US00RE48731E

(19) United States
(12) Reissued Patent
Flynn et al.

(10) Patent Number: US RE48,731 E
(45) Date of Reissued Patent: Sep. 14, 2021

(54) DIHYDRONAPHTHYRIDINES AND RELATED COMPOUNDS USEFUL AS KINASE INHIBITORS FOR THE TREATMENT OF PROLIFERATIVE DISEASES

(71) Applicant: Deciphera Pharmaceuticals, LLC, Lawrence, KS (US)

(72) Inventors: Daniel L. Flynn, Lawrence, KS (US); Michael D. Kaufman, Lawrence, KS (US); Peter A. Petillo, Lawrence, KS (US)

(73) Assignee: Deciphera Pharmaceuticals, LLC, Waltham, MA (US)

(21) Appl. No.: 16/387,315

(22) Filed: Apr. 17, 2019

Related U.S. Patent Documents

Reissue of:
(64) Patent No.: 8,940,756
Issued: Jan. 27, 2015
Appl. No.: 13/801,753
Filed: Mar. 13, 2013

U.S. Applications:
(62) Division of application No. 13/491,394, filed on Jun. 7, 2012, now Pat. No. 8,461,179.

(51) Int. Cl.
*A61K 31/4375* (2006.01)
*C07D 471/04* (2006.01)
*A01N 43/42* (2006.01)

(52) U.S. Cl.
CPC ..... *C07D 471/04* (2013.01); *A01N 43/42* (2013.01)

(58) Field of Classification Search
None
See application file for complete search history.

(56) References Cited

U.S. PATENT DOCUMENTS

| | | | |
|---|---|---|---|
| 3,528,980 | A | 9/1970 | Islip |
| 3,818,024 | A | 6/1974 | Krenzer |
| 3,939,122 | A | 2/1976 | Merten et al. |
| 3,949,002 | A | 4/1976 | Feasey et al. |
| 4,093,624 | A | 6/1978 | Revankar et al. |
| 4,296,237 | A | 10/1981 | Cragoe, Jr. et al. |
| 4,366,189 | A | 12/1982 | Burdeska et al. |
| 4,432,992 | A | 2/1984 | Cragoe, Jr. et al. |
| 4,525,450 | A | 6/1985 | Itoh et al. |
| 4,816,454 | A | 3/1989 | Zoller et al. |
| 5,103,014 | A | 4/1992 | Musser et al. |
| 5,162,360 | A | 11/1992 | Creswell et al. |
| 5,189,045 | A | 2/1993 | Peglion et al. |
| 5,319,099 | A | 6/1994 | Kamata et al. |
| 5,494,925 | A | 2/1996 | Court et al. |
| 5,614,532 | A | 3/1997 | Carling et al. |
| 5,621,010 | A | 4/1997 | Sueda et al. |
| 5,658,924 | A | 8/1997 | Matsuura et al. |
| 5,721,231 | A | 2/1998 | Moriwaki et al. |
| 5,811,456 | A | 9/1998 | Seman et al. |
| 6,020,357 | A | 2/2000 | Pinto et al. |
| 6,028,085 | A | 2/2000 | Bromidge |
| 6,080,763 | A | 6/2000 | Regan et al. |
| 6,147,088 | A | 11/2000 | Goulet et al. |
| 6,197,599 | B1 | 3/2001 | Chin et al. |
| 6,235,786 | B1 | 5/2001 | Dai et al. |
| 6,294,573 | B1 | 9/2001 | Curtin et al. |
| 6,319,921 | B1 | 11/2001 | Cirillo et al. |
| 6,410,254 | B1 | 6/2002 | Finer et al. |
| 6,500,628 | B1 | 12/2002 | Robison |
| 6,525,046 | B1 | 2/2003 | Cirillo et al. |
| 6,645,990 | B2 | 11/2003 | Askew et al. |
| 6,916,924 | B2 | 7/2005 | Tan et al. |
| 7,030,128 | B2 | 4/2006 | Blackaby et al. |
| 7,071,199 | B1 | 7/2006 | Hirst et al. |
| 7,135,550 | B2 | 11/2006 | Come et al. |
| 7,144,911 | B2 | 12/2006 | Flynn et al. |
| 7,202,257 | B2 | 4/2007 | Flynn et al. |
| 7,211,575 | B2 | 5/2007 | Moss et al. |
| 7,342,037 | B2 | 3/2008 | Flynn et al. |
| 7,531,566 | B2 | 5/2009 | Flynn et al. |
| 7,790,756 | B2 | 9/2010 | Flynn et al. |
| 8,163,756 | B2 | 4/2012 | Flynn et al. |
| 8,188,113 | B2 | 5/2012 | Flynn et al. |
| 8,278,331 | B2 | 10/2012 | Flynn et al. |
| 8,461,179 | B1 | 6/2013 | Flynn et al. |
| 8,569,319 | B2 | 10/2013 | Flynn et al. |
| 8,586,565 | B2 | 11/2013 | Flynn et al. |

(Continued)

FOREIGN PATENT DOCUMENTS

| | | | |
|---|---|---|---|
| CN | 101528744 | A | 9/2009 |
| CN | 101553232 | A | 10/2009 |

(Continued)

OTHER PUBLICATIONS

Hou, Y.-Y., et al. World J. Gastroenterol. (2004), 10(9); 1310-1314.*
Palmisano, M., et al. Hematology (2008), 13(1); 1-12.*
McIntyre, A., et al. Cancer Res. (2005), 65(18); 8085-8089.*
Gotlib, J., et al. Blood (2005), 106(8); 2865-2870.*
Palmer, Brian, D. et al: "Structure-Activity Relationships for 2-Anilino-6-Phenylpyrido[2,3-d]Pyrimidin-7(8H)-Ones As Inhibitors of the Cellular Checkpoint Kinase Wee1" Bioorganic & Medicinal Chemistry Letters, 15(7), 1931-1935 Coden: BMCLE8; ISSN: 0960-894X, 2005, XP004789411 p. 1933.
Kettle et al., "Discovery of N-(4-{[5-Fluoro-7-(2-methoxyethoxy)quinazolin-4-yl]amino}phenyl)-2-[4-(propan-2-yl)-1H-1,2,3-triazol-1-yl]acetamide (AZD3229), a Potent Pan-KIT Mutant Inhibitor for the Treatment of Gastrointestinal Stromal Tumors" Journal of Medicinal Chemistry (2018), 61(19), 8797-8810.
Lim et al., "Current research and treatment for gastrointestinal stromal tumors" World Journal of Gastroenterology (2017), 23(27), 4856-4866 Publisher: Baishideng Publishing Group Inc.

(Continued)

*Primary Examiner* — Kevin S Orwig
(74) *Attorney, Agent, or Firm* — Goodwin Procter LLP

(57) ABSTRACT

The invention relates to dihydronaphthyridines and related compounds; compositions comprising an effective amount of a dihydronaphthyridine or a related compound; and methods for treating or preventing proliferative diseases comprising the administration of an effective amount of a dihydronaphthyridine or a related compound.

4 Claims, No Drawings

Specification includes a Sequence Listing.

(56) References Cited

U.S. PATENT DOCUMENTS

| | | | |
|---|---|---|---|
| 8,637,672 | B2 | 1/2014 | Flynn et al. |
| 8,921,565 | B2 | 12/2014 | Flynn et al. |
| 9,012,635 | B2 | 4/2015 | Flynn et al. |
| 9,133,183 | B2 | 9/2015 | Flynn et al. |
| 9,181,223 | B2 | 11/2015 | Kaufman et al. |
| 9,187,474 | B2 | 11/2015 | Flynn et al. |
| 9,193,719 | B2 | 11/2015 | Flynn et al. |
| 9,309,224 | B2 | 4/2016 | Flynn et al. |
| 9,334,267 | B2 | 5/2016 | Flynn et al. |
| 9,382,228 | B2 | 7/2016 | Flynn et al. |
| 9,387,202 | B2 | 7/2016 | Flynn et al. |
| 9,457,019 | B2 | 10/2016 | Flynn et al. |
| 2002/0058678 | A1 | 5/2002 | Cirillo et al. |
| 2002/0077486 | A1 | 6/2002 | Scarborough et al. |
| 2003/0060455 | A1 | 3/2003 | Moss et al. |
| 2003/0105139 | A1 | 6/2003 | Gaster et al. |
| 2003/0207870 | A1 | 11/2003 | Dumas et al. |
| 2003/0232865 | A1 | 12/2003 | Cirillo et al. |
| 2004/0043388 | A1 | 3/2004 | Come et al. |
| 2004/0157827 | A1 | 8/2004 | Pevarello et al. |
| 2004/0167224 | A1 | 8/2004 | Ozaki et al. |
| 2004/0171075 | A1 | 9/2004 | Flynn et al. |
| 2004/0180906 | A1 | 9/2004 | Flynn et al. |
| 2004/0229937 | A1 | 11/2004 | Dumas et al. |
| 2005/0014753 | A1 | 1/2005 | Ding et al. |
| 2005/0165024 | A1 | 7/2005 | Milanov et al. |
| 2005/0165031 | A1 | 7/2005 | Grotzfeld et al. |
| 2005/0192314 | A1 | 9/2005 | Mehta et al. |
| 2005/0197371 | A1 | 9/2005 | Milanov et al. |
| 2005/0256174 | A1 | 11/2005 | Wood et al. |
| 2005/0267182 | A1 | 12/2005 | Milanov et al. |
| 2005/0288286 | A1 | 12/2005 | Flynn et al. |
| 2006/0229337 | A1 | 10/2006 | Brittelli et al. |
| 2007/0037794 | A1 | 2/2007 | Ungashe et al. |
| 2007/0078121 | A1 | 4/2007 | Flynn et al. |
| 2007/0155764 | A1 | 7/2007 | Lang et al. |
| 2007/0191336 | A1 | 8/2007 | Flynn et al. |
| 2007/0293685 | A1 | 12/2007 | Fritch et al. |
| 2008/0045531 | A1 | 2/2008 | Flynn et al. |
| 2008/0045706 | A1 | 2/2008 | Flynn et al. |
| 2008/0064717 | A1 | 3/2008 | Iyengar et al. |
| 2008/0090856 | A1 | 4/2008 | Flynn et al. |
| 2008/0113967 | A1 | 5/2008 | Flynn et al. |
| 2008/0114006 | A1 | 5/2008 | Flynn et al. ..... A61P 37/02 514/264.1 |
| 2008/0132506 | A1 | 6/2008 | Flynn et al. |
| 2008/0176846 | A1 | 7/2008 | Chianelli et al. |
| 2008/0187978 | A1 | 8/2008 | Flynn et al. |
| 2008/0194836 | A1 | 8/2008 | Gharbaoui et al. |
| 2008/0200530 | A1 | 8/2008 | Unett et al. |
| 2008/0220497 | A1 | 9/2008 | Flynn et al. |
| 2008/0248487 | A1 | 10/2008 | Flynn et al. |
| 2008/0248548 | A1 | 10/2008 | Flynn et al. |
| 2009/0069310 | A1 | 3/2009 | Flynn et al. |
| 2009/0075986 | A1 | 3/2009 | Flynn et al. |
| 2009/0099190 | A1 | 4/2009 | Flynn et al. |
| 2009/0105230 | A1 | 4/2009 | Flynn et al. |
| 2009/0137021 | A1 | 5/2009 | Flynn et al. |
| 2009/0312349 | A1 | 12/2009 | Flynn et al. |
| 2010/0160292 | A1 | 6/2010 | Whitney et al. |
| 2010/0209420 | A1 | 8/2010 | Lamb et al. |
| 2010/0298290 | A1 | 11/2010 | Anand et al. |
| 2011/0124640 | A1 | 5/2011 | Liu et al. |
| 2011/0183997 | A1 | 7/2011 | Chianelli et al. |
| 2012/0214808 | A1 | 8/2012 | Bloxham et al. |
| 2012/0289540 | A1 | 11/2012 | Flynn et al. |
| 2014/0088075 | A1 | 3/2014 | Flynn et al. |
| 2014/0107100 | A1 | 4/2014 | Rice et al. |
| 2014/0147415 | A1 | 5/2014 | Moussy et al. |
| 2015/0031648 | A1 | 1/2015 | Le Tiran et al. |
| 2015/0073141 | A1 | 3/2015 | Teegarden et al. |
| 2015/0320759 | A1 | 11/2015 | Flynn et al. |
| 2016/0009709 | A1 | 1/2016 | Cheve et al. |
| 2016/0166679 | A1 | 6/2016 | Low et al. |
| 2016/0222012 | A1 | 8/2016 | Ruan |
| 2016/0374990 | A1 | 12/2016 | Teegarden et al. |
| 2019/0091217 | A1 | 3/2019 | Flynn et al. |

FOREIGN PATENT DOCUMENTS

| | | | |
|---|---|---|---|
| CN | 102731385 | A | 10/2012 |
| CN | 105461699 | A | 4/2016 |
| DE | 4343831 | | 6/1995 |
| EP | 0021228 | | 1/1981 |
| EP | 0025232 | | 3/1981 |
| EP | 0661276 | | 7/1995 |
| EP | 0692483 | | 1/1996 |
| EP | 0739884 | | 10/1996 |
| EP | 0867435 | | 9/1998 |
| EP | 0927555 | | 7/1999 |
| EP | 0928790 | | 7/1999 |
| EP | 0956855 | | 11/1999 |
| EP | 1281399 | | 2/2003 |
| EP | 2858646 | A1 | 4/2015 |
| FR | 2337554 | | 9/1977 |
| FR | 2396549 | | 3/1979 |
| GB | 971307 | | 9/1964 |
| GB | 1410279 | | 10/1975 |
| GB | 2220206 | | 1/1990 |
| JP | 59-015247 | | 1/1984 |
| JP | 59-177557 | | 10/1984 |
| JP | 09-221476 | | 8/1997 |
| JP | 2000-275886 | | 10/2000 |
| JP | 2001-002687 | | 1/2001 |
| WO | WO 91/19708 | | 12/1991 |
| WO | WO 92/08693 | | 5/1992 |
| WO | WO 94/18176 | | 8/1994 |
| WO | WO 94/21617 | | 9/1994 |
| WO | WO 94/24095 | | 10/1994 |
| WO | 1995/006044 | A1 | 3/1995 |
| WO | WO 95/15954 | | 6/1995 |
| WO | WO 95/29902 | | 11/1995 |
| WO | WO 95/34540 | | 12/1995 |
| WO | WO 96/16046 | | 5/1996 |
| WO | WO 96/19477 | | 6/1996 |
| WO | 1996/023783 | A1 | 8/1996 |
| WO | WO 97/34900 | | 9/1997 |
| WO | 1997/037989 | A2 | 10/1997 |
| WO | WO 97/40028 | | 10/1997 |
| WO | 1997/045400 | A1 | 12/1997 |
| WO | WO 98/22103 | | 5/1998 |
| WO | WO 98/52558 | | 11/1998 |
| WO | WO 99/15164 | | 4/1999 |
| WO | WO 99/23091 | | 5/1999 |
| WO | WO 99/23093 | | 5/1999 |
| WO | WO 99/32106 | | 7/1999 |
| WO | WO 99/32110 | | 7/1999 |
| WO | WO 99/32111 | | 7/1999 |
| WO | WO 99/32455 | | 7/1999 |
| WO | WO 99/37622 | | 7/1999 |
| WO | WO 99/59959 | | 11/1999 |
| WO | WO 00/06550 | | 2/2000 |
| WO | WO 00/07980 | | 2/2000 |
| WO | WO 00/18738 | | 4/2000 |
| WO | WO 00/21927 | | 4/2000 |
| WO | WO 00/41698 | | 7/2000 |
| WO | WO 00/42012 | | 7/2000 |
| WO | WO 00/43384 | | 7/2000 |
| WO | WO 00/55139 | | 9/2000 |
| WO | WO 00/59506 | | 10/2000 |
| WO | WO 01/12621 | | 2/2001 |
| WO | WO 01/14372 | | 3/2001 |
| WO | WO 01/74771 | | 10/2001 |
| WO | WO 01/96298 | | 12/2001 |
| WO | WO 02/14291 | | 2/2002 |
| WO | WO 02/14311 | | 2/2002 |
| WO | WO 02/28835 | | 4/2002 |
| WO | WO 02/34727 | | 5/2002 |
| WO | WO 02/060869 | | 8/2002 |
| WO | WO 02/060876 | | 8/2002 |
| WO | WO 02/062763 | | 8/2002 |
| WO | WO 03/068223 | | 8/2002 |
| WO | WO 02/070662 | | 9/2002 |

(56) References Cited

FOREIGN PATENT DOCUMENTS

| | | | |
|---|---|---|---|
| WO | WO 03/005999 | | 1/2003 |
| WO | WO 03/053368 | | 7/2003 |
| WO | WO 03/059373 | | 7/2003 |
| WO | WO 03/068229 | | 8/2003 |
| WO | WO 03/072577 | | 9/2003 |
| WO | WO 03/084539 | | 10/2003 |
| WO | WO 2004/004720 | | 1/2004 |
| WO | WO 2004/056783 | | 7/2004 |
| WO | WO 2004/060306 | | 7/2004 |
| WO | WO 2004/061084 | | 7/2004 |
| WO | WO 2004/078128 | | 9/2004 |
| WO | WO 2004/113352 | | 12/2004 |
| WO | WO 2005/002673 | | 1/2005 |
| WO | 2005/012254 | A1 | 2/2005 |
| WO | 2005/024755 | A2 | 3/2005 |
| WO | WO 2005/034869 | | 4/2005 |
| WO | 2005/103011 | A1 | 11/2005 |
| WO | WO 2005/110994 | | 11/2005 |
| WO | 2006/018662 | A2 | 2/2006 |
| WO | WO 2006/014290 | | 2/2006 |
| WO | WO 2006/046552 | | 5/2006 |
| WO | 2006/078610 | A1 | 7/2006 |
| WO | WO 2006/071940 | | 7/2006 |
| WO | 2006/081335 | A2 | 8/2006 |
| WO | WO 2006/081034 | | 8/2006 |
| WO | 2006/099075 | A2 | 9/2006 |
| WO | WO 2007/008917 | | 1/2007 |
| WO | 2007/042321 | A2 | 4/2007 |
| WO | WO 2007/076473 | | 7/2007 |
| WO | 2007/137107 | A2 | 11/2007 |
| WO | 2008/033858 | A2 | 3/2008 |
| WO | WO 2008/033999 | | 3/2008 |
| WO | WO 2008/034008 | | 3/2008 |
| WO | WO 2008/046003 | | 4/2008 |
| WO | WO 2008/051757 | | 5/2008 |
| WO | WO-2008/051757 | A1 | 5/2008 |
| WO | 2008/131227 | A1 | 10/2008 |
| WO | 2008/131253 | A1 | 10/2008 |
| WO | WO 2008/131276 | | 10/2008 |
| WO | 2008/140895 | A1 | 11/2008 |
| WO | 2009/076454 | A2 | 6/2009 |
| WO | 2010/011837 | A1 | 1/2010 |
| WO | 2010/051373 | A1 | 5/2010 |
| WO | 2010/135524 | A1 | 11/2010 |
| WO | 2011/067306 | A1 | 6/2011 |
| WO | 2011/137342 | A1 | 11/2011 |
| WO | 2011/139891 | A1 | 11/2011 |
| WO | 2012/019015 | A2 | 2/2012 |
| WO | 2012/071519 | A1 | 5/2012 |
| WO | 2013/078295 | A2 | 5/2013 |
| WO | 2013/134243 | A1 | 9/2013 |
| WO | 2013/134252 | A1 | 9/2013 |
| WO | 2013/134298 | A1 | 9/2013 |
| WO | 2013/184119 | A1 | 12/2013 |
| WO | 2014/037480 | A1 | 3/2014 |
| WO | 2014/040242 | A1 | 3/2014 |
| WO | 2014/040549 | A1 | 3/2014 |
| WO | 2014/102376 | A1 | 7/2014 |
| WO | 2014/102377 | A1 | 7/2014 |
| WO | 2014/145004 | A1 | 9/2014 |
| WO | 2014/145015 | A2 | 9/2014 |
| WO | 2014/145023 | A1 | 9/2014 |
| WO | 2014/145025 | A2 | 9/2014 |
| WO | 2014/145028 | A2 | 9/2014 |
| WO | 2014/145029 | A2 | 9/2014 |
| WO | 2015/011399 | A1 | 1/2015 |
| WO | 2015/069266 | A1 | 5/2015 |
| WO | 2015/092423 | A1 | 6/2015 |
| WO | 2016/061228 | A1 | 4/2016 |
| WO | 2016/061231 | A1 | 4/2016 |
| WO | 2016/154524 | A1 | 9/2016 |
| WO | 2018/222173 | A1 | 12/2018 |

OTHER PUBLICATIONS

Deciphera Pharmaceuticals LLC, "DCC-2618, a small molecule inhibitor of normal and mutant KIT kinase for treatment of refractory gastrointestinal stromal tumors (GIST)" (Presented on Sep. 24, 2011 at GIST Summit 2011 on "Gastrointestinal stromal tumors.").

"A Safety, Tolerability and PK Study of DCC-2618 in Patients With Advanced Malignancies," ClinicalTrials.gov, Jan. 12, 2018, pp. 1-11. Retrieved from the Internet: URL: <https://clinicaltrials.gov/ct2/show/NC>.

Database Registry [Online] Chemical Abstracts Service, Columbus, Ohio, US; May 27, 2010, XP002777425, retrieved from STN accession No. 1225278-16-9 RN (2 pages).

Janku Filip et al., "Pharmacokinetic-driven phase I study of DCC-2618 a pan-KIT and PDGFR inhibitor in patients (pts) with gastrointestinal stromal tumor (GIST) and other solid tumors," *J. Clin. Oncol.* (2017) No. 15, Suppl 2515.

Schneeweiss Mathias, et al., "The KIT and PDGFRA switch-control inhibitor DCC-2618 blocks growth and survival of multiple neoplastic cell types in advanced mastocytosis," *Haematologica* (2018) vol. 103, No. 5, pp. 799-809.

Schneeweiss Mathias, et al., "The Multi-Kinase Inhibitor DCC-2618 Inhibits Proliferation and Survival of Neoplastic Mast Cells and Other Cell Types Involved in Systemic Mastocytosis," *Blood* (2016) vol. 128, No. 22, pp. 1965.

Bai et al., "Targeting the KITactivating switch control pocket: a novel mechanism to inhibit neoplastic mast cell proliferation and mast cell activation," Leukemia (2013), vol. 27, pp. 278-285.

'Smith et al., "Ripretinib (DCC-2618) is a switch control kinase inhibitor of a broad spectrum of oncogenic and drug-resistant KIT and PDGFRA variants," Cancer Cell (2019), vol. 35, No. 5, pp. 738-759.

U.S. Appl. No. 12/268,997, filed Nov. 11, 2008, Flynn et al.

International Preliminary Report on Patentability for International Application No. PCT/US2007/078408, dated Mar. 17, 2009.

International Search Report and Written Opinion for International Application No. PCT/US2007/078408, mailed Apr. 11, 2008.

Supplementary European Search Report for European Application No. 07842438.9, mailed Sep. 1, 2010.

International Search Report and Written Opinion for International Application No. PCT/US2012/041378, mailed Sep. 17, 2012.

Office Action for U.S. Appl. No. 13/491,394, mailed Oct. 23, 2012.

Office Action for U.S. Appl. No. 13/491,394, mailed Sep. 7, 2012.

"Additions and Corrections," Journal of Medicinal Chemistry, 32(12):2583 (1989).

Aklilu et al., "Increased PTHRP Production by a Tyrosine Kinase Oncogene, Tpr-Met: Rose of the Ras Signaling Pathway," American Journal of Physiology—Endocrinology and Metabolism, 271(2) pp. E277-E283 (1996).

Albericio et al., "Synthesis of a Sulfaydantion Library," J. Comb. Chem., 3:290-300 (2001).

Almerico et al., "On the Preparation of 1-aryl-2-heteroaryl- and 2-aryl-1-heteroaryl-pyrroles as Useful Building Blocks for Biologically Interesting Heterocycles," Arkivoc (vi), Rudy Abramovitch Issue, pp. 129-142 (2001).

Antonescu et al., "Acquired Resistance to Imatinib in Gastrointestinal StromalTumor Occurs Through Secondary Gene Mutation," Clin. Cancer Res., 11(11):4182-4190 (Jun. 2005).

Anzai et al., "Alkyl- and Arylthiation of Uracil and Indole," J. Heterocyclic Chem., 16:567-569 (1979).

Askew et al., "Molecular Recognition with Convergent Functional Groups: 6. Synthetic and Structural Studies with a Model Receptor for Nucleic Acid Components," J. Am. Chem., 111:1082-1090 (1989).

Avruch, J. et al., "Ras Activation of the Raf Kinase: Tyrosine Kinase Recruitment of the MAP Kinase Cascade," Recent Prog. Horm. Res., 56:127-155 (2001).

Bais et al., "Inhibition of Endogenous Wxalate Production: Biochemical Consideration of the Roles of Glycollate Oxidase and Lactate Dehydrogenase," Clinical Science, 76:303-309 (1989).

Baker et al., "Irreversible Enzyme Inhibitors. 188. Inhibition of Mammalian Thymidine Phosphorylase," Journal of Medicinal Chemistry, 14:812-816 (1971).

(56) References Cited

OTHER PUBLICATIONS

Barker et al., "Characterization of pp60c-src Tyrosine Kinase Activities Using a Continuous Assay: Autoactivation of the Enzyme is an Intermolecular Autophosphorylation Process," Biochemistry, 35:14843-14851 (1995).
Barvian et al, "Pyrido[2,3-d]pyrimidin-7-one Inhibitors of Cyclin-Dependent Kinases," J. Med Chem., 43:4606-4616 (2000).
Bausch et al., "Proton-Transfer Chemistry of Urazoles and Related Imides, and Diacyl Hydrazides," J. Org. Chem., 56:5643-5651 (1991).
Beghini et al., "C-kit mutations in core binding factor leukemias," Blood, 95(2):726-727 (Jan. 2000).
Benvenuti et al., "Crystallization of Soluble Proteins in Vapor Diffusion for X-Ray Crystallography," Nature Protocols, 2(7):1633-1651 (2007).
Bolton et al, "Chapter 17. Ras Oncogene Directed Approaches in Cancer Chemotherapy," Ann. Rep. Med. Chem., 29:165-174 (1994).
Bosca et al., "Circular Dichroism Analysis of Ligand-Induced Conformational Changes in Protein Kinase C," Biochem. J., 290:827-832 (1993).
Boschelli et al., "4-Anilino-3-quinolinecarbonitriles: An Emerging Class of Kinase Inhibitors," Current Topics in Medicinal Chemistry, 2:1051-1063 (2002).
Bourdonnec et al., "Synthesis and Pharmacological Evaluation of New Pyrazolidine-3,5-diones as AT1 Angiotensin II Receptor Antagonists," J. Med. Chem., 43:2685-2697 (2000).
Boyer, "Small Molecule Inhibitors of Kdr (Vegfr-2) Kinase: an Overview of Structure Activity Relationships," Current Topics in Medicinal Chemisty, 2:973-1000 (2002).
Brady et al., "Fast Prediction and Visualization of Protein Binding Pockets with PASS," Journal of Computer-Aided Molecular Design, 14:383-401 (2000).
Brasher et al., "C-Abul has High Intrinsic Tyrosine Kinase Activity that is Stimulated by Mutation of the Src Homology 3 Domain and by Autophosphorylation at Two Distinct Regulatory Tyrosines," Journal of Biological Chemistry, 275:35631-35637 (2000).
Bullock et al., "Prospects for Kinase Activity Modulators in the Treatment of Diabetes and Diabetic Complications," Current Topics in Medicinal Chemistry, 2:915-938 (2002).
Byron et al., "The Synthesis of some Substituted Biphenyl-4-carboxylic Acids, 4-Biphenylylacetic Acids, and 4-Aminobiphenyls," J. Chem. Soc. (C), Organic, pp. 840-845 (1966).
Cardillo et al., "Sulle 1,2-difenil-3.5-dichetopirazolidine," Gazz. Chim., Ital., 9:973-985 (1966) (English Summary).
Chan et al, "Copper promoted C—N. And C—O bond dross-coupling with phenyl and pyridylboronates," Tetrahedron Lett., 44:3863-3865 (2003).
Chan et al, "New N- and 0-Arylations with Phenylboronic Acids and Cupric Acetate," Tetrahedron Lett., 39:2933-2936 (1998).
Chan, D. M. T., "Promotion of Reaction of N—H Bonds with Triarylbismuth and Cuprie Acetate," Tetrahedron Lett., 37(50):9013-9016 (1996).
Charmm, "NHLBI LBC Computational Biophysics Section," CHARMM Documentation Index, http://www.lobos.nih.gov/Charmm/chmdoc.html, printed Mar. 4, 2005 (1 page).
Chen et al., "Biochemical Evidence for the Autophosphorylation and Transphosphorylation of Transforming Growth Factor b Receptor Kinases," Proc. Natl. Acad. Sci. USA, 92:1565-1569 (1995).
Cheng et al., "Novel Solution Phase Strategy for the Synthesis of Chemical Libraries Containing Small Organic Molecules," J. Am. Chem. Soc., 118:2567-2573 (1996).
Cheng et al., "Synthesis and SAR of Heteroaryl-phenyl-substituted Pyrazole Derivatives as Highly Selective and Potent Canine COX-2 Inhibitors," Bioorganic & Medicinal Chemistry Letters, 16:2076-2080 (2006).
Chu et al., "Using Affinity Capillary Electrophoresis to Determine Binding Stoichiometries of Protein-Ligand Interactions," Biochemistry, 33:10616-10621 (1994).
Cirillo et al. "The Non-Diaryl Heterocycle Classes of p38 MAP Kinase Inhibitors," Current Topics in Medicinal Chemistry, 2:1021-1035 (2002).
Closier et al., "Nitrofuryl Heterocyclics. 1," Journal of Medicinal Chemistry, 13(4):638-640 (1970).
Cockerill et al., "Small Molecule Inhibitors of the Class 1 Receptor Tyrosine Kinase Family," Current Topics in Medicinal Chemistry, 2:1001-1010 (2002).
Colton et al., "Affinity Capillary Electrophoresis: A Physical-Organic Tool for Studying Interactions in Biomolecular Recognition," Electrophoresis, 19:367-382 (1998).
Corless et al., "Biology of gastrointestinal stromal tumors," Journal of Clinical Oncology, 22:3813-3825 (Sep. 2004).
Cortes et al., "Results of Imatinib Mesylate Therapy in Patients with Refractory or Recurrent Acute Myeloid Leukemia, High-Risk Myelodysplastic Syndrime, and Myeloproliferative Disorders," Cancer, 97(11):2760-2766 (2003).
Cross et al., "Inhibition of Glycogen Synthase Kinase-3 by Insulin Mediated by Protein Kinase B," Nature, 378:785-789 (1995).
Dajani et al., "Crystal Structure of Glycogen Synthase Kinas 3b: Structural Basis for Phosphate-Primed Substrate Specificity and Autoinhibition," Cell, 105:721-732 (2001).
Dajani et al., "Structural Basis for Recruitment of Glycogen Synthase Kinase 3b to the Axin-APC Scaffold Complex," EMBO J., 22(3):494-501 (2003).
Daley et al., "Induction of Chronic Myelogenous Leukemia in Mice by the P210bcr/abl Gene of the Philadelphia Chromosome," Science, 247:824-830 (1990).
Davies, H. et al, "Mutations of the BRAF gene in human cancer," Nature, 417:949-954 (Jun. 2002).
Davis et al., "Iterative Size-Exclusion Chromatography Coupled with Liquid Chromatographic Mass Spectrometry to Enrich and Identify Tight-Binding Ligands from Complex Mixtures," Tetrahedron, 55:11653-11667 (1999).
de Boer et al., "Synthesis and Characterization of Conjugated Mono- and Dithiol Oligomers and Characterization of Their Self-Assembled Monolayers," Langmuir, 19:4272-4284 (2003).
de Silva et al., "Gastrointestinal Stromal Tumors (GIST): C-kit Mutations, CD117 Expression, Differential Diagnosis and Targeted Cancer Therapy with Imatinib," Pathology Oncology Research, 9(1):13-19 (2003).
Debiec-Rychter et al., "Mechanisms of Resistance to Imatinib Mesylate in Gastrointestinal Stromal Tumors and Activity of the PKC412 Inhibitor Against Imatinib-Resistant Mutants," Gastroenterology, 128:270-279 (2005).
Deng et al., "Expression, Characterization, and Crystallization of the Pyrophosphate-Dependent Phosphofructo-1-Kinase of Borrelia Burgdorferi," Archives of Biochemistry and Biophysics, 371(2):326-331 (1999).
Dess et al., "A Useful 12-I-5 Triacetoxyperiodiane (the Dess-Martin Periodiane) for Selective Oxidation of Primary or Secondary Alcohols and a Variety of Related 12-I-5 Species," J. Am. Chem., Soc., 113:7277-7287 (1991).
Dumas, "Preface," Current Topics in Medicinal Chemistry 2(9):i (2002) (1 Page).
Dumas, "Protein Kinase Inhibitors: Emerging Pharmacophores," Exp. Opin. Ther. Patents, 11(3):405-429 (2001).
Dumas et al., "Discovery of a New Class of p38 Kinase Inhibitors," Bioorganic & Medicinal Chemistry Letters, 10:2047-2050 (2000).
Dumas, J. et al, "Recent developments in the discovery of protein kinase inhibitors from the urea class," Current Opinion in Drug Discovery & Development, 7(5):600-616 (2004).
Ettmayer et al, "Lessons Learned from Marketed and Investigational Prodrugs," J. Med. Chem., 47(10):2393-2404 (May 2004).
Ewing, "Critical Evaluation of Search Algorithms for Automated Molecular Docking and Database Screening," Journal of Computational Chemistry, 18(9):1175-1189 (1997).
Farooqui et al., "Interactions Between Neural Membrane Glycerophospholipid and Sphingolipid Mediators: A Recipe for Neural Cell Survival or Suicide," Journal of Neuroscience Research, 85:1834-1850 (2007).

(56) References Cited

OTHER PUBLICATIONS

Fathalla, "Synthesis of New Pyrazolo[1,5-a]pyrimidine Derivative Using 5-Aminouracil and Ketene Dithiacetal," Arch Pharm Res, 22(6):571-574 (1999).
Fathalla et al., "Synthesis of New Uracil-5-Sulfonamide Derivatives and Immuno-Stimulatory Effect of a Chemically Modified Hemolymph of Biomphalaria Alexandrine on Schistosoma Manosi Infected Mice," Arch Pharm Res., 26(5):358-366 (2003).
Fathalla et al., "Synthesis of New Uracil-5-Sulphonamide-p-Phenyl Derivatives and Their Effect on Biomphalaria alexandrine Snail's Nucleoproteins," Arch. Pharm. Res., 23(2):128-138 (2000).
Flatt et al., "Synthesis of thiol substituted oligoanilines for molecular device candidates," Tetrahedron Letters, 44:6699-6702 (2003).
Fletcher et al., "Diagnosis of Gastrointestinal Stromal Tumors: a Consensus Approach," Human Pathology, 33(5):459-465 (2002).
Fletcher et al., "KIT Mutations in GIS," Current Opinion in Genetics & Development, 17:3-7 (2007).
Frame et al., "A Common Phosphate Binding Site Explains the Unique Substrate Specificity of GSK3 and Its Inactivation by Phosphorylation," Molecular Cell, 7:1321-1327 (2001).
Furuya et al., "Addition of 4-Ethoxyimidazoles to Dimethyl Acetylenedicarboxylate and Transformation of the Adducts to Pyrimidian-5-yl Acetates," Chem. Pharm. Bull., 36(5):1669-1675 (1988).
Gajiwala et al., "KIT kinase mutants show unique mechanisms of drug resistance to imatinib and sunitinib in gastrointestinal stromal tumor patients," PNAS Early Edition (2009), p. 1-6.
Garcia-Tellado et al., "Molecular Recognition in the Solid Waste State: Controlled Assembly of Hydrogen-Bonded Molecular Sheets," J. Am. Chem. Soc., 113:9265-9269 (1991).
Gishizky et al., "Efficient Transplantation of BCR-ABL-Induced Chronic Myelogenous Leukemia-Like Syndrome in Mice," Proceedings of the National Academy of Sciences of the United States of America, 90(8):3755-3759 (1993).
Greene et al., "Chapter 7: Protection for the Amino Group," In: Protective Groups in Organic Synthesis, Third Edition, John Wiley: New York, pp. 494-653 (1999).
Griffith et al., "TPAP: Tetra-n-propylammonium Perruthenate, A Mild and Convenient Oxidant for Alcohols," Aldrichimica Acta, 23(1):13-19 (1990).
Guzel, "Investigation of the Relationship Between the Inhibitory Activity of Glycolic Acid Oxidase (GAO) and its Chemical Structure: Electron-Topological Approach," Journal of Molecular Structure, 366:131-137 (1996).
Haar et al., "Structure of GSK3b Reveals a Primed Phosphorylation Mechanism," Nature Structural Biology, 8(7):593-596 (2001).
Haesslein et al., "Recent Advances in Cyclin-Dependent Kinase Inhibition. Purine-Based Derivatives as Anti-Cancer Agents. Roles and Perspectives for the Future," Current Topics in Medicinal Chemistry, 2:1037-1050 (2002).
Heegaard et al., "Affinity Capillary Electrophoresis: Important Application Areas and Some Recent Developments," Journal of Chromatography B, 715:29-54 (1998).
Heinrich et al., "Molecular Correlates of Imatinib Resistance in Gastrointestinal Stromal Tumors," Journal of Clinical Oncology, 24(29):4764-4774 (Oct. 2006).
Heinrich et al., "Primary and Secondary Kinase Genotypes Correlate With the Biological and Clinical Activity of Sunitinib in Imatinib-Resistant Gastrointestinal Stromal Tumor," Journal of Clinical Oncology, 26(33):5352-5359 (Nov. 2008).
Honda et al., "Determination of the Association Constant of Monovalent Mode Protein-Sugar Interaction by Capillary Zone Electrophoresis," Journal of Chromatography, 597:377-382 (1992).
Hu et al., "Capillary Electrophoresis for the Analysis of Biopolymers," Anal., Chem., 74:2833-2850 (2002).
Huang et al., "Inhibition of Nucleoside Transport by Protein Kinase Inhibitors," The Journal of Pharmacology and Experimental Therapeutics, 304(2):753-760 (2003).
Hubbard, "Crystal Structure of the Activated Insulin Receptor Tyrosine Kinase in Complex with Peptide Substrate and ATP Analog," EMBO J., 16(18):5573-5581 (1997).
Hubbard et al., "Crystal Structure of the Tyrosine Kinase Domain of the Human Insulin Receptor," Nature, 372:746-754 (1994).
Hughes et al., "Modulation of the Glycogen Synthase Kinase-3 Family by Tyrosine Phosphorylation," EMBO J., 12(2):803-808 (1993).
Huse et al., "The TGFb Receptor Activation Process: An Inhibitor-to Substrate-Binding Switch," Molecular Cell, 8:671-682 (2001).
Huse, M. et al, "The Conformational Plasticity of Protein Kinases," Cell, 109:275-282 (May 2002).
Igarashi et al., "Antimicrobial Activities of 2-arylthio-N-alkylmaleimides," Journal of Industrial Microbiology, 9:91-96 (1992).
International Human Genome Sequencing Consortium, "Initial Sequencing and Analysis of the Human Genome," Nature, 409:860-921 (2001).
Ishida et al., "Molecular Arrangement and Electrical Conduction of Self-Assembled Monolayers Made from Terphenyl Thiols," Surface Science, 514:187-193 (2002).
Islip et al., "Nitrofuryl Heterocyclics 3," Journal of Medicinal Chemistry, 16(11):1308-1310 (1973).
Jackson et al., "N-Terminal Mutations Activate the Leukemogenic Potential of the Myristoylated form of c-abl," EMBO, 8(2):449-456 (1989).
Jackson et al., "Pyridinylimidazole Based p38 MAP Kinase Inhibitors," Current Topics in Medicinal Chemistry, 2:1011-1020 (2002).
Jiang et al., ""Soft Docking": Matching of Molecular Surface Cubes," J. Mol. Biol., 219:79-102 (1991).
Jiang et al., "Synthesis and SAR Investigations for Novel Melanin-Concentrating Hormone 1 Receptor (MCH1) Antagonists Part 1. The Discovery of Arylacetamides as Viable Replacements for the Dihydropyrimidione Moiety of an HTS Hit," J. Med. Chem., 50:3870-3882 (2007).
Johnson, "Circular Dichroism Spectroscopy and The Vacuum Ultraviolet Region," Ann. Rev. Phys. Chem., 29:93-114 (1978).
Johnson, "Protein Secondary Structure and Circular Dichroism: A Practical Guide," Proteins: Structure, Function, and Genetics, 7:205-214 (1990).
Johnson et al., "An Evaluation of the Effect of Light Stabilisers on the Exterior Durability of Polyester Powder Coatings for the Architectural Market," Surface Coatings International, 3:134-141 (1999).
Johnson et al., "The Stereochemistry of Oxidation at Sulfur Oxidation of 2-Thiabicyclo[2.2.1]Hpetane," Tetrahedron, 25:5649-5653 (1969).
Kallander et al., "4-Aryl-1,2,3-triazole: A Novel Template for a Reversible Methionine Aminopeptidase 2 Inhibitor, Optimized to Inhibit Angiogenesis in Vivo," J. Med. Chem., 48:5644-5647 (2005).
Katritzky et al., "Novel Chromophoric Heterocycles Based on Maleimide and Naphthoquinone," J. Heterocyclic Chem., 26:885-892 (1989).
Kern et al., "Synthese von Makromolekeln einheitlicher Brobe. II Mitt: Syntheses neuer Diol-oligo-urethane nach dem Duplikationsverfahren," Makromolekulara Chemie, 16:89-107 (1955) (English Summary) (20 pages).
Kim, ct al., "Solid Phase Synthesis of Benzamidine and Butylamine-Derived Hydantoin Libraries," Molecular Diversity, 3:129-132 (1998).
Klayman et al., "The Reaction of S-Methiodide Derivatives of Activated Thioureas with Hydroxylic Compounds. A Novel Synthesis of Mercaptans," J. Org. Chem., 37(10):1532-1537 (1972).
Kleywegt et al., "Detection, Delineation, Measurement and Display of Cavities in Macromolecular Structures," Acta Cryst, D50:178-185 (1994).
Koch et al., "QSAR and Molecular Modelling for a Series of Isomeric X-Sulfanilamido-1-phenylpyrazoles," Quant. Struct. Act. Relat., 12:373-382 (1993).
Kolch, W., "Meaningful relationships: the regulation of the Ras/Raf/MEK/ERK pathway by protein interactions," Biochem. J., 351:289-305 (2000).
Krasovitskii et al., "Synthesis and Spectral-Luminescence Properties of Hetarylethylene Derivatives of 2,5-Diphenyloxazole and 2,5-Diphenyl-1,3,4-Oxadiazole," Khimiya Geterotsiklicheskikh Soedinenii, 5:617-621 (1982) (English Translation) (10 pages).
Kuhn et al., "The Genesis of High-Throughput Structure-Based Drug Discovery using Protein Crystallography," Analytical Techniques, Current Opinion in Chemical Biology, 6:704-710 (2002).

(56) References Cited

OTHER PUBLICATIONS

Kumar et al., "P38 Map Kinases: Key Signalling Molecules as Therapeutic Targets for Inflammatory Diseases," Nature Reviews Drug Discovery, 2:717-726 (2003).
Kundrot, "Which Strategy for a Protein Crystallization Project," CMLS, Cell. Mol. Life Sci., 61:525-536 (2004).
Kundu et al., "Depropargylation Under Palladium-Copper Catalysis: Synthesis of Diaryl Sulfides," Tetrahedron, 57:5885-5895 (2001).
Kurogi et al., "Discovery of Novel Mesangial Cell Proliferation Inhibitors Using a Three-Dimensional Database Searching Method," J. Med. Chem., 44:2304-2307 (2001).
Kuse et al., "Synthesis of azide-fluoro-dehydrocoelenterazine analog as a photoaffinity-labeling probe and photolysis of azide-fluoro-coelenterazine," Tetrahedron Lett., 61:5754-5762 (2005).
Kwong et al., "A General, Efficient, and Inexpensive Catalyst System for the Coupling Aryl Iodides and Thiols," Organic Letters, 4(20):3517-3520 (2002).
Laskowski, "Surfnet: A Program for Visualizing Molecular Surfaces, Cavities, and Intermolecular Interactions," Journal of Molecular Graphics, 13:323-330 (1995).
Leca et al., "A New Practical One-Pot Access to Sulfonimidates," Organic Letters, 4(23):4093-4095 (2002).
Lefevre et al., "Roles of Stem Cell Factor/c-Kit and Effects of Gliveca/STI571 in Human Uveal Melanoma Cell Tumorigenesis," Journal of Biological Chemistry, 279(30):31769-31779 (2004).
Lesort et al., "Insulin Transiently Increases Tau Phosphorylation: Involvement of Glycogen Synthase Kinase-3b and Fyn Tyrosine Kinase," Journal of Neurochemistry, 72(2):576-584 (1999).
Leung et al., "The Difluoromethylensulfonic Acid Groups as a Monoanionic Phosphate Surrogate for Obtaining PTP1B Inhibitors," Bioorganic & Medicinal Chemistry, 10:2309-2323 (2002).
Li et al., "Targeting Serine/Threonine Protein Kinase B/Akt and Cell-cycle Checkpoint Kinases for Treating Cancer," Current Topics in Medicinal Chemistry, 2:939-971 (2002).
Li et al., "The P190, P210, and P230 Forms of the BCR/ABL Oncogene Induce a Similar Chronic Myeloid Leukemia-like Syndrome in Mice but Have Different Lymphoid Leukemogenic Activity," J. Exp. Med., 189(9):1399-1412 (1999).
Link et al., "Synthesis of 8-Substituted 5-Deazaflavins," J. Heterocyclic Chem, 22:841-848 (1985).
Lipinski et al., "Experimental and Computational Approaches to Estimate Solubility and Permeability in Drug Discovery and Development Settings," Advanced Drug Delivery Reviews, 23:3-25 (1997).
Lohse et al., The Palladium Catalyzed Suzuki Coupling of 2- and 4-Chloropyridines, Synlett 1:45-48 (1999).
Longley et al., "Somatic c-KIT activating mutation ini urticaria pigmentosa and aggressive mastocytosis: establishment of clonality in a human mast cell neoplasm," Nature Genetics, p. 312-314 (Mar. 1996).
Loren et al., "NH-1,2,3-Triazoles from Azidomethyl Pivalate and Carbamates: Base-Labile N-Protecting Groups," Synlett, 18:2847-2850 (2005).
Lorenzi et al, "Amino Acid Ester Prodrugs of 2-Bromo-5,6-dichloro-1-(.beta.-D-ribofuranosyl)benzimidazole Enhance Metabolic Stability in Vitro and in Vivo," J. Pharm. Exp. Therpeutics, 314(2):883-890 (2005).
Lowinger et al, "Design and Discovery of Small Molecules Targeting Raf-1 Kinase," Current Pharmaceutical Design, 8:2269-2278 (2002).
Ma et al., "c-MET Mutational Analysis in Small Cell Lung Cancer: Novel Juxtamembrane Domain Mutations Regulating Cytoskeletal Functions," Cancer Research, 63:6272-6281 (2003).
Ma et al., "c-MET: Structure, Functions and Potential for Therapeutic Inhibition," Cancer and Metastasis Reviews, 22:309-325 (2003).
Magnuson et al, "The Raf-1 serine/threonine protein kinase," Seminars in Cancer Biology, 5:247-253 (1994).
Mallakpour et al., "Uncatalyzed Polymerization of Bistriazolinediones with Electron-Rich Aromatic Compounds via Electrophilic Aromatic Substitution," Journal of Polymer Science: Part A: Polymer Chemistry, 27:217-235 (1989).
Mamaev et al., "Synthesis of 2,5'-Bipyrimidines from Substituted 5-Cyanopyrimidines," Khimiya Geterotsiklicheskikh Soedinenni, 24(3):371-375 (1988) (English Translation).
March, J., Chaper 2, Tautomerism, In: Advanced Organic Chemistry, Reactions, Mechanisms, and Structure, Fourth Edition, John Wiley & Sons, Inc. (1992), pp. 69-74.
Martinez et al., "First Non-ATP Competitive Glycogen Synthase Kinase 3b (GSK-3b) Inhibitors: Thiadizolidinones (TDZD) as Potential Drugs for the Treatment of Alzheimers Disease," J. Med. Chem., 45:1292-1299 (2002).
Mattsson et al., "Six X-Linked Agammaglobulinemia-Causing Missense Mutations in the Src Homology 2 Domain of Bruton's Tyrosine Kinase: Phosphotyrosine-Binding and Circular Dichroism Analysis," Journal of Immunology, 64:4170-4177 (2000).
McMahon, G. et al., "VEGF receptor signaling in tumor angiogenesis," The Oncologist, 5(1):3-10 (2000).
McPherson, "Current Approaches to Macromolecular Crystallization," Eur. J. Biochem, 189:1-23 (1990).
Medebielle et al., "A Convenient Synthesis of Perfluoroalkylated and Fluorinated-Aryl Nitrogen Bases by Electrochemically Induced SRN1 Substitution," J. Org. Chem., 61:1331-1340 (1996).
Medebielle et al., "A New Convenient Synthesis of 5-Aryl Uracils Using SRN1 Aromatic Nucleophilic Substitution," Tetrahedron Letters, 34(21):3409-3412 (1993).
Mikhaleva et al., "Relative Reactivities of the Chlorine Atoms of 2,2',4-Trichloro-4',5-Dipyrimidinyl in its Reaction with Piperidine," Khimiya Geterotsiklicheskikh Soedinenii, 6:821-826 (1979) (English Translation) (12 pages).
Mol, "Structural Basis for the Autoinhibition and STI-571 Inhibition of c-Kit Tyrosine Kinase," The Journal of Biological Chemistry, 279(30):31655-31663 (Jul. 2004).
Morris et al., "Automated Docking of Flexible Ligands to Macromolecules," AutoDock Website, www.scripps.edu/mb/olson/doc/autodock/, printed Mar. 3, 2005 (3 pages).
Morris et al., "Automated Docking Using a Lamarckian Genetic Algorithm and an Empirical Binding Free Energy Function," Journal of Computational Chemistry, 19(14):1639-1662 (1998).
Morstyn et al., "Stem Cell Factor Is a Potent Synergistic Factor in Hematopoiesis," Oncology, 51:205-214 (1994).
Moss et al., "Basic Terminology of Stereochemistry," International Union of Pure and Applied Chemistry, 68(12):2193-2222 (1996).
Muller et al., "A General Synthesis of 4-Substituted 1,1-Dioxo-1,2,5-thiadiazolidin-3-ones Derived from a-Amino Acids," J. Org. Chem., 54:4471-4473 (1989).
Muller, "Glossary of Terms Used in Physical Organic Chemistry," International Union of Pure and Applied Chemistry, Pure & Appl. Chem., 66(5):1077-1184 (1994).
Murayama et al., "JNK (c-Jun NH2 Terminal Kinase) and p38 During Ischemia Reperfusion Injury in the Small Intestine" Transplantation, 81(9):1325-1330 (2006).
Mutlib et al., "Disposition of 1-[3-(Aminomethyl)phenyl]-N-[3-fluoro-2'-(methylsulfony1)-[1,1'-biphenyl]- -4-yl]- 3(trifluomethyl)-1H-pyrazole-5-carboxamide (DPC 423) by Novel Metabolic Pathways. Characterization of Unusual Metabolites by Liquid Chromatography/Mass Spectrometry and NMR," Chem. Res. Toxicol., 15:48-62 (2002).
Mutlib et al., "P450-Mediated Metabolism of 1-[3-(Aminomethyl)phenyl]-N-[3-fluoro-2'-(methylsulfony1)-[1,1'-biphenyl]- - -4-yl]-3(trifluomethyl)-1H-pyrazole-5-carboxamide (DCP 423) and Its Analogues to Aldoximes. Characterization of Glutathione Conjugates of Postulated Intermediates Derived from Aloximes," Chem. Res. Toxicol., 15:63-75 (2002).
Nagano, M. et al. "Studies on Organic Sulfur Compounds. XIV. The Reaction of N-alkoxy-carbonyl-N'-(2- thiazolyl)thioureas with some oxidants," Chemical and Pharmaceutical Bulletin, 21(11):2408-2416 (Nov. 1973).
Nagar et al., "Crystal Structures of the Kinase Domain of c-Abl in Complex with the Small Molecule Inhibitors PD173955 and Imatinib (STI-571)," Cancer Research, 62:4236-4243 (2002).

(56) References Cited

OTHER PUBLICATIONS

Nagar et al., "Structural Basis for the Autoinhibition of c-Abl Tyrosine Kinase," Cell, 112:859-871 (2003).
Nagata et al., "Identification of a point mutation ini the catalytic domain of the protooncogene c-kit in peripheral blood mononuclear cells of patients who have mastocytosis with an associated hematologic disorder," Proc. Natl. Acad. Sci. USA, 92:10560-10564 (Nov. 1995).
Nakopoulou et al., "c-Met Tyrosine Kinase Receptor Expression is Associated with Abnormal b-catenin Expression and Favourable Prognostic Factors in Invasive Breast Carcinoma," Histopathology, 36:313-325 (2000).
Nantka-Namirski, P. et al., "Condensation Reaction of Ethyl (4-Uracil)-Acetate with Ethyl Orthoformate," ACTA Polon. Pharm XXVII(5):455-463 (1971).
National Academy of Sciences, "Abstracts of Papers Presented at the Autumn Meeting, Nov. 14-16, 1960," Science, 132:1488-1501 (1960) (15 pages).
Nicolaou et al., "Molecular Design and Chemical Synthesis of a Highly Potent Epothilone," ChemMedChem, 1:41-44 (2006).
Nikolaev et al., "Solubility Polytherm in the System HNO3-H20-(C4H90)P0(C4H9)2," Doklady Akademii Nauk SSSR, 160(4):841-844 (1965) (English Translation).
Ning et al., "Activating Mutations of c-Kit at Codon 816 Confer Drug Resistance in Human Leukemia Cells," Leukemia and Lymphoma, 41(5-6):513-522 (2001).
Nofal et al., "Synthesis of Novel Uracil-5-Sulphonamide Derivatives of Possible Biological Activity," Egypt J. Chem., 33(4):375-380 (1990).
O'Dell et al., "Treatment of Rheumatoid Arthritis with Methotrexate Alone, Sulfasalazine and Hydroxychloroquine, or a Combination of All Three Medications," New England J. Med., 334(20):1287-1291(1996).
Okano et al., "o-Bromophenylzinc Compound: a Readily Available and Efficient Synthetic Equivalent of o-Phenylene 1-Anion 2-Cation," Tetrahedron Letters 39:3001-3004 (1998).
Okishio et al., "Differential Ligand Recognition by the Src and Phosphatidylinositol 3-Kinase Src Homology 3 Domains: Circular Dichroism and Ultraviolet Resonance Raman Studies," Biochemistry, 42:208-216 (2003).
Okishio et al., "Identification of Tyrosine Residues Involved in Ligand Recognition by the Phosphatidylinositol 3-Kinase Src Homology 3 Domain: Circular Dichroism and UV Resonance Raman Studies," Biochemistry, 40:15797-15804 (2001).
Okishio et al., "Role of the Conserved Acidic Residue Asp21 in the Structure of Phosphatidylinositol 3-Kinase Src Homolgy 3 Domain: Circular Dichroism and Nuclear Magnetic Resonance Studies," Biochemistry 40:119-129 (2001).
O'Neill, "Targeting Signal Transduction as a Strategy to Treat Inflammatory Diseases," Nature Review Drug Discovery, Published Online Jun. 9, 2006, www.nature.com/reviews/drugdisc (15 pages).
Parang et al., "Mechanism-based Design of a Protein Kinase Inhibitor," Nature Structural Biology, 8(1):37-41 (2001).
Pargellis et al., "Inhibition of p38 MAP Kinase by Utilizing a Novel Allosteric Binding Site," Nature Structural Biology, 9(4):268-272 (2002).
Park et al., "Mechanism of met Oncogene Activation," Cell, 45:895-904 (1986).
Pearlman et al., "Assisted Model Building with Energy Refinement," Amber Home Page, amber.scripts.edu (2005), 9 pages.
Pedersen, "The Preparation of Some N-Methyl-1,2,3-Triazoles," Acta Chimica Scandinavica, 13(5):888-892 (1959).
Peng et al., "Identification of Novel Inhibitors of BCR-ABL Tyrosine Kinase via Virtual Screening," Bioorganic & Medicinal Chemistry Letters, 13:3693-3699 (2003).
Pereira et al., "The Role of c-kit and Imatinib Mesylate in Uveal Melonoma," Journal of Carcinogenesis, 4:19 (2005), 8 pages.
Peyssonnaux, C. et al, "The Raf/MEK/ERK pathway: new concepts of activation," Biol. Cell, 93:53-62 (2001).
Picard et al., "Inhibitors of Acyl-CoA: Cholesterol 0-Acyltrasferase. 17. Structure-Activity Relationships of Several Series of Compounds Derived from N-Chlorosulfonyl Isocyanate," J. Med. Chem., 39:1243-1252 (1996).
Pierrat et al, "Solid Phase Synthesis of Pyridine-Based Derivatives from a 2-Chloro-5-Bromopyridine Scaffold," J. Comb. Chem., 7(6):879-886 (2005).
Pinedo, H. M. et al., "Translation research: the role of VEGF in tumor angiogenesis," the Oncologist, 5(1):1-2 (2000).
Pluk et al., "Autoinhibition of c-Abl," Cell, 108:247-259 (2002).
Ponzetto et al., "A Novel Recognition Motif for Phosphatidylinositol 3-Kinase Binding Mediates Its Association with the Hepatocyte Growth Factor/Scatter Factor Receptor," Molecular and Cellular Biology, 13(8):4600-4608 (1993).
Raimbault et al., "Effects of pH and KCI on the Conformations of Creatine Kinase from Rabbit Muscle," Eur. J. Biochem., 234:570-578 (1995).
Ranatunge et al, "Synthesis and Selective Cyclooxygenase-2 Inhibitory Activity of a Series of Novel, Nitric Oxide Donor-Containing Pyrazoles," J. Med Chem., 47:2180-2193 (2004).
Rebek et al. "Convergent Functional Groups: Synthetic and Structural Studies," J. Am. Chem. Soc., 107:7476-7481 (1985).
Rebek et al., "Convergent Functional Groups. 2. Structure and Selectivity in Olefin Epoxidation with Peracids," J. Org. Chem., 51:1649-1653 (1986).
Reed et al., "Circular Dichroic Evidence for an Ordered Sequence Ligand/Binding Site Interactions in the Catalytic Reaction of the cAMP-Dependent Protein Kinase," Biochemistry, 24:2967-2973 (1985).
Regan et al., "Pyrazole Urea-Based Inhibitors of p38 MAP Kinase: From Lead Compound to Clinical Candidate," J. Med. Chem., 45:2994-3008 (2002).
Regan et al., "Structure-Activity Relationships of the p38a MAP Kinase Inhibitor 1-)5-tert-Butyl-2-p-tolyl-2H-pyrazol-3-yl)-3[4-(2-morpholin-4-- yl-ethoxy)naph-thalen-1-yl]urea (BIRB 796)," J. Med. Chem., 46:4676-4686 (2003).
Rooney et al., "Inhibitors of Gylcolic Acid Oxidase. 4-Substituted 3-Hydroxy-1H-pyrrole-2,5-dione Derivatives," J. Med. Chem., 26(5):700-714 (1983).
Roux et al., "ERK and p38 MAPK-Activated Protein Kinases: a Family of Protein Kinases with Diverse Biological Functions," Microbiology and Molecular Biology Reviews, 68(2):320-344 (2004).
Rowley, "A New Consistent Chromosomal Abnormality in Chronic Myelogenous Leukaemia Identified by Quinacrine Fluorescence and Giemsa Staining," Nature, 243:290-293 (1973).
Rubin et al., "Gastrointestinal stromal tumour," Lancet, 369:1731-1741 (May 2007).
Russell et al., "3-[3-(Piperdin-1-yl)propyl]indoles as Highly Selective h5-HT1D Receptor," J. Med. Chem., 42:4981-5001 (1999).
Saiga et al., "Consecutive Cross-Coupling of o-Phenylenedizinc Compound with Acyl and/or Aryl Halides in the Presence of Pd(0)-tris(2,4,6-trimethoxyphenyl)phosphine," Tetrahedron Letters, 41:4629-4632 (2000).
Sakamoto et al., "Condensed Heteroaromatic Ring Systems. XIX. Synthesis and Reactions of 5-(Tributylstannyl)Isoxazoles," Tetrahedron, 47(28):5111-5118 (1991).
Sakuma et al., "c-kit Gene Mutations in Intracranial Germinomas," Cancer Sci, 95(9):716-720 (2004).
Salgia, R., "Studies on c-Kit and c-Met in Lung Cancer with Similarities to Stem Cells," Microscopy and Microanalysis, 11 (Suppl. 22), 1 page. (2005).
Satsangi et al., "1-(4-Substituted-thiazol-2-yl)hydatoins as Anti-inflammatory and CNS-Active Agents," Pharmazie, 38:341-342 (1983).
Schiering, et al, "Crystal Structure of the Tyrosine Kinase Domain of the Hepatocyte Growth Factor Receptor c-Met and its Complex with the Microbial Alkaloid K-252a," Proc. Nat'l Acad. Sci 100(22): 12654-12659 (2003).
Schindler, et al, "Structural Mechanism for STI-571 Inhibition of Abelson Tyrosine Kinase," Science, 289:1938-1942 (Sep. 2000).
Schlosser et al., "Regiochemically Flexible Substitutions of Di-, Tri-, and Tetrahalopyridines: The Trialkylsily Trick," J. Org. Chem., 70:2494-2502 (2005).

(56) References Cited

OTHER PUBLICATIONS

Schmidt et al., "Germline and Somatic Mutations in the Tyrosine Kinase Domain of the MET proto-oncogene in Papillary Renal Carcinomas," Nature Genetics, 16:68-73 (1997).
Schmidt et al., "Novel Mutations of the MET Proto-oncogene in Papillary Renal Carcinomas," Oncogene, 18:2343-2350 (1999).
Seimiya et al., "Telomere Shortening and Growth Inhibition of Human Cancer Cells by Novel Synthetic Telomerase Inhibitors MST-312, MST-295, and MST-199," Molecular Cancer Therapeutics, 1:657-665 (2002).
Seminario et al., "Theoretical Study of a Molecular Resonant Tunneling Diode," J. Am. Chem. Soc., 122:3015-3020 (2000).
Seto et al., "2-Substituted-4-aryl-6,7,8,9-tetrahydro-5H-pyrimido [4,5-b][1,5]oxazocin-5-one as a structurally new NK.sub.1 antagonist," Biorg. Med. Chem. Lett., 15:1485-1488 (2005).
Shah et al., "Circular Dichroic Studies of Protein Kinase C and its Interactions with Calcium and Lipid Vesicles," Biochimica et Biophysica Acta, 1119:19-26 (1992).
Shi et al., "Abnormal Diels-Alder Reaction of 5-Alkoxythiazoles with Highly Reactive Dienophiles; 4-Phenyl-3H-1,2,4-triazole-3,5(4H)-dione, Diethyl Azodicarboxylate, and Diethyl Oxomalonate," Bull. Chem. Soc. Jpn., 65:3315-3321 (1992).
Shinkai et al., "Coenzyme Models. Part 45. Synthesis of Atropisomeric Flavins and their Novel Redox-induced Racernisation," J. Chem. Soc. Perkin Trans., pp. 313-319 (1988).
Shiozaki et al., "Impaired Differentiation of Endocrine and Exocrine Cells of the Pancreas in Transgenic Mouse Expressing the Truncated Type II Activin Receptor," Biochimica et Biophysica Acta, 1450:1-11 (1999).
Sihto et al., "KIT and Platelet-Derived Growth Factor Receptor Alpha Tyrosine Kinase Gene Mutations and KIT Amplifications in Human Solid Tumors," Journal of Clinical Oncology, 23(1):49-57 (Jan. 1, 2005).
Smith et al., "Classification of Reactions by Type of Compound Synthesized," March's Advanced Organic Chemistry: Reactions, Mechanisms, and Structure, Fifth Edition, Smith and March Editors, Wiley-Interscience Publication (2001), pp. 1654-1655.
Smith et al., "Tautomerism," from March's Advanced Organic Chemistry, Fifth Edition, Smith and March Editors, Wiley-Interscience Publication (2001), pp. 69-74.
Stout et al., "High-Throughput Structural Biology in Drug Discovery: Protein Kinases," Current Pharmaceutical Design, 10:1069-1082 (2004).
Sugden et al., ""Stress-Responsive" Mitogen-Activated Protein Kinases (c-Jun N-Terminal Kinases and p38 Mitogen-Activated Protein Kinases) in the Myocardium," Circulation Research—Journal of the American Heart Association, 83:345-352 (1998).
Tanis et al., "Two Distinct Phosphorylation Pathways Have Additive Effects on Abl Family Kinase Activation," Molecular and Cellular Biology, 23(11):3884-3896 (2003).
Tarn et al., "Analysis of KIT Mutations in Sporadic and Familial Gastrointestinal Stromal Tumors: Therapeutic Implications through Protein Modeling," Clinical Cancer Research, 11:3668-3677 (2005).
Teague, "Implications of Protein Flexibility for Drug Discovery," Nature Reviews Drug Discovery, 2:527-541 (2003).
Tian et al., "Activating c-kit Gene Mutations in Human Germ Cell Tumors," American Journal of Pathology, 154(6):1643-1647 (Jun. 1999).
Tominaga et al., "General model for Estimation of the Inhibition of Protein Kinases Using Monte Carlo Simulations," J. Med. Chem., 47:2534-2549 (2004).
Tremblay et al., "Efficient Solid-Phase Synthesis of Sulfahydantoins," J. Comb. Chem., 4:429-435 (2002).
"Trilateral Project WM4-Comparative Studies in New Technologies: Report on Comparative Study on Protein 3-Dimensional Structure Related Claims—ANNEX 3: Comments of the USPTO," Vienna, Austria, Nov. 4-8, pp. 58-79 (2002).
Tsuzuki et al., "Synthesis and Structure-Activity Relationships of Novel 7-Substituted 1,4-Dihydro-4-oxo-1-(2-thiazoly1)-1,8-napthyridine-3-carboxylic Acids as Antitumor Agents. Part 2," J. Med. Chem., 47:2097-2109 (2004).
Van Etten, "Cycling, Stressed-Out and Nervous: Cellular Functions of c-Abl," Trends in Cell Biology, 9:179-186 (1999).
Venter et al., "The Sequence of the Human Genome," Science, 291:1304-1351 (Feb. 16, 2001); Erratum (Jun. 8, 2001), 49 pages.
Waetzig et al., "Review Article: Mitogen-Activated Protein Kinases in Chronic Intestinal Inflammation—Targeting Ancient Pathways to Treat Modern Diseases," Aliment Pharmacol Ther, 18:17-32 (2003).
Wan, P. T. C. et al, "Mechanism of Activation of the RAF-ERK Signaling Pathway by Oncogenic Mutations of B-RAF," Cell, 116:855-867 (2004).
Wardelmann, "Acquired resistance to imatinib in gastrointestinal stromal tumours caused by multiple KIT mutations," The Lancet Oncology, 6:249-251 (2005).
Welker et al., "Glucocorticoid-Induced Modulation of Cytokine Secretion from Normal and Leukemic Human Myelomonocytic Cells," Int. Arch. Allergy Immunol, 109:110-115 (1996).
Wentland et al., "3-Quinolinecarboxamides. A Series of Novel Orally-Active Antiherpetic Agents," J. Med. Chem., 36:1580-1596 (1993).
Wilson et al., "The Structural Basis for the Specificity of Pyridinylimidazole Inhibitors of p38 MAP Kinase," Chemistry & Biology, 4(6):423-431 (1997).
Wilson, et el., "Laser-Jet Delayed Trapping: Electron-Transfer Trapping of the Photoenol from 2-Methylbenzophenone," J. Am. Chem. Soc., 109:4743-4745 (1987).
Wolter et al., "Copper-Catalyzed Coupling of Aryl Iodides with Aliphatic Alcohols," Organic Letters, 4(6):973-976 (2002).
Wrana et al., "Mechanism of Activation of the TGF-b Receptor," Nature, 370:341-347 (1994).
Wu et al., "Discovery of a Novel Family of CDK Inhibitors with the Program LIDAEUS: Structual Basis for Ligand-Induced Disordering of the Acivation Loop," Structure, 11:399-410 (2003).
Yang et al., "Molecular Mechanism for the Regulation of Protein Kinase B/Akt by Hydrophobic Motif Phosphorylation," Molecular Cell, 9:1227-1240 (2002).
Yang et al., "Palladium-Catalyzed Amination of Any Halides and Sulfonates," Journal of Organometallic Chemistry, 576:125-146 (1999).
Yarden et al., "Human Proto-oncogene c-kit: a New Cell Surface Receptor Tyrosine Kinase for an Unidentified Ligand," The EMBO Journal, 6(11):3341-3351 (1987).
Yoneda et al., "A New Synthesis of Purines," J.C.S. Chem. Comm., 464:551 (1974).
Yonezawa et al., "Synthesis of Sequentially Controlled Isomeric, Wholly aromatic Polyketones Composed of 2-trifluoromethylbiphenylene and 2,2'-dimethoxybiphenylene Units," Reactive & Functional Polymers, 52:19-30 (2002).
Yoshimoto et al., "Correlation Analysis of Baker's Studies on Enzyme Inhibition. 2. Chymotrypsin, Trypsin, Thymidine Phosphorylase, Uridine Phosphorylase, Thimidylate Synthetase, Cytosine Nucleoside Deaminase, Dihodrofolate Reductase, Malate Dehydrogenase, Glutamate Dehydrogenase, Lactate Dehydrogenase, and Glyceraldehyde-phosphate Dehydrogenase," Journal of Medicinal Chemistry, 19(1):71-98 (1976).
Yoshino et al., "Organic Phosphorous Compounds. 2. Synthesis and Coronary Vasodilator Activity of (Benzothiazolybenzyl) Phosphonate Derivatives," J. Med. Chem., 32:1528-1532 (1989).
Yu et al., "Frequency of TPR-MET Rearrangement in Patients with Gastric Carcinoma and in First-Degree Relatives," Cancer, 88(8):1801-1806 (2000).
Zaidi et al., "New Anti-Mycobacterial Hydantoins," Pharmazie, 35:755-756 (1980).
Zhen et al., "Structural and Functional Domains Critical for Constitutive Activation of the HGF-Receptor (Met)," Oncogene, 9(6):1691-1697 (1994).
Zvilichovsky et al., "Aminolysis and Polymerization of 3-(p-Toluenesulfonoxy) Hydantoin," Israel Journal of Chemistry, 7:547-554 (1969).

* cited by examiner

DIHYDRONAPHTHYRIDINES AND RELATED COMPOUNDS USEFUL AS KINASE INHIBITORS FOR THE TREATMENT OF PROLIFERATIVE DISEASES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATION

This application is a divisional application of U.S. patent application Ser. No. 13/491,394, filed on Jun. 7, 2012, entitled "DIHYDRONAPHTHYRIDINES AND RELATED COMPOUNDS USEFUL AS KINASE INHIBITORS FOR THE TREATMENT OF PROLIFERATIVE DISEASES," which is incorporated herein by reference in its entirety.

BACKGROUND OF THE INVENTION c-KIT (also known as KIT, CD117, and stem cell factor receptor) is a 145 kDa transmembrane tyrosine kinase protein that acts as a type-III receptor (Pereira et al. J. Carcin. 2005, 4, pg. 19). The c-KIT proto-oncogene, located on chromosome 4q11-21, encodes the c-KIT receptor, whose ligand is the stem cell factor (SCF, steel factor, kit ligand, mast cell growth factor, Morstyn, G. et al. Oncology 1994, 51 (2), pg. 205; Yarden, Y. et al. Embo. J. 1987, 6 (11), pg. 3341). The receptor has tyrosine-protein kinase activity and binding of the ligand SCF leads to the autophosphorylation of c-KIT and its association with substrates such as phosphatidylinositol 3-kinase (PI3K). Tyrosine phosphorylation by protein tyrosine kinases is of particular importance in cellular signaling and can mediate signals for major cellular processes, such as proliferation, survival, differentiation, apoptosis, attachment, invasiveness and migration. Defects in c-KIT are a cause of piebaldism, an autosomal dominant genetic developmental abnormality of pigmentation characterized by congenital patches of white skin and hair that lack melanocytes. Gain-of-function mutations of the c-KIT gene and the expression of constitutively phosphorylated c-KIT are found in most gastrointestinal stromal tumors GIST) and mastocytosis. Further, almost all gonadal seminomas/dysgerminomas exhibit c-KIT membranous staining, and several reports have clarified that some (10-25%) have a c-KIT gene mutation (Sakuma, Y. et al. Cancer Sci. 2004, 95 (9), pg. 716). c-KIT defects have also been associated with testicular tumors including germ cell tumors (GCT) and testicular germ cell tumors (TGCT).

The role of c-KIT expression has been studied in hematologic and solid tumors, such as acute leukemias (Cortes, J. et al. Cancer 2003, 97 (11), pg. 2760) and GIST (Fletcher, J. et al. Hum. Pathol. 2002, 33 (5), pg. 459). The clinical importance of c-KIT expression in malignant tumors relies on studies with Gleevec® (imatinib mesylate, STI571 (signal transduction inhibitor number 571), Novartis Pharma AG Basel, Switzerland) that specifically inhibits tyrosine kinase receptors (Lefevre, G. et al. J. Biol. Chem. 2004, 279 (30), pg. 31769). Moreover, a clinically relevant breakthrough has been the finding of anti-tumor effects of this compound in GIST, a group of tumors regarded as being generally resistant to conventional chemotherapy (de Silva, C. M.; Reid, R. Pathol. Oncol. Res. 2003, 9 (1), pp. 13-19). Most GISTs have primary activating mutations in the genes encoding the closely related RTKs c-KIT (75-80% of GIST) or PDGFRα (8% of the non-c-KIT mutated GIST). c-KIT and PDGFRα mutations are mutually exclusive in GIST (Rubin et al. Lancet 2007, 369, pg. 1731). The majority of primary GIST-causing c-KIT mutations affect the juxtamembrane (JM) region of the protein encoded by exon 11 (i.e. V560D) and consist of in-frame deletions or insertions, or missense mutations. c-KIT exon 11 mutations have been identified as primary mutations in approximately 75% of GISTs. Such JM domain mutations disrupt the autoinhibition mechanism of c-KIT kinase, leading to constitutive kinase activity and cell-transforming events causative of GIST (Chen, L. L. et al. Clin. Cancer Res. 2005, 11, pg. 3668-3677; Mol, C. D., et al. J. Biol. Chem. 2004, 279, pg. 31655-31663).

GIST most often become Gleevec® resistant, and molecularly targeted small molecule therapies that target c-KIT secondary mutations remain elusive. GIST patients who relapse after treatment with Gleevec® or Sutent® have disease still driven by c-KIT mutations. These secondary mutations occur on the same alleles as the primary JM-region mutation, and thus represent even more aggressive activated forms of c-KIT than the original primary mutation. These secondary mutants of c-KIT identified in GIST lead to acquired drug resistance. Secondary mutations are found in the extracellular domain of c-KIT (exon 9, i.e. AY501-502 duplication/insertion), ATP binding pocket (exon 13, i.e. K642E, V654A; exon 14, i.e. T670I), and activation loop (exon 17, i.e. N822K, D816H, D816V, D820A). These various secondary c-KIT mutations have been reported: Heinrich, M. C. et al. J. Clin. Oncol. 2006, 24, pg. 4764-4774; Debiec-Rychter, M., et al. Gastroenterology 2005, 128, pg. 270-279; Wardelmann, E., et al. Lancet Oncol. 2005, 6, pg. 249-251; Antonescu, C. R., et al. Clin. Cancer. Res. 2005, 11, pg. 4182-4190. Sunitinib malate (Sutent™, Pfizer) is an inhibitor of multiple RTKs, notably in this context, c-KIT and PDGFRα, and has been shown to be effective against certain imatinib-resistant c-KIT mutants, such as the ATP-binding pocket mutants V654A and T670I. Certain Gleevec®-resistant mutants are also resistant to sunitinib, such as D816H and D816V which are located in the activation loop of the c-KIT catalytic domain encoded by exon 17 (Corless et al. J. Clin. Oncol. 2004, 22, pg. 3813; Heinrich et al. J. Clin. Oncol. 2008, 26, pg. 5352; Gajiwala et al. Proc. Natl. Acad. Sci. USA 2009, 106:1542). Median survival after progression due to Gleevec®-resistance remains relatively short.

It has been demonstrated that complex, multiple secondary c-KIT mutations can arise and vary within individual patients, such variation in mutational status of c-KIT being demonstrated by biopsy samples obtained from different progressing metastases within each patient (Wardelmann, E., et al. Lancet Oncol. 2005, 6, pg. 249-251; Fletcher, J. A. and Rubin, B. P., Curr. Opin in Genetics & Develop., 2007, 17, pg. 3-7). This complex c-KIT mutational heterogeneity within individual patients underscores an unmet medical need to identify inhibitors of c-KIT kinase that are effective across a broad spectrum of c-KIT primary and secondary mutations. Such a broad spectrum c-KIT inhibitor would be of high therapeutic value in the treatment of refractory GIST patients.

SUMMARY OF THE INVENTION

The present invention discloses the unexpected utility of compounds that inhibit c-KIT kinase across a broad range of c-KIT mutations, including complex occurrences of primary mutations (KIT exon 9 or 11) and secondary KIT mutations (exons 13, 14, 17 and 18) that may arise in individual, refractory GIST patients. Also unexpected is the utility of compounds of the present invention to inhibit the problematic exon 17 D816V c-KIT mutation, for which there is currently no effective therapy. D816 mutations in c-KIT have been demonstrated to cause mastocytosis, mast cell leukemia, seminomas, dysgerminomas, lymphomas, and intracranial teratomas (Ning, A. Q, Li, J., and Arceci, R. J. Leuk Lymphoma, 2001, 41, pg. 513-522; Beghini, A , et al. Blood, 2000, 95, pg. 726-727; Tian, Q., et al. Am J. Pathol. 1999, 154, pg. 1643-1647; Nagata, H., et al. Proc. Natl. Acad. Sci. USA, 1995, 92, 10560-10564; Longley, B. J., et al. Nat. Genet., 1996, 12, pg. 312-314). The present invention also discloses new compounds for the treatment of diseases caused by c-KIT mutation, including new compounds for the treatment of refractory GIST, mast cell leukemia, or mastocytosis.

One aspect of the present invention provides a method of treating a disease caused by the kinase activity of c-KIT, oncogenic forms thereof, aberrant fusion proteins thereof or polymorphs thereof, comprising the administration of a compound of formula Ia

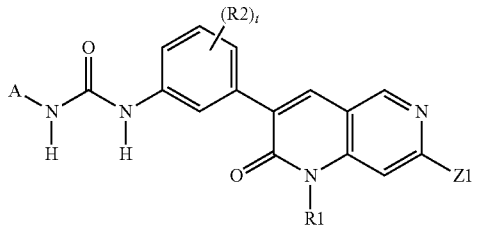

Ia or a pharmaceutically acceptable salt thereof, wherein:

A is selected from the group consisting of phenyl, naphthyl, and benzothienyl;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, tetrahydropyranyl, dioxalinyl, piperidinyl, and morpholinyl;

when A has one or more substitutable sp2-hybridized carbon atom, each respective sp2 hybridized carbon atom may be optionally substituted with a Z3 substituent;

Z1 is selected from the group consisting of —NH(R4), and —NHCOR8;

in the event that Z1 contains an alkyl or alkylene moiety, such moieties may be further substituted with one or more C1-C6alkyls;

each Z2 is independently and individually selected from the group consisting of hydrogen, C1-C6alkyl, C3-C8carbocyclyl, C1-C6 alkoxy, hydroxyl, hydroxyC1-C6alkyl-, cyano, $(R3)_2N$—, and —$(CH_2)_nR5$;

in the event that Z2 contains an alkyl or alkylene moiety, such moieties may be further substituted with one or more C1-C6alkyls;

each Z3 is independently and individually selected from the group consisting of H, methyl, ethyl, isopropyl, C3-C4 carbocyclyl, halogen, cyano, —$(CH_2)_k$—$N(R3)_2$, and —$(CH_2)_k$—R5;

R1 is selected from the group consisting of C1-C4alkyl, branched C3-C5alkyl, and C3-C5carbocyclyl;

each R2 is independently and individually selected from the group consisting of hydrogen, methyl, ethyl, halogen, fluoroalkyl wherein the alkyl moiety can be partially or fully fluorinated, cyano, and C2-C3alkynyl;

each R3 is independently and individually selected from the group consisting of H, C1-C6alkyl, branched C3-C7alkyl, and C3-C8carbocyclyl;

each R4 is independently and individually selected from the group consisting of H, C1-C6alkyl, hydroxyC2-C6alkyl, C1-C6alkoxyC2-C6alkyl, branched C3-C7alkyl, branched hydroxyC2-C6alkyl, branched C1-C6alkoxyC2-C6alkyl, —$(CH_2)_q$—$N(R7)_2$, —$(CH_2)_q$—R5, —$(CH_2)_n$C(O)R5, C3-C8carbocyclyl, hydroxyl substituted C3-C8carbocyclyl, alkoxy substituted C3-C8carbocyclyl, and —$(CH_2)_n$—R17;

each R5 is independently and individually selected from the group consisting of

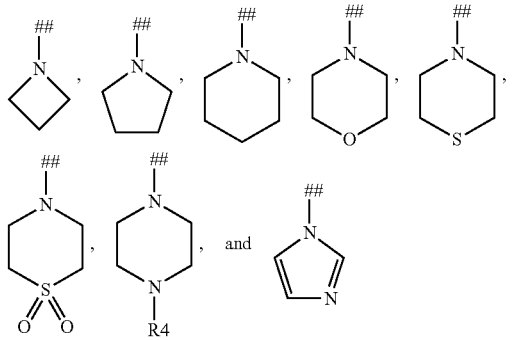

and wherein the symbol (##) is the point of attachment of the R5 moiety;

each R5 may be optionally substituted with one or two R10 substituents;

each R7 is independently and individually selected from the group consisting of H, C1-C6alkyl, hydroxyC2-C6alkyl, C1-C6alkoxyC2-C6alkyl, branched C3-C7alkyl, branched hydroxyC2-C6 alkyl, branched C1-C6alkoxyC2-C6alkyl, —$(CH_2)_q$—R5, —$(CH_2)_n$—C(O)R5, —$(CH_2)_n$—C(O)OR3, C3-C8carbocyclyl, hydroxyl substituted C3-C8carbocyclyl, alkoxy substituted C3-C8carbocyclyl, and —$(CH_2)_n$—R17;

each R8 is independently and individually selected from the group consisting of hydrogen, C1-C6alkyl, branched C3-C7alkyl, fluoroalkyl wherein the alkyl moiety is partially or fully fluorinated, C3-C8carbocyclyl, Z3-substituted phenyl, Z3-substituted G1, Z3-substituted G1-C1-C6alkyl, Z2-substituted G4, Z2-substituted G4-C1-C6alkyl, C1-C6alkoxy, C1-C6alkoxyC1-C6alkyl, cyanoC1-C6alkyl, —$N(R4)_2$, and R5;

each R10 is independently and individually selected from the group consisting of $CO_2H$, $CO_2$C1-C6alkyl, CO—$N(R4)_2$, OH, C1-C6alkoxy, C1-C6alkyl, and —$N(R4)_2$;

each R17 is taken from the group comprising phenyl, naphthyl, pyrrolyl, furyl, thienyl, oxazolyl, thiazolyl, isoxazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, pyrrolidinyl, and piperidinyl;

wherein R17 can be further substituted with one or more Z2 or Z3 moieties;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3.

In one embodiment, the invention provides a method of treating a disease caused by the kinase activity of c-KIT, oncogenic forms thereof, aberrant fusion proteins thereof or polymorphs thereof, wherein c-KIT contains a missense mutatation, insertion mutation, or a deletion mutation encoded by exons comprising Exon 9, Exon 11, Exon 13, Exon 14, Exon 17, or Exon 18, presenting either individually or in combination, comprising the administration of a compound of formula Ia or a pharmaceutically acceptable salt thereof.

A second aspect of the present invention provides a method of treating a disease selected from gastrointestinal stromal tumors, ovarian cancer, pancreatic cancer, prostate cancer, lung cancers, breast cancers, melanoma, renal cancers, hepatic cancers, cervical carcinomas, metastasis of primary tumor sites, papillary thyroid carcinoma, non-small cell lung cancer, mesothelioma, hypereosinophilic syndrome, colonic cancers, acute myeloid leukemia, germ cell tumors of the seminoma or dysgerminoma, teratomas, mastocytosis, or mast cell leukemia, said method comprising administering a therapeutically effective amount of a compound of Formula Ia, or a pharmaceutically acceptable salt thereof, to a patient.

A third aspect of the present invention provides a pharmaceutical composition comprising a compound of Formula Ia, or a pharmaceutically acceptable salt thereof, in association with a pharmaceutically acceptable carrier, with the proviso that the compound is not 1-(5-(1-ethyl-7-(methylamino)-2-oxo-1,2-dihydro-1,6-naphthyridin-3-yl)-2-fluoro-4-methylphenyl)-3-(naphthalen-1-yl)urea, 1-(5-(1-ethyl-7-(methylamino)-2-oxo-1,2-dihydro-1,6-naphthyridin-3-yl)-2-fluorophenyl)-3-(naphthalen-1-yl)urea, 1-(4-chloro-5-(1-ethyl-7-(methylamino)-2-oxo-1,2-dihydro-1,6-naphthyridin-3-yl)-2-fluorophenyl)-3-phenylurea, 1-(4-chloro-5-(1-ethyl-7-(methylamino)-2-oxo-1,2-dihydro-1,6-naphthyridin-3-yl)-2-fluorophenyl)-3-(2,3-difluorophenyl) urea, 1-(2-fluoro-5-(1-isopropyl-7-(methylamino)-2-oxo-1,2-dihydro-1,6-naphthyridin-3-yl)phenyl)-3-phenylurea, 1-(4-chloro-5-(1-ethyl-7-(methylamino)-2-oxo-1,2-dihydro-1,6-naphthyridin-3-yl)-2-fluorophenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-phenylurea, 1-(4-chloro-2-fluoro-5-(1-methyl-7-(methylamino)-2-oxo-1,2-dihydro-1,6-naphthyridin-3-yl) phenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-(3-cyanophenyl)urea, or 1-(4-chloro-2-fluoro-5-(1-methyl-7-(methylamino)-2-oxo-1,2-dihydro-1,6-naphthyridin-3-yl)phenyl)-3-(2,3-difluorophenyl)urea.

A fourth aspect of the present invention provides use of a compound of Formula Ia or a pharmaceutically acceptable salt thereof, for the manufacture of a medicament for the treatment of a disease selected from gastrointestinal stromal tumors, ovarian cancer, pancreatic cancer, prostate cancer, lung cancers, breast cancers, melanoma, renal cancers, hepatic cancers, cervical carcinomas, metastasis of primary tumor sites, papillary thyroid carcinoma, non-small cell lung cancer, mesothelioma, hypereosinophilic syndrome, colonic cancers, acute myeloid leukemia, germ cell tumors of the seminoma or dysgerminoma, teratomas, mastocytosis, or mast cell leukemia.

A fifth aspect of the present invention provides a compound of formula Ia

Ia

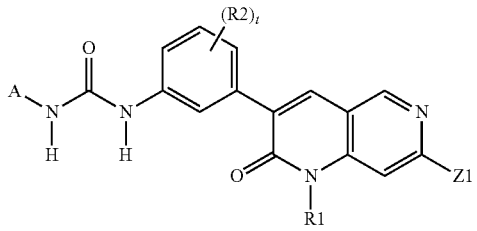

or a pharmaceutically acceptable salt thereof, wherein:

A is selected from the group consisting of phenyl, naphthyl, and benzothienyl;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, tetrahydropyranyl, dioxalinyl, piperidinyl, and morpholinyl;

when A has one or more substitutable sp2-hybridized carbon atom, each respective sp2 hybridized carbon atom may be optionally substituted with a Z3 substituent;

Z1 is selected from the group consisting of —NH(R4), and —NHCOR8;

in the event that Z1 contains an alkyl or alkylene moiety, such moieties may be further substituted with one or more C1-C6alkyls;

each Z2 is independently and individually selected from the group consisting of hydrogen, C1-C6alkyl, C3-C8carbocyclyl, C1-C6 alkoxy, hydroxyl, hydroxyC1-C6alkyl-, cyano, $(R3)_2N$—, and —$(CH_2)_nR5$;

in the event that Z2 contains an alkyl or alkylene moiety, such moieties may be further substituted with one or more C1-C6alkyls;

each Z3 is independently and individually selected from the group consisting of H, methyl, ethyl, isopropyl, C3-C4 carbocyclyl, halogen, cyano, —$(CH_2)_k$—$N(R3)_2$, and —$(CH_2)_k$—R5;

R1 is selected from the group consisting of C1-C4alkyl, branched C3-C5alkyl, and C3-C5carbocyclyl;

each R2 is independently and individually selected from the group consisting of hydrogen, methyl, ethyl, halogen, fluoroalkyl wherein the alkyl moiety can be partially or fully fluorinated, cyano, and C2-C3alkynyl;

each R3 is independently and individually selected from the group consisting of H, C1-C6alkyl, branched C3-C7alkyl, and C3-C8carbocyclyl;

each R4 is independently and individually selected from the group consisting of H, C1-C6alkyl, hydroxyC2-C6alkyl, C1-C6alkoxyC2-C6alkyl, branched C3-C7alkyl, branched hydroxyC2-C6alkyl, branched C1-C6alkoxyC2-C6alkyl, —$(CH_2)_q$—$N(R7)_2$, —$(CH_2)_q$—R5, —$(CH_2)_n$C(O)R5, C3-C8carbocyclyl, hydroxyl substituted C3-C8carbocyclyl, alkoxy substituted C3-C8carbocyclyl, and —$(CH_2)_n$—R17;

each R5 is independently and individually selected from the group consisting of

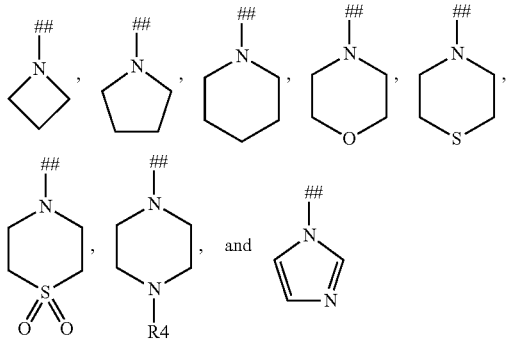

and wherein the symbol (##) is the point of attachment of the R5 moiety;

each R5 may be optionally substituted with one or two R10 substituents;

each R7 is independently and individually selected from the group consisting of H, C1-C6alkyl, hydroxyC2-C6alkyl, C1-C6alkoxyC2-C6alkyl, branched C3-C7alkyl, branched hydroxyC2-C6 alkyl, branched C1-C6alkoxyC2-C6alkyl, —$(CH_2)_q$—R5, —$(CH_2)_n$—C(O)R5, —$(CH_2)_n$—C(O)OR3, C3-C8carbocyclyl, hydroxyl substituted C3-C8carbocyclyl, alkoxy substituted C3-C8carbocyclyl, and —$(CH_2)_n$—R17;

each R8 is independently and individually selected from the group consisting of hydrogen, C1-C6alkyl, branched C3-C7alkyl, fluoroalkyl wherein the alkyl moiety is partially or fully fluorinated, C3-C8carbocyclyl, Z3-substituted phenyl, Z3-substituted G1, Z3-substituted G1-C1-C6alkyl, Z2-substituted G4, Z2-substituted G4-C1-C6alkyl, C1-C6alkoxy, C1-C6alkoxyC1-C6alkyl, cyanoC1-C6alkyl, —$N(R4)_2$, and R5;

each R10 is independently and individually selected from the group consisting of $CO_2H$, $CO_2$C1-C6alkyl, CO—$N(R4)_2$, OH, C1-C6alkoxy, C1-C6alkyl, and —$N(R4)_2$;

each R17 is taken from the group comprising phenyl, naphthyl, pyrrolyl, furyl, thienyl, oxazolyl, thiazolyl, isoxazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, pyrrolidinyl, and piperidinyl;

wherein R17 can be further substituted with one or more Z2 or Z3 moieties;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3;

with the proviso that the compound is not 1-(5-(1-ethyl-7-(methylamino)-2-oxo-1,2-dihydro-1,6-naphthyridin-3-yl)-2-fluoro-4-methylphenyl)-3-(naphthalen-1-yl)urea, 1-(5-(1-ethyl-7-(methylamino)-2-oxo-1,2-dihydro-1,6-naphthyridin-3-yl)-2-fluorophenyl)-3-(naphthalen-1-yl) urea, 1-(4-chloro-5-(1-ethyl-7-(methylamino)-2-oxo-1,2-dihydro-1,6-naphthyridin-3-yl)-2-fluorophenyl)-3-phenylurea, 1-(4-chloro-5-(1-ethyl-7-(methylamino)-2-oxo-1,2-dihydro-1,6-naphthyridin-3-yl)-2-fluorophenyl)-3-(2,3-difluorophenyl)urea, 1-(2-fluoro-5-(1-isopropyl-7-(methylamino)-2-oxo-1,2-dihydro-1,6-naphthyridin-3-yl) phenyl)-3-phenylurea, 1-(4-chloro-5-(1-ethyl-7-(methylamino)-2-oxo-1,2-dihydro-1,6-naphthyridin-3-yl)-2-fluorophenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-phenylurea, 1-(4-chloro-2-fluoro-5-(1-methyl-7-(methylamino)-2-oxo-1,2-dihydro-1,6-naphthyridin-3-yl)phenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-(3-cyanophenyl) urea, or 1-(4-chloro-2-fluoro-5-(1-methyl-7-(methylamino)-2-oxo-1,2-dihydro-1,6-naphthyridin-3-yl)phenyl)-3-(2,3-difluorophenyl)urea.

In any of the foregoing aspects:

In one embodiment, the compound of Formula Ia is a compound wherein: A is phenyl; or a pharmaceutically acceptable salt thereof.

In one embodiment, the compound of Formula Ia is a compound wherein: A is naphthyl; or a pharmaceutically acceptable salt thereof.

In one embodiment, the compound of Formula Ia is a compound wherein: A is benzothienyl; or a pharmaceutically acceptable salt thereof.

In one embodiment, the compound of Formula Ia is a compound wherein: R1 is taken from the group consisting of C1-C4alkyl, branched C3-C5alkyl, and C3-C5carbocyclyl; or a pharmaceutically acceptable salt thereof.

In one embodiment, the compound of Formula Ia is a compound wherein: R1 is C1-C4alkyl; or a pharmaceutically acceptable salt thereof.

In one embodiment, the compound of Formula Ia is a compound wherein: R1 is branched C3-C5alkyl; or a pharmaceutically acceptable salt thereof.

In one embodiment, the compound of Formula Ia is a compound wherein: R1 is C3-C5carbocyclyl; or a pharmaceutically acceptable salt thereof.

In one embodiment, the compound of Formula Ia is a compound wherein: Z1 is selected from the group consisting of —NH(R4) and —NHCOR8; or a pharmaceutically acceptable salt thereof.

In one embodiment, the compound of Formula Ia is a compound wherein: Z1 is —NH(R4); or a pharmaceutically acceptable salt thereof.

In one embodiment, the compound of Formula Ia is a compound wherein: Z1 is —NH(R4) and R4 is H or C1-C6 alkyl; or a pharmaceutically acceptable salt thereof.

In one embodiment, the compound of Formula Ia is a compound wherein: Z1 is —NH(R4) and R4 is H; or a pharmaceutically acceptable salt thereof.

In one embodiment, the compound of Formula Ia is a compound wherein: Z1 is —NH(R4) and R4 is C1-C6alkyl; or a pharmaceutically acceptable salt thereof.

In one embodiment, the compound of Formula Ia is a compound wherein: Z1 is —NH(R4) and R4 is methyl; or a pharmaceutically acceptable salt thereof.

In one embodiment, the compound of Formula Ia is a compound wherein: Z1 is —NR4COR8; or a pharmaceutically acceptable salt thereof.

In one embodiment, the compound of Formula Ia is a compound wherein: Z1 is —NHCOR8; or a pharmaceutically acceptable salt thereof.

In one embodiment, the compound of Formula Ia is a compound wherein: Z1 is —NHCOR8 and R8 is hydrogen, C1-C6alkyl, branched C3-C7alkyl, C3-C8carbocyclyl, —N(R4)2, or R5; or a pharmaceutically acceptable salt thereof.

In one embodiment, the compound of Formula Ia is a compound wherein: Z1 is —NHCOR8 and R8 is C1-C6alkyl; or a pharmaceutically acceptable salt thereof.

In one embodiment, the compound of Formula Ia is a compound wherein: Z1 is —NHCOR8 and R8 is branched C3-C7alkyl; or a pharmaceutically acceptable salt thereof.

In one embodiment, the compound of Formula Ia is a compound wherein: Z1 is —NHCOR8 and R8 is C3-C8carbocyclyl; or a pharmaceutically acceptable salt thereof.

In one embodiment, the compound of Formula Ia is a compound wherein: Z1 is —NHCOR8 and R8 is —N(R4)$_2$; or a pharmaceutically acceptable salt thereof.

In one embodiment, the compound of Formula Ia is a compound wherein: Z1 is —NHCOR8 and R8 is R5; or a pharmaceutically acceptable salt thereof.

In one embodiment, the compound of Formula Ia is a compound wherein: each R2 is independently hydrogen, methyl, or halogen and t is 2; or a pharmaceutically acceptable salt thereof.

In one embodiment, the compound of Formula Ia is a compound of Formula Ib

Ib

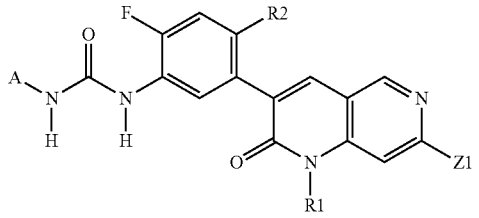

wherein:

R2 is hydrogen, methyl, or halogen; or a pharmaceutically acceptable salt thereof.

In one embodiment, the compound of Formula Ia is a compound of Formula Ib wherein: R2 is hydrogen; or a pharmaceutically acceptable salt thereof.

In one embodiment, the compound of Formula Ia is a compound of Formula Ib wherein: R2 is methyl; or a pharmaceutically acceptable salt thereof.

In one embodiment, the compound of Formula Ia is a compound of Formula Ib wherein: R2 is halogen; or a pharmaceutically acceptable salt thereof.

In one embodiment, the compound of Formula Ia is a compound of Formula Ib wherein: A is phenyl, R1 is C1-C4alkyl, branched C3-C5alkyl, or C3-C5carbocyclyl, R2 is hydrogen, methyl, or halogen, and Z1 is —NH(R4) or —NHCOR8; or a pharmaceutically acceptable salt thereof.

In one embodiment, the compound of Formula Ia is a compound of Formula Ib wherein: A is phenyl, R1 is C1-C4alkyl, R2 is methyl or halogen, and Z1 is —NH(R4) or —NHCOR8; or a pharmaceutically acceptable salt thereof.

In one embodiment, the compound of Formula Ia is a compound of Formula Ib wherein: A is phenyl, R1 is ethyl, R2 is methyl or halogen, and Z1 is —NH(R4) or —NHCOR8;

or a pharmaceutically acceptable salt thereof.

In one embodiment, the compound of Formula Ia is a compound of Formula Ib wherein: A is phenyl, R1 is ethyl, R2 is methyl or halogen, Z1 is —NH(R4) and R4 is methyl; or a pharmaceutically acceptable salt thereof.

In one embodiment, the compound of Formula Ia is a compound of Formula Ib wherein: A is phenyl, R1 is ethyl, R2 is methyl, Z1 is —NH(R4) and R4 is methyl; or a pharmaceutically acceptable salt thereof.

In one embodiment, the compound of Formula Ia is a compound of Formula Ib wherein: A is phenyl, R1 is ethyl, R2 is halogen, Z1 is —NH(R4) and R4 is methyl; or a pharmaceutically acceptable salt thereof.

In one embodiment, the compound of Formula Ia is a compound of Formula Ib wherein: A is naphthyl, R1 is C1-C4alkyl, branched C3-C5alkyl, or C3-C5carbocyclyl, R2 is hydrogen, methyl, or halogen, and Z1 is —NH(R4) or —NHCOR8; or a pharmaceutically acceptable salt thereof.

In one embodiment, the compound of Formula Ia is a compound of Formula Ib wherein: A is naphthyl, R1 is C1-C4alkyl, R2 is methyl or halogen, and Z1 is —NH(R4) or —NHCOR8; or a pharmaceutically acceptable salt thereof.

In one embodiment, the compound of Formula Ia is a compound of Formula Ib wherein: A is naphthyl, R1 is ethyl, R2 is methyl or halogen, and Z1 is —NH(R4) or —NHCOR8; or a pharmaceutically acceptable salt thereof.

In one embodiment, the compound of Formula Ia is a compound of Formula Ib wherein: A is naphthyl, R1 is ethyl, R2 is methyl or halogen, Z1 is —NH(R4) and R4 is methyl; or a pharmaceutically acceptable salt thereof.

In one embodiment, the compound of Formula Ia is a compound of Formula Ib wherein: A is naphthyl, R1 is ethyl, R2 is methyl, Z1 is —NH(R4) and R4 is methyl; or a pharmaceutically acceptable salt thereof.

In one embodiment, the compound of Formula Ia is a compound of Formula Ib wherein: A is naphthyl, R1 is ethyl, R2 is halogen, Z1 is —NH(R4) and R4 is methyl; or a pharmaceutically acceptable salt thereof.

In one embodiment, the compound of Formula Ia is a compound of Formula Ib wherein: A is benzothienyl, R1 is C1-C4alkyl, branched C3-C5alkyl, or C3-C5carbocyclyl, R2 is hydrogen, methyl, or halogen, and Z1 is —NH(R4) or —NHCOR8; or a pharmaceutically acceptable salt thereof.

In one embodiment, the compound of Formula Ia is a compound of Formula Ib wherein: A is benzothienyl, R1 is C1-C4alkyl, R2 is methyl or halogen, and Z1 is —NH(R4) or —NHCOR8; or a pharmaceutically acceptable salt thereof.

In one embodiment, the compound of Formula Ia is a compound of Formula Ib wherein: A is benzothienyl, R1 is ethyl, R2 is methyl or halogen, and Z1 is —NH(R4) or —NHCOR8; or a pharmaceutically acceptable salt thereof.

In one embodiment, the compound of Formula Ia is a compound of Formula Ib wherein: A is benzothienyl, R1 is ethyl, R2 is methyl or halogen, Z1 is —NH(R4) and R4 is methyl; or a pharmaceutically acceptable salt thereof.

In one embodiment, the compound of Formula Ia is a compound of Formula Ib wherein: A is benzothienyl, R1 is ethyl, R2 is methyl, Z1 is —NH(R4) and R4 is methyl; or a pharmaceutically acceptable salt thereof.

In one embodiment, the compound of Formula Ia is a compound of Formula Ib wherein: A is benzothienyl, R1 is ethyl, R2 is halogen, Z1 is —NH(R4) and R4 is methyl; or a pharmaceutically acceptable salt thereof.

In some embodiments, the present invention provides a method treating a disease caused by c-KIT kinase comprising gastrointestinal stromal tumors, ovarian cancer, melanoma, cervical carcinomas, acute myeloid leukemia, germ cell tumors of the seminoma or dysgerminoma, teratomas, mastocytosis, or mast cell leukemia, said method comprising administering to a patient a therapeutically effective amount of a compound selected from 1-(5-(1-ethyl-7-(methylamino)-2-oxo-1,2-dihydro-1,6-naphthyridin-3-yl)-2-fluoro-4-methylphenyl)-3-(naphthalen-1-yl)urea, 1-(5-(1-ethyl-7-(methylamino)-2-oxo-1,2-dihydro-1,6-naphthyridin-3-yl)-2-fluorophenyl)-3-(naphthalen-1-yl)urea, 1-(4-chloro-5-(1-ethyl-7-(methylamino)-2-oxo-1,2-dihydro-1,6-naphthyridin-3-yl)-2-fluorophenyl)-3-phenylurea, 1-(4-chloro-5-(1-ethyl-7-(methylamino)-2-oxo-1,2-dihydro-1,6-naphthyridin-3-yl)-2-fluorophenyl)-3-(2,3-difluorophenyl)urea, 1-(2-fluoro-5-(1-isopropyl-7-(methylamino)-2-oxo-1,2-dihydro-1,6-naphthyridin-3-yl)phenyl)-3-phenylurea, 1-(4-chloro-5-(1-ethyl-7-(methylamino)-2-oxo-1,2-dihydro-1,6-naphthyridin-3-yl)-2-fluorophenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-phenylurea, 1-(4-chloro-2-fluoro-5-(1-methyl-7-(methylamino)-2-oxo-1,2-dihydro-1,6-naphthyridin-3-yl)phenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-(3-cyanophenyl)urea, 1-(4-chloro-2-fluoro-5-(1-methyl-7-(methylamino)-2-oxo-1,2-dihydro-1,6-naphthyridin-3-yl)phenyl)-3-(2,3-difluorophenyl)urea, 1-(4-chloro-3-(1-methyl-7-(methylamino)-2-oxo-1,2-dihydro-1,6-naphthyridin-3-yl)phenyl)-3-(3-cyanophenyl)urea, 1-(3-cyanophenyl)-3-(5-(1-ethyl-7-(methylamino)-2-oxo-1,2-dihydro-1,6-naphthyridin-3-yl)-2-fluorophenyl)urea, 1-(benzo[b]thiophen-3-yl)-3-(2-fluoro-4-methyl-5-(1-methyl-7-(methylamino)-2-oxo-1,2-dihydro-1,6-naphthyridin-3-yl)phenyl)urea, 1-(benzo[b]thiophen-3-yl)-3-(2,4-difluoro-5-(1-methyl-7-(methylamino)-2-oxo-1,2-dihydro-1,6-naphthyridin-3-yl)phenyl)urea, 1-(5-(1-ethyl-7-(methylamino)-2-oxo-1,2-dihydro-1,6-naphthyridin-3-yl)-2,4-difluorophenyl)-3-(3-fluorophenyl)urea, 1-(5-(1-ethyl-7-(methylamino)-2-oxo-1,2-dihydro-1,6-naphthyridin-3-yl)-2,4-difluorophenyl)-3-phenylurea, 1-(3-chlorophenyl)-3-(5-(1-ethyl-7-(methylamino)-2-oxo-1,2-dihydro-1,6-naphthyridin-3-yl)-2,4-difluorophenyl)urea, 1-(3-cyanophenyl)-3-(5-(1-ethyl-7-(methylamino)-2-oxo-1,2-dihydro-1,6-naphthyridin-3-yl)-2,4-difluorophenyl)urea, 1-(benzo[b]thiophen-3-yl)-3-(5-(1-ethyl-7-(methylamino)-2-oxo-1,2-dihydro-1,6-naphthyridin-3-yl)-2,4-difluorophenyl)urea, 1-(5-(7-amino-1-ethyl-2-oxo-1,2-dihydro-1,6-naphthyridin-3-yl)-4-chloro-2-fluorophenyl)-3-(3-fluorophenyl)urea, 1-(5-(7-amino-1-ethyl-2-oxo-1,2-dihydro-1,6-naphthyridin-3-yl)-4-chloro-2-fluorophenyl)-3-phenylurea, 1-(4-chloro-2-fluoro-5-(1-isopropyl-7-(methylamino)-2-oxo-1,2-dihydro-1,6-naphthyridin-3-yl)phenyl)-3-phenylurea, 1-(5-(1-ethyl-7-(methylamino)-2-oxo-1,2-dihydro-1,6-naphthyridin-3-yl)-2-fluoro-4-methylphenyl)-3-phenylurea, 1-[4-chloro-5-(1-ethyl-7-methylamino-2-oxo-1,2-dihydro-[1,6]naphthyridin-3-yl)-2-fluoro-phenyl]-3-(3-fluoro-phenyl)-urea, 1-[4-chloro-5-(1-ethyl-7-methylamino-2-oxo-1,2-dihydro-[1,6]naphthyridin-3-yl)-2-fluoro-phenyl]-3-(2-fluoro-phenyl)-urea, 1-(4-chloro-3-(1-ethyl-7-(methylamino)-2-oxo-1,2-dihydro-1,6-naphthyridin-3-yl)-2-fluorophenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-(3-fluorophenyl)urea, 1-(4-chloro-5-(7-(2-(dimethylamino)ethylamino)-1-ethyl-2-oxo-1,2-dihydro-1,6-naphthyridin-3-yl)-2-fluorophenyl)-3-phenylurea, 1-(4-chloro-5-(7-(3-(dimethylamino)propylamino)-1-ethyl-2-oxo-1,2-dihydro-1,6-naphthyridin-3-yl)-2-fluorophenyl)-3-phenylurea, 1-(4-bromo-5-(1-ethyl-7-(methylamino)-2-oxo-1,2-dihydro-1,6-naphthyridin-3-yl)-2-fluorophenyl)-3-phenylurea, 1-(benzo[b]thiophen-3-yl)-3-(4-chloro-5-(1-ethyl-7-(methylamino)-2-oxo-1,2,4a,8a-tetrahydro-1,6-naphthyridin-3-yl)-2-fluorophenyl)urea, 1-(4-chloro-3-(1-ethyl-7-(methylamino)-2-oxo-1,2-dihydro-1,6-naphthyridin-3-yl)phenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-(4-fluorophenyl)urea, 1-(4-chloro-5-(1-ethyl-7-(2-methoxyethylamino)-2-oxo-1,2-dihydro-1,6-naphthyridin-3-yl)-2-fluorophenyl)-3-(2-fluorophenyl)urea, 1-(5-(1-ethyl-7-(2-methoxyethylamino)-2-oxo-1,2-dihydro-1,6-naphthyridin-3-yl)-2,4-difluorophenyl)-3-phenylurea, 1-(5-(1-ethyl-7-(2-methoxyethylamino)-2-oxo-1,2-dihydro-1,6-naphthyridin-3-yl)-2-fluoro-4-methylphenyl)-3-phenylurea, 1-(5-(1-ethyl-7-(methylamino)-2-oxo-1,2-dihydro-1,6-naphthyridin-3-yl)-2-fluoro-4-methylphenyl)-3-(2-fluorophenyl)urea, 1-(4-chloro-5-(1-ethyl-7-(3-methoxypropylamino)-2-oxo-1,2-dihydro-1,6-naphthyridin-3-yl)-2-fluorophenyl)-3-phenylurea, 1-(2,4-difluoro-5-(1-isopropyl-7-(methylamino)-2-oxo-1,2-dihydro-1,6-naphthyridin-3-yl)phenyl)-3-(3-fluorophenyl)urea, 1-(2-fluoro-5-(1-isopropyl-7-(methylamino)-2-oxo-1,2-dihydro-1,6-naphthyridin-3-yl)-4-methylphenyl)-3-(3-fluorophenyl)urea, 1-(4-chloro-5-(1-ethyl-2-oxo-7-(tetrahydro-2H-pyran-4-ylamino)-1,2-dihydro-1,6-naphthyridin-3-yl)-2-fluorophenyl)-3-phenylurea, (S)-1-(4-chloro-5-(1-ethyl-7-(1-methoxypropan-2-ylamino)-2-oxo-1,2-dihydro-1,6-naphthyridin-3-yl)-2-fluorophenyl)-3-phenylurea, 1-(5-(1-ethyl-7-(methylamino)-2-oxo-1,2-dihydro-1,6-naphthyridin-3-yl)-2-fluoro-4-methylphenyl)-3-(3-fluorophenyl)urea, 1-(5-(7-(cyclopropylamino)-1-ethyl-2-oxo-1,2-dihydro-1,6-naphthyridin-3-yl)-2-fluoro-4-methylphenyl)-3-(3-fluorophenyl)urea, 1-(4-chloro-5-(1-ethyl-7-(1-methylpiperidin-4-ylamino)-2-oxo-1,2-dihydro-1,6-naphthyridin-3-yl)-2-fluorophenyl)-3-phenylurea, 1-(4-chloro-5-(1-ethyl-2-oxo-7-(THF-3-ylamino)-1,2-dihydro-1,6-naphthyridin-3-yl)-2-fluorophenyl)-3-phenylurea, 1-(4-chloro-5-(1-ethyl-7-(2-(methylsulfonyl)ethylamino)-2-oxo-1,2-dihydro-1,6-naphthyridin-3-yl)-2-fluorophenyl)-3-phenylurea, 1-(4-chloro-5-(1-ethyl-7-(1-methylpyrrolidin-3-ylamino)-2-oxo-1,2-dihydro-1,6-naphthyridin-3-yl)-2-fluorophenyl)-3-phenylurea, 1-(4-bromo-5-(1-ethyl-7-(methylamino)-2-oxo-1,2-dihydro-1,6-naphthyridin-3-yl)-2-fluorophenyl)-3-(3-fluorophenyl)urea, 1-(4-bromo-5-(1-ethyl-7-(2-methoxyethylamino)-2-oxo-1,2-dihydro-1,6-naphthyridin-3-yl)-2-fluorophenyl)-3-phenylurea, 1-(4-bromo-5-(1-ethyl-7-(2-(methylsulfonyl)ethylamino)-2-oxo-1,2-dihydro-1,6-naphthyridin-3-yl)-2-fluorophenyl)-3-phenylurea, 1-(5-(7-acetamido-1-ethyl-2-oxo-1,2-dihydro-1,6-naphthyridin-3-yl)-4-bromo-2-fluorophenyl)-3-phenylurea, 1-(5-(7-acetamido-1-ethyl-2-oxo-1,2-dihydro-1,6-naphthyridin-3-yl)-4-chloro-2-fluorophenyl)-3-phenylurea, 1-(4-chloro-5-(1-ethyl-7-(methylamino)-2-oxo-1,2-dihydro-1,6-naphthyridin-3-yl)-2-fluorophenyl)-3-(3,5-difluorophenyl)urea, 1-(4-bromo-2-fluoro-5-(1-methyl-7-(methylamino)-2-oxo-1,2-dihydro-1,6-naphthyridin-3-yl)phenyl)-3-phenylurea, 1-(5-(7-amino-1-ethyl-2-oxo-1,2-dihydro-1,6-naphthyridin-3-yl)-4-bromo-2-fluorophenyl)-3-phenylurea, 1-(5-(7-amino-1-ethyl-2-oxo-1,2-dihydro-1,6-naphthyridin-3-yl)-2-fluoro-4-methylphenyl)-3-(3-fluorophenyl)urea, 1-(benzo[b]thiophen-3-yl)-3-(5-(1-ethyl-7-(methylamino)-2-oxo-1,2-dihydro-1,6-naphthyridin-3-yl)-2-fluoro-4-methylphenyl)urea, 1-(3,5-difluorophenyl)-3-(5-(1-ethyl-7-(methylamino)-2-oxo-1,2-dihydro-1,6-naphthyridin-3-yl)-2-fluoro-4-methylphenyl)urea, 1-(2,5-difluorophenyl)-3-(5-

(1-ethyl-7-(methylamino)-2-oxo-1,2-dihydro-1,6-naphthyridin-3-yl)-2-fluoro-4-methylphenyl)urea, 1-(2,5-difluorophenyl)-3-(5-(1-ethyl-7-(methylamino)-2-oxo-1,2,4a,8a-tetrahydro-1,6-naphthyridin-3-yl)-2,4-difluorophenyl)urea, 1-(3,5-difluorophenyl)-3-(5-(1-ethyl-7-(methylamino)-2-oxo-1,2,4a,8a-tetrahydro-1,6-naphthyridin-3-yl)-2,4-difluorophenyl)urea, N-(3-(2-bromo-4-fluoro-5-(3-phenylureido)phenyl)-1-ethyl-2-oxo-1,2-dihydro-1,6-naphthyridin-7-yl)-2-cyanoacetamide, N-(3-(2-chloro-4-fluoro-5-(3-phenylureido)phenyl)-1-ethyl-2-oxo-1,2-dihydro-1,6-naphthyridin-7-yl)-2-cyanoacetamide, 1-(5-(7-acetamido-1-ethyl-2-oxo-1,2-dihydro-1,6-naphthyridin-3-yl)-2,4-difluorophenyl)-3-phenylurea, N-(3-(2-chloro-5-(3-(3,5-difluorophenyl)ureido)-4-fluorophenyl)-1-ethyl-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(2,5-difluorophenyl)urea, 1-(3-chloro-5-fluorophenyl)-3-(5-(1-ethyl-7-(methylamino)-2-oxo-1,2-dihydro-1,6-naphthyridin-3-yl)-2-fluoro-4-methylphenyl)urea, 3-(3-(2-chloro-4-fluoro-5-(3-phenylureido)phenyl)-1-ethyl-2-oxo-1,2-dihydro-1,6-naphthyridin-7-yl)-1,1-dimethylurea, 1-(4-chloro-5-(1-ethyl-7-(methylamino)-2-oxo-1,2-dihydro-1,6-naphthyridin-3-yl)-2-fluorophenyl)-3-(3-chloro-5-fluorophenyl)urea, 1-(4-chloro-5-(1-ethyl-7-(methylamino)-2-oxo-1,2-dihydro-1,6-naphthyridin-3-yl)-2-fluorophenyl)-3-(3-fluoro-5-methylphenyl)urea, methyl (3-(2-chloro-4-fluoro-5-(3-phenylureido)phenyl)-1-ethyl-2-oxo-1,2-dihydro-1,6-naphthyridin-7-yl)carbamate, N-(3-(2-chloro-4-fluoro-5-(3-phenylureido)phenyl)-1-ethyl-2-oxo-1,2-dihydro-1,6-naphthyridin-7-yl)-2-methoxyacetamide, 2-cyano-N-(3-(2,4-difluoro-5-(3-phenylureido)phenyl)-1-ethyl-2-oxo-1,2-dihydro-1,6-naphthyridin-7-yl)acetamide, 1-(4-cyano-5-(1-ethyl-7-(methylamino)-2-oxo-1,2-dihydro-1,6-naphthyridin-3-yl)-2-fluorophenyl)-3-phenylurea, 1-(4-chloro-2-fluoro-5-(1-isopropyl-7-(methylamino)-2-oxo-1,2-dihydro-1,6-naphthyridin-3-yl)phenyl)-3-(3-fluorophenyl)urea, N-(1-ethyl-3-(4-fluoro-5-(3-(3-fluorophenyl)ureido)-2-methylphenyl)-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea, N-(1-ethyl-3-(4-fluoro-2-methyl-5-(3-phenylureido)phenyl)-2-oxo-1,2-dihydro-1,6-naphthyridin-7-yl)acetamide, N-(3-(2-chloro-4-fluoro-5-(3-phenylureido)phenyl)-1-ethyl-2-oxo-1,2-dihydro-1,6-naphthyridin-7-yl)-3-hydroxyazetidine-1-carboxamide, 1-(5-(1-ethyl-7-(methylamino)-2-oxo-1,2-dihydro-1,6-naphthyridin-3-yl)-2-fluoro-4-methylphenyl)-3-(3-((4-methylpiperazin-1-yl)methyl)phenyl)urea, 1-(4-bromo-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea, (R)—N-(3-(2-chloro-4-fluoro-5-(3-phenylureido)phenyl)-1-ethyl-2-oxo-1,2-dihydro-1,6-naphthyridin-7-yl)-3-(dimethylamino) pyrrolidine-1-carboxamide, (S)—N-(3-(2-chloro-4-fluoro-5-(3-phenylureido)phenyl)-1-ethyl-2-oxo-1,2-dihydro-1,6-naphthyridin-7-yl)pyrrolidine-2-carboxamide, N-(3-(2-chloro-4-fluoro-5-(3-phenylureido)phenyl)-1-isopropyl-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(4-fluoro-3-((4-methylpiperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-fluoro-5-((4-methylpiperazin-1-yl)methyl)phenyl)urea, 1-(5-(1-ethyl-7-(methylamino)-2-oxo-1,2-dihydro-1,6-naphthyridin-3-yl)-2-fluoro-4-methylphenyl)-3-(4-fluoro-3-((4-methylpiperazin-1-yl)methyl)phenyl)urea, 1-(5-(1-ethyl-7-(methylamino)-2-oxo-1,2-dihydro-1,6-naphthyridin-3-yl)-2,4-difluorophenyl)-3-(4-fluoro-3-((4-methylpiperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-cyanophenyl)urea, 1-(4-chloro-5-(1-ethyl-7-((3-morpholinopropyl)amino)-2-oxo-1,2-dihydro-1,6-naphthyridin-3-yl)-2-fluorophenyl)-3-phenylurea, 1-(5-(7-amino-1-ethyl-2-oxo-1,2-dihydro-1,6-naphthyridin-3-yl)-2-fluoro-4-methylphenyl)-3-(4-fluoro-3-((4-methylpiperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-((dimethylamino) methyl)-4-fluorophenyl)urea, 1-(4-chloro-5-(1-ethyl-7-(methylamino)-2-oxo-1,2-dihydro-1,6-naphthyridin-3-yl)-2-fluorophenyl)-3-(4-fluoro-3-(morpholinomethyl)phenyl) urea, (S)—N-(3-(2-chloro-4-fluoro-5-(3-phenylureido) phenyl)-1-ethyl-2-oxo-1,2-dihydro-1,6-naphthyridin-7-yl)-3-(dimethylamino)pyrrolidine-1-carboxamide, 1-(4-chloro-5-(1-ethyl-7-(methylamino)-2-oxo-1,2-dihydro-1,6-naphthyridin-3-yl)-2-fluorophenyl)-3-(4-fluoro-3-(pyrrolidin-1-ylmethyl)phenyl)urea, 3-(3-(2-chloro-4-fluoro-5-(3-(3-fluorophenyl)ureido)phenyl)-1-isopropyl-2-oxo-1,2-dihydro-1,6-naphthyridin-7-yl)-1,1-dimethylurea, N-(3-(2-chloro-4-fluoro-5-(3-(3-fluorophenyl)ureido)phenyl)-1-isopropyl-2-oxo-1,2-dihydro-1,6-naphthyridin-7-yl) acetamide, N-(1-ethyl-3-(4-fluoro-5-(3-(4-fluoro-3-((4-methyl)piperazin-1-yl)methyl)phenyl)ureido)-2-methylphenyl)-2-oxo-1,2-dihydro-1,6-naphthyridin-7-yl) formamide, 3-(1-ethyl-3-(4-fluoro-2-methyl-5-(3-phenylureido)phenyl)-2-oxo-1,2-dihydro-1,6-naphthyridin-7-yl)-1,1-dimethylurea, N-(3-(2-chloro-4-fluoro-5-(3-phenylureido)phenyl)-1-ethyl-2-oxo-1,2-dihydro-1,6-naphthyridin-7-yl)-3-(dimethylamino)azetidine-1-carboxamide, 3-(3-(2-chloro-4-fluoro-5-(3-phenylureido) phenyl)-1-isopropyl-2-oxo-1,2-dihydro-1,6-naphthyridin-7-yl)-1,1-dimethylurea, 3-(3-(5-(3-(benzo[b]thiophen-3-yl) ureido)-4-fluoro-2-methylphenyl)-1-ethyl-2-oxo-1,2-dihydro-1,6-naphthyridin-7-yl)-1,1-dimethylurea, 3-(3-(2-bromo-4-fluoro-5-(3-phenylureido)phenyl)-1-ethyl-2-oxo-1,2-dihydro-1,6-naphthyridin-7-yl)-1,1-dimethylurea, 3-(1-ethyl-3-(4-fluoro-5-(3-(3-fluorophenyl)ureido)-2-methylphenyl)-2-oxo-1,2-dihydro-1,6-naphthyridin-7-yl)-1,1-dimethylurea, N-(3-(2-chloro-4-fluoro-5-(3-(4-fluoro-3-(morpholinomethyl)phenyl)ureido)phenyl)-1-ethyl-2-oxo-1,2-dihydro-1,6-naphthyridin-7-yl)formamide, 3-(3-(5-(3-(3,5-difluorophenyl)ureido)-4-fluoro-2-methylphenyl)-1-ethyl-2-oxo-1,2-dihydro-1,6-naphthyridin-7-yl)-1,1-dimethylurea, N-(3-(4-fluoro-2-methyl-5-(3-phenylureido) phenyl)-1-isopropyl-2-oxo-1,2-dihydro-1,6-naphthyridin-7-yl)azetidine-1-carboxamide, N-(1-ethyl-3-(4-fluoro-2-methyl-5-(3-phenylureido)phenyl)-2-oxo-1,2-dihydro-1,6-naphthyridin-7-yl)azetidine-1-carboxamide, 1-(5-(1-ethyl-7-((6-methylpyridin-3-yl)amino)-2-oxo-1,2-dihydro-1,6-naphthyridin-3-yl)-2-fluoro-4-methylphenyl)-3-phenylurea, 3-(3-(2,4-difluoro-5-(3-phenylureido)phenyl)-1-ethyl-2-oxo-1,2-dihydro-1,6-naphthyridin-7-yl)-1,1-dimethylurea, 3-(dimethylamino)-N-(1-ethyl-3-(4-fluoro-2-methyl-5-(3-phenylureido)phenyl)-2-oxo-1,2-dihydro-1,6-naphthyridin-7-yl)azetidine-1-carboxamide, 1-(5-(1-ethyl-7-(methylamino)-2-oxo-1,2-dihydro-1,6-naphthyridin-3-yl)-2-fluoro-4-iodophenyl)-3-phenylurea, and 1-(5-(1-ethyl-7-((1-methyl-1H-pyrazol-4-yl)amino)-2-oxo-1,2-dihydro-1,6-naphthyridin-3-yl)-2-fluoro-4-methylphenyl)-3-phenylurea; or a pharmaceutically acceptable salt thereof.

In some embodiments, the present invention comprises a compound selected from the group consisting of 1-(4-chloro-3-(1-methyl-7-(methylamino)-2-oxo-1,2-dihydro-1,6-naphthyridin-3-yl)phenyl)-3-(3-cyanophenyl)urea, 1-(3-cyanophenyl)-3-(5-(1-ethyl-7-(methylamino)-2-oxo-1,2-dihydro-1,6-naphthyridin-3-yl)-2-fluorophenyl)urea, 1-(benzo[b]thiophen-3-yl)-3-(2-fluoro-4-methyl-5-(1-methyl-7-(methylamino)-2-oxo-1,2-dihydro-1,6-naphthyridin-3-yl)phenyl)urea, 1-(benzo[b]thiophen-3-yl)-3-(2,4-difluoro-5-(1-methyl-7-(methylamino)-2-oxo-1,2-dihydro-1,6-naphthyridin-3-yl)phenyl)urea, 1-(5-(1-ethyl-7-(methylamino)-2-oxo-1,2-dihydro-1,6-naphthyridin-3-yl)-2,4-difluorophenyl)-3-(3-fluorophenyl)urea, 1-(5-(1-ethyl-7-(methylamino)-2-oxo-1,2-dihydro-1,6-naphthyridin-3-yl)-2,4-difluorophenyl)-3-phenylurea, 1-(3-chlorophenyl)-3-(5-(1-ethyl-7-(methylamino)-2-oxo-1,2-dihydro-1,6-naphthyridin-3-yl)-2,4-difluorophenyl)urea, 1-(3-cyanophenyl)-3-(5-(1-ethyl-7-(methylamino)-2-oxo-1,2-dihydro-1,6-naphthyridin-3-yl)-2,4-difluorophenyl)urea, 1-(benzo[b]thiophen-3-yl)-3-(5-(1-ethyl-7-(methylamino)-2-oxo-1,2-dihydro-1,6-naphthyridin-3-yl)-2,4-difluorophenyl)urea, 1-(5-(7-amino-1-ethyl-2-oxo-1,2-dihydro-1,6-naphthyridin-3-yl)-4-chloro-2-fluorophenyl)-3-(3-fluorophenyl)urea, 1-(5-(7-amino-1-ethyl-2-oxo-1,2-dihydro-1,6-naphthyridin-3-yl)-4-chloro-2-fluorophenyl)-3-phenylurea, 1-(4-chloro-2-fluoro-5-(1-isopropyl-7-(methylamino)-2-oxo-1,2-dihydro-1,6-naphthyridin-3-yl)phenyl)-3-phenylurea, 1-(5-(1-ethyl-7-(methylamino)-2-oxo-1,2-dihydro-1,6-naphthyridin-3-yl)-2-fluoro-4-methylphenyl)-3-phenylurea, 1-[4-chloro-5-(1-ethyl-7-methylamino-2-oxo-1,2-dihydro-[1,6]naphthyridin-3-yl)-2-fluoro-phenyl]-3-(3-fluoro-phenyl)-urea, 1-[4-chloro-5-(1-ethyl-7-methylamino-2-oxo-1,2-dihydro-[1,6]naphthyridin-3-yl)-2-fluoro-phenyl]-3-(2-fluoro-phenyl)-urea, 1-(4-chloro-3-(1-ethyl-7-(methylamino)-2-oxo-1,2-dihydro-1,6-naphthyridin-3-yl)-2-fluorophenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-(3-fluorophenyl)urea, 1-(4-chloro-5-(7-(2-(dimethylamino)ethylamino)-1-ethyl-2-oxo-1,2-dihydro-1,6-naphthyridin-3-yl)-2-fluorophenyl)-3-phenylurea, 1-(4-chloro-5-(7-(3-(dimethylamino)propylamino)-1-ethyl-2-oxo-1,2-dihydro-1,6-naphthyridin-3-yl)-2-fluorophenyl)-3-phenylurea, 1-(4-bromo-5-(1-ethyl-7-(methylamino)-2-oxo-1,2-dihydro-1,6-naphthyridin-3-yl)-2-fluorophenyl)-3-phenylurea, 1-(benzo[b]thiophen-3-yl)-3-(4-chloro-5-(1-ethyl-7-(methylamino)-2-oxo-1,2,4a,8a-tetrahydro-1,6-naphthyridin-3-yl)-2-fluorophenyl)urea, 1-(4-chloro-3-(1-ethyl-7-(methylamino)-2-oxo-1,2-dihydro-1,6-naphthyridin-3-yl)phenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-(4-fluorophenyl)urea, 1-(4-chloro-5-(1-ethyl-7-(2-methoxyethylamino)-2-oxo-1,2-dihydro-1,6-naphthyridin-3-yl)-2-fluorophenyl)-3-(2-fluorophenyl)urea, 1-(5-(1-ethyl-7-(2-methoxyethylamino)-2-oxo-1,2-dihydro-1,6-naphthyridin-3-yl)-2,4-difluorophenyl)-3-phenylurea, 1-(5-(1-ethyl-7-(2-methoxyethylamino)-2-oxo-1,2-dihydro-1,6-naphthyridin-3-yl)-2-fluoro-4-methylphenyl)-3-phenylurea, 1-(5-(1-ethyl-7-(methylamino)-2-oxo-1,2-dihydro-1,6-naphthyridin-3-yl)-2-fluoro-4-methylphenyl)-3-(2-fluorophenyl)urea, 1-(4-chloro-5-(1-ethyl-7-(3-methoxypropylamino)-2-oxo-1,2-dihydro-1,6-naphthyridin-3-yl)-2-fluorophenyl)-3-phenylurea, 1-(2,4-difluoro-5-(1-isopropyl-7-(methylamino)-2-oxo-1,2-dihydro-1,6-naphthyridin-3-yl)phenyl)-3-(3-fluorophenyl)urea, 1-(2-fluoro-5-(1-isopropyl-7-(methylamino)-2-oxo-1,2-dihydro-1,6-naphthyridin-3-yl)-4-methylphenyl)-3-(3-fluorophenyl)urea, 1-(4-chloro-5-(1-ethyl-2-oxo-7-(tetrahydro-2H-pyran-4-ylamino)-1,2-dihydro-1,6-naphthyridin-3-yl)-2-fluorophenyl)-3-phenylurea, (S)-1-(4-chloro-5-(1-ethyl-7-(1-methoxypropan-2-ylamino)-2-oxo-1,2-dihydro-1,6-naphthyridin-3-yl)-2-fluorophenyl)-3-phenylurea, 1-(5-(1-ethyl-7-(methylamino)-2-oxo-1,2-dihydro-1,6-naphthyridin-3-yl)-2-fluoro-4-methylphenyl)-3-(3-fluorophenyl)urea, 1-(5-(7-(cyclopropylamino)-1-ethyl-2-oxo-1,2-dihydro-1,6-naphthyridin-3-yl)-2-fluoro-4-methylphenyl)-3-(3-fluorophenyl)urea, 1-(4-chloro-5-(1-ethyl-7-(1-methylpiperidin-4-ylamino)-2-oxo-1,2-dihydro-1,6-naphthyridin-3-yl)-2-fluorophenyl)-3-phenylurea, 1-(4-chloro-5-(1-ethyl-2-oxo-7-(THF-3-ylamino)-1,2-dihydro-1,6-naphthyridin-3-yl)-2-fluorophenyl)-3-phenylurea, 1-(4-chloro-5-(1-ethyl-7-(2-(methylsulfonyl)ethylamino)-2-oxo-1,2-dihydro-1,6-naphthyridin-3-yl)-2-fluorophenyl)-3-phenylurea, 1-(4-chloro-5-(1-ethyl-7-(1-methylpyrrolidin-3-ylamino)-2-oxo-1,2-dihydro-1,6-naphthyridin-3-yl)-2-fluorophenyl)-3-phenylurea, 1-(4-bromo-5-(1-ethyl-7-(methylamino)-2-oxo-1,2-dihydro-1,6-naphthyridin-3-yl)-2-fluorophenyl)-3-(3-fluorophenyl)urea, 1-(4-bromo-5-(1-ethyl-7-(2-methoxyethylamino)-2-oxo-1,2-dihydro-1,6-naphthyridin-3-yl)-2-fluorophenyl)-3-phenylurea, 1-(4-bromo-5-(1-ethyl-7-(2-(methylsulfonyl)ethylamino)-2-oxo-1,2-dihydro-1,6-naphthyridin-3-yl)-2-fluorophenyl)-3-phenylurea, 1-(5-(7-acetamido-1-ethyl-2-oxo-1,2-dihydro-1,6-naphthyridin-3-yl)-4-bromo-2-fluorophenyl)-3-phenylurea, 1-(5-(7-acetamido-1-ethyl-2-oxo-1,2-dihydro-1,6-naphthyridin-3-yl)-4-chloro-2-fluorophenyl)-3-phenylurea, 1-(4-chloro-5-(1-ethyl-7-(methylamino)-2-oxo-1,2-dihydro-1,6-naphthyridin-3-yl)-2-fluorophenyl)-3-(3,5-difluorophenyl)urea, 1-(4-bromo-2-fluoro-5-(1-methyl-7-(methylamino)-2-oxo-1,2-dihydro-1,6-naphthyridin-3-yl)phenyl)-3-phenylurea, 1-(5-(7-amino-1-ethyl-2-oxo-1,2-dihydro-1,6-naphthyridin-3-yl)-4-bromo-2-fluorophenyl)-3-phenylurea, 1-(5-(7-amino-1-ethyl-2-oxo-1,2-dihydro-1,6-naphthyridin-3-yl)-2-fluoro-4-methylphenyl)-3-(3-fluorophenyl)urea, 1-(benzo[b]thiophen-3-yl)-3-(5-(1-ethyl-7-(methylamino)-2-oxo-1,2-dihydro-1,6-naphthyridin-3-yl)-2-fluoro-4-methylphenyl)urea, 1-(3,5-difluorophenyl)-3-(5-(1-ethyl-7-(methylamino)-2-oxo-1,2-dihydro-1,6-naphthyridin-3-yl)-2-fluoro-4-methylphenyl)urea, 1-(2,5-difluorophenyl)-3-(5-(1-ethyl-7-(methylamino)-2-oxo-1,2-dihydro-1,6-naphthyridin-3-yl)-2-fluoro-4-methylphenyl)urea, 1-(2,5-difluorophenyl)-3-(5-(1-ethyl-7-(methylamino)-2-oxo-1,2,4a,8a-tetrahydro-1,6-naphthyridin-3-yl)-2,4-difluorophenyl)urea, 1-(3,5-difluorophenyl)-3-(5-(1-ethyl-7-(methylamino)-2-oxo-1,2,4a,8a-tetrahydro-1,6-naphthyridin-3-yl)-2,4-difluorophenyl)urea, N-(3-(2-bromo-4-fluoro-5-(3-phenylureido)phenyl)-1-ethyl-2-oxo-1,2-dihydro-1,6-naphthyridin-7-yl)-2-cyanoacetamide, N-(3-(2-chloro-4-fluoro-5-(3-phenylureido)phenyl)-1-ethyl-2-oxo-1,2-dihydro-1,6-naphthyridin-7-yl)-2-cyanoacetamide, 1-(5-(7-acetamido-1-ethyl-2-oxo-1,2-dihydro-1,6-naphthyridin-3-yl)-2,4-difluorophenyl)-3-phenylurea, N-(3-(2-chloro-5-(3-(3,5-difluorophenyl)ureido)-4-fluorophenyl)-1-ethyl-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(2,5-difluorophenyl)urea, 1-(3-chloro-5-fluorophenyl)-3-(5-(1-ethyl-7-(methylamino)-2-oxo-1,2-dihydro-1,6-naphthyridin-3-yl)-2-fluoro-4-methylphenyl)urea, 3-(3-(2-chloro-4-fluoro-5-(3-phenylureido)phenyl)-1-ethyl-2-oxo-1,2-dihydro-1,6-naphthyridin-7-yl)-1,1-dimethylurea, 1-(4-chloro-5-(1-ethyl-7-(methylamino)-2-oxo-1,2-dihydro-1,6-naphthyridin-3-yl)-2-fluorophenyl)-3-(3-chloro-5-fluorophenyl)urea, 1-(4-chloro-5-(1-ethyl-7-(methylamino)-2-oxo-1,2-dihydro-1,6-naphthyridin-3-yl)-2-fluorophenyl)-3-(3-fluoro-5-methylphenyl)urea, methyl (3-(2-chloro-4-fluoro-5-(3-phenylureido)phenyl)-1-ethyl-2-oxo-1,2-dihydro-1,6-naphthyridin-7-yl)carbamate, N-(3-(2-chloro-4-fluoro-5-(3-phenylureido)phenyl)-1-ethyl-2-oxo-1,2-dihydro-1,6-naphthyridin-7-yl)-2-methoxyacetamide, 2-cyano-N-(3-(2,4-difluoro-5-(3-phenylureido)phenyl)-1-ethyl-2-oxo-1,2-dihydro-1,6-naphthyridin-7-yl)acetamide, 1-(4-cyano-5-(1-ethyl-7-(methylamino)-2-oxo-1,2-dihydro-1,6-naphthyridin-3-yl)-2-fluorophenyl)-3-phenylurea, 1-(4-chloro-2-fluoro-5-(1-isopropyl-7-(methylamino)-2-oxo-1,2-dihydro-1,6-naphthyridin-3-yl)phenyl)-3-(3-fluorophenyl)urea, N-(1-ethyl-3-(4-fluoro-5-(3-(3-fluorophenyl)ureido)-2-methylphenyl)-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea, N-(1-ethyl-3-(4-fluoro-2-methyl-5-(3-phenylureido)phenyl)-2-oxo-1,2-dihydro-1,6-naphthyridin-7-yl)acetamide, N-(3-(2-chloro-4-fluoro-5-(3-phenylureido)phenyl)-1-ethyl-2-oxo-1,2-dihydro-1,6-naphthyridin-7-yl)-3-hydroxyazetidine-1-carboxamide, 1-(5-(1-ethyl-7-(methylamino)-2-oxo-1,2-dihydro-1,6-naphthyridin-3-yl)-2-fluoro-4-methylphenyl)-3-(3-((4-methyl)piperazin-1-yl)methyl)phenyl)urea, 1-(4-bromo-5-(1-ethyl-7-(methylamino)-2-oxo-1,2-dihydro-1,6-naphthyridin-3-yl)-2-fluorophenyl)-3-(3-((4-methyl)piperazin-1-yl)methyl)phenyl)urea, (R)—N-(3-(2-chloro-4-fluoro-5-(3-phenylureido)phenyl)-1-ethyl-2-oxo-1,2-dihydro-1,6-naphthyridin-7-yl)-3-(dimethylamino)pyrrolidine-1-carboxamide, (S)—N-(3-(2-chloro-4-fluoro-5-(3-phenylureido)phenyl)-1-ethyl-2-oxo-1,2-dihydro-1,6-naphthyridin-7-yl)pyrrolidine-2-carboxamide, N-(3-(2-chloro-4-fluoro-5-(3-phenylureido)phenyl)-1-isopropyl-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(4-fluoro-3-((4-methyl)piperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-fluoro-5-((4-methylpiperazin-1-yl)methyl)phenyl)urea, 1-(5-(1-ethyl-7-(methylamino)-2-oxo-1,2-dihydro-1,6-naphthyridin-3-yl)-2-fluoro-4-methylphenyl)-3-(4-fluoro-3-((4-methyl)piperazin-1-yl)methyl)phenyl)urea, 1-(5-(1-ethyl-7-(methylamino)-2-oxo-1,2-dihydro-1,6-naphthyridin-3-yl)-2,4-difluorophenyl)-3-(4-fluoro-3-((4-methyl)piperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-cyanophenyl)urea, 1-(4-chloro-5-(1-ethyl-7-((3-morpholinopropyl)amino)-2-oxo-1,2-dihydro-1,6-naphthyridin-3-yl)-2-fluorophenyl)-3-phenylurea, 1-(5-(7-amino-1-ethyl-2-oxo-1,2-dihydro-1,6-naphthyridin-3-yl)-2-fluoro-4-methylphenyl)-3-(4-fluoro-3-((4-methylpiperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-((dimethylamino)methyl)-4-fluorophenyl)urea, 1-(4-chloro-5-(1-ethyl-7-(methylamino)-2-oxo-1,2-dihydro-1,6-naphthyridin-3-yl)-2-fluorophenyl)-3-(4-fluoro-3-(morpholinomethyl)phenyl)urea, (S)—N-(3-(2-chloro-4-fluoro-5-(3-phenylureido)phenyl)-1-ethyl-2-oxo-1,2-dihydro-1,6-naphthyridin-7-yl)-3-(dimethylamino)pyrrolidine-1-carboxamide, 1-(4-chloro-5-(1-ethyl-7-(methylamino)-2-oxo-1,2-dihydro-1,6-naphthyridin-3-yl)-2-fluorophenyl)-3-(4-fluoro-3-(pyrrolidin-1-ylmethyl)phenyl)urea, 3-(3-(2-chloro-4-fluoro-5-(3-(3-fluorophenyl)ureido)phenyl)-1-isopropyl-2-oxo-1,2-dihydro-1,6-naphthyridin-7-yl)-1,1-dimethylurea, N-(3-(2-chloro-4-fluoro-5-(3-(3-fluorophenyl)ureido)phenyl)-1-isopropyl-2-oxo-1,2-dihydro-1,6-naphthyridin-7-yl)acetamide, N-(1-ethyl-3-(4-fluoro-5-(3-(4-fluoro-3-((4-methylpiperazin-1-yl)methyl)phenyl)ureido)-2-methylphenyl)-2-oxo-1,2-dihydro-1,6-naphthyridin-7-yl)formamide, 3-(1-ethyl-3-(4-fluoro-2-methyl-5-(3-phenylureido)phenyl)-2-oxo-1,2-dihydro-1,6-naphthyridin-7-yl)-1,1-dimethylurea, N-(3-(2-chloro-4-fluoro-5-(3-phenylureido)phenyl)-1-ethyl-2-oxo-1,2-dihydro-1,6-naphthyridin-7-yl)-3-(dimethylamino)azetidine-1-carboxamide, 3-(3-(2-chloro-4-fluoro-5-(3-phenylureido)phenyl)-1-isopropyl-2-oxo-1,2-dihydro-1,6-naphthyridin-7-yl)-1,1-dimethylurea, 3-(3-(5-(3-(benzo[b]thiophen-3-yl)ureido)-4-fluoro-2-methylphenyl)-1-ethyl-2-oxo-1,2-dihydro-1,6-naphthyridin-7-yl)-1,1-dimethylurea, 3-(3-(2-bromo-4-fluoro-5-(3-phenylureido)phenyl)-1-ethyl-2-oxo-1,2-dihydro-1,6-naphthyridin-7-yl)-1,1-dimethylurea, 3-(1-ethyl-3-(4-fluoro-5-(3-(3-fluorophenyl)ureido)-2-methylphenyl)-2-oxo-1,2-dihydro-1,6-naphthyridin-7-yl)-1,1-dimethylurea, N-(3-(2-chloro-4-fluoro-5-(3-(4-fluoro-3-(morpholinomethyl)phenyl)ureido)phenyl)-1-ethyl-2-oxo-1,2-dihydro-1,6-naphthyridin-7-yl)formamide, 3-(3-(5-(3-(3,5-difluorophenyl)ureido)-4-fluoro-2-methylphenyl)-1-ethyl-2-oxo-1,2-dihydro-1,6-naphthyridin-7-yl)-1,1-dimethylurea, N-(3-(4-fluoro-2-methyl-5-(3-phenylureido)phenyl)-1-isopropyl-2-oxo-1,2-dihydro-1,6-naphthyridin-7-yl)azetidine-1-carboxamide, N-(1-ethyl-3-(4-fluoro-2-methyl-5-(3-phenylureido)phenyl)-2-oxo-1,2-dihydro-1,6-naphthyridin-7-yl)azetidine-1-carboxamide, 1-(5-(1-ethyl-7-((6-methylpyridin-3-yl)amino)-2-oxo-1,2-dihydro-1,6-naphthyridin-3-yl)-2-fluoro-4-methylphenyl)-3-phenylurea, 3-(3-(2,4-difluoro-5-(3-phenylureido)phenyl)-1-ethyl-2-oxo-1,2-dihydro-1,6-naphthyridin-7-yl)-1,1-dimethylurea, 3-(dimethylamino)-N-(1-ethyl-3-(4-fluoro-2-methyl-5-(3-phenylureido)phenyl)-2-oxo-1,2-dihydro-1,6-naphthyridin-7-yl)azetidine-1-carboxamide, 1-(5-(1-ethyl-7-(methylamino)-2-oxo-1,2-dihydro-1,6-naphthyridin-3-yl)-2-fluoro-4-iodophenyl)-3-phenylurea, and 1-(5-(1-ethyl-7-((1-methyl-1H-pyrazol-4-yl)amino)-2-oxo-1,2-dihydro-1,6-naphthyridin-3-yl)-2-fluoro-4-methylphenyl)-3-phenylurea; or a pharmaceutically acceptable salt thereof.

For convenience, certain terms employed in the specification, examples and claims are collected here. Unless defined otherwise, all technical and scientific terms used in this disclosure have the same meanings as commonly understood by one of ordinary skill in the art to which this disclosure belongs. The initial definition provided for a group or term provided in this disclosure applies to that group or term throughout the present disclosure individually or as part of another group, unless otherwise indicated.

The compounds of this disclosure include any and all possible isomers, stereoisomers, enantiomers, diastereomers, tautomers, pharmaceutically acceptable salts, and solvates thereof, as well as crystalline polymorphic forms of the disclosed compounds and any and all possible isomers, stereoisomers, enantiomers, diastereomers, tautomers, pharmaceutically acceptable salts, and solvates thereof. Thus, the terms "compound," "compounds," "test compound," or "test compounds" as used in this disclosure refer to the compounds of this disclosure and any and all possible isomers, stereoisomers, enantiomers, diastereomers, tautomers, pharmaceutically acceptable salts, solvates, and crystalline polymorphs thereof.

DEFINITIONS

The term "alkyl" as used herein refers to straight chain alkyl, wherein alkyl chain length is indicated by a range of numbers, In exemplary embodiments, "alkyl" refers to an alkyl chain as defined above containing 1, 2, 3, 4, 5, or 6 carbons (i.e., C1-C6 alkyl). Examples of an alkyl include, but are not limited to, methyl, ethyl, propyl, butyl, pentyl, and hexyl.

The term "branched alkyl" as used herein refers to an alkyl chain wherein a branching point in the chain exists, and the total number of carbons in the chain is indicated by a range of numbers. In exemplary embodiments, "branched alkyl" refers to an alkyl chain as defined above containing 3, 4, 5, 6, or 7 carbons (i.e., C3-C7 branched alkyl). Examples of branched alkyl include, but are not limited to, iso-propyl, iso-butyl, secondary-butyl, tertiary-butyl, 2-pentyl, 3-pentyl, 2-hexyl, and 3-hexyl.

The term "alkoxy" as used herein refers to —O-(alkyl), wherein "alkyl" is as defined above.

The term "branched alkoxy" as used herein refers to —O-(branched alkyl), wherein "branched alkyl" is as defined above.

The term "alkylene" as used herein refers to an alkyl moiety interposed between two other atoms. In exemplary embodiments, "alkylene" refers to an alkyl moiety as defined above containing 1, 2, or 3 carbons. Examples of an alkylene group include, but are not limited to $—CH_2—$, $—CH_2CH_2—$, and $—CH_2CH_2CH_2—$. In exemplary embodiments, alkylene groups are branched.

The term "alkynyl" as used herein refers to a carbon chain containing one carbon-carbon triple bond. In exemplary embodiments, "alkynyl" refers to a carbon chain as described above containing 2 or 3 carbons (i.e., C2-C3 alkynyl). Examples of an alkynyl group include, but are not limited to, ethyne and propyne.

The term "aryl" as used herein refers to a cyclic hydrocarbon, where the ring is characterized by delocalized π electrons (aromaticity) shared among the ring members, and wherein the number of ring atoms is indicated by a range of numbers. In exemplary embodiments, "aryl" refers to a cyclic hydrocarbon as described above containing 6, 7, 8, 9, or 10 ring atoms (i.e., C6-C10 aryl). Examples of an aryl group include, but are not limited to, benzene, naphthalene, tetralin, indene, and indane.

The term "cycloalkyl" as used herein refers to a monocyclic saturated carbon ring, wherein the number of ring atoms is indicated by a range of numbers. In exemplary embodiments, "cycloalkyl" refers to a carbon ring as defined above containing 3, 4, 5, 6, 7, or 8 ring atoms (i.e., C3-C8 cycloalkyl). Examples of a cycloalkyl group include, but are not limited to, cyclopropyl, cyclobutyl, cyclopentyl, cyclohexyl, cycloheptyl, and cyclooctyl.

The term "halogen" or "halo" as used herein refers to fluorine, chlorine, bromine, and iodine.

The term "heterocycle" or "heterocyclyl" as used herein refers to a cyclic hydrocarbon, wherein at least one of the ring atoms is an O, N, or S, wherein the number of ring atoms is indicated by a range of numbers. Heterocyclyl moieties as defined herein have C or N bonding hands. For example, in some embodiments, a ring N atom from the heterocyclyl is the bonding atom of the heterocylic moiety. In exemplary embodiments, "heterocyclyl" refers to a cyclic hydrocarbon as described above containing 4, 5, or 6 ring atoms (i.e., C4-C6 heterocyclyl). Examples of a heterocycle group include, but are not limited to, aziridine, oxirane, thiirane, azetidine, oxetane, thietane, pyrrolidine, tetrahydrofuran, pyran, thiopyran, thiomorpholine, thiomorpholine S-oxide, thiomorpholine S-dioxide, oxazoline, tetrahydrothiophene, piperidine, tetrahydropyran, thiane, imidazolidine, oxazolidine, thiazolidine, dioxolane, dithiolane, piperazine, oxazine, dithiane, and dioxane.

The term "heteroaryl" as used herein refers to a cyclic hydrocarbon, where at least one of the ring atoms is an O, N, or S, the ring is characterized by delocalized π electrons (aromaticity) shared among the ring members, and wherein the number of ring atoms is indicated by a range of numbers. Heteroaryl moieties as defined herein have C or N bonding hands. For example, in some embodiments, a ring N atom from the heteroaryl is the bonding atom of the heteroaryl moiety. In exemplary embodiments, "heteroaryl" refers to a cyclic hydrocarbon as described above containing 5 or 6 ring atoms (i.e., C5-C6 heteroaryl). Examples of a heteroaryl group include, but are not limited to, pyrrole, furan, thiene, oxazole, thiazole, isoxazole, isothiazole, imidazole, pyrazole, oxadiazole, thiadiazole, triazole, tetrazole, pyridine, pyrimidine, pyrazine, pyridazine, and triazine.

The term "substituted" in connection with a moiety as used herein refers to a further substituent which is attached to the moiety at any acceptable location on the moiety. Unless otherwise indicated, moieties can bond through a carbon, nitrogen, oxygen, sulfur, or any other acceptable atom.

The term "salts" as used herein embraces pharmaceutically acceptable salts commonly used to form alkali metal salts of free acids and to form addition salts of free bases. The nature of the salt is not critical, provided that it is pharmaceutically acceptable. Suitable pharmaceutically acceptable acid addition salts may be prepared from an inorganic acid or from an organic acid. Exemplary pharmaceutical salts are disclosed in Stahl, P. H., Wermuth, C. G., Eds. Handbook of Pharmaceutical Salts: Properties, Selection and Use; Verlag Helvetica Chimica Acta/Wiley-VCH: Zurich, 2002, the contents of which are hereby incorporated by reference in their entirety. Specific non-limiting examples of inorganic acids are hydrochloric, hydrobromic, hydroiodic, nitric, carbonic, sulfuric and phosphoric acid. Appropriate organic acids include, without limitation, aliphatic, cycloaliphatic, aromatic, arylaliphatic, and heterocyclyl containing carboxylic acids and sulfonic acids, for example formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, 3-hydroxybutyric, galactaric or galacturonic acid. Suitable pharmaceutically acceptable salts of free acid-containing compounds disclosed herein include, without limitation, metallic salts and organic salts. Exemplary metallic salts include, but are not limited to, appropriate alkali metal (group Ia) salts, alkaline earth metal (group IIa) salts, and other physiological acceptable metals. Such salts can be made from aluminum, calcium, lithium, magnesium, potassium, sodium and zinc. Exemplary organic salts can be made from primary amines, secondary amines, tertiary amines and quaternary ammonium salts, for example, tromethamine, diethylamine, tetra-N-methylammonium, N,N'-dibenzylethylenediamine, chloroprocaine, choline, diethanolamine, ethylenediamine, meglumine (N-methylglucamine) and procaine.

The terms "administer," "administering, or "administration" as used herein refer to either directly administering a compound or pharmaceutically acceptable salt of the compound or a composition to a subject.

The term "carrier" as used herein encompasses carriers, excipients, and diluents, meaning a material, composition or vehicle, such as a liquid or solid filler, diluent, excipient, solvent or encapsulating material involved in carrying or transporting a pharmaceutical agent from one organ, or portion of the body, to another organ or portion of the body.

The term "disorder" is used in this disclosure to mean, and is used interchangeably with, the terms disease, condition, or illness, unless otherwise indicated.

The terms "effective amount" and "therapeutically effective amount" are used interchangeably in this disclosure and refer to an amount of a compound that, when administered to a subject, is capable of reducing a symptom of a disorder in a subject. The actual amount which comprises the "effective amount" or "therapeutically effective amount" will vary depending on a number of conditions including, but not limited to, the particular disorder being treated, the severity of the disorder, the size and health of the patient, and the route of administration. A skilled medical practitioner can readily determine the appropriate amount using methods known in the medical arts.

The terms "isolated" and "purified" as used herein refer to a component separated from other components of a reaction mixture or a natural source. In certain embodiments, the isolate contains at least about 50%, at least about 55%, at least about 60%, at least about 65%, at least about 70%, at least about 75%, at least about 80%, at least about 85%, at least about 90%, at least about 95%, or at least about 98% of the compound or pharmaceutically acceptable salt of the compound by weight of the isolate.

The phrase "pharmaceutically acceptable" as used herein refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used in this disclosure, the terms "patient" or "subject" include, without limitation, a human or an animal. Exemplary animals include, but are not limited to, mammals such as mouse, rat, guinea pig, dog, cat, horse, cow, pig, monkey, chimpanzee, baboon, or rhesus monkey.

"Therapeutically effective amount" or "effective amount" means the dosage of the compound, or pharmaceutically acceptable salt thereof, or pharmaceutical composition containing an exemplified compound of Formula I, or pharmaceutically acceptable salt thereof, necessary to inhibit c-KIT signaling in a cancer patient, and either destroy the target cancer cells or slow or arrest the progression of the cancer in a patient. The exact dosage required to treat a patient and the length of treatment time will be determined by a physician in view of the stage and severity of the disease as well as the specific needs and response of the individual patient and the particular compound administered. Although expressed as dosage on a per day basis, the dosing regimen may be adjusted to provide a more optimal therapeutic benefit to a patient. In addition to daily dosing, twice-a-day (BID) or thrice-a-day (TID) dosing may be appropriate. BID dosing is currently preferred.

The terms "treatment," "treat," and "treating," are meant to include the full spectrum of intervention for the cancer from which the patient is suffering, such as administration of the active compound to alleviate, slow or reverse one or more of the symptoms and to delay progression of the cancer even if the cancer is not actually eliminated. Treating can be curing, improving, or at least partially ameliorating the disorder. The patient to be treated is a mammal, in particular a human being.

The term "hydrate" as used herein refers to a compound disclosed herein which is associated with water in the molecular form, i.e., in which the H—OH bond is not split, and may be represented, for example, by the formula $R.H_2O$, where R is a compound disclosed herein. A given compound may form more than one hydrate including, for example, monohydrates ($R.H_2O$), dihydrates ($R.2H_2O$), trihydrates ($R.3H_2O$), and the like.

The term "solvate" as used herein refers to a compound disclosed herein which is associated with solvent in the molecular form, i.e., in which the solvent is coordinatively bound, and may be represented, for example, by the formula R.(solvent), where R is a compound disclosed herein. A given compound may form more than one solvate including, for example, monosolvates (R.(solvent)) or polysolvates (R.n(solvent)) wherein n is an integer greater than 1) including, for example, disolvates (R.2(solvent)), trisolvates (R.3 (solvent)), and the like, or hemisolvates, such as, for example, R.n/2(solvent), R.n/3(solvent), R.n/4(solvent) and the like, wherein n is an integer. Solvents herein include mixed solvents, for example, methanol/water, and as such, the solvates may incorporate one or more solvents within the solvate.

The term "acid hydrate" as used herein refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

Structural, chemical and stereochemical definitions are broadly taken from IUPAC recommendations, and more specifically from Glossary of Terms used in Physical Organic Chemistry (IUPAC Recommendations 1994) as summarized by Müller, P. Pure Appl. Chem. 1994, 66, pp. 1077-1184 and Basic Terminology of Stereochemistry (IUPAC Recommendations 1996) as summarized by Moss, G. P. Pure Appl. Chem. 1996, 68, pp. 2193-2222.

Atropisomers are defined as a subclass of conformers which can be isolated as separate chemical species and which arise from restricted rotation about a single bond.

Regioisomers or structural isomers are defined as isomers involving the same atoms in different arrangements.

Enantiomers are defined as one of a pair of molecular entities which are mirror images of each other and non-superimposable.

Diastereomers or diastereoisomers are defined as stereoisomers other than enantiomers. Diastereomers or diastereoisomers are stereoisomers not related as mirror images. Diastereoisomers are characterized by differences in physical properties, and by some differences in chemical behavior towards achiral as well as chiral reagents.

The term "tautomer" as used herein refers to compounds produced by the phenomenon wherein a proton of one atom of a molecule shifts to another atom. See March, Advanced Organic Chemistry: Reactions, Mechanisms and Structures, 4th Ed., John Wiley & Sons, pp. 69-74 (1992). Tautomerism is defined as isomerism of the general form

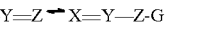

where the isomers (called tautomers) are readily interconvertible; the atoms connecting the groups X, Y and Z are typically any of C, H, O, or S, and G is a group which becomes an electrofuge or nucleofuge during isomerization. The most common case, when the electrofuge is $H^+$, is also known as "prototropy." Tautomers are defined as isomers that arise from tautomerism, independent of whether the isomers are isolable.

The exemplified compounds of the present invention are preferably formulated as a pharmaceutical composition using a pharmaceutically acceptable carrier and administered by a variety of routes. Preferably, such compositions are for oral administration. Such pharmaceutical compositions and processes for preparing them are well known in the art. See, e.g., REMINGTON: THE SCIENCE AND PRACTICE OF PHARMACY (A. Gennaro, et al., eds., 19$^{th}$ ed., Mack Publishing Co., 1995). In a particular embodiment, the pharmaceutical composition comprises 1-(3,3-dimethylbutyl)-3-{2-fluoro-4-methyl-5-[7-methyl-2-(methylamino) pyrido[2,3-d]pyrimidin-6-yl]phenyl}urea, or a pharmaceutically acceptable salt thereof, together with a pharmaceutically acceptable carrier and optionally other therapeutic ingredients particularly for treatment of cancer generally or a specific cancer type.

The exemplified compounds of the present invention are capable of reaction with a number of inorganic and organic acids to form pharmaceutically acceptable acid addition salts. Such pharmaceutically acceptable salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2002); S. M. Berge, et al., "Pharmaceutical Salts," Journal of Pharmaceutical Sciences, Vol. 66, No. 1, January 1977.

The compounds of Formula Ia, or a pharmaceutically acceptable salt thereof, may be prepared by a variety of procedures known in the art, as well as those described below. The specific synthetic steps may be combined in different ways to prepare the Formula Ia compounds, or a pharmaceutically acceptable salt thereof.

The compounds employed as initial starting materials in the synthesis of the compounds of Formula Ia are well known and, to the extent not commercially available, are readily synthesized using specific references provided, by standard procedures commonly employed by those of ordinary skill in the art, or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

ChemDraw version 10 or 12 (CambridgeSoft Corporation, Cambridge, Mass.) was used to name the structures of intermediates and exemplified compounds.

The following abbreviations are used in this disclosure and have the following definitions: "ADP" is adenosine diphosphate, "AIBN" is azobisisobutyronitrile, "ATP" is adenosine triphosphate, "BippyPhos" is 5-(di-tert-butylphosphino)-1',3',5'-triphenyl-1'H-[1,4']bipyrazole, "BrettPhos Palladacycle" is chloro[2-(dicyclohexylphosphino)-3,6-dimethoxy-2'-4'-6'-tri-1-propyl-1,1'-biphenyl][2-(2-aminoethyl)phenyl]palladium(II), "conc." is concentrated, "DBU" is 1,8-diazabicyclo[5.4.0]undec-7-ene, "DCM" is dichloromethane, "DIEA" is N,N-diisopropylethylamine, "DMA" is N,N-dimethylacetamide, "DMAP" is 4-(dimethylamino)pyridine, "DMF" is N,N-dimethylformamide, "DMSO" is dimethylsulfoxide, "DPPA" is diphenylphosphryl azide, "DTT" is dithiothreitol, "ESI" is electrospray ionization, "$Et_2O$" is diethylether, "EtOAc" is ethyl acetate, "EtOH" is ethanol, "GST" is glutathione S-transferase, "h" is hour or hours, "Hex" is hexane, "$IC_{50}$" is half maximal inhibitory concentration, "IPA" refers to isopropyl alcohol, "$KF/Al_2O_3$" is potassium fluoride on alumina, "mCPBA" is 3-chloroperbenzoic acid, "MeCN" is acetonitrile, "MeOH" is methanol, "MHz" is megahertz, "min" is minute or minutes, "MS" is mass spectrometry, "MTBE" is methyl tert-butyl ether, "NADH" is nicotinamide adenine dinucleotide, "NBS" is N-bromosuccinimide, "NMP" is 1-methyl-2-pyrrolidinone, "NMR" is nuclear magnetic resonance, "PBS" is phosphate buffered saline, "Pd/C" is palladium on carbon, "$Pd(OAc)_2$" is palladium(II) acetate, "$Pd_2(dba)_3$" is tris(dibenzylideneacetone)dipalladium(0), "pet ether" is petroleum ether, "prep-HPLC" is preparative high performance liquid chromatography, "prep-TLC" is preparative thin layer chromatography, "RT" is room temperature which is also known as "ambient temp," which will be understood to consist of a range of normal laboratory temperatures ranging from 15-25° C., "satd." is saturated, "t-butyl-X-Phos" is 2-di-tert-butylphosphino-2',4',6'-triisopropylbiphenyl, "TEA" is triethylamine, "TFA" is trifluoroacetic acid, "THF" is tetrahydrofuran, "Tris" is tris(hydroxymethyl)aminomethane, "Xantphos" is 4,5-bis (diphenylphosphino)-9,9-dimethylxanthene, and "X-Phos" is 2-dicyclohexylphosphino-2',4',6'-triisopropylbiphenyl.

General Chemistry

The compounds of Formula Ia (1) are prepared by the general synthetic methods illustrated in the schemes below and the accompanying examples. Suitable reaction conditions for the steps of these schemes are well known in the art and appropriate substitutions of solvents and co-reagents are within the skill of the art. Those skilled in the art will understand that synthetic intermediates may be isolated and/or purified by well known techniques as needed or desired, and that it will be possible to use various intermediates directly in subsequent synthetic steps with little or no purification. Furthermore, those skilled in the art will appreciate that in some instances, the order in which moieties are introduced is not critical. The particular order of steps required to produce the compounds of Formula I is dependent upon the particular compound being synthesized, the starting compound, and the relative liability of the substituted moieties, as is well appreciated by the ordinary skilled chemist. All substituents, unless otherwise indicated, are as defined above.

The compounds of Formula Ia (1) frequently contain —NH moieties in the Z1 position. It will be understood by those skilled in the art that in some instances it may be advantageous to use an amine protecting group during synthesis to temporarily mask one or more —NH moieties. Said protecting group can be removed from any subsequent intermediate leading to the synthesis of compound I, using standard conditions that effect removal of said protecting group, said conditions of which will be familiar to those skilled in the art. When not specified in a scheme, it will be understood by those skilled in the art that the Z1 moiety represented in the schemes below may optionally contain a standard NH-protecting group that can be removed at any opportune time in the synthetic sequence. For example, intermediates wherein Z1 is aminomethyl, may be obtained directly by the introduction of methylamine into a synthetic scheme, or alternately by introduction of a "protected" form of methylamine, for example 1-(4-methoxyphenyl)-N-methylmethanamine to provide intermediates wherein Z1 is 1-(4-methoxyphenyl)-N-methylmethanamino. Even if not specifically drawn, the schemes below implicitly include de-protection of any protected Z1 moiety immediately after introduction, or optionally at any subsequent step of the synthesis.

Scheme 1

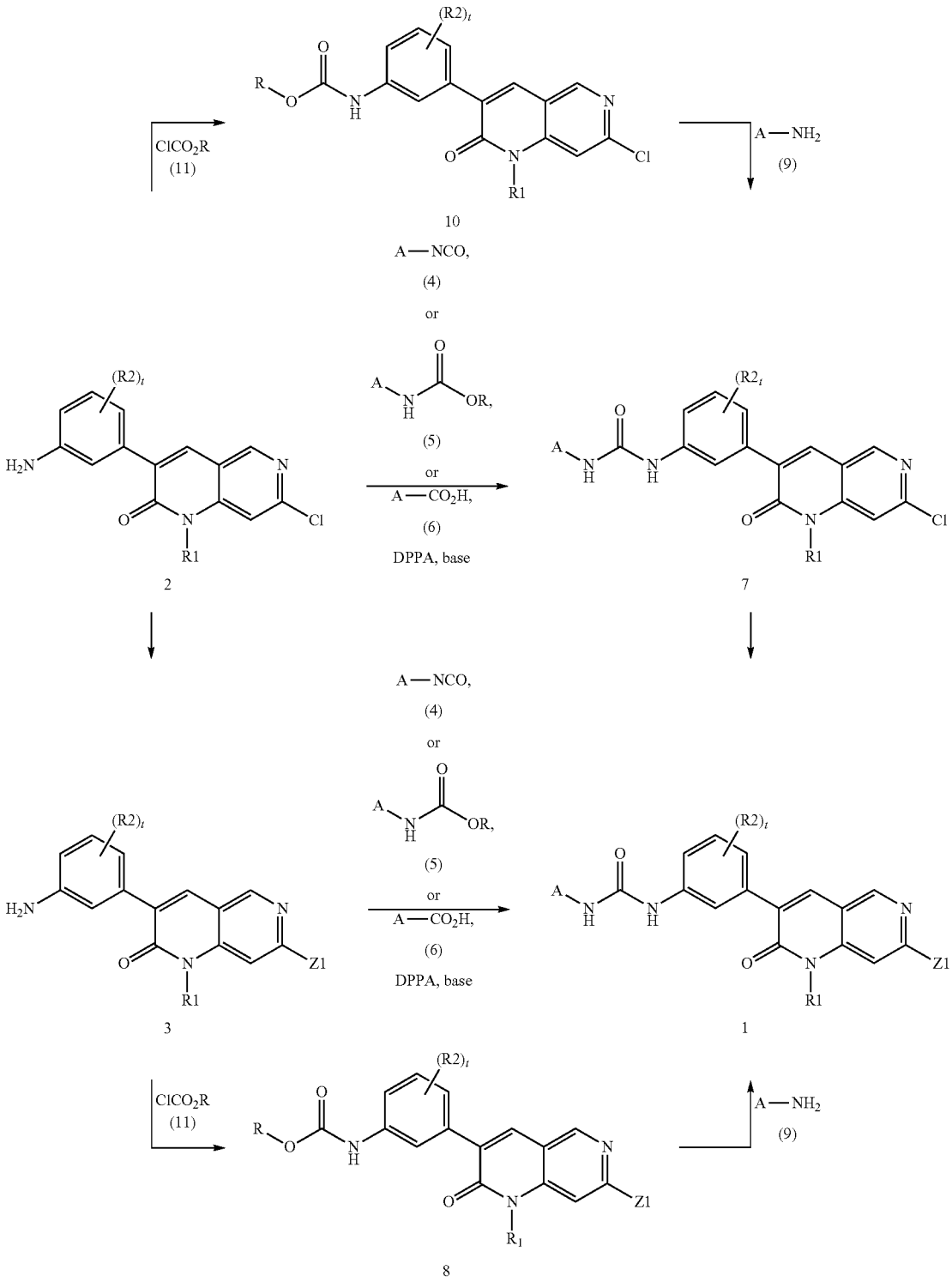

Scheme 1 illustrates general preparations of compounds of formula 1 from 7-chloro-naphthyridinone 2. Conversion of chloride 2 to Z1-substituted intermediate 3 can be accomplished by numerous methods familiar to those skilled in art, the choice of which is dictated by the specific nature of Z1. Further conversion of intermediate 3 to ureas of formula 1 is accomplished by one of three methods. In one embodiment, reaction of 3 with isocyanates of formula 4 provides ureas of formula 1. Many isocyanates (4) are commercially available and those that are not can be readily prepared from the corresponding amines (9) by reaction of said amines with phosgene or an equivalent such as triphosgene or carbonyl diimidazole. Conditions to effect the transformation of 3 to 1 include treating 3 with 4 in an aprotic solvent such as DCM, THF or EtOAc, optionally in the presence of a base, for example pyridine, and optionally while heating said mixtures. In a second embodiment, reaction of 3 with carbamates of formula 5 also affords ureas of formula 1. Conditions to effect the transformation of 3 to 1 include treating 3 with 5 in an aprotic solvent such as 1,4-dioxane, THF or DMSO, in the presence of a base, for example N-methylpyrrolidine, diisopropylethylamine, or triethylamine, and heating the resulting mixture. Suitable carbamates (5) include isopropenyl, 2,2,2,-trichloroethyl and phenyl (or substituted phenyl) carbamates. These carbamates 5 can be readily prepared by reaction with amines 9 with the appropriate chloroformate as familiar to those skilled in the art. In a third embodiment, carboxylic acids of formula 5 can be subjected to a Curtius rearrangement in the presence of amine 3 to provide ureas of formula 1. Conditions to effect said transformation include combining amine 3, carboxylic acid 5 and diphenylphosphoryl azide (DPPA), and a base, for example triethylamine, and heating said mixture in an aprotic solvent, such as 1,4-dioxane, in a temperature range of 50-120° C. to effect the rearrangement.

In addition to these methods, compound 3 can also be converted to 1 via two-step process by first converting 3 to carbamate 8, followed by reaction of carbamate 8 with amine 9. As before, suitable carbamates (8) include isopropenyl, 2,2,2,-trichloroethyl and phenyl (or substituted phenyl) carbamates. These carbamates 8 can be readily prepared by reaction of amine 3 with the appropriate chloroformate 11 (for example, R=2-propenyl, 2,2,2-trichloroethyl, or phenyl). In one embodiment, reaction of amine 3 with isopropenyl chloroformate and sodium bicarbonate in a mixed solvent of EtOAc and water provides carbamate 8 (R=2-propenyl). Further treatment of carbamate 8 with amine 9 in an aprotic solvent such as 1,4-dioxane, THF or DMSO, in the presence of a base, for example N-methylpyrrolidine, diisopropylethylamine, or triethylamine, and heating the resulting mixture provides compounds of formula 1.

By analogy to the conversion of 3 to 1 or 3 to 8, 7-chloro-naphthyridinone 2 can also be converted to urea 7 or carbamate 10, respectively. Further conversion of urea 7 to urea 1 is then accomplished by reaction of 7 with a generic Z1 amine, amide, urea or carbamic acid in the presence of a Palladium catalyst (Buchwald-type coupling), as further illustrated below.

Scheme 2

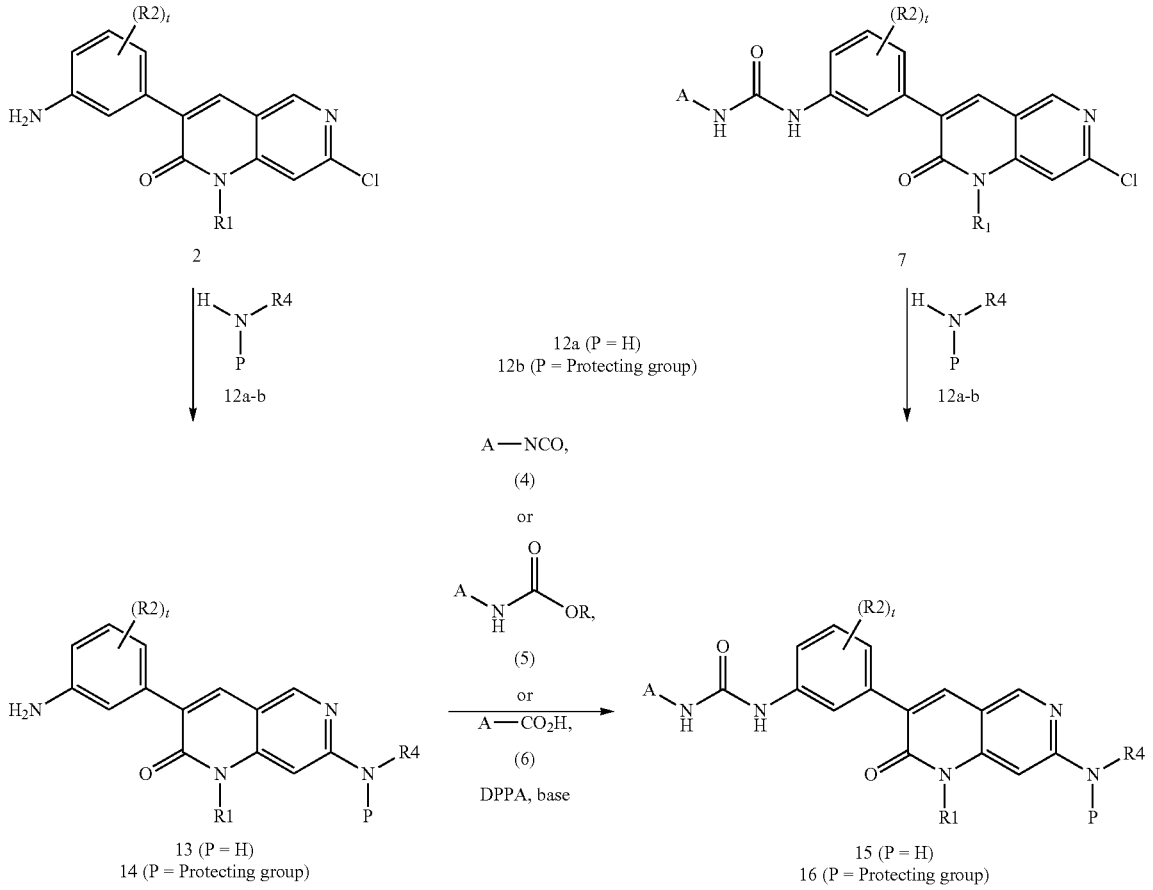

-continued

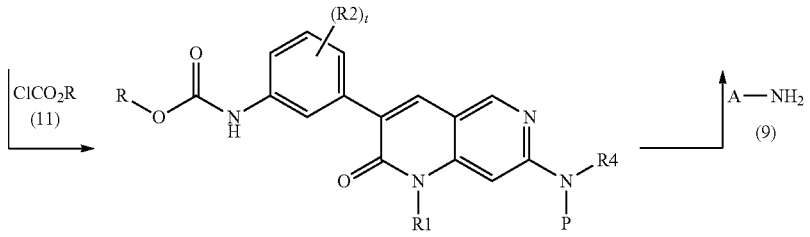

17 (P = H)
18 (P = Protecting group)

Scheme 2 illustrates the preparation of compounds of formula 15, compounds of formula 1 wherein Z1 is —NHR4. In one embodiment, 7-chloro-naphthyridinone 2 is reacted with amine 12a (P=H), or 12b (P is a standard amine protecting group such as 4-methoxybenzyl or tert-butoxycarbonyl) to provide 13 or 14 respectively. Conditions for the conversion of 2 to 13 or 14 include heating an amine of formula 12a or 12b with chloride 2, optionally in the presence of an additional base, for example DBU (1,8-diazabicyclo[5.4.0]undec-7-ene), and optionally in the presence of microwave irradiation. When "P" represents a protecting group, said group of 14 may be removed by suitable conditions familiar to the skilled chemist, for example by treatment with TFA when "P" is 4-methoxybenzyl, to provide 13. Using one of the three methods described for scheme 1, compound 13 or 14 can be converted to ureas 15 or 16, respectively. In the event that "P" represents a protecting group, said group of 16 may be removed by suitable conditions familiar to the skilled chemist to provide 15. Alternately, as described in scheme 1, amines 13 or 14 can be converted to carbamates 17 or 18. Further reaction of these carbamates with amine 9 provides ureas 15 or 16. Finally, ureas 15 or 16 can also be prepared from chloride 7 (scheme 1) by reaction with amine 12a or 12b in the presence of a suitable palladium catalyst, for example the catalyst prepared from $Pd(OAc)_2$ or $Pd_2(dba)_3$ [tris(dibenzylideneacetone)dipalladium] and a ligand such as Xantphos [4,5-bis(diphenylphosphino)-9,9-dimethylxanthene] or BippyPhos [5-(di-tert-butylphosphino)-1',3',5'-triphenyl-1'H-[1,4']bipyrazole] in the presence of a base, for example $K_2CO_3$.

Scheme 3

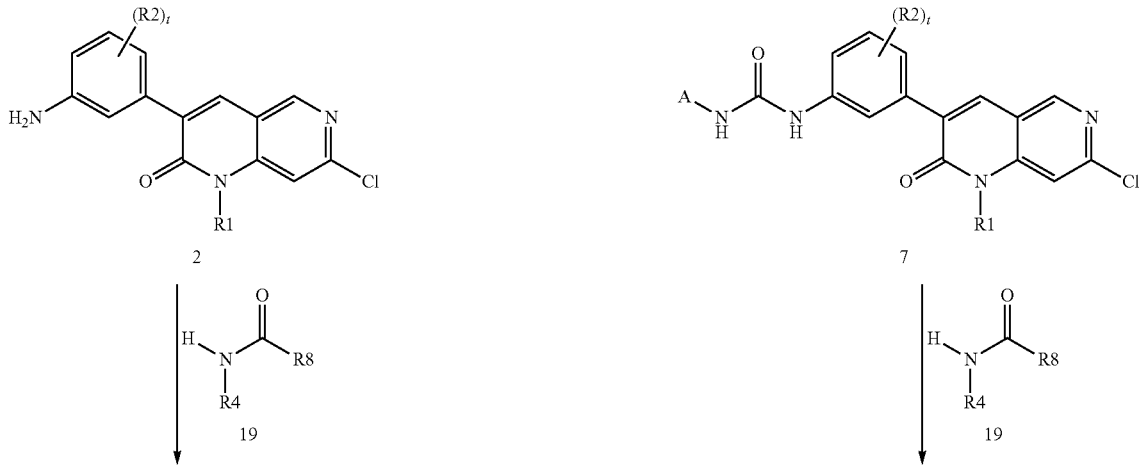

-continued

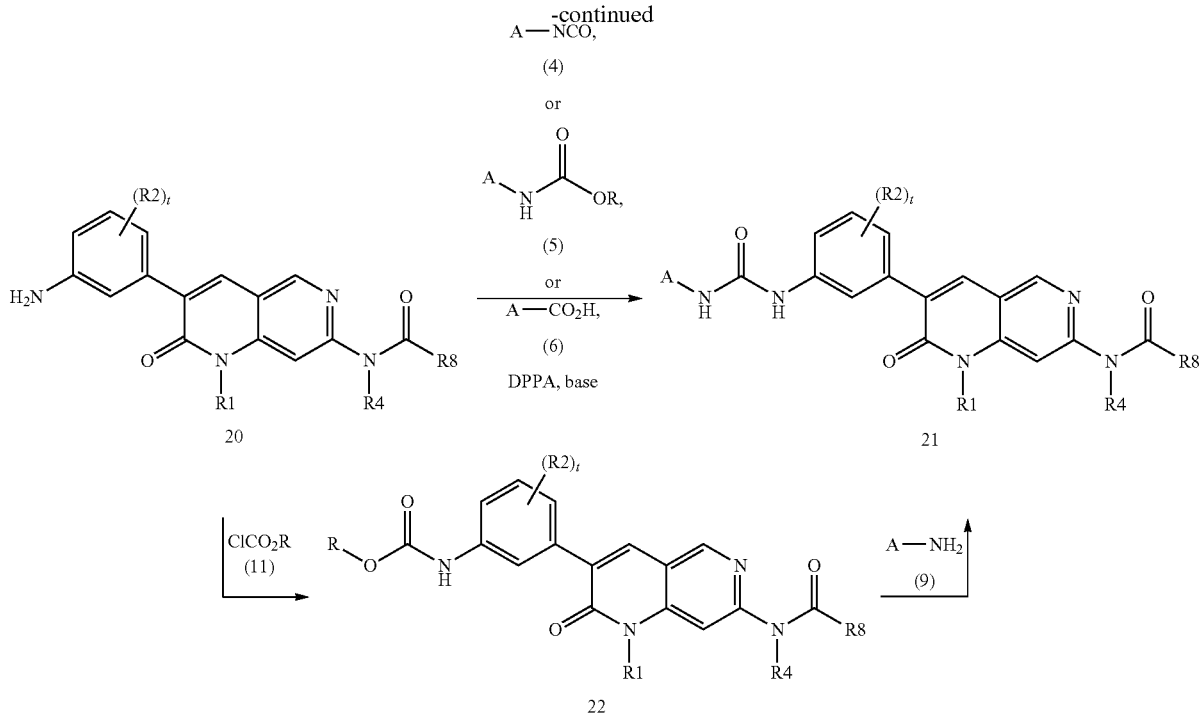

Scheme 3 illustrates the preparation of 21, a compound of formula 1 wherein Z1 is —N(R4)COR8. Using methods described in scheme 2, treatment of chlorides 2 or 7 with generic carbonylamine 19 in the presence of a suitable palladium catalyst provides amides, ureas, or carbamates (according to the R8 moiety) of formula 20 or 21 respectively. Further conversion of 20 to 21 is accomplished, as described above, by treatment of 20 with 4, 5, or 6. Alternately, 20 can first be converted to carbamate 22. As described above, further treatment of 22 with amine 9 provides urea 21.

Scheme 4

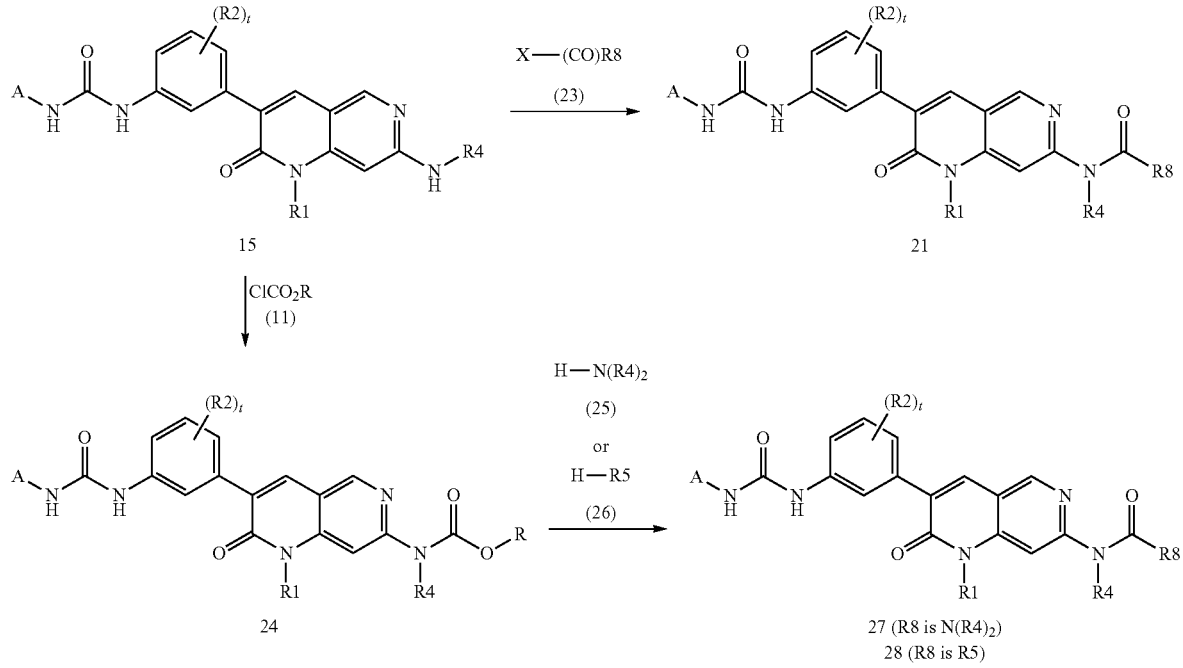

Scheme 4 illustrates alternate preparations of 21, 27 and 28 starting from intermediate 15 (scheme 2). Treatment of 15 with a carbonylation reagent 23 according to conditions familiar to the skilled artisan affords urea 21. The X-moiety of 23 represents a generalized leaving group. Examples of X—(CO)R8 23 include acid chlorides (X=Cl, R8=alkyl) or anhydrides (X=O(CO)R8), and chloroformates (X=Cl, R8=alkoxy). Those skilled in the art will recognize that in the instance in which R8 is —NHR4, isocyanates of formula R4-NCO can be substituted for 23. Additionally, when R8 is an amine, the resulting ureas 27 and 28 can be prepared by reaction of a suitable carbamate 24 with amine 25 or heterocyclic amine 26, respectively. Suitable carbamates include alkyl, isopropenyl, 2,2,2,-trichloroethyl and phenyl (or substituted phenyl) carbamates. These carbamates 24 can be readily prepared by reaction of amine 15 with the appropriate chloroformate 11 (for example, R=2-propenyl, 2,2,2-trichloroethyl, or phenyl).

Scheme 5

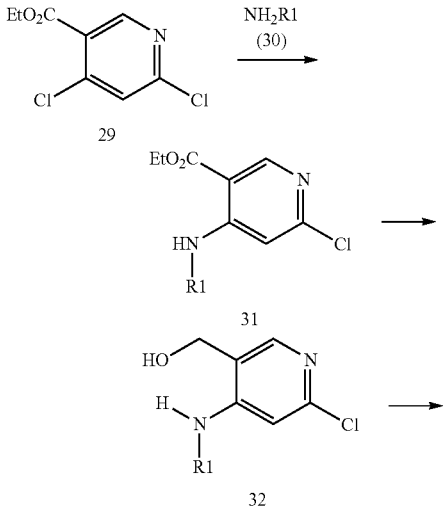

-continued

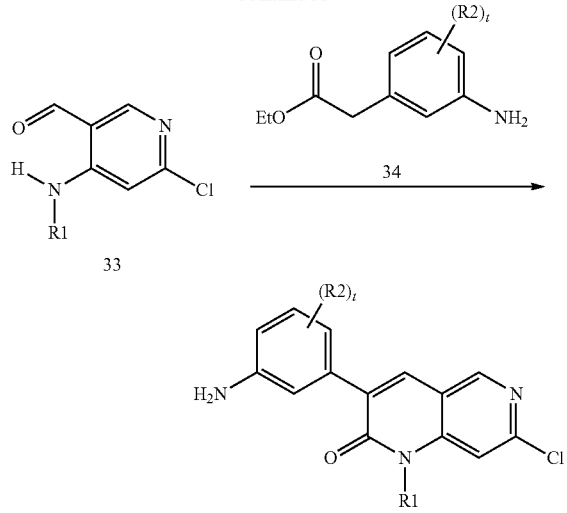

Scheme 5 illustrates the general preparation of 7-chloronaphthyridinones 2. Treatment of ethyl 4,6-dichloronicotinate (29, see: Example C3) with R1-$NH_2$ 30 provides the 4-aminopyridine 31. Conditions for this transformation include polar solvents such as DMF, THF, acetonitrile, dioxane, water or mixtures thereof in the presence of optionally added bases such as triethylamine at temperatures between 0° C. and 100° C. Reduction of 31, for example by treatment with lithium aluminum hydride in THF at temperatures ranging from 0° C. to room temp, provides alcohol 32. Oxidation of 32 with manganese dioxide provides aldehyde 33. Condensation of 33 with phenylacetate 34 provides general intermediate 2. Conditions for this transformation include combining 33 and 34 in DMF or DMAc in the presence of potassium carbonate or cesium carbonate with optional heating (30-150° C.) for a period of time ranging from 1 h to 4 days. Alternate conditions include combining 33, 34 and alumina-supported potassium fluoride in DMAc with stirring and/or optional sonication and/or optional heating (30-150° C.) for a period of 10 min to 48 h.

Scheme 6

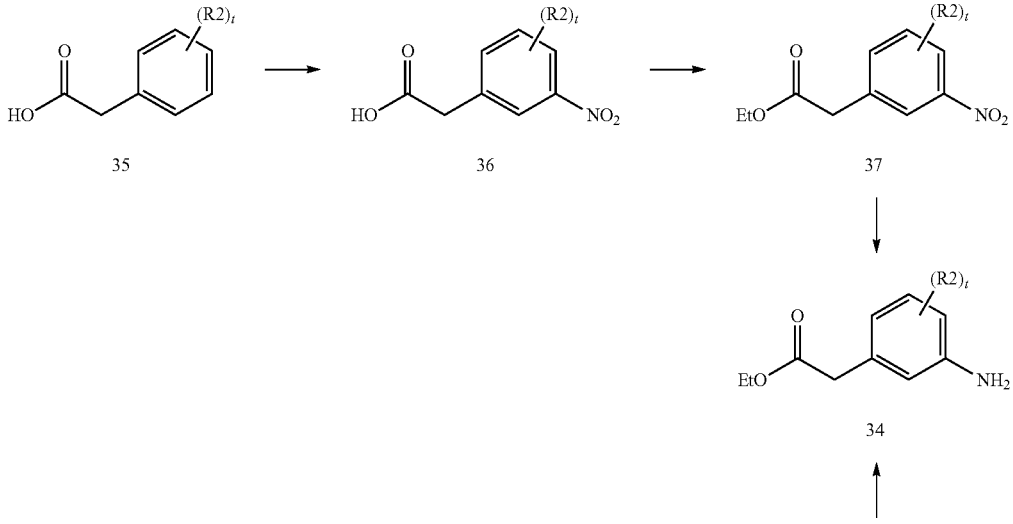

-continued

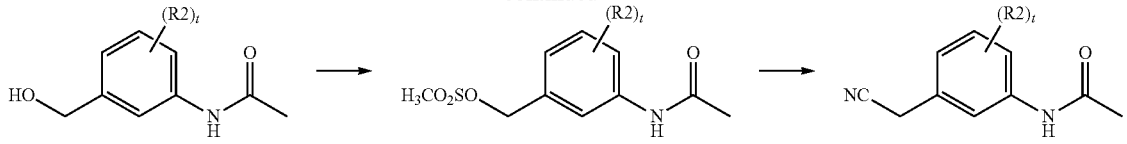

Scheme 6 illustrates a general preparation of ester 34. Nitration of R2-substituted phenylacetic acid 35, for example by treatment with nitric acid and sulfuric acid provides 36. Acid 36 in turn is converted to ethyl ester 37, for example by heating in EtOH in the presence of an acid, such as sulfuric acid. Finally, reduction of the nitro group provides 34. Suitable conditions for this transformation include both hydrogenation over a palladium or nickel catalyst, or reduction with iron or zinc powder in the presence of a proton source, for example ethanolic HCl, acetic acid, or ammonium formate. Those skilled in the art will recognize the existence of numerous alternative preparations of general ethyl phenylacetate 34. One additional method is illustrated by the conversion of benzyl alcohol 38 to mesylate 39, homologation of mesylate 39 with cyanide to benzonitrile 40, and conversion of nitrile 40 to ethyl ester 34 by treatment with EtOH and HCl. Alcohol 38 can be obtained from the reduction of a suitably substituted benzoic acid or aldehyde, a sample preparation of which is disclosed below (Example A45).

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

General Method A:

To a stirring solution of carboxylic acid (0.50 mmol, 1.00 eq) and DPPA (0.75 mmol, 1.50 eq) in 1,4-dioxane (5.0 mL) at RT was added TEA (1.5 mmol, 3.00 eq). After stirring for 30 min at RT, the appropriate amine (0.76 mmol, 1.50 eq) was added and the mixture was heated at 100° C. After 2 h, the completed reaction was cooled to RT, diluted with brine and extracted with EtOAc (2×). The combined organics were washed with 3M HCl (1×), satd. $NaHCO_3$ (2×), and brine (1×), dried ($MgSO_4$), concentrated in vacuo to give the crude product which was purified by flash column chromatography to afford the target urea.

General Method B:

To a stirring suspension of isocyanate (0.51 mmol, 1.00 eq) and pyridine (0.0418 mL, 0.51 mmol, 1.00 eq) in DCM (5 mL) at RT was added the appropriate amine (0.51 mmol, 1.00 eq). A thick suspension gradually formed. After 3.5 h, the solids were collected by filtration, rinsed well with DCM and dried on the filter to afford the desired urea.

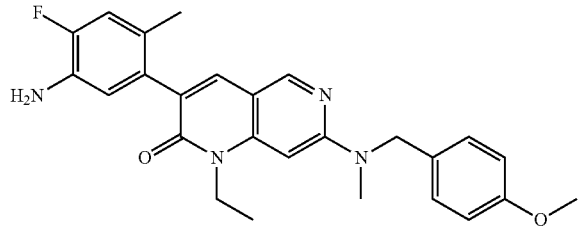

Example A1

Example A6 (1.61 g, 4.85 mmol), 4-methoxy-N-methylbenzylamine (1.10 g, 7.28 mmol) and DBU (1.09 mL, 7.28 mmol) were combined in NMP (20 mL) and heated at 180° C. under Ar overnight. The mixture was cooled to RT, poured into $H_2O$ (200 mL) and the resulting solids were collected by filtration and rinsed well with $H_2O$. The solids were dried on the filter to dampness, dissolved in EtOAc, dried ($MgSO_4$), and evaporated to afford 3-(5-amino-4-fluoro-2-methylphenyl)-1-ethyl-7-((4-methoxybenzyl)(methyl)amino)-1,6-naphthyridin-2(1H)-one (2.06 g) as a brittle brown foam contaminated slightly with EtOAc and NMP. It was used as is in the next reaction.

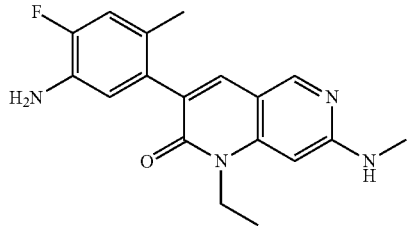

Example A2

Using a procedure analogous to Example A8, Example A1 (2.06 g, 4.61 mmol) was converted to 3-(5-amino-4-fluoro-2-methylphenyl)-1-ethyl-7-(methylamino)-1,6-naphthyridin-2(1H)-one (1.16 g, 73% yield for 2 steps). $^1$H NMR (400 MHz, DMSO-$d_6$): δ 8.36 (s, 1H), 7.58 (s, 1H), 6.94-6.92 (m, 1H), 6.83 (d, J=12.0 Hz, 1H), 6.57 (d, J=9.6 Hz, 1H), 4.87 (br s, 2H), 4.12 (q, J=6.8 Hz, 2H), 2.84 (d, J=4.8 Hz, 3H), 1.94 (s, 3H), 1.19 (t, J=7.2 Hz, 3H); MS (ESI) m/z: 327.2 $[M+H]^+$.

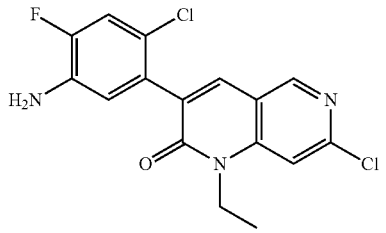

Example A3

A suspension mixture of Example B1 (3.5 g, 0.019 mol), Example C2 (4.4 g, 0.019 mol) and $KF/Al_2O_3$ (10 g) in DMA was stirred at RT for 10 min, poured into water, and extracted with EtOAc (3×). The combined organic phases were washed with brine, dried ($Na_2SO_4$), concentrated in vacuo and purified by silica gel chromatography to give 3-(5-amino-2-chloro-4-fluorophenyl)-7-chloro-1-ethyl-1,6-naphthyridin-2(1H)-one (4 g, 60% yield). $^1$H NMR (400 MHz, DMSO-$d_6$): δ 8.75 (s, 1H), 8.01 (s, 1H), 7.72 (s, 1H), 7.24 (d, J=10.8 Hz, 1H), 6.76 (d, J=9.2 Hz, 1H), 5.40 (s, 2H), 4.26-4.24 (m, 2H), 1.18 (t, J=6.8 Hz, 3H); MS (ESI) m/z: 352.1 $[M+H]^+$.

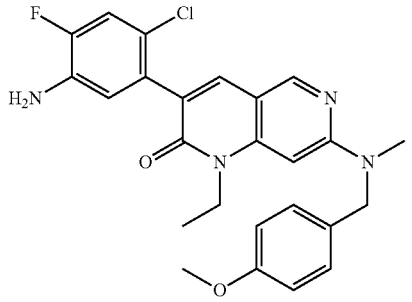

Example A4

A mixture of Example A3 (3 g, 8.5 mmol) and 1-(4-methoxyphenyl)-N-methylmethanamine (20 mL) was charged in a sealed vessel, and then the mixture was heated at 200° C. overnight. Volatiles were removed and the residue was purified by column chromatography to give 7-((4-methoxybenzyl)(methyl)amino)-3-(5-amino-2-chloro-4-fluorophenyl)-1-ethyl-1,6-naphthyridin-2(1H)-one (3 g, 73% yield). $^1$H NMR (400 MHz, DMSO-$d_6$): δ 8.47 (s, 1H), 7.70 (s, 1H), 7.18-7.17 (m, 3H), 6.86 (d, J=8.4 Hz, 2H), 6.73 (d, J=9.6 Hz, 1H), 6.30 (s, 1H), 5.31 (s, 2H), 4.84 (s, 2H), 4.17 (q, J=7.1 Hz, 2H), 3.70 (s, 3H), 3.12 (s, 3H), 1.11 (t, J=7.0 Hz, 3H); MS (ESI) m/z: 467.2 $[M+H]^+$.

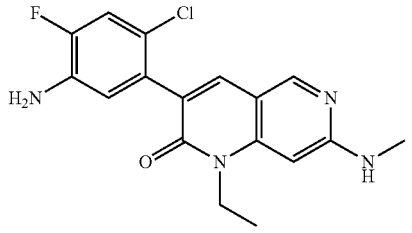

Example A5

To a solution of Example A4 (3 g, 6.2 mmol) in DCM (100 mL) was added TFA (20 mL) at RT, and the resulting mixture was stirred at RT for 6 h. The mixture was extracted with water (2×) and the combined aqueous layers were neutralized with $NH_3H_2O$. The resulting precipitate was collected by filtration and dried to give 3-(5-amino-2-chloro-4-fluorophenyl)-1-ethyl-7-(methylamino)-1,6-naphthyridin-2(1H)-one (1 g, 44% yield). $^1$H NMR (400 MHz, DMSO-$d_6$): δ 8.46 (s, 1H), 7.75 (s, 1H), 7.1 (d, J=11.2 Hz, 1H), 7.0 (m, 1H), 6.73 (d, J=9.6 Hz, 1H), 6.43 (s, 1H), 4.95 (br s, 2H), 4.14 (m, 2H), 2.92 (s, 3H), 1.14 (t, J=6.8 Hz, 3H); MS (ESI) m/z: 347.2 $[M+H]^+$.

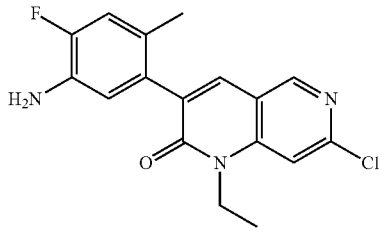

Example A6

Example C1 (1.32 g, 6.25 mmol, 1.00 eq), Example B1 (1.15 g, 6.25 mmol, 1.00 eq) and $KF/Al_2O_3$ (40.00 wt %, 9.08 g, 62.5 mmol, 10.00 eq) were combined in DMA (35 mL) and sonicated for 2 h. The solids were removed via filtration through diatomaceous earth and washed with EtOAc. The combined filtrates were washed with $H_2O$ (3×) and the combined aqueous layers were back-extracted with EtOAc (1×). The combined organics were washed with brine (2×), dried ($MgSO_4$), evaporated and purified by silica gel chromatography (EtOAc/Hex) to afford 3-(5-amino-4-fluoro-2-methylphenyl)-7-chloro-1-ethyl-1,6-naphthyridin-2(1H)-one (1.61 g, 78% yield) as a brittle foam. MS (ESI) m/z: 332.0 $[M+H]^+$.

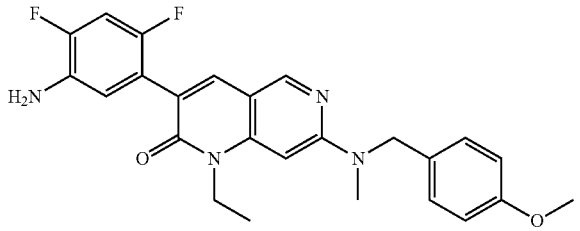

Example A7

A solution of Example A18 (22 g, 65.7 mmol), (4-methoxy-benzyl)-methyl-amine (14.9 g, 98.5 mmol) and DBU (15 g, 98.5 mmol) in NMP (120 mL) was heated at 160° C. for 5 h. The mixture was poured into 200 mL of water while stirring and the resulting solids were collected by filtration, washed with water, dried and then washed with $Et_2O$ to give 3-(5-amino-2,4-difluoro-phenyl)-1-ethyl-7-[(4-methoxy-benzyl)-methyl-amino]-1H-[1,6]naphthyridin-2-one (25 g, yield 85% yield). $^1$H NMR (300 MHz, DMSO-$d_6$): δ 8.51 (s, 1H), 7.80 (s, 1H), 7.19-7.17 (d, J=8.7 Hz, 2H), 7.06 (t, J=10.2 Hz, 1H), 6.90-6.81 (m, 3H), 6.32 (s, 1H), 5.02 (s, 2H), 4.86 (s, 2H), 4.19 (q, J=6.9 Hz, 2H), 3.72 (s, 3H), 3.14 (s, 3H), 1.14 (t, J=6.9 Hz, 3H); MS (ESI): m/z 451.1 $[M+H]^+$.

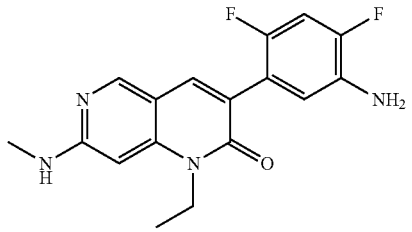

Example A8

TFA (3.64 g, 32.0 mmol) was added to Example A7 (0.48 g, 1.06 mmol) and the mixture was stirred for 90 min at RT. Water (50 mL) was added and the reaction mixture was carefully treated with solid $Na_2CO_3$ until it was weakly basic. The product was extracted with EtOAc (3×), the combined organics were washed with water (1×), then brine and dried ($Na_2SO_4$) to afford crude product which was stirred with DCM (2 mL) for 2 h. The resultant suspension was filtered, washed with DCM and dried to afford 3-(5-amino-2,4-difluorophenyl)-1-ethyl-7-(methylamino)-1,6-naphthyridin-2(1H)-one as an off-white solid. (0.28 g, 60% yield). $^1$H NMR (400 MHz, DMSO-$d_6$): δ 8.39 (s, 1H), 7.73 (s, 1H), 7.06-7.01 (m, 2H), 6.79 (dd, J=10.0, 7.6 Hz, 1H), 6.21 (s, 1H), 4.99 (s, 2H), 4.12 (q, J=7.2 Hz, 2H), 2.84 (d, J=5.2 Hz, 3H), 1.19 (t, J=7.2 Hz, 3H); MS (ESI) m/z: 331.0 $[M+H]^+$.

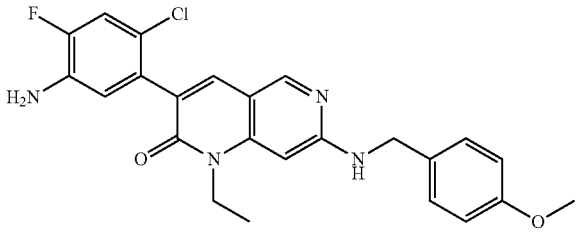

Example A9

A solution of Example A3 (1.90 g, 5.39 mmol), 4-methoxybenzylamine (1.110 g, 8.09 mmol) and DBU (1.232 g, 8.09 mmol) in NMP (15 mL) was heated at 150° C. overnight. After cooling to RT, the mixture was diluted with EtOAc (100 mL) and water (100 mL). The organic phase was washed with water, then brine, dried ($Na_2SO_4$), concentrated in vacuo and purified by reverse phase chromatography (MeCN/$H_2O$ with 0.1% TFA) to give the TFA salt of 7-(4-methoxybenzylamino)-3-(5-amino-2-chloro-4-fluorophenyl)-1-ethyl-1,6-naphthyridin-2(1H)-one. The salt was treated with satd. $NaHCO_3$ (15 mL), allowed to stand and the resulting solid was collected by filtration, washed with water and dried in vacuo to give 7-(4-methoxybenzylamino)-3-(5-amino-2-chloro-4-fluorophenyl)-1-ethyl-1,6-naphthyridin-2(1H)-one (901 mg, 36% yield). $^1$H NMR (400 MHz, DMSO-$d_6$), δ 1.10 (t, 3H), 3.69 (s, 3H), 4.05-4.00 (m, 2H), 4.50-4.45 (s, 2H), 5.30 (s, 2H), 6.28 (s, 1H), 6.71-6.69 (m, 1H), 6.87-6.85 (m, 2H), 7.18-7.15 (m, 1H), 7.28-7.26 (m, 2H), 7.52 (s, 1H), 7.64 (s, 1H), 8.36 (s, 1H); MS (ES-API) m/z: 453.2 $[M+H]^+$.

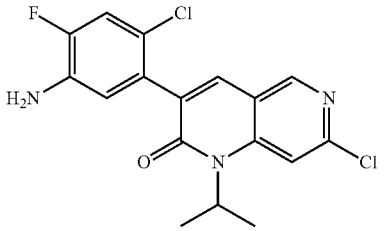

Example A10

Example B2 (0.701 g, 3.53 mmol), Example C2 (0.817 g, 3.53 mmol), and 40% KF on alumina (3.59 g, 24.7 mmol) were combined in DMA (5 mL) and the mixture was sonicated for 2 h. The mixture was diluted with EtOAc (10 mL), the solids removed via filtration through diatomaceous earth and washed with EtOAc. The filtrate was washed with water (2×), and brine, dried ($Na_2SO_4$), concentrated in vacuo and purified by silica gel chromatography (EtOAc\Hex) to afford 3-(5-amino-2-chloro-4-fluorophenyl)-7-chloro-1-isopropyl-1,6-naphthyridin-2(1H)-one (0.99 g, 77% yield) as a white foam. $^1$H NMR (400 MHz, DMSO-$d_6$): δ 8.87 (s, 1H), 8.10 (s, 1H), 7.96 (s, 1H), 7.38 (d, J=11.2 Hz, 1H), 6.89 (d, J=9.2 Hz, 1H), 5.55 (s, 2H), 5.23 (br s, 1H), 1.65 (d, J=6.4 Hz, 6H); MS (ESI) m/z: 366.0 $[M+H]^+$.

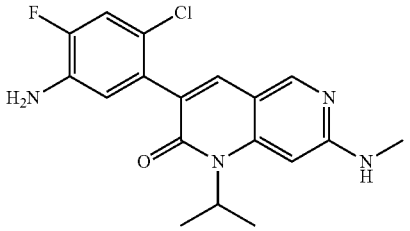

Example A11

(4-Methoxyphenyl)-N-methylmethanamine (0.56 g, 3.75 mmol) and DBU (0.52 mL, 3.75 mmol) were added to a solution of Example A10 (0.98 g, 2.68 mmol) in NMP (10 mL) and the mixture was heated under Ar at 155° C. for 24 h. The mixture was cooled to RT, poured into water (50 mL) and extracted with EtOAc (2×). The combined organics were washed with brine, dried ($Na_2SO_4$), concentrated in vacuo and purified by chromatography (EtOAc\DCM) to afford 7-(4-methoxybenzyl)(methyl)amino)-3-(5-amino-2-chloro-4-fluorophenyl)-1-isopropyl-1,6-naphthyridin-2(1H)-one (0.78 g, 60% yield) as a white foam. MS (ESI) m/z: 481.0 $(M+H^+)$ TFA (5.55 g, 48.7 mmol) was added to 7-((4-methoxybenzyl)(methyl)amino)-3-(5-amino-2-chloro-4-fluorophenyl)-1-isopropyl-1,6-naphthyridin-2(1H)-one (0.78 g, 1.62 mmol) and the reaction was stirred for 90 min at RT. Water (50 mL) was added and the reaction mixture was carefully treated with solid $Na_2CO_3$ until it was faintly basic. The solution was extracted with EtOAc (2×), and the combined organics were washed with brine, dried ($Na_2SO_4$), concentrated in vacuo and purified by silica gel chromatography (MeOH/DCM) to afford 3-(5-amino-2-chloro-4-fluorophenyl)-1-isopropyl-7-(methylamino)-1,6-naphthyridin-2(1H)-one (0.42 g, 72% yield) as a white amorphous solid. $^1$H NMR (400 MHz, DMSO-$d_6$): δ 8.34 (s, 1H), 7.60 (s, 1H), 7.17 (d, J=11.2 Hz, 1H), 6.95 (q, J=4.8 Hz, 1H), 6.71 (d, J=9.6 Hz, 1H), 6.41 (s, 1H), 5.30 (s, 2H), 5.08 (br s, 1H), 2.84 (d, J=4.8 Hz, 3H), 1.49 (d, J=6.8 Hz, 6H); MS (ESI) m/z: 361.0 [M+H]$^+$.

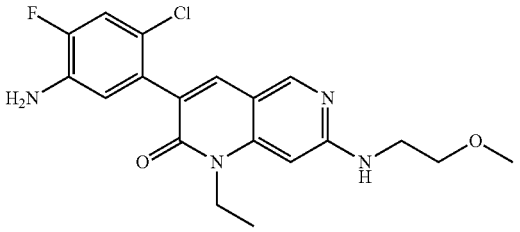

Example A12

A suspension of Example A3 (1.50 g, 4.26 mmol) in 2-methoxyethylamine (3 mL, 34.51 mm) was heated at 120° C. for 12 h. The reaction mixture was diluted with water and extracted with EtOAc (3×). The combined organic layers were washed with brine, dried ($Na_2SO_4$), and concentrated to provide 3-(5-amino-2-chloro-4-fluorophenyl)-1-ethyl-7-(2-methoxyethylamino)-1,6-naphthyridin-2(1H)-one (1.56 g, 94% yield) as a white solid. $^1$H NMR (400 MHz, DMSO-$d_6$): δ 8.36 (s, 1H), 7.65 (s, 1H), 7.18 (d, J=11 Hz, 1H), 7.03 (m, 1H), 6.72 (d, J=9.5 Hz, 1H), 6.38 (s, 1H), 5.30 (s, 2H), 4.07 (m, 2H), 3.47 (m, 4H), 3.25 (s, 3H), 1.20 (s, 3H); MS (ESI) m/z: 391.1 [M+H]$^+$.

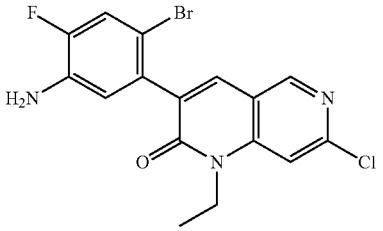

Example A13

A mixture of Example C5 (2.191 g, 7.94 mmol), Example B1 (1.538 g, 8.33 mmol) and KF on alumina (40 wt %) (9.22 g, 63.5 mmol) in DMA (40 mL) was sonicated for 2 h. The mixture was filtered through a shallow bed of silica gel and rinsed well with EtOAc. The filtrate was washed with satd. $NaHCO_3$ (1×), 5% LiCl (2×), then brine (1×), dried ($MgSO_4$), and concentrated to dryness to afford 3-(5-amino-2-bromo-4-fluorophenyl)-7-chloro-1-ethyl-1,6-naphthyridin-2(1H)-one (2.793 g, 89% yield) as a brown solid. $^1$H NMR (400 MHz, DMSO-$d_6$): δ 8.77 (s, 1H), 8.00 (s, 1H), 7.74 (s, 1H), 7.37 (d, 1H), 6.77 (d, 1H), 5.45 (s, 2H), 4.27 (q, 2H), 1.20 (t, 3H); MS (ESI) m/z: 398.0 [M+H]$^+$.

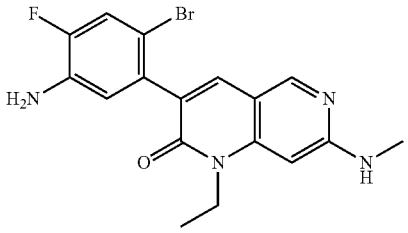

Example A14

A suspension of Example A13 (1.50 g, 3.78 mmol) in dioxane (15 mL) was treated with methylamine (40% in water) (26.4 mL, 303 mmol) in a pressure tube and heated to 100° C. overnight. The mixture was cooled to RT, treated with a large amount of brine, then diluted with EtOAc until all of the solids dissolved. The layers were separated, the aqueous layer extracted with additional EtOAc (1×) and the combined organics were washed with satd. $NaHCO_3$ (1×), dried ($MgSO_4$) and concentrated to dryness. The resulting solid was suspended in MeCN/$H_2O$, frozen and lyophilized to afford 3-(5-amino-2-bromo-4-fluorophenyl)-1-ethyl-7-(methylamino)-1,6-naphthyridin-2(1H)-one (1.32 g, 89% yield) as a light brown solid. $^1$H NMR (400 MHz, DMSO-$d_6$): δ 8.37 (s, 1H), 7.62 (s, 1H), 7.30 (d, 1H), 6.99 (q, 1H), 6.73 (d, 1H), 6.21 (s, 1H), 5.33 (s, 2H), 4.11 (q, 2H), 2.84 (d, 3H), 1.19 (t, 3H); MS (ESI) m/z: 393.0 [M+H]$^+$.

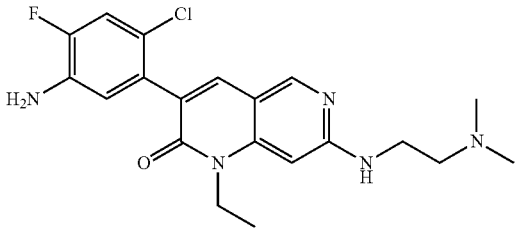

Example A15

To a solution of Example A3 (1.00 g, 2.84 mmol) in DMF (10 mL) was added N,N-dimethylethanediamine (0.250 g, 2.84 mmol) and the resulting reaction mixture was heated at 100° C. for 36 h. The reaction mixture was diluted with water and extracted with EtOAc (3×). The combined organic layers were washed with brine, dried ($MgSO_4$), and the solvent evaporated. The residue was crystallized from IPA to provide 3-(5-amino-2-chloro-4-fluorophenyl)-7-(2-(dimethylamino)ethylamino)-1-ethyl-1,6-naphthyridin-2(1H)-one (0.98 g, 85% yield) as a white solid. $^1$H NMR (400 MHz, DMSO-$d_6$): δ 8.36 (s, 1H), 7.64 (s, 1H), 7.17 (d, J=11 Hz, 1H), 6.84 (m, 1H), 6.72 (d, J=9 Hz, 1H), 6.37 (s, 1H), 5.30 (s, 2H), 4.08 (m, 2H), 3.40 (m, 2H), 2.41 (t, J=6 Hz, 2H), 2.20 (s, 6H), 1.18 (t, J=6 Hz, 3H); MS (ESI) m/z: 404.2 $[M+H]^+$.

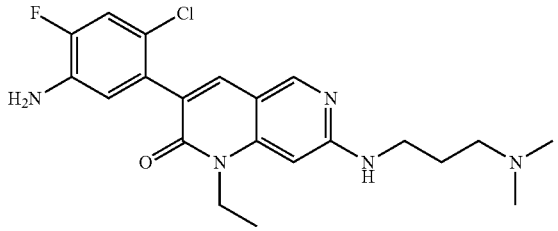

Example A16

To a solution of Example A3 (1.00 g, 2.84 mmol) in DMF (10 mL) was added N,N-dimethylpropaneamine (0.870 g, 8.52 mmol) and the resulting reaction mixture was heated at 100° C. for 36 h. The mixture was diluted with water and extracted with EtOAc (3×). The combined organic layers were washed with brine, dried ($MgSO_4$), and the solvent evaporated to provide 3-(5-amino-2-chloro-4-fluorophenyl)-7-(3-(dimethylamino)propylamino)-1-ethyl-1,6-naphthyridin-2(1H)-one (1.10 g, 93% yield) as an orange foam. $^1$H NMR (400 MHz, DMSO-$d_6$): δ 8.36 (s, 1H), 7.64 (s, 1H), 7.20 (d, J=11 Hz, 1H), 7.03 (m, 1H), 6.76 (d, J=9 Hz, 1H), 6.27 (s, 1H), 5.30 (s, 2H), 4.08 (m, 2H), 3.30 (m, 2H), 2.26 (t, J=6 Hz, 2H), 2.05 (m, 6H), 1.66 (m, 2H), 1.18 (t, J=6 Hz, 3H); MS (ESI) m/z: 418.2.2 $[M+H]^+$.

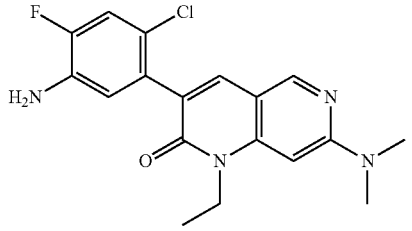

Example A17

A solution of Example A3 (0.25 g, 0.710 mmol) in THF (6 mL) was treated with dimethylamine (2M in THF, 2.84 mL, 5.68 mmol) and heated at 80° C. overnight. Additional dimethylamine (2M in THF, 5.68 mL, 11.36 mmol) was added over 3 days and the reaction mixture was heated at 80° C. The mixture was partitioned between DCM and satd. $NaHCO_3$ and extracted with DCM (3×). The combined organic extracts were dried ($MgSO_4$) and evaporated. The crude product was purified by silica gel chromatography (EtOAc/Hex) to give 3-(5-amino-2-chloro-4-fluorophenyl)-7-(dimethylamino)-1-ethyl-1,6-naphthyridin-2(1H)-one (0.21 g, 82% yield). $^1$H NMR (400 MHz, DMSO-$d_6$): δ 8.45 (s, 1H), 7.69 (s, 1H), 7.18 (d, 1H), 6.73 (d, 1H), 6.29 (s, 1H), 5.31 (br s, 2H), 4.21 (q, 2H), 3.14 (s, 6H), 1.18 (t, 3H); MS (ESI) m/z: 361.1 $[M+H]^+$.

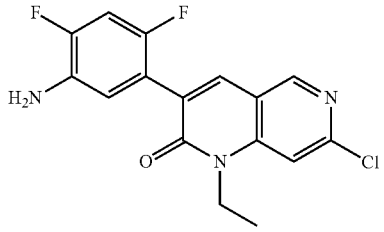

Example A18

To a solution of Example B1 (19 g, 103.3 mmol) and Example C4 (20.3 g, 103.3 mmol) in DMF (150 mL) was added $K_2CO_3$ (28.5 g, 206.6 mmol), and the reaction mixture was heated at 90° C. overnight. The mixture was poured into water (300 mL), stirred at RT for 10 min and the resulting precipitate collected by filtration, washed with water and dried to give 3-(5-amino-2,4-difluoro-phenyl)-7-chloro-1-ethyl-1H-[1,6]naphthyridin-2-one (22 g, 65% yield). $^1$H NMR (400 MHz, DMSO-$d_6$): δ 8.76 (s, 1H), 8.07 (s, 1H), 7.71 (s, 1H), 7.11 (t, J=10.4 Hz, 1H), 8.84 (dd, J=10.0, 7.6 Hz, 1H), 5.09 (s, 2H), 4.25 (q, J=6.8 Hz, 2H), 1.19 (t, J=6.8 Hz, 3H).

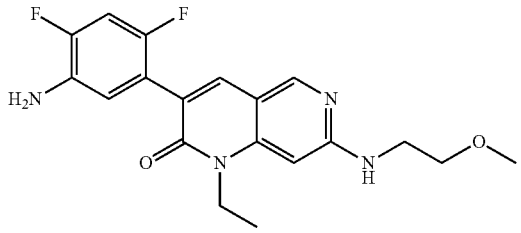

Example A19

To a suspension of Example A18 (0.180 g, 0.536 mmol) in dioxane (5 mL) was added 2-methoxyethylamine (0.462 mL, 5.36 mmol) and the mixture was heated at 100° C. for 20 h. Solvent from the reaction mixture was evaporated and the residue was stirred with water (50 mL). The solids were filtered, washed and dried to provide 3-(5-amino-2,4-difluorophenyl)-1-ethyl-7-(2-methoxyethylamino)-1,6-naphthyridin-2(1H)-one (0.185 g, 92% yield) as a white solid. MS (ESI) m/z: 375.1 $[M+H]^+$.

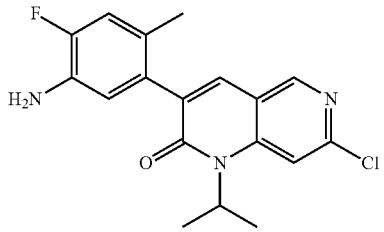

Example A20

A mixture of Example B2 (5 g, 25 mmol), Example C1 (5.3 g, 25 mmol) and $Cs_2CO_3$ (21.4 g, 66 mmol) in DMF (50 mL) was heated at 100° C. overnight. The solid was removed by filtration and the filter cake was washed with DMF. The organics were concentrated and the residue was purified by silica gel chromatography (EtOAc/pet ether) to give 3-(5-amino-4-fluoro-2-methylphenyl)-7-chloro-1-isopropyl-1,6-naphthyridin-2(1H)-one (1.7 g, 20% yield). $^1$H NMR (400 MHz, DMSO-$d_6$): δ 8.69 (s, 1H), 7.84 (s, 1H), 7.78 (s, 1H), 6.87-6.84 (d, J=12.4 Hz, 1H), 6.61-6.58 (d, J=9.6 Hz, 1H), 5.11-5.08 (br s, 1H), 4.93 (s, 2H), 1.93 (s, 3H), 1.50-1.48 (d, J=6.8 Hz, 6H); MS (ESI) m/z: 346 [M+H]

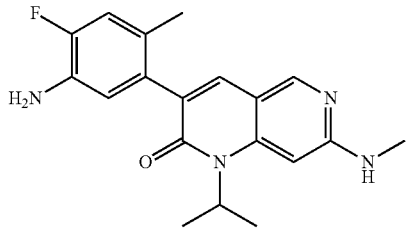

Example A21

A mixture of Example A20 and (4-methoxy-benzyl)-methyl-amine (4.5 g, 30 mmol) was heated to 180° C. under a $N_2$ atmosphere for 8 h. The excess (4-methoxy-benzyl)-methyl-amine was removed under reduced pressure to give the crude product, which was suspended in 50% aqueous acetic acid and stirred for 30 min. The mixture was extracted with EtOAc (3×) and the combined organics were washed with brine, dried ($MgSO_4$) and concentrated to give 7-((4-methoxybenzyl)(methyl)amino)-3-(5-amino-4-fluoro-2-methylphenyl)-1-isopropyl-1,6-naphthyridin-2(1H)-one (1.0 g, 76.9% yield), which was used in the next step without further purification.

To a solution of 7-((4-methoxybenzyl)(methyl)amino)-3-(5-amino-4-fluoro-2-methylphenyl)-1-isopropyl-1,6-naphthyridin-2(1H)-one (1.0 g, 2.2 mmol) in DCM (10 mL) was added TFA (3 mL) at RT. The resulting mixture was stirred at RT for 6 h, then washed with $H_2O$ (6×). The combined aqueous layers were neutralized with $NH_3H_2O$, extracted with DCM (3×) and the combined organic layers were washed with brine, dried ($Na_2SO_4$), filtered and concentrated to give 3-(5-amino-4-fluoro-2-methylphenyl)-1-isopropyl-7-(methylamino)-1,6-naphthyridin-2(1H)-one (0.5 g, 66.8% yield). $^1$H NMR (400 MHz, DMSO-$d_6$): δ 8.41 (s, 1H), 7.60 (s, 1H), 6.95 (m, 1H), 6.90 (d, J=12.4 Hz, 1H), 6.65 (d, J=9.2 Hz, 1H), 6.50 (s, 1H), 5.21 (br s, 1H), 4.95 (s, 2H), 2.92 (d, J=4.8 Hz, 3H), 2.02 (s, 3H), 1.58 (d, J=6.8 Hz, 6H); MS (ESI) m/z: 341.2[M+H]$^+$.

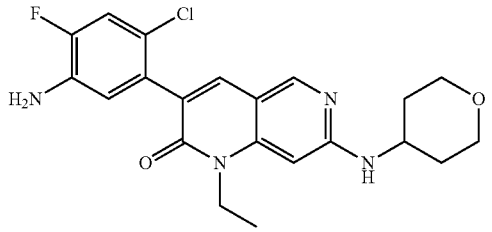

Example A22

Example A3 (0.50 g, 1.420 mmol), 4-aminotetrahydropyran (0.431 g, 4.26 mmol) and TEA (0.394 mL, 2.84 mmol) were combined in NMP (5 mL) and the mixture was heated at 180° C. under microwave irradiation for 6 h. Additional 4-aminotetrahydropyran (0.2 mL) was added and the mixture was heated at 180° C. under microwave irradiation for 3 h more. The mixture was quenched with water and extracted with EtOAc (3×). The organics were washed with 5% LiCl, then brine, dried ($Na_2SO_4$), concentrated to dryness and purified by silica gel column chromatography (MeOH/DCM) to obtain 3-(5-amino-2-chloro-4-fluorophenyl)-1-ethyl-7-(tetrahydro-2H-pyran-4-ylamino)-1,6-naphthyridin-2(1H)-one (0.31 g, 52% yield). MS (ESI) m/z: 417.1 [M+H]$^+$.

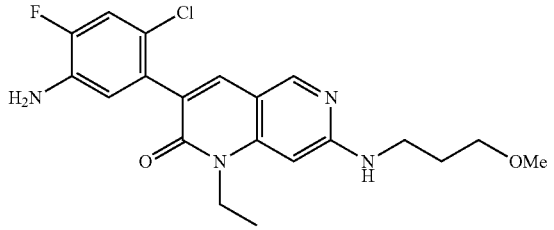

Example A23

Example A3 (0.4 g, 1.14 mmol) and 3-methoxypropylamine (0.5 g, 5.69 mmol) were combined in NMP (5 mL) and heated at 120° C. for 24 h. The mixture was poured in water, extracted with EtOAc (2×) and the combined organics were washed with brine, dried ($Na_2SO_4$), concentrated to dryness and purified by silica gel chromatography (MeOH/DCM) to afford 3-(5-amino-2-chloro-4-fluorophenyl)-1-ethyl-7-(3-methoxypropylamino)-1,6-naphthyridin-2(1H)-one (409 mg, 89% yield) as an orange solid. $^1$H NMR (400 MHz, DMSO-$d_6$): δ 8.36 (s, 1H), 7.64 (s, 1H), 7.18 (d, J=11.2 Hz, 1H), 7.04 (t, J=5.6 Hz, 1H), 7.20 (d, J=8.8 Hz, 1H), 6.27 (s, 1H), 5.30 (s, 2H), 4.09 (q, J=6.8 Hz, 2H), 3.41-3.30 (m, 4H), 3.23 (s, 3H), 1.80-1.73 (m, 2H), 1.18 (t, J=6.8 Hz, 3H); MS (ESI) m/z: 405.1 [M+H]$^+$.

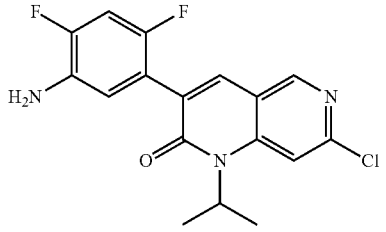

Example A24

A solution of Example C4 (5 g, 23.2 mmol), Example B2 (4.6 g, 23.2 mmol) and $Cs_2CO_3$ (15 g, 2 eq) in DMF were heated at 80° C. overnight. The mixture was poured into water and extracted with EtOAc. The combined organic layers were washed with brine, dried ($Na_2SO_4$), concentrated to dryness and purified by silica gel chromatography to give 3-(5-amino-2,4-difluorophenyl)-7-chloro-1-isopropyl-1,6-naphthyridin-2(1H)-one (4 g, 49% yield). MS (ESI) m/z: 350.2 [M+H]$^+$.

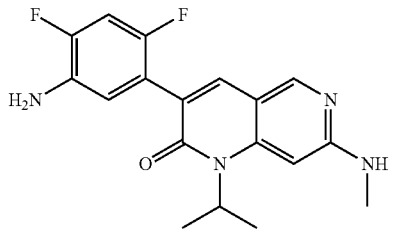

Example A25

A mixture of Example A24 (4 g, 11.5 mmol) and methylamine (30 mL) was heated to 100° C. in a sealed vessel for 12 h, then cooled to RT. The mixture was concentrated and residue was washed with EtOAc to give 3-(5-amino-2,4-difluorophenyl)-1-isopropyl-7-(methylamino)-1,6-naphthyridin-2(1H)-one (3.5 g, 90% yield). $^1$H NMR (400 MHz, DMSO-$d_6$), δ 8.40 (s, 1H), 7.70 (s, 1H), 7.05 (t, J=10 Hz, 1H), 6.98 (m, 1H), 6.81 (t, J=7.6 Hz, 1H), 6.45 (s, 1H), 5.10 (br s, 1H), 5.06 (s, 2H), 2.87 (d, J=4.8 Hz, 3H), 1.53 (d, J=6.8 Hz, 6H); MS (ESI) m/z: 345.1 [M+H]$^+$.

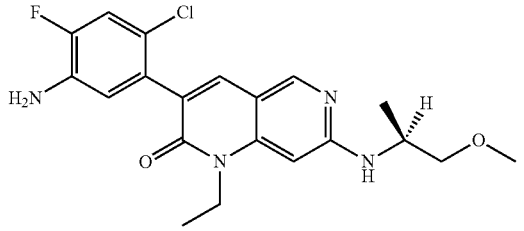

Example A26

Example A3 (0.150 g, 0.426 mmol) and (S)-(+)-1-methoxy-2-propylamine (0.228 g, 2.56 mmol) were combined in NMP (4 mL) and heated in the microwave at 180° C. for 18 h. After cooling, the reaction was diluted with satd. LiCl and extracted with EtOAc (2×). The combined organics were washed successively with satd. LiCl (1×), $H_2O$ (1×), and brine (1×), dried ($MgSO_4$), filtered and evaporated. The crude product was purified by silica gel chromatography (EtOAc/Hex) to afford (S)-3-(5-amino-2-chloro-4-fluorophenyl)-1-ethyl-7-(1-methoxypropan-2-ylamino)-1,6-naphthyridin-2(1H)-one (0.13 g, 75% yield). MS (ESI) m/z: 405.1 (M+H$^+$), 407.1 (M+2+H$^+$).

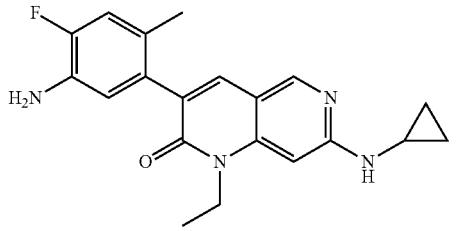

Example A27

A solution of Example A6 (500 mg, 1.507 mmol) and cyclopropylamine (860 mg, 15.07 mmol) in EtOH (15 mL) was heated at 100° C. in a sealed vessel. After 20 h the reaction mixture was treated with additional cyclopropylamine (860 mg, 15.07 mmol) and catalytic DMAP (10 mg) and heated at 100° C. for 23 h, then 115° C. for 10 days. The mixture was cooled to RT, concentrated to dryness and the resulting residue dissolved in EtOAc (30 mL) and washed successively with water (30 mL), satd. $NaHCO_3$ (30 mL) and brine (30 mL). The organic phase was dried over $Na_2SO_4$, concentrated to dryness and purified by reverse phase chromatography (MeCN/$H_2O$ with 0.1% TFA). The aqueous solution was treated with satd. $NaHCO_3$ (5 mL) and allowed to stand. A solid formed which was collected by filtration to yield 3-(5-amino-4-fluoro-2-methylphenyl)-7-(cyclopropylamino)-1-ethyl-1,6-naphthyridin-2(1H)-one (124 mg, 23% yield). $^1$H NMR (400 MHz, DMSO-$d_6$): δ 8.36 (s, 1H), 7.60 (s, 1H), 7.28 (s, 1H), 6.83 (d, 1H), 6.58 (d, 1H), 6.38 (s, 1H), 4.87 (s, 2H), 4.18-4.12 (m, 2H), 2.59 (m, 1H), 1.94 (s, 3H), 1.21 (t, 3H), 0.75 (m, 2H), 0.47 (m, 2H); MS (ES-API) m/z: 353.1 [M+H]$^+$.

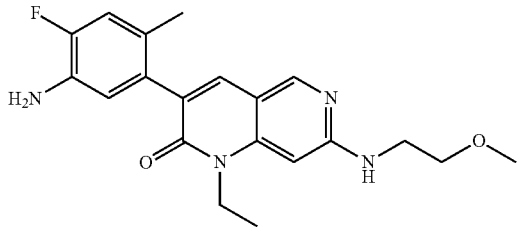

Example A28

To a suspension of Example A6 (0.500 g, 1.507 mmol) in dioxane (10 mL) was added 2-methoxyethylamine (2 mL, 23.22 mmol) and the mixture was heated at 100° C. for 40 h. Solvent from the reaction mixture was evaporated and the residue was diluted with water (50 mL) and extracted with EtOAc (3×). The combined organic layers were washed with brine, dried, and the solvent evaporated to provide 3-(5-amino-4-fluoro-2-methylphenyl)-1-ethyl-7-(2-methoxyethylamino)-1,6-naphthyridin-2(1H)-one (405 mg, 73% yield) as an orange-yellow solid. MS (ESI) m/z: 371.2 [M+H]$^+$.

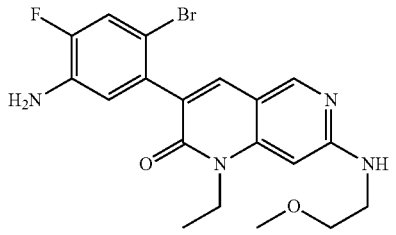

Example A29

A solution of Example A13 (0.500 g, 1.261 mmol) and 2-methoxy ethylamine (0.947 g, 12.61 mmol) in NMP (5 mL) was heated at 120° C. After 4 h the reaction mixture was cooled and partitioned between EtOAc and water. The organic layer was separated and the aqueous layer was extracted with additional EtOAc (1×). The combined organic layers were washed with brine, dried and the solvent evaporated to provide 3-(5-amino-2-bromo-4-fluorophenyl)-1-ethyl-7-(2-methoxyethylamino)-1,6-naphthyridin-2(1H)-one (0.486 g, 89% yield) as brownish mass. $^1$H NMR (400 MHz, DMSO-$d_6$): δ 8.37 (s, 1H), 7.62 (s, 1H), 7.30 (d, J=12 Hz, 1H), 7.04 (m, 1H), 6.72 (d, J=10 Hz, 1H) 6.39 (s, 1H), 5.33 (s, 2H), 4.08 (m, 2H), 3.50 (m, 4H), 3.27 (s, 3H), 1.18 (t, J=6 Hz, 3H); MS (ESI) m/z: 435.1/437.1 $[M+H]^+$.

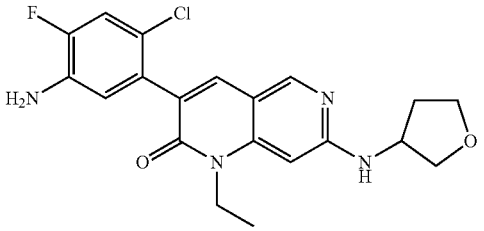

Example A30

To a solution of Example A3 (2.0 g, 5.7 mmol) in NMP (10 mL) was added tetrahydro-furan-3-ylamine (1.5 g, 17.2 mmol) and DBU (1.7 g, 11.4 mmol). Nitrogen was bubbled through the mixture for 5 min and then it was heated in the microwave at 180° C. for 1 h. The reaction mixture was cooled to RT, poured into water and extracted with EtOAc (3×). The combined organics were washed with brine, dried over $Na_2SO_4$, concentrated under reduced pressure and purified by silica gel chromatography to give 3-(5-amino-2-chloro-4-fluorophenyl)-1-ethyl-7-(tetrahydrofuran-3-ylamino)-1,6-naphthyridin-2(1H)-one (0.57 g, 25% yield). $^1$H NMR (400 MHz, DMSO-$d_6$): δ 8.39 (s, 1H), 7.66 (s, 1H), 7.27 (d, J=6.4 Hz, 1H), 7.18 (d, J=11.2 Hz, 1H), 6.72 (d, J=9.6 Hz, 1H), 6.33 (s, 1H), 5.31 (s, 2H), 4.46-4.42 (m, 1H), 4.08 (q, J=6.8 Hz, 2H), 3.89-3.81 (m, 2H), 3.75-3.69 (m, 1H), 3.55-3.52 (m, 1H), 2.22-2.17 (m, 1H), 1.83-1.79 (m, 1H), 1.20 (t, J=6.8 Hz, 3H).

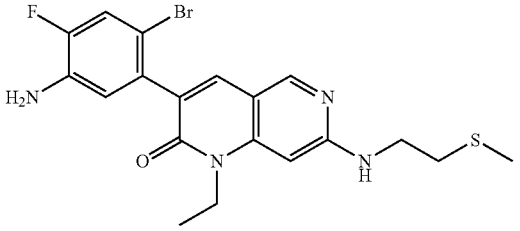

Example A31

Example A13 (0.165 g, 0.416 mmol) and 2-(thiomethyl) ethylamine (0.38 g, 4.16 mmol) were combined in NMP (2 mL) and the solution was heated in the microwave at 180° C. for 5 h. The mixture was poured into water (30 mL) and the resultant suspension was filtered, washed with water and dried to afford 3-(5-amino-2-bromo-4-fluorophenyl)-1-ethyl-7-(2-(methylthio)ethylamino)-1,6-naphthyridin-2(1H)-one (0.19 g, 100% yield) as an off-white solid. $^1$H NMR (400 MHz, DMSO-$d_6$): δ 8.37 (s, 1H), 7.62 (s, 1H), 7.30 (d, J=10.8 Hz, 1H), 7.15 (t, J=6.8 Hz, 1H), 7.32 (d, J=8.8 Hz, 1H), 6.33 (s, 1H), 5.33 (s, 2H), 4.09 (q, J=7.2 Hz, 2H), 3.53 (q, J=7.2 Hz, 2H), 2.66 (t, J=6.8 Hz, 2H), 2.10 (s, 3H), 1.18 (t, J=7.2 Hz, 3H); MS (ESI) m/z: 451.1 $[M+H]^+$.

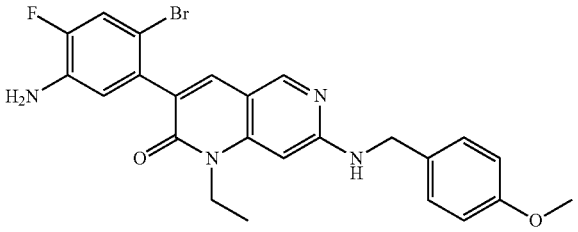

Example A32

Example A13 (2.5 g, 6.35 mmol) and 4-methoxybenzylamine (50 mL) were combined and heated at 140° C. overnight. The reaction mixture was cooled to RT, then poured into water. The resulting solid was collected via filtration, dried and purified by silica gel chromatography (EtOAc/pet ether) to give 7-(4-methoxybenzylamino)-3-(5-amino-2-bromo-4-fluorophenyl)-1-ethyl-1,6-naphthyridin-2(1H)-one (2.5 g, 81% yield). $^1$H NMR (400 MHz, DMSO-$d_6$): δ 8.35 (s, 1H), 7.59 (s, 1H), 7.51-7.48 (t, J=5.6 Hz, 1H), 7.29 (s, 1H), 7.26 (d, J=8.4 Hz, 2H), 6.85 (d, J=8.4 Hz, 2H), 6.70 (d, J=9.6 Hz, 1H), 6.27 (s, 1H), 5.31 (s, 2H), 4.45 (d, J=5.6 Hz, 2H), 4.06-4.01 (q, J=6.8 Hz, 2H), 3.53 (s, 3H), 1.10-1.07 (t, J=6.8 Hz, 3H).

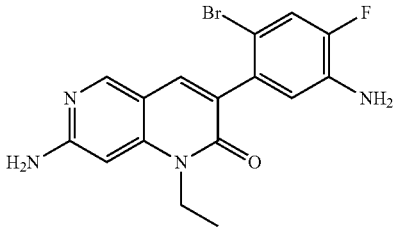

Example A33

Example A32 (2.5 g, 13.8 mmol) in TFA (30 mL) was stirred at 50-60° C. for 2 days. The mixture was concentrated, dissolved in EtOAc (100 mL) and washed with satd. $NaHCO_3$ (3×), then brine (3×). The organic layer was dried with $Na_2SO_4$, and concentrated to obtain crude product. Hydrochloric acid (6 M, 100 mL) was added to the residue and the solution was washed with EtOAc (3×). The aqueous layer was neutralized with satd. $NaHCO_3$ and then extracted with EtOAc (3×). The organic layers were washed with brine (1×), dried and concentrated to give 7-amino-3-(5-amino-2-bromo-4-fluorophenyl)-1-ethyl-1,6-naphthyridin-2(1H)-one (1 g, 53% yield). $^1$H NMR (400 MHz, DMSO-$d_6$): δ 8.56 (s, 1H), 7.79 (s, 1H), 7.73 (s, 2H), 7.37 (d, J=10.8 Hz, 1H), 6.77 (s, 1H), 6.73 (d, J=7.6 Hz, 1H), 5.89-5.03 (br s, 2H), 4.14-4.08 (q, J=6.8 Hz, 2H), 1.25-1.21 (t, J=6.8 Hz, 3H).

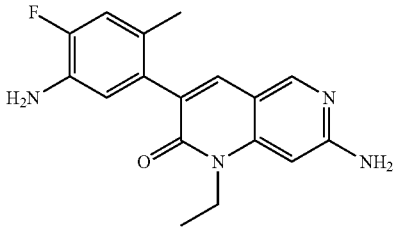

Example A34

A solution of Example A6 (2.5 g, 7.5 mmol) and 4-methoxybenzylamine (30 mL) was refluxed at 140° C. for 2 h. After cooling to RT, the reaction mixture was poured into a 20% aq. solution of acetic acid and stirred for 0.5 h. The mixture was filtered to provide 7-(4-methoxybenzylamino)-3-(5-amino-4-fluoro-2-methylphenyl)-1-ethyl-1,6-naphthyridin-2(1H)-one.

TFA (2 mL, 26.9 mmol) was added to a solution of 7-(4-methoxybenzylamino)-3-(5-amino-4-fluoro-2-methylphenyl)-1-ethyl-1,6-naphthyridin-2(1H)-one in DCM (10 mL) and the reaction mixture was refluxed at 50° C. for 2 h. After cooling to RT, the reaction mixture was washed with water and the combined aqueous layers were neutralized with satd. $NaHCO_3$. The aqueous layer was extracted with EtOAc (3×) and the extracts were dried ($Na_2SO_4$) and concentrated to give 7-amino-3-(5-amino-4-fluoro-2-methylphenyl)-1-ethyl-1,6-naphthyridin-2(1H)-one (0.9 g, 46% yield, over 2 steps). $^1$H NMR (300 MHz, DMSO-$d_6$): δ 8.30 (s, 1H), 7.56 (s, 1H), 6.83 (d, J=12.3 Hz, 1H), 6.57 (d, J=9.6 Hz, 1H), 6.40 (s, 2H), 6.32 (s, 1H), 4.85 (s, 2H), 4.07 (q, J=6.9 Hz, 2H), 1.94 (s, 3H), 1.19 (t, J=6.9 Hz, 3H); MS (ESI) m/z: 313.3 $[M+H]^+$.

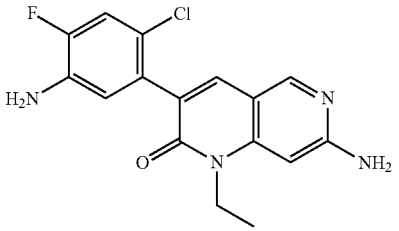

Example A35

Example A9 (2 g, 4.4 mmol) in TFA (10 mL) was stirred at 60° C. overnight, cooled to RT, added to water (10 mL) and extracted with EtOAc (3×). The combined organics layers were washed with brine, dried over $Na_2SO_4$, concentrated in vacuo, and purified by silica gel chromatography to afford 7-amino-3-(5-amino-2-chloro-4-fluorophenyl)-1-ethyl-1,6-naphthyridin-2(1H)-one (870 mg, 59% yield). $^1$H NMR (400 MHz, DMSO-$d_6$): δ 8.35 (s, 1H), 7.68 (s, 1H), 7.21 (d, J=10.8 Hz, 1H), 6.75 (d, J=9.6 Hz, 1H), 6.52 (s, 2H), 6.35 (s, 1H), 5.33 (s, 2H), 4.09 (q, J=6.8 Hz, 2H), 1.22 (t, J=6.8 Hz, 3H); MS (ESI) m/z: 333.2 $[M+H]^+$.

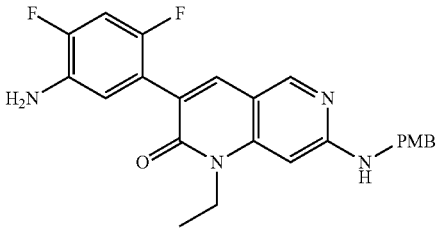

Example A36

A solution of Example A18 (1 g, 3 mmol) in (4-methoxyphenyl)methanamine (10 mL) was heated at 130° C. overnight. The mixture was cooled to RT, poured into a mixture of 1:1 acetic acid and water (10 mL), stirred for 30 minutes, and extracted with EtOAc (2×). The combined organic layers were washed with brine, dried over $Na_2SO_4$, filtered, and the filtrate concentrated to give a crude product which was purified by silica gel chromatography to give 7-(4-methoxybenzylamino)-3-(5-amino-2,4-difluorophenyl)-1-ethyl-1,6-naphthyridin-2(1H)-one (1 g, 69% yield). $^1$H NMR (400 MHz, DMSO-$d_6$): δ 8.40 (s, 1H), 7.74 (s, 1H), 7.57-7.54 (m, 1H), 7.30 (d, J=8.4 Hz, 2H), 7.08-7.03 (m, 1H), 6.90 (d, J=4.4 Hz, 2H), 6.78-6.72 (m, 1H), 6.30 (s, 1H), 5.02 (s, 2H), 4.49 (d, J=6.0 Hz, 2H), 4.11-4.09 (q, J=7.2 Hz, 2H), 3.72 (s, 3H), 1.14-1.11 (t, J=6.8 Hz, 3H).

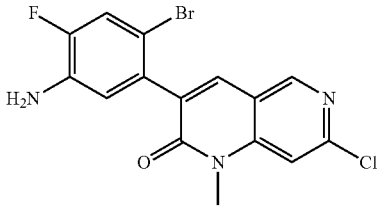

Example A37

To a solution of Example B3 (1 g, 5.5 mmol) and Example C5 (1.53 g, 5.5 mmol) in DMA (10 mL) was added $KF/Al_2O_3$ (3 g), and the mixture was stirred at RT for 10 min. The reaction mixture was filtered, the filtrate concentrated and the residue poured into water. The resulting solid was collected via filtration, washed with water, dried under vacuum and washed with MTBE to give 3-(5-amino-2-bromo-4-fluoro-phenyl)-7-chloro-1-methyl-1H-[1,6]naphthyridin-2-one (1.5 g, 67% yield). $^1$H NMR (400 MHz, DMSO-$d_6$): δ 8.76 (s, 1H), 7.99 (s, 1H), 7.66 (s, 1H), 7.37 (d, J=11.2, 1H), 6.75 (d, J=9.6 Hz, 1H), 5.44 (s, 2H), 3.62 (s, 3H).

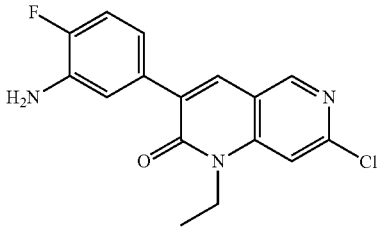

Example A38

A solution of Example B1 (6.0 g, 0.033 mol), ethyl 2-(3-amino-4-fluorophenyl)acetate (6.4 g, 0.033 mol) and $K_2CO_3$ (9.17 g, 0.066 mol) in DMF (100 mL) was heated to 80° C. overnight. The reaction mixture was poured into the water and extracted with EtOAc (3×). The combined extracts were washed with brine (3×), dried ($MgSO_4$), concentrated in vacuo and purified by chromatography to provide 3-(3-amino-4-fluorophenyl)-7-chloro-1-ethyl-1,6-naphthyridin-2(1H)-one (7.0 g, 68% yield). $^1$H NMR (400 MHz, DMSO-$d_6$): δ 8.75 (s, 1H), 8.07 (s, 1H), 7.67 (s, 1H), 7.13 (dd, J=8.8, 2.0 Hz, 1H), 7.02 (dd, J=11.6, 8.4 Hz, 1H), 6.80 (m, 1H), 5.20 (s, 2H), 4.25 (q, J=6.8 Hz, 2H), 1.19 (t, J=6.8 Hz, 3H); MS (ESI) m/z: 318.2 $[M+H]^+$.

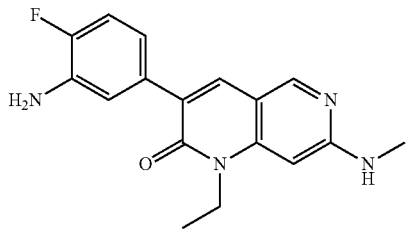

Example A39

Using the 2-step procedure of Example A4 and A5, Example A38 (0.85 g, 2.7 mmol) and 4-methoxybenzylmethylamine (10 mL) were combined to provide 3-(3-amino-4-fluorophenyl)-1-ethyl-7-(methylamino)-1,6-naphthyridin-2(1H)-one (0.45 g, 32% yield, 2 steps). $^1$H NMR (300 MHz, DMSO-$d_6$): δ 8.40 (s, 1H), 7.77 (s, 1H), 7.11 (d, J=9.0 Hz, 1H), 6.95 (m, 2H), 6.76 (m, 1H), 6.19 (s, 1H), 5.09 (s, 2H), 4.14 (m, 2H), 2.85 (br s, 3H), 1.20 (t, J=6.0, 3H); MS (ESI) m/z ($M+H^+$): 313.3.

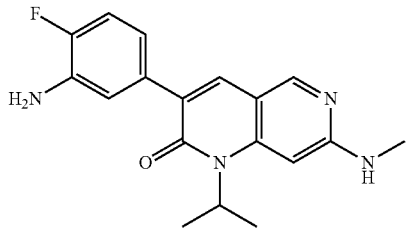

Example A40

$KF/Al_2O_3$ (40 wt %, 10 g, 69 mmol) was added to a solution of Example B2 (6 g, 30 mmol) and ethyl (3-amino-4-fluorophenyl)acetate (6 g, 30 mmol) in DMA (80 mL) and stirred at RT for 1 h. The mixture was filtered and the filtrate was concentrated under vacuum. The residue was poured into water, and the precipitate was collected by filtration, washed with $Et_2O$, and dried in vacuo to give 3-(3-amino-4-fluorophenyl)-7-chloro-1-isopropyl-1,6-naphthyridin-2(1H)-one (7 g, 70% yield). $^1$H NMR (400 Hz, DMSO-$d_6$): δ 8.71 (s, 1H), 8.00 (s, 1H), 7.76 (s, 1H), 7.11 (dd, J=9.2, 2.4 Hz, 1H), 7.05 (dd, J=11.6, 8.4 Hz, 1H), 6.76 (m, 1H), 5.18 (s, 2H), 5.15 (m, 1H), 1.52 (d, J=7.2 Hz, 1H); MS (ESI) m/z: 332.0 $[M+H]^+$.

A mixture of 3-(3-amino-4-fluorophenyl)-7-chloro-1-isopropyl-1,6-naphthyridin-2(1H)-one (4 g, 12.1 mmol) and (4-methoxybenzyl)methylamine (15 mL) was degassed under reduced pressure, then heated to 180° C. under $N_2$ for 4 h. After cooling, the reaction mixture was diluted with $Et_2O$. The precipitate was filtered, washed with $Et_2O$ and dried in vacuo to give 3-(3-amino-4-fluoro-phenyl)-1-isopropyl-7-[(4-methoxybenzyl)-methyl-amino]-1H-[1,6]naphthyridin-2-one (5.3 g) as a solid contaminated with (4-methoxybenzyl)methylamine HCl salt.

The above prepared 3-(3-amino-4-fluoro-phenyl)-1-isopropyl-7-[(4-methoxy-benzyl)-methyl-amino]-1H-[1,6]naphthyridin-2-one (5.3 g) was combined with TFA (50 mL) in DCM (150 mL) and heated at reflux overnight. The volatiles were removed under reduced pressure, the residue dissolved in 10% HCl and washed with EtOAc (3×). The aqueous layer was made basic (pH=11), extracted with EtOAc and the combined organics were dried ($Na_2SO_4$) and concentrated to give 3-(3-amino-4-fluoro-phenyl)-1-isopropyl-7-methylamino-1H-[1,6]naphthyridin-2-one (1.26 g, 32% yield over two steps). $^1$H NMR (400 MHz, DMSO-$d_6$): δ 8.36 (s, 1H), 7.70 (s, 1H), 7.06 (dd, J=8.4, 2.0 Hz, 1H), 6.94 (dd, J=11.6, 8.4 Hz, 1H), 6.88 (m, 1H), 6.72 (m, 1H), 6.39 (s, 1H), 5.07 (m, 1H), 5.06 (s, 2H), 2.83 (d, J=4.8 Hz, 1H), 1.51 (d, J=6.8 Hz, 6H); MS (ESI) m/z: 327.1 $[M+H]^+$.

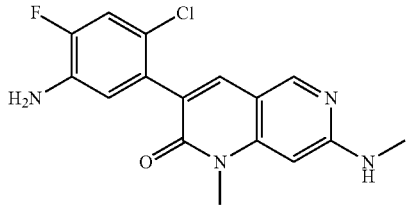

Example A41

Example C2 (3 g, 12.9 mmol), Example B3 (2.2 g, 12.9 mmol) and $KF/Al_2O_3$ (40%, 6 g, 41 mmol) were combined in DMA (40 mL) and the resultant mixture was stirred at RT for 1 h. The mixture was filtered and the filtrate was concentrated in vacuo. The residue was washed with $Et_2O$ to give 3-(5-amino-2-chloro-4-fluorophenyl)-7-chloro-1-methyl-1,6-naphthyridin-2(1H)-one (2.6 g, 60% yield). $^1$H NMR (300 MHz, DMSO-$d_6$): δ 8.74 (s, 1H), 8.00 (s, 1H), 7.63 (s, 1H), 7.23 (d, J=11.2 Hz, 1H), 6.75 (d, J=9.2 Hz, 1H), 5.40 (s, 2H), 3.60 (s, 3H); MS (ESI) m/z: 338.1$[M+H]^+$.

A mixture of 3-(5-amino-2-chloro-4-fluorophenyl)-7-chloro-1-methyl-1,6-naphthyridin-2(1H)-one (2.5 g, 7.4 mmol) and 4-methoxy-N-methylbenzylamine (4 mL) was heated to 180° C. under $N_2$ for 3 h. After cooling, the reaction mixture was diluted with $Et_2O$. The precipitate was filtered, washed with water, and dried to give 7-((4-methoxybenzyl)(methyl)amino)-3-(5-amino-2-chloro-4-fluorophenyl)-1-methyl-1,6-naphthyridin-2(1H)-one (3 g, 89% yield). $^1$H NMR (400 MHz, DMSO-$d_6$): δ 8.47 (s, 1H), 7.77 (s, 1H) 7.22 (m, 2H), 7.17 (d, J=8.0 Hz, 2H), 6.86 (d, J=8.4 Hz, 2H), 5.86 (d, J=9.6 Hz, 1H), 6.30 (s, 1H), 5.32 (s, 2H) 4.87 (s, 1H), 3.72 (s, 3H), 3.52 (s, 3H), 3.09 (s, 3H); MS (ESI) m/z: 453.2$[M+H]^+$.

A solution of 7-((4-methoxybenzyl)(methyl)amino)-3-(5-amino-2-chloro-4-fluorophenyl)-1-methyl-1,6-naphthyridin-2(1H)-one (3 g, 6.6 mmol) in DCM (50 mL) was treated with TFA (20 mL) and the mixture was heated to reflux overnight. The mixture was concentrated under reduced pressure, the residue was dissolved in 10% HCl (50 mL), washed with EtOAc, neutralized with satd. $NaHCO_3$ and extracted with EtOAc (3×). The combined organics were washed with brine, dried ($Na_2SO_4$) and concentrated in vacuo to give 3-(5-amino-2-chloro-4-fluorophenyl)-1-methyl-7-(methylamino)-1,6-naphthyridin-2(1H)-one (1.6 g, 72% yield) $^1$H NMR (300 MHz, DMSO-$d_6$): δ 8.36 (s, 1H), 7.66 (s, 1H), 7.17 (d, J=10.8 Hz, 1H), 7.05 (m, 1H), 6.71 (d, J=9.6 Hz, 1), 6.15 (s, 1H), 5.30 (s, 2H), 3.47 (s, 3H), 3.42 (s, 1H), 2.84 (d, J=4.4 Hz, 3H); MS (ESI) m/z: 333.1 $[M+H]^+$

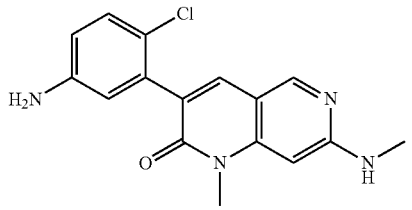

Example A42

Example B3 (3.2 g, 18.8 mmol), Example C6 (4.0 g, 18.8 mmol) and $Cs_2CO_3$ (12.3 g, 37.6 mmol) were combined in DMF (80 mL) and heated to 80° C. for 4 h. The reaction mixture was poured into water (600 mL) and the precipitate was collected by filtration and dried under reduced pressure to give 3-(5-amino-2-chlorophenyl)-7-chloro-1-methyl-1,6-naphthyridin-2(1H)-one (5.0 g, 83% yield). $^1$H NMR (400 MHz, DMSO-$d_6$): δ 8.74 (s, 1H), 7.97 (s, 1H), 7.63 (s, 1H), 7.09 (d, J=8.4 Hz, 1H), 6.57 (dd, J=8.4 Hz, 2.8 Hz, 1H), 6.52 (s, 1H), 5.31 (s, 2H), 3.60 (s, 3H).

A mixture of 3-(5-amino-2-chlorophenyl)-7-chloro-1-methyl-1,6-naphthyridin-2(1H)-one (5 g, 15.67 mmol), 4-methoxybenzylmethylamine (3.6 g, 23.5 mmol) and DBU (3.7 g, 23.5 mmol) in NMP (80 mL) was heated at 180° C. under $N_2$ for 4 h. The reaction was cooled to RT and poured into water (600 mL). The precipitate was collected by filtration and dried in vacuo to give 7-((4-methoxybenzyl)(methyl)amino)-3-(5-amino-2-chlorophenyl)-1-methyl-1,6-naphthyridin-2(1H)-one (6.5 g, 95% yield). $^1$H NMR (400 MHz, DMSO-$d_6$): δ 8.46 (s, 1H), 7.68 (s, 1H), 7.16 (d, J=8.8 Hz, 2H), 7.06 (d, J=8.4 Hz, 1H), 6.85 (d, J=8.8 Hz, 2H), 6.54-6.51 (m, 2H), 6.29 (s, 1H), 5.23 (s, 2H), 4.85 (s, 2H), 3.69 (s, 3H), 3.51 (s, 3H), 3.07 (s, 3H).

TFA (10 mL, 134 mmol) was added to a solution of 7-((4-methoxybenzyl)(methyl)amino)-3-(5-amino-2-chlorophenyl)-1-methyl-1,6-naphthyridin-2(1H)-one (4 g, 9.2 mmol) in DCM (50 mL) and heated to reflux for 3 h. The reaction mixture was concentrated under reduced pressure, dissolved in HCl, washed with EtOAc (3×), neutralized with satd. $Na_2CO_3$ and extracted with EtOAc (3×). The combined extracts were washed with brine, dried over $Na_2SO_4$, concentrated under reduced pressure and purified by chromatography to give 3-(5-amino-2-chlorophenyl)-1-methyl-7-(methylamino)-1,6-naphthyridin-2(1H)-one (1.7 g, 58% yield). $^1$H NMR (400 MHz, DMSO-$d_6$): δ 8.36 (s, 1H), 7.63 (s, 1H), 7.06-7.00 (m, 2H), 6.54-6.50 (m, 2H), 6.14 (s, 1H), 5.21 (s, 2H), 3.48 (s, 3H), 2.84 (d, J=4.8 Hz, 3H); MS (ESI) m/z: 314.9 $[M+H]^+$.

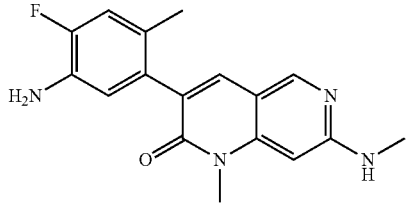

Example A43

A solution of Example B3 (2 g, 11.8 mmol) in DMA (40 mL) was treated with Example C1 (2.5 g, 11.8 mmol), followed by KF/$Al_2O_3$ (40 wt %, 10 g, 68 mmol) and stirred at RT for 2 h. The mixture was filtered, the filtrate poured into water and the precipitate was collected by filtration and dried to give 3-(5-amino-4-fluoro-2-methylphenyl)-7-chloro-1-methyl-1,6-naphthyridin-2(1H)-one (2.5 g, 69% yield). $^1$H NMR (300 MHz, DMSO-$d_6$): δ 8.72 (s, 1H), 7.90 (s, 1H), 7.62 (s, 1H), 6.88 (d, J=12.3 Hz, 1H), 6.60 (d, J=6 Hz, 1H), 4.95 (s, 2H), 3.60 (s, 3H), 1.95 (s, 3H); MS (ESI) m/z: 318.0 $[M+H]^+$.

3-(5-amino-4-fluoro-2-methylphenyl)-7-chloro-1-methyl-1,6-naphthyridin-2(1H)-one (1.36 g, 4.28 mmol, 1.00 eq), 4-methoxy-N-methylbenzylamine (0.971 g, 6.42 mmol, 1.50 eq) and DBU (0.960 mL, 6.42 mmol, 1.50 eq) were combined in NMP (20 mL) and heated at 180° C. under Ar overnight. The mixture was cooled to RT and poured onto $H_2O$ (200 mL). The resulting solids were collected by filtration, rinsed very well with $H_2O$, dried on the filter to dampness and then dissolved in EtOAc. The solution was dried ($MgSO_4$), filtered and evaporated to afford 7-((4-methoxybenzyl)(methyl)amino)-3-(5-amino-4-fluoro-2-methylphenyl)-1-methyl-1,6-naphthyridin-2(1H)-one (1.86 g, 100% yield) as a brittle brown foam which was used as is in the next reaction. $^1$H NMR (400 MHz, DMSO-$d_6$): δ 8.45 (s, 1H), 7.63 (s, 1H), 7.16 (d, J=8.8 Hz, 2H), 6.85 (d, J=8.8 Hz, 2H), 6.86-6.82 (m, 1H), 6.57 (d, J=9.6 Hz, 1H), 6.29 (s, 1H), 4.88 (br s, 2H), 4.85 (s, 2H), 3.69 (s, 3H), 3.52 (s, 3H), 3.07 (s, 3H), 1.94 (s, 3H); MS (ESI) m/z: 433.3 $[M+H]^+$.

7-((4-methoxybenzyl)(methyl)amino)-3-(5-amino-4-fluoro-2-methylphenyl)-1-methyl-1,6-naphthyridin-2(1H)-one (1.86 g, 4.3 mmol) and TFA (9.5 mL, 121 mmol) were combined and stirred at RT overnight. The mixture was treated slowly with 2M $Na_2CO_3$ until the mixture was just faintly basic, then stirred at RT for 1 h. The solids were collected by filtration, washed thoroughly with $H_2O$, dried partially in the air and then under high vacuum at 65° C. The crude product was purified by flash column chromatography (THF/EtOAc) to afford 3-(5-amino-4-fluoro-2-methylphenyl)-1-methyl-7-(methylamino)-1,6-naphthyridin-2(1H)-one (0.86 g, 64% yield) as an off-white solid. $^1$H NMR (400 MHz, DMSO-$d_6$): δ 8.35 (s, 1H), 7.58 (s, 1H), 6.99 (q, J=4.8 Hz, 1H), 6.56 (d, J=12.0 Hz, 1H), 6.56 (d, J=9.2 Hz, 1H), 6.15 (s, 1H), 4.87 (br s, 2H), 3.48 (s, 3H), 2.84 (d, J=5.2 Hz, 3H), 1.94 (s, 3H); MS (ESI) m/z: 313.2 $[M+H]^+$.

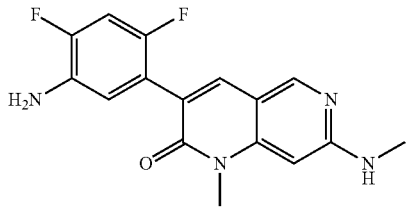

Example A44

Example B3 (2 g, 9.3 mmol), Example C4 (1.6 g, 9.3 mmol) and KF/$Al_2O_3$ (40%, 5 g, 34.4 mmol) were combined in DMA and stirred for 10 min. The reaction mixture was poured into water and extracted with EtOAc. The combined organic layers were washed with brine, dried ($Na_2SO_4$) and concentrated in vacuo. The residue was purified by chromatography to give 3-(5-amino-2,4-difluorophenyl)-7-chloro-1-methyl-1,6-naphthyridin-2(1H)-one (2 g, 68% yield). $^1$H NMR (300 MHz, DMSO-$d_6$): δ 8.41 (s, 1H), 7.73 (s, 1H), 7.06-7.03 (m, 1H), 6.81-6.75 (m, 1H), 6.15 (s, 1H), 4.98 (s, 2H), 3.48 (s, 3H); MS (ESI) m/z: 322.7 $[M+H]^+$.

3-(5-Amino-2,4-difluorophenyl)-7-chloro-1-methyl-1,6-naphthyridin-2(1H)-one (2.4 g, 7.5 mmol) and 4-methoxy-N-methylbenzylamine (10 mL) were combined in a sealed vessel and heated to 200° C. overnight. The volatiles were removed in vacuo and the residue was purified by column chromatography to give 7-(4-methoxybenzyl)(methyl)amino)-3-(5-amino-2,4-difluorophenyl)-1-methyl-1,6-naphthyridin-2(1H)-one (3 g, 91% yield), which was used in the next step without further purification.

A solution of 7-(4-methoxybenzyl)(methyl)amino)-3-(5-amino-2,4-difluorophenyl)-1-methyl-1,6-naphthyridin-2(1H)-one (3 g, 6.8 mmol) in DCM (100 mL) was treated with TFA (20 mL) and stirred at RT for 6 h. The mixture was extracted with water and the combined aqueous layers were neutralized with $NH_3H_2O$. The precipitate was collected by filtration and dried to give 3-(5-amino-2,4-difluorophenyl)-1-methyl-7-(methylamino)-1,6-naphthyridin-2(1H)-one (661 mg, 30% yield). $^1H$ NMR (300 MHz, DMSO-$d_6$): δ 8.39 (s, 1H), 7.78 (s, 1H), 7.08-6.93 (m, 2H), 6.80 (dd, J=10.2, 8.1 Hz, 1H), 6.16 (s, 1H), 5.00 (s, 2H), 3.50 (s, 3H), 2.84 (d, J=4.8 Hz, 3H); MS (ESI) m/z: 317.0 $[M+H]^+$.

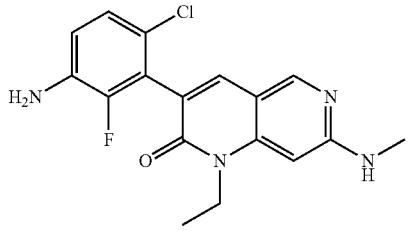

Example A45

A solution of 4-chloro-2-fluoroaniline (5.0 g, 34.3 mmol) in acetic acid (3 mL) was treated with acetic anhydride (6.45 mL, 68.7 mmol) and stirred at RT for 2 h. The mixture was poured onto ice water, stirred for 2 h and the resulting solid collected via filtration and dried to afford N-(4-chloro-2-fluorophenyl)acetamide (6.12 g, 95% yield). $^1H$ NMR (400 MHz, DMSO-$d_6$): δ 9.80 (s, 1H), 7.91 (t, J=8.7 Hz, 1H), 7.45 (dd, J=10.8, 2.4 Hz, 1H), 7.22 (d, J=8.9 Hz, 1H), 2.07 (s, 3H).

A −78° C. solution of N-(4-chloro-2-fluorophenyl)acetamide (2.00 g, 10.66 mmol) in THF (40 mL), under Ar, was treated with butyl lithium (16.66 mL, 26.7 mmol), stirred at −78° C. for 2.5 h, treated slowly with DMF (1.651 mL, 21.32 mmol), stirred for 15 min at −78° C. and slowly warmed to RT. The mixture was stirred for 2 h, treated with satd. $NH_4Cl$, the layers separated and the aqueous layer extracted with EtOAc (1×). The combined organics were washed with brine, dried over $Na_2SO_4$, concentrated to dryness and purified via silica gel chromatography (EtOAc/Hex) to afford N-(4-chloro-2-fluoro-3-formylphenyl)acetamide (1.1 g, 48% yield) as an off-white solid. MS (ESI) m/z: 216.0 $[M+H]^+$.

A 0° C. solution of N-(4-chloro-2-fluoro-3-formylphenyl)acetamide (1.1 g, 5.10 mmol) in MeOH (10 mL) was treated portion-wise with sodium borohydride (0.193 g, 5.10 mmol), stirred at 0° C. for 0.5 h, then warmed to RT and concentrated to dryness. The residue was treated with water, extracted with EtOAc (2×) and the combined organics were washed with brine, dried over $Na_2SO_4$ and concentrated to dryness to afford N-(4-chloro-2-fluoro-3-(hydroxymethyl)phenyl)acetamide (1.05 g, 95% yield) as a white solid. MS (ESI) m/z: 218.0 $[M+H]^+$.

A 0° C. of N-(4-chloro-2-fluoro-3-(hydroxymethyl)phenyl)acetamide (1.05 g, 4.82 mmol) and TEA (1.003 mL, 7.24 mmol) in DCM (30 mL) was treated slowly with methanesulfonyl chloride (0.414 mL, 5.31 mmol), warmed to RT and stirred for 2 h. The mixture was treated with satd. $NaHCO_3$, extracted with DCM (2×) and the combined organics were washed with brine, dried over $Na_2SO_4$ and concentrated to dryness to afford 3-acetamido-6-chloro-2-fluorobenzyl methanesulfonate (1.31 g, 74% yield) as an off-white solid. MS (ESI) m/z: 296.0 $[M+H]^+$.

A solution of 3-acetamido-6-chloro-2-fluorobenzyl methanesulfonate (1.31 g, 3.54 mmol) in DMSO (10 mL) was treated with sodium cyanide (0.868 g, 17.72 mmol), stirred at RT overnight, treated with water and extracted with EtOAc (2×). The combined organics were washed with brine, dried over $Na_2SO_4$, concentrated to dryness and purified via silica gel chromatography (EtOAc/Hex) to afford N-(4-chloro-3-(cyanomethyl)-2-fluorophenyl)acetamide (630 mg, 78% yield) as a yellow solid. MS (ESI) m/z: 227.0 $[M+H]^+$.

HCl gas was bubbled into 0° C. EtOH (30 mL), added to N-(4-chloro-3-(cyanomethyl)-2-fluorophenyl)acetamide (0.28 g, 1.235 mmol) and heated at 80° C. for 7 h. The mixture was cooled to RT, concentrated to dryness and the residue neutralized with satd. $NaHCO_3$. The mixture was extracted with EtOAc (2×) and the combined organics were washed with brine, dried over $Na_2SO_4$ and purified via silica gel chromatography (EtOAc/Hex) to afford ethyl 2-(3-amino-6-chloro-2-fluorophenyl)acetate (250 mg, 87% yield) as an off-white solid. MS (ESI) m/z: 232.1 $[M+H]^+$.

A solution of ethyl 2-(3-amino-6-chloro-2-fluorophenyl)acetate (0.252 g, 1.089 mmol) in DMA (5 mL) was treated with Example B1 (0.201 g, 1.089 mmol) and KF on alumina (40%, 1.107 g, 7.62 mmol) and sonicated for 1 h. The mixture was diluted with EtOAc, filtered through diatomaceous earth and rinsed well with EtOAc. The filtrate was washed with water, then brine, dried over $Na_2SO_4$ and concentrated to dryness to afford crude 3-(3-amino-6-chloro-2-fluorophenyl)-7-chloro-1-ethyl-1,6-naphthyridin-2(1H)-one (450 mg, 117% yield) as a white amorphous solid which was used without further purification. MS (ESI) m/z: 352.0 $[M+H]^+$.

A solution of 3-(3-amino-6-chloro-2-fluorophenyl)-7-chloro-1-ethyl-1,6-naphthyridin-2(1H)-one (0.45 g, 1.150 mmol) in dioxane (5 mL) was treated with methylamine (40% in water, 7.14 g, 92 mmol) and heated at 100° C. overnight. The mixture was cooled to RT, treated with brine and extracted with EtOAc (2×). The combined organics were dried over $Na_2SO_4$, concentrated to dryness and purified via silica gel chromatography (MeOH/DCM) to afford 3-(3-amino-6-chloro-2-fluorophenyl)-1-ethyl-7-(methylamino)-1,6-naphthyridin-2(1H)-one (350 mg, 88% yield) as a white amorphous solid. $^1H$ NMR (500 MHz, DMSO-$d_6$): δ 8.41 (s, 1H), 7.74 (s, 1H), 7.07 (q, J=4.9 Hz, 1H), 7.03 (dd, J=8.7, 1.3 Hz, 1H), 6.77 (t, J=9.0 Hz, 1H), 6.25 (s, 1H), 5.30 (s, 2H), 4.15-4.13 (q, J=7.0 Hz, 2H), 2.87 (d, J=4.9 Hz, 3H), 1.21 (t, J=7.0 Hz, 3H); MS (ESI) m/z: 347.1 $[M+H]^+$.

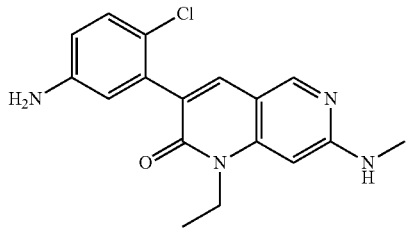

Example A46

Using the three-step procedure of Example A42, Example B1 (3.5 g, 18.8 mmol), Example C6 (4.0 g, 18.8 mmol), $Cs_2CO_3$ (12.3 g, 37.6 mmol), 4-methoxybenzylmethylamine (3.6 g, 23.5 mmol) and TFA (10 mL, 134 mmol) were combined to provide 3-(5-amino-2-chlorophenyl)-1-ethyl-7-(methylamino)-1,6-naphthyridin-2(1H)-one (1.68 g, 27% yield over 3 steps). $^1$H NMR (400 MHz, DMSO-$d_6$): δ 8.36 (s, 1H), 7.62 (s, 1H), 7.05 (dd, J=7.2, 2.0 Hz, 1H), 6.96 (q, J=4.8 Hz, 1H), 6.54-6.50 (m, 2H), 6.21 (s, 1H), 5.21 (s, 2H), 4.11 (q, J=7.2 Hz, 2H), 2.84 (d, J=4.8 Hz, 3H), 1.18 (t, J=7.2 Hz, 3H); MS (ESI) m/z: 329.2[M+H]$^+$.

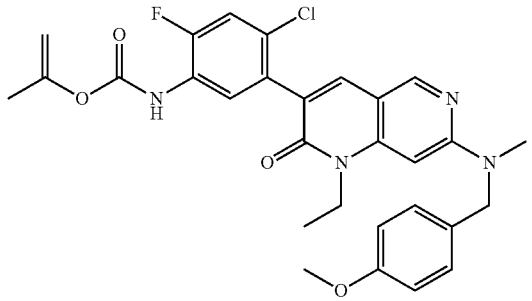

Example A47

A bi-phasic mixture of Example A4 (1.00 g, 2.142 mmol) in EtOAc (25 mL) and satd. $NaHCO_3$ (25 mL) was treated with isopropenyl chloroformate (516 mg, 4.28 mmol) and stirred vigorously at RT for 3 h. Hexane (10 mL) was added and the resulting solid collected via filtration and dried. The layers of the filtrate were separated, the organic layer washed with brine, dried over $Na_2SO_4$, concentrated to dryness and combined with the above-isolated solid to afford prop-1-en-2-yl (4-chloro-5-(1-ethyl-7-((4-methoxybenzyl)(methyl)amino)-2-oxo-1,2-dihydro-1,6-naphthyridin-3-yl)-2-fluorophenyl)carbamate (1.168 g, 98% yield). MS (ESI) m/z: 551.2 [M+H]$^+$.

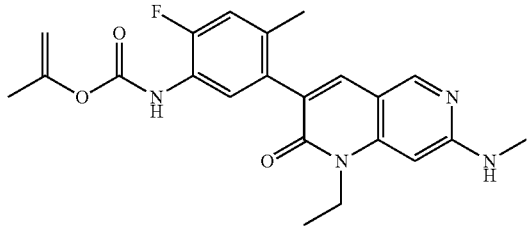

Example A48

A biphasic solution of Example A2 (300 mg, 0.919 mmol) in EtOAc (10 mL) and satd. $NaHCO_3$ (10 mL) was treated with isopropenyl chloroformate (138 mg, 1.149 mmol) and stirred at RT for 6 h. Additional isopropenyl chloroformate (50 μL) was added and the mixture stirred at RT overnight. The layers were separated, the organic layer washed with brine, dried over $Na_2SO_4$ and concentrated to dryness to afford prop-1-en-2-yl (5-(1-ethyl-7-(methylamino)-2-oxo-1,2-dihydro-1,6-naphthyridin-3-yl)-2-fluoro-4-methylphenyl) carbamate (378 mg, 100% yield). MS (ESI) m/z: 411.2 [M+H]$^+$.

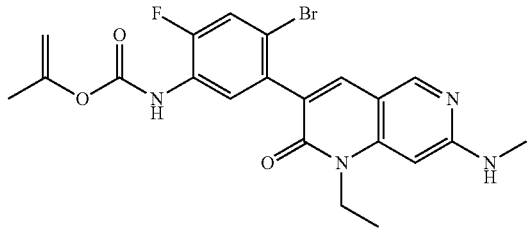

Example A49

A 0° C. solution of Example A14 (0.75 g, 1.917 mmol) in a biphasic mixture of 1:1:1 EtOAc/THF/satd. $NaHCO_3$ (90 mL) was treated with isopropenyl chloroformate (0.220 mL, 2.013 mmol), allowed to warm to RT and stirred overnight. Additional isopropenyl chloroformate (0.220 mL, 2.013 mmol) was added, the mixture stirred at RT for 3 h, then placed in the refrigerator overnight. The mixture was extracted with EtOAc (2×) and the combined organics were washed with brine, dried over $Na_2SO_4$ and concentrated to dryness to afford prop-1-en-2-yl (4-bromo-5-(1-ethyl-7-(methylamino)-2-oxo-1,2-dihydro-1,6-naphthyridin-3-yl)-2-fluorophenyl)carbamate (960 mg, 105% yield). $^1$H NMR (400 MHz, DMSO-$d_6$): δ 9.81 (s, 1H), 8.39 (s, 1H), 7.72-7.61 (m, 3H), 7.04 (m, 1H), 6.23 (s, 1H), 4.72 (d, J=9.5 Hz, 2H), 4.13 (m, 2H), 2.85 (d, J=4.8 Hz, 3H), 1.91 (s, 3H), 1.20 (t, J=7.0 Hz, 3H); MS (ESI) m/z: 475.1 [M+H]$^+$.

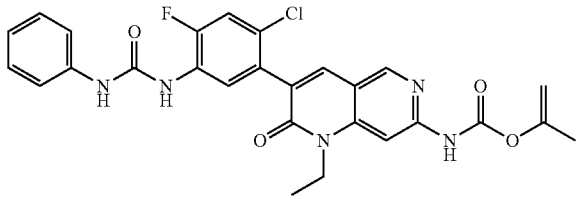

Example A50

A solution of Example 21 (0.1 g, 0.221 mmol) in pyridine (5 mL) was treated with isopropenyl chloroformate (0.027 mL, 0.243 mmol) and stirred at RT overnight. Water was added and the resulting solid was collected via filtration and dried to afford prop-1-en-2-yl (3-(2-chloro-4-fluoro-5-(3-phenylureido)phenyl)-1-ethyl-2-oxo-1,2-dihydro-1,6-naphthyridin-7-yl)carbamate (105 mg, 89% yield). $^1$H NMR (400 MHz, DMSO-$d_6$): δ 10.82 (s, 1H), 9.10 (s, 1H), 8.72 (d, J=2.6 Hz, 1H), 8.70 (s, 1H), 8.23 (d, J=8.6 Hz, 1H), 7.99 (s, 1H), 7.91 (s, 1H), 7.57 (d, J=11.0 Hz, 1H), 7.41 (dd, J=8.2, 1.2 Hz, 2H), 7.26 (m, 2H), 6.97 (t, J=7.4 Hz, 1H), 4.80-4.79 (m, 2H), 4.21 (q, J=7.1 Hz, 2H), 1.96 (s, 3H), 1.25 (t, J=7.1 Hz, 3H); MS (ESI) m/z: 536.1 $[M+H]^+$.

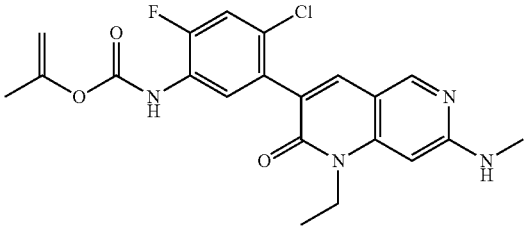

Example A51

A suspension of Example A5 (0.154 g, 0.444 mmol) in EtOAc (2.5 mL) was treated with satd. $NaHCO_3$ (2.5 mL) and isopropenyl chloroformate (0.046 mL, 0.422 mmol) and the biphasic mixture stirred vigorously at RT for 3.5 h. Additional isopropenyl chloroformate (20 μL) was added and the mixture was stirred at RT overnight. The mixture was diluted with additional EtOAc and satd. $NaHCO_3$ and the layers separated. The organic layer was washed with brine, dried over $MgSO_4$ and concentrated to dryness. The resulting residue was dissolved in pyridine (1.5 mL), cooled to 0° C., treated with isopropenyl chloroformate (15 μL) and allowed to warm to RT. The mixture was re-cooled to 0° C., treated with additional isopropenyl chloroformate (7 μL) and allowed to warm to RT. The mixture was once again cooled to 0° C., treated with isopropenyl chloroformate (5 μL), allowed to warm to RT and stirred overnight. The mixture was concentrated to dryness, treated with brine and extracted with EtOAc (2×). The combined organics were dried over $MgSO_4$, concentrated to dryness and purified via silica gel chromatography (EtOAc/Hex) to afford prop-1-en-2-yl (4-chloro-5-(1-ethyl-7-(methylamino)-2-oxo-1,2-dihydro-1,6-naphthyridin-3-yl)-2-fluorophenyl)carbamate (141 mg, 74% yield). $^1$H NMR (400 MHz, DMSO-$d_6$): δ 9.80 (s, 1H), 8.40 (s, 1H), 7.75 (s, 1H), 7.64 (s, 1H), 7.55 (d, J=10.5 Hz, 1H), 7.05 (d, J=5.0 Hz, 1H), 6.23 (s, 1H), 4.73 (m, 2H), 4.13 (q, J=7.1 Hz, 2H), 2.85 (d, J=4.9 Hz, 3H), 1.91 (s, 3H), 1.20 (t, J=7.0 Hz, 3H), MS (ESI) m/z: 431.1 $[M+H]^+$.

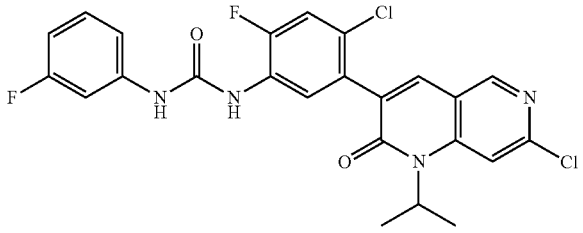

Example A52

A mixture of Example A10 (200 mg, 0.546 mmol) and pyridine (173 mg, 2.184 mmol) in THF (5 mL) was treated with 3-fluorophenyl isocyanate (90 mg, 0.655 mmol) and stirred at RT overnight. The mixture was treated with water and EtOAc and most of the aqueous layer was removed. DMF was added, the mixture concentrated to dryness and purified via reverse-phase chromatography (MeCN/$H_2O$ with 0.1% TFA). The organics were removed under reduced pressure and the aqueous residue was treated with satd. $NaHCO_3$ and allowed to stand at RT. The resulting solid was collected via filtration and dried to afford 1-(4-chloro-5-(7-chloro-1-isopropyl-2-oxo-1,2-dihydro-1,6-naphthyridin-3-yl)-2-fluorophenyl)-3-(3-fluorophenyl)urea (153 mg, 56% yield). $^1$H NMR (400 MHz, DMSO-$d_6$): δ 9.31 (s, 1H), 8.80 (s, 1H), 8.76 (s, 1H), 8.20 (d, J=8.4 Hz, 1H), 8.04 (s, 1H), 7.84 (s, 1H), 7.59 (d, J=10.9 Hz, 1H), 7.46 (d, J=11.9 Hz, 1H), 7.29 (m, 1H), 7.07 (d, J=8.2 Hz, 1H), 6.79 (m, 1H), 5.12 (m, 1H), 1.52 (d, J=6.6 Hz, 6H); MS (ESI) m/z: 503.1 $[M+H]^+$.

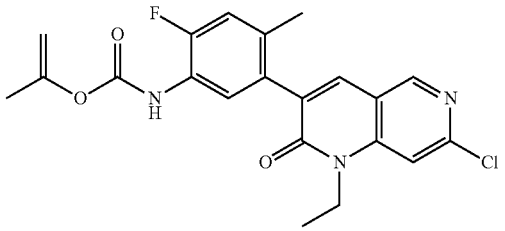

Example A53

A suspension of Example A6 (0.161 g, 0.485 mmol) in EtOAc (2.5 mL) was treated with satd. $NaHCO_3$ (2.5 mL) followed by isopropenyl chloroformate (0.080 mL, 0.728 mmol) and the bi-phasic mixture stirred vigorously at RT for 2 h. The layers were separated, the organic layer washed with brine dried over $MgSO_4$ and concentrated to dryness to afford prop-1-en-2-yl (5-(7-chloro-1-ethyl-2-oxo-1,2-dihydro-1,6-naphthyridin-3-yl)-2-fluoro-4-methylphenyl)carbamate (100% yield assumed). MS (ESI) m/z: 416.1 $[M+H]^+$.

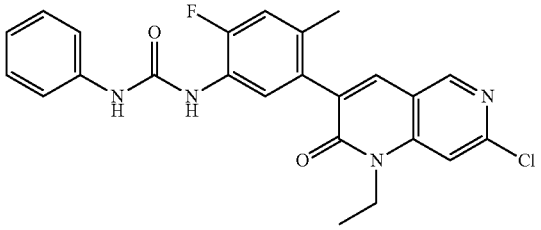

Example A54

A solution of Example A6 (0.200 g, 0.603 mmol) and TEA (0.126 mL, 0.904 mmol) in THF (6 mL) was treated with phenyl isocyanate (0.066 mL, 0.603 mmol and stirred at RT overnight. The resulting solid was collected via filtration and dried to afford 1-(5-(7-chloro-1-ethyl-2-oxo-1,2-dihydro-1,6-naphthyridin-3-yl)-2-fluoro-4-methylphenyl)-3-phenylurea (211 mg, 78% yield). $^1$H NMR (400 MHz, DMSO-$d_6$): δ 9.01 (s, 1H), 8.77 (s, 1H), 8.51 (d, J=2.3 Hz, 1H), 8.01-7.98 (m, 2H), 7.73 (s, 1H), 7.41 (dd, J=8.3, 1.2 Hz, 2H), 7.25 (dd, J=8.5, 7.3 Hz, 2H), 7.17 (d, J=12.2 Hz, 1H), 6.97-6.90 (m, 1H), 4.27 (q, J=7.1 Hz, 2H), 2.07 (s, 3H), 1.21 (t, J=7.0 Hz, 3H); MS (ESI) m/z: 451.1 $[M+H]^+$.

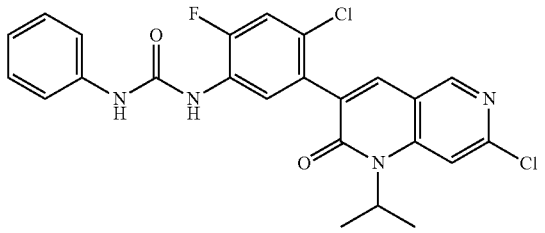

Example A55

A mixture of Example A10 (700 mg, 1.911 mmol) and pyridine (605 mg, 7.65 mmol) in THF (15 mL) was treated with phenyl isocyanate (250 mg, 2.103 mmol) and stirred at RT for 19 h. The mixture was diluted with EtOAc, washed with satd. $NaHCO_3$, then brine, dried over $Na_2SO_4$, concentrated to dryness and purified via reverse-phase chromatography (MeCN/$H_2O$ with 0.1% TFA). The organics were removed under reduced pressure, the aqueous residue treated with satd. $NaHCO_3$ and allowed to stand at RT. The resulting solid was collected via filtration and dried to afford 1-(4-chloro-5-(7-chloro-1-isopropyl-2-oxo-1,2-dihydro-1,6-naphthyridin-3-yl)-2-fluorophenyl)-3-phenylurea (325 mg, 35% yield). $^1$H NMR (400 MHz, DMSO-$d_6$): δ 9.10 (s, 1H), 8.76 (s, 1H), 8.73 (m, 1H), 8.23 (d, J=8.6 Hz, 1H), 8.04 (s, 1H), 7.84 (s, 1H), 7.58 (d, J=11.0 Hz, 1H), 7.41 (d, J=8.0 Hz, 2H), 7.27 (t, J=7.9 Hz, 2H), 6.97 (t, J=7.4 Hz, 1H), 5.11 (m, 1H), 1.52 (d, J=6.7 Hz, 6H); MS (ESI) m/z: 485.1 [M+H]$^+$.

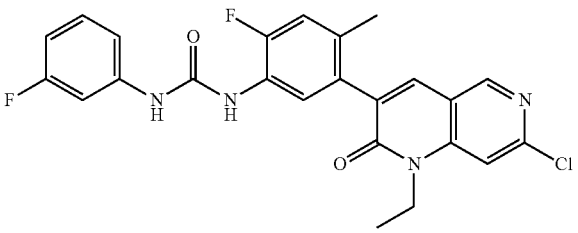

Example A56

A solution of Example A6 (0.200 g, 0.603 mmol) and TEA (0.126 mL, 0.904 mmol) in THF (6 mL) was treated with 3-fluorophenyl isocyanate (0.083 ml, 0.723 mmol) and stirred at RT for 4 h. The mixture was concentrated to dryness and purified via silica gel chromatography (EtOAc/Hex). The material was treated with DCM and the solid collected via filtration. The filtrate was concentrated to dryness, re-purified via silica gel chromatography (MeOH/DCM) and combined with the isolated solid to afford 1-(5-(7-chloro-1-ethyl-2-oxo-1,2-dihydro-1,6-naphthyridin-3-yl)-2-fluoro-4-methylphenyl)-3-(3-fluorophenyl)urea (88 mg, 31% yield). $^1$H NMR (400 MHz, DMSO-$d_6$): δ 9.23 (s, 1H), 8.77 (s, 1H), 8.58 (d, J=2.3 Hz, 1H), 8.00 (s, 1H), 7.97 (d, J=8.4 Hz, 1H), 7.73 (s, 1H), 7.46 (dt, J=12.0, 2.3 Hz, 1H), 7.28 (m, 1H), 7.18 (d, J=12.2 Hz, 1H), 7.05 (ddd, J=8.2, 2.0, 0.9 Hz, 1H), 6.77 (td, J=8.3, 2.5 Hz, 1H), 4.27 (q, J=7.1 Hz, 2H), 2.07 (s, 3H), 1.21 (t, J=7.0 Hz, 3H); MS (ESI) m/z: 469.1 [M+H]$^+$.

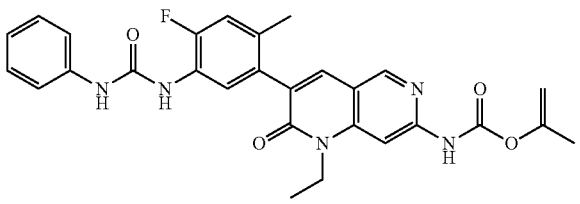

Example A57

A mixture of Example A34 (0.3 g, 0.960 mmol), phenyl isocyanate (0.137 g, 1.153 mmol) and TEA (0.134 ml, 0.960 mmol) in THF (5 mL) was stirred at RT for 4 h. The mixture was treated with 30% EtOAc/Hex, stirred for several minutes and the resulting solid was collected via filtration and dried to afford 1-(5-(7-amino-1-ethyl-2-oxo-1,2-dihydro-1,6-naphthyridin-3-yl)-2-fluoro-4-methylphenyl)-3-phenylurea (350 mg, 84% yield). $^1$H NMR (400 MHz, DMSO-$d_6$): δ 9.01 (s, 1H), 8.47 (s, 1H), 8.34 (s, 1H), 7.93 (d, J=8.5 Hz, 1H), 7.65 (s, 1H), 7.41 (dd, J=8.3, 1.2 Hz, 2H), 7.24-7.26 (m, 2H), 7.12 (d, J=12.2 Hz, 1H), 6.95 (t, J=7.4 Hz, 1H), 6.47 (s, 2H), 6.34 (s, 1H), 4.09 (q, J=7.3 Hz, 2H), 2.06 (s, 3H), 1.20 (t, J=7.0 Hz, 3H); MS (ESI) m/z: 432.1 [M+H]$^+$.

A solution of 1-(5-(7-amino-1-ethyl-2-oxo-1,2-dihydro-1,6-naphthyridin-3-yl)-2-fluoro-4-methylphenyl)-3-phenylurea (0.35 g, 0.811 mmol) in pyridine (5 mL) was treated with isopropenyl chloroformate (0.147 g, 1.217 mmol) and stirred at RT for 1 h. Water was added, the mixture stirred for 10 minutes and the resulting solid was collected via filtration and dried to afford prop-1-en-2-yl (1-ethyl-3-(4-fluoro-2-methyl-5-(3-phenylureido)phenyl)-2-oxo-1,2-dihydro-1,6-naphthyridin-7-yl)carbamate (360 mg, 86% yield). MS (ESI) m/z: 516.2 [M+H]$^+$.

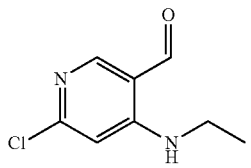

Example B1

A 0° C. solution of Example C3 (4.4 g, 20 mmol) in MeCN (50 mL) was treated drop-wise with a solution of 65% ethylamine in water (2.7 g, 39 mmol), warmed to RT and stirred. The reaction was concentrated and the residue was washed with water to give ethyl 6-chloro-4-(ethylamino)nicotinate (3.9 g, 91% yield). $^1$H NMR (400 MHz, DMSO-$d_6$): δ 8.51 (s, 1H), 8.08 (s, 1H), 6.53 (m, 1H), 4.19 (q, J=7.2 Hz, 2H), 2.78 (q, J=7.2 Hz, 2H), 1.28 (t, J=7.2 Hz, 3H), 1.13 (t, J=7.2 Hz, 3H); MS (ESI) m/z: 229.1[M+H]$^+$.

A −50° C. solution of ethyl 6-chloro-4-(ethylamino)nicotinate (3.9 g, 17 mmol) in THF (50 mL) was treated with $LiAlH_4$ (3.6 g, 95 mmol), allowed to warm to 0° C. and stirred for 1 h. The mixture was quenched with 10% NaOH (3.6 mL), filtered and the filtrate treated with water and extracted with EtOAc (3×). The combined organics were washed with brine, dried ($MgSO_4$) and concentrated in vacuo to provide (6-chloro-4-(ethylamino)pyridin-3-yl) methanol (2.5 g, 79% yield). $^1$H NMR (400 MHz, DMSO- $d_6$): δ 7.84 (s, 1H), 6.55 (s, 1H), 6.17 (m, 1H), 5.25 (t, J=5.2 Hz, 1H), 4.44 (q, J=7.2 Hz, 2H), 3.23 (m, 2H), 1.23 (t, J=7.2 Hz, 3H).

To a solution of (6-chloro-4-(ethylamino)pyridin-3-yl) methanol (2.5 g, 13.4 mmol) in DCM (30 mL) was added $MnO_2$ (5.8 g, 67 mmol) and the reaction mixture was stirred at RT overnight. The reaction mixture was filtered and the filtrate was concentrated in vacuo to give 6-chloro-4-(ethylamino)nicotinaldehyde (2.2 g, 89% yield). $^1$H NMR (400 MHz, $CDCl_3$): δ 9.82 (s, 1H), 8.51 (br s, 1H), 8.27 (s, 1H), 6.56 (s, 1H), 3.28 (m, 2H), 1.31 (t, J=7.2 Hz, 3H); MS (ESI) m/z: 185.0 $[M+H]^+$.

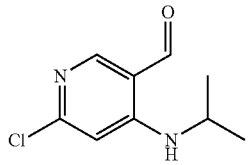

Example B2

Using the three-step procedure of Example B1, Example C3 (20 g, 91 mmol) and isopropylamine (60% in water, 18 g, 182 mmol) were converted to 6-chloro-4-(isopropylamino)nicotinaldehyde (16 g, 81% yield). $^1$H NMR (400 MHz, DMSO-$d_6$): δ 9.82 (s, 1H), 8.43-8.39 (m, 2H), 6.83 (s, 1H), 3.84 (m, 1H), 1.17 (d, J=6.4 Hz, 6H).

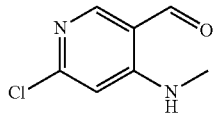

Example B3

A 0° C. solution of ethyl 4,6-dichloronicotinate (5 g, 22.8 mmol) in MeCN (30 mL) was treated drop-wise with aqueous methylamine (65%, 5.2 g, 45.6 mmol), warmed to RT and stirred for 8 h. The mixture was concentrated to dryness, the residue suspended in $H_2O$ and extracted with EtOAc (3×). The combined extracts were washed with brine, dried ($MgSO_4$) and concentrated to give ethyl 6-chloro-4-(methylamino)nicotinate (4 g, 82% yield), which was used in the next step without further purification. $^1$H NMR (300 MHz, DMSO-$d_6$): δ 8.48 (s, 1H), 8.04 (d, J=4.5 Hz, 1H), 6.71 (s, 1H), 4.27 (q, J=6.9 Hz, 2H), 2.85 (d, J=5.1 Hz, 3H), 1.29 (t, J=6.9 Hz, 3H).

A 0° C. solution of ethyl 6-chloro-4-(methylamino)nicotinate (4 g, 18.7 mmol) in THF (40 mL), under a $N_2$ atmosphere, was treated portion-wise with $LiAlH_4$ (1.4 g, 37.4 mmol), stirred for 20 min, then carefully treated with water followed by 2 N NaOH. The suspension was filtered and the filtrate was concentrated to afford (6-chloro-4-(methylamino)pyridin-3-yl)methanol (2.9 g, 91% yield), which was used in next step without purification. $^1$H NMR (400 MHz, DMSO-$d_6$): δ 7.96 (s, 1H), 6.63 (s, 1H), 6.46 (s, 1H), 5.04 (s, 1H), 4.39 (m, 2H), 2.81-2.68 (m, 3H).

A mixture of (6-chloro-4-(methylamino)pyridin-3-yl) methanol (2.9 g, 16.7 mmol) and $MnO_2$ (11.7 g, 133.6 mmol) in anhydrous DCM (25 mL) was stirred at 30° C. for 6 h. The reaction mixture was cooled to RT and filtered. The filtrate was concentrated in vacuo to give 6-chloro-4-(methylamino)nicotinaldehyde (2.5 g, 87% yield). $^1$H NMR (400 MHz, DMSO-$d_6$): δ 9.83 (s, 1H), 8.52 (br s, 1H), 8.40 (s, 1H), 6.75 (s, 1H), 2.87 (d, J=5.8 Hz, 3H); MS (ESI) m/z: 171.0 $[M+H]^+$.

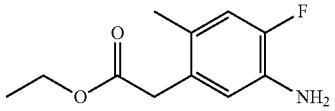

Example C1

To stirring fuming $HNO_3$ (90 wt %, 30.0 mL, 643 mmol) at −15° C. was added 4-fluoro-2-methylphenylacetic acid (15 g, 89.2 mmol) in portions such that the internal temperature remained below −10° C. After completing the addition the reaction was stirred with warming to 5° C. over 15 min. The mixture was poured onto ice (400 g), stirred vigorously until the ice had completely melted and the resulting solid was collected by filtration, rinsed well with $H_2O$ and dried on the filter to afford 2-(4-fluoro-2-methyl-5-nitrophenyl)acetic acid (18.43 g, 97% yield) as a pale yellow solid. $^1$H NMR (400 MHz, acetone-$d_6$): δ 8.06 (d, J=7.6 Hz, 1H), 7.36 (d, J=12.0 Hz, 1H), 3.84 (s, 2H), 2.44 (s, 3H).

2-(4-Fluoro-2-methyl-5-nitrophenyl)acetic acid (18.43 g, 86.5 mmol) and conc. $H_2SO_4$ (4.00 mL) were combined in EtOH (300 mL) and heated at 85° C. for 2.5 h. The mixture was cooled to RT, concentrated, the residue dissolved in MTBE and washed with $H_2O$ (2×), then brine (2×), dried ($MgSO_4$), and evaporated to afford ethyl 2-(4-fluoro-2-methyl-5-nitrophenyl)acetate (16.79 g, 81% yield) as a dark orange oil which was used without further purification. MS (ESI) m/z: 242.0 $(M+H)^+$.

A solution of ethyl 2-(4-fluoro-2-methyl-5-nitrophenyl) acetate (16.79 g, 69.6 mmol) in EtOH (60 mL) was treated with 10% Pd/C (50% wet, 7.41 g, 3.48 mmol) and hydrogenated (3.5 atm) for 2 h. The solids were removed via filtration through diatomaceous earth, rinsed with EtOH and the filtrate was concentrated to afford ethyl 2-(5-amino-4-fluoro-2-methylphenyl)acetate (13.18 g, 90% yield) as a brown oil. $^1$H NMR (400 MHz, DMSO-$d_6$): δ 6.80 (d, J=12.4 Hz, 1H), 6.59 (d, J=9.6 Hz, 1H), 4.86 (s, 2H), 4.05 (q, J=7.2 Hz, 2H), 3.46 (s, 2H), 2.05 (s, 3H), 1.17 (t, J=7.2 Hz, 3H); MS (ESI) m/z: 212.2 $(M+H)^+$.

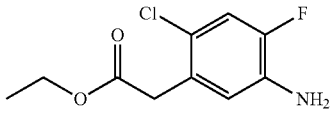

Example C2

$HNO_3$ (10.35 g, 98.6 mmol) was added drop-wise to a −10° C. solution of 2-(2-chloro-4-fluorophenyl)acetic acid (16.9 g, 89.6 mmol) in conc. $H_2SO_4$ (60 mL), stirred at 0° C. for 10 min, then carefully poured into ice water. The off-white solid was collected by filtration and dried to give 2-(2-chloro-4-fluoro-5-nitrophenyl)acetic acid (20.5 g, 98% yield). $^1$H NMR (400 Hz, DMSO-$d_6$): δ 12.71 (br s, 1H), 8.33 (d, J=8.0 Hz, 1H), 7.92 (d, J=11.2 Hz, 1H), 3.85 (s, 2H).

A 0° C. solution of 2-(2-chloro-4-fluoro-5-nitrophenyl) acetic acid (20.5 g, 88 mmol) in EtOH (150 mL) was treated with sulfuryl dichloride (21 g, 0.17 mol), then heated to reflux for 1 h. The reaction mixture was concentrated under reduced pressure and treated with satd. $Na_2CO_3$ to pH 7-8. The resultant mixture was extracted with EtOAc (3×) and the combined organic layers were washed with brine, dried ($MgSO_4$) and concentrated to give ethyl 2-(2-chloro-4-fluoro-5-nitrophenyl)acetate (22.5 g, 98% yield). $^1$H NMR (400 Hz, DMSO-$d_6$): δ 8.32 (d, J=8.0 Hz, 1H), 7.91 (d, J=11.2 Hz, 1H), 4.09 (q, J=7.2 Hz, 2H), 3.92 (s, 2H), 1.17 (t, J=7.2 Hz, 3H).

A solution of ethyl 2-(2-chloro-4-fluoro-5-nitrophenyl) acetate (22.5 g, 86.2 mmol) in EtOH (200 mL) was stirred with Raney Ni (20% slurry in water, 5.0 g, 17 mmol) under a hydrogen atmosphere (30 psi) for 5 h. The catalyst was removed by filtration and the filtrate was concentrated to give ethyl 2-(5-amino-2-chloro-4-fluorophenyl)acetate (19 g, 95% yield). $^1$H NMR (400 MHz, DMSO-$d_6$): δ 7.10 (d, J=11.2 Hz, 1H), 6.71 (d, J=9.2 Hz, 1H), 5.27 (s, 2H), 4.05 (q, J=6.8 Hz, 2H), 3.57 (s, 2H), 1.14 (t, J=6.8 Hz, 3H); MS (ESI) m/z: 232.0 $[M+H]^+$.

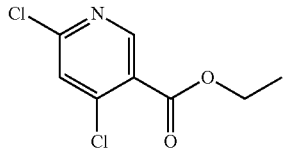

Example C3

3-Oxo-pentanedioic acid diethyl ester (101 g, 0.5 mmol), triethyl orthoformate (81.4 g, 0.55 mol) and acetic anhydride (102 g, 1 mol) were combined and heated to 120° C. for 2 h. The resulting mixture was cooled to RT and dissolved in DCM (1 L). After further cooling to 0° C., ammonia (30%, 80 mL) was added and the reaction mixture was allowed to warm to RT overnight. The product was extracted with water (2×) and the aqueous layer was acidified to pH 5 with conc. HCl. The precipitate was collected by filtration to afford ethyl 4,6-dihydroxynicotinate (60.0 g, 60% yield). $^1$H NMR (400 MHz, DMSO-$d_6$): δ 7.99 (s, 1H), 5.58 (s, 1H), 4.23 (q, J=6.8, 14.0 Hz, 2H), 1.25 (t, J=7.2 Hz, 3H); MS (ESI) m/z: 184.1 $[M+H]^+$.

Ethyl 4,6-dihydroxynicotinate (60 g, 0.328 mol) was added slowly to $POCl_3$ (500 mL), then heated to reflux for 2 h. The resulting mixture was distilled under reduced pressure to remove excess $POCl_3$. The residue was poured into ice water and stirred for 30 minutes before extracting with EtOAc (3×). The combined extracts were washed with brine, dried ($MgSO_4$) and concentrated in vacuo to give ethyl 4,6-dichloronicotinate (65 g, 90%, yield). $^1$H NMR (300 MHz, DMSO-$d_6$): δ 8.80 (s, 1H), 7.95 (s, 1H), 4.34 (q, J=6.9 Hz, 2H), 1.31 (t, J=6.9 Hz, 3H); MS (ESI) m/z: 220.1 $[M+H]^+$.

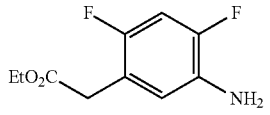

Example C4

A 0° C. solution of (2,4-difluoro-phenyl)acetic acid (14.5 g, 0.084 mol) in $H_2SO_4$ (60 mL) was treated drop-wise with 69% $HNO_3$ (6 mL), stirred at 0° C. for 35 min, then poured into ice water. The aqueous layer was extracted with EtOAc, and the organic extracts were washed with brine, dried ($Na_2SO_4$), concentrated in vacuo and purified by silica gel chromatography to give (2,4-difluoro-5-nitro-phenyl)acetic acid (16 g, 88% yield). $^1$H NMR (400 MHz, DMSO-$d_6$): δ 8.30 (t, J=8.0 Hz, 1H), 7.68 (m, 1H), 3.75 (s, 2H).

A solution of (2,4-difluoro-5-nitro-phenyl)acetic acid (16 g, 74 mmol) in EtOH (200 mL) and 98% $H_2SO_4$ (14 mL) was refluxed at 80'C for 2.5 h under a $N_2$ atmosphere. The reaction mixture was poured into ice water, and the resultant solution was extracted with $Et_2O$. The combined organic extracts were washed with brine, dried ($Na_2SO_4$), concentrated in vacuo and purified by silica gel chromatography to give ethyl 2-(2,4-difluoro-5-nitrophenyl)acetate (16 g, 89% yield). $^1$H NMR (300 MHz, DMSO-$d_6$): δ 8.22 (t, J=8.1 Hz, 1H), 7.55 (t, J=11.1 Hz, 1H), 4.06 (m, 2H), 3.77 (s, 2H), 1.13 (t, J=6.9 Hz, 3H).

A mixture of ethyl 2-(2,4-difluoro-5-nitrophenyl)acetate (16 g, 130 mmol) and 10% Pd/C (1.6 g, 1.5 mmol) in EtOAc was hydrogenated (30 psi) at RT for 12 h. The catalyst was filtered off and the filtrate was evaporated. The residue was purified by column chromatography to give ethyl 2-(5-amino-2,4-difluorophenyl)acetate (14 g, 99% yield). $^1$H NMR (300 MHz, DMSO-$d_6$): δ 6.98 (t, J=9.9 Hz, 1H), 6.70 (t, J=7.8 Hz, 1H), 4.50 (s, 2H), 4.06 (m, 2H), 3.53 (s, 2H), 1.16 (t, J=6.9 Hz, 3H); MS (ESI) m/z: 216.2 $[M+H]^+$.

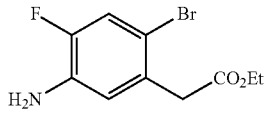

Example C5

Nitric acid (16.00 mL, 322 mmol) was cooled to −15° C. and treated portion-wise with 2-bromo-4-fluorophenylacetic acid (10.00 g, 42.9 mmol) maintaining an internal temperature of −10° C. to −5° C. Once the addition was complete the mixture was warmed to 5° C. over −15 minutes, poured onto ice (200 mL), stirred vigorously until all of the ice melted, and then filtered and rinsed with water. The resulting solid was dissolved in EtOAc, washed with brine, dried ($MgSO_4$) and concentrated to dryness to afford 2-(2-bromo-4-fluoro-5-nitrophenyl)acetic acid (10.93 g, 92% yield) as a bright yellow solid. $^1$H NMR (400 MHz, DMSO-$d_6$): δ 8.29 (d, 1H), 8.04 (d, 1H), 3.85 (s, 2H).

A solution of 2-(2-bromo-4-fluoro-5-nitrophenyl)acetic acid (5.00 g, 17.98 mmol) in EtOH (100 mL) was treated with concentrated sulfuric acid (0.999 mL, 17.98 mmol) and heated at 85° C. overnight. The mixture was cooled to RT and the EtOH was removed under reduced pressure. The resulting oil was dissolved in MTBE, washed with water (2×) then brine (2×), dried ($MgSO_4$), and concentrated to dryness. The material was purified by silica gel chromatography (EtOAc/Hex) to afford ethyl 2-(2-bromo-4-fluoro-5-nitrophenyl)acetate (2.679 g, 49% yield) as a yellow oil. $^1$H NMR (400 MHz, DMSO-$d_6$): δ 8.33 (d, 1H), 8.08 (d, 1H), 4.12 (q, 2H), 3.96 (s, 2H), 1.20 (t, 3H); MS (ESI) m/z: 308.0 $[M+H]^+$.

A solution of ethyl 2-(2-bromo-4-fluoro-5-nitrophenyl) acetate (2.127 g, 6.95 mmol) in EtOH (70 mL) was treated with iron powder (3.88 g, 69.5 mmol) and satd ammonium chloride (14.48 mL, 69.5 mmol) and heated to 55° C. for 1 h. The mixture was cooled to RT, filtered through a pad of diatomaceous earth, rinsed well with EtOH and the organics concentrated under reduced pressure. The resulting aqueous residue was treated with satd. $NaHCO_3$, extracted with EtOAc (2×) and the combined organics were washed with water, dried ($MgSO_4$), and concentrated to afford ethyl 2-(5-amino-2-bromo-4-fluorophenyl)acetate (1.792 g, 93% yield) as an amber oil. $^1$H NMR (400 MHz, DMSO-$d_6$): δ 7.25 (d, 1H), 6.76 (d, 1H), 5.35 (s, 2H), 4.08 (q, 2H), 3.61 (s, 2H), 1.18 (t, 3H); MS (ESI) m/z: 278.0 $[M+H]^+$.

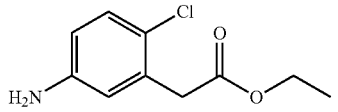

Example C6

A mixture of (2-chlorophenyl)acetic acid (15 g, 88 mmol) in conc. $H_2SO_4$ (100 mL) was cooled to −20° C. and treated drop-wise with conc. $HNO_3$ (9.4 g, 97 mmol). The resulting mixture was stirred at −20° C. for 0.5 h, poured into the ice-water, and extracted with EtOAc (3×). The combined organics were washed with brine, dried over $Na_2SO_4$ and concentrated in vacuo to give (2-chloro-5-nitrophenyl)acetic acid (15 g, 79% yield). $^1$H NMR (400 MHz, DMSO-$d_6$): δ 8.58 (s, 1H), 8.35 (m, 1H), 7.96 (m, 1H), 4.12 (s, 2H).

Thionyl chloride (16.7 g, 0.14 mol) was added drop-wise to a 0° C. solution of (2-chloro-5-nitro-phenyl)acetic acid (15 g, 0.07 mol) in EtOH (300 mL) and the resultant mixture was heated at reflux overnight. The reaction mixture was concentrated under reduced pressure, the residue poured into ice water, and extracted with EtOAc (2×). The combined organics were washed with brine, then satd. $NaHCO_3$, dried over $Na_2SO_4$ and concentrated in vacuo to give ethyl 2-(2-chloro-5-nitrophenyl)acetate (17 g, 99% yield). $^1$H NMR (400 MHz, DMSO-$d_6$): δ 8.35 (d, J=2.8 Hz, 1H), 8.12 (dd, J=8.4, 2.8 Hz, 1H), 7.72 (d, J=8.4 Hz, 1H), 4.10 (q, J=7.2 Hz, 2H), 3.96 (s, 2H), 1.15 (t, J=7.2 Hz, 3H).

Iron powder (2.5 g, 44.7 mmol) was added portion-wise to a solution of ethyl 2-(2-chloro-5-nitrophenyl)acetate (8 g, 4.68 mmol) and conc. HCl (12 M, 3.9 mL, 46.8 mmol) in EtOH (100 mL). The resultant mixture was heated at 50° C. for 2 h. The mixture was filtered and the filtrate cake was washed with satd. $Na_2CO_3$ until pH 8. The filter cake was further washed with EtOAc and the combined filtrates were partitioned between EtOAc and water. The organics were dried over $Na_2SO_4$ and concentrated in vacuo to provide ethyl 2-(5-amino-2-chlorophenyl)acetate (5.6 g, 56% yield). $^1$H NMR (400 MHz, DMSO-$d_6$): δ 7.00 (d, J=8.4 Hz, 1H), 6.50 (s, J=2.8 Hz, 1H), 6.44 (dd, J=8.4 Hz, 2.8 Hz, 1H), 5.20 (s, 2H), 4.05 (q, J=7.2 Hz, 2H), 3.56 (s, 2H), 1.15 (t, J=7.2 Hz, 3H).

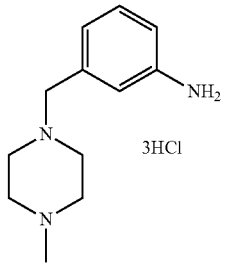

Example D1

A −20° C. mixture of N-methylpiperazine (233 μL, 2.097 mmol) and DIEA (452 mg, 3.49 mmol) in THF (12 mL) was treated drop-wise with a solution of t-butyl (3-bromomethyl) phenylcarbamate (500 mg, 1.747 mmol) in THF (3 mL) and stirred overnight as the cooling bath expired. The mixture was diluted with EtOAc, washed with satd. $NaHCO_3$, then brine, dried over $Na_2SO_4$ and concentrated to dryness to afford tert-butyl (3-((4-methylpiperazin-1-yl)methyl)phenyl)carbamate (544 mg, 102% yield). MS (ESI) m/z: 306.2 $[M+H]^+$.

A solution of tert-butyl (3-((4-methylpiperazin-1-yl) methyl)phenyl)carbamate (544 mg, 1.781 mmol) in dioxane (10 mL) was treated with HCl (g) for 10 min, then stirred at RT for 3 h. The mixture was concentrated to dryness to afford crude 3-((4-methylpiperazin-1-yl)methyl)aniline trihydrochloride (505 mg, 90% yield) which was used without further purification. MS (ESI) m/z: 306.2 $[M+H]^+$.

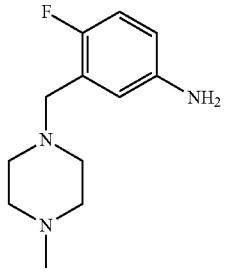

Example D2

A mixture of 2-fluoro-5-nitrotoluene (0.750 g, 4.83 mmol), NBS (1.549 g, 8.70 mmol) and AIBN (0.159 g, 0.967 mmol) in trifluorotoluene (15 ml) was heated to reflux overnight. The mixture was cooled RT, the solids removed via filtration and the filtrate concentrated to dryness and purified via silica gel chromatography (EtOAc/Hex) to afford ~80% pure 2-(bromomethyl)-1-fluoro-4-nitrobenzene (956 mg, 63% yield).

A solution of ~80% pure 2-(bromomethyl)-1-fluoro-4-nitrobenzene (0.956 g, 3.27 mmol) in THF (10 mL) was added slowly drop-wise to a −20° C. solution of 1-methylpiperazine (0.393 g, 3.92 mmol) and DIEA (1.142 mL, 6.54 mmol) in THF (20 mL), the mixture allowed to warm slowly to RT and stirred overnight. The resulting solid was removed via filtration and the filtrate was concentrated to dryness and purified via silica gel chromatography (EtOAc, MeOH/DCM) to afford 1-(2-fluoro-5-nitrobenzyl)-4-methylpiperazine (577 mg, 70% yield). $^1$H NMR (400 MHz, DMSO-$d_6$): δ 8.28 (dd, J=6.2, 3.0 Hz, 1H), 8.21 (ddd, J=9.0, 4.4, 3.0 Hz, 1H), 7.47 (t, J=9.1 Hz, 1H), 3.60 (s, 2H), 2.48-2.25 (br m, 8H), 2.14 (s, 3H); MS (ESI) m/z: 254.1 $[M+H]^+$.

A solution of 1-(2-fluoro-5-nitrobenzyl)-4-methylpiperazine (0.577 g, 2.278 mmol) in EtOH (7 mL) was treated with satd. $NH_4Cl$ (4.75 mL, 22.78 mmol) followed by iron (powder) (1.272 g, 22.78 mmol) and the mixture heated at 55° C. overnight. The mixture was cooled to RT and gravity-filtered through filter paper, rinsing well with MeOH and DCM. The filtrate was concentrated to dryness. The residue was treated with EtOAc and water, then concentrated to dryness again. The resulting material was treated with THF (20 mL), sonicated for several hours and the solvent decanted from the solids. The solids were treated with additional THF (20 mL), sonicated again and the solvent decanted. The solids were treated with THF (20 mL) for a third time, stirred vigorously overnight, then the liquid was decanted. The combined decanted liquids were concentrated to dryness, treated with DCM, filtered to remove solids and concentrated to dryness to afford very hydroscopic 4-fluoro-3-((4-methylpiperazin-1-yl)methyl)aniline (382 mg, 75% yield). $^1H$ NMR (400 MHz, DMSO-$d_6$): δ 6.81 (m, 1H), 6.49 (m, 2H), 4.99 (s, 2H), 3.44 (s, 2H), 3.32 (s, 8H), 2.69 (s, 3H); MS (ESI) m/z: 224.2 $[M+H]^+$.

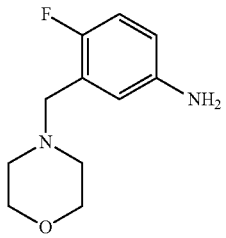

Example D3

A mixture of 1-fluoro-2-methyl-4-nitrobenzene (2.5 g, 16.12 mmol) and NBS (3.16 g, 17.73 mmol) in trifluorotoluene (45 mL) was treated with AIBN (66 mg, 0.403 mmol) and heated at 80° C. overnight. The mixture was cooled to RT, the solids removed via filtration and the filtrate concentrated to dryness. The residue was dissolved in EtOAc, washed with water, then brine, dried over $Na_2SO_4$, concentrated to dryness and purified via silica gel chromatography (EtOAc/Hex) to afford 2-(bromomethyl)-1-fluoro-4-nitrobenzene (1.915 g, 50% yield). $^1H$ NMR (400 MHz, DMSO-$d_6$): δ 8.53-8.52 (m, 1H), 8.28 (ddd, J=9.1, 4.4, 3.0 Hz, 1H), 7.55 (t, J=9.2 Hz, 1H), 4.80 (s, 2H).

A −20° C. mixture of DIEA (552 mg, 4.27 mmol) and morpholine (242 mg, 2.78 mmol) in THF (5 mL) was treated drop-wise with a solution of 2-(bromomethyl)-1-fluoro-4-nitrobenzene (500 mg, 2.137 mmol) in THF (5 mL) and stirred overnight as the cooling bath expired. The mixture was treated with EtOAc, washed with water, then brine, dried over $Na_2SO_4$ and concentrated to dryness to afford 4-(2-fluoro-5-nitrobenzyl)morpholine (414 mg, 81% yield). $^1H$ NMR (400 MHz, DMSO-$d_6$): δ 8.30 (dd, J=6.2, 3.0 Hz, 1H), 8.21 (ddd, J=9.0, 4.4, 3.0 Hz, 1H), 7.48 (t, J=9.1 Hz, 1H), 3.61 (s, 2H), 3.56 (t, J=4.6 Hz, 4H), 2.40 (t, J=4.4 Hz, 4H); MS (ESI) m/z: 241.1 $[M+H]^+$.

A mixture of 4-(2-fluoro-5-nitrobenzyl)morpholine (414 mg, 1.723 mmol) in EtOAc (15 mL) was treated with 10% Pd/C (100 mg) and hydrogenated (1 atm) for 3 h. The solids were removed via filtration, rinsed with EtOAc and the filtrate concentrated to dryness to afford 4-fluoro-3-(morpholinomethyl)aniline (200 mg, 55% yield). MS (ESI) m/z: 211.1 $[M+H]^+$.

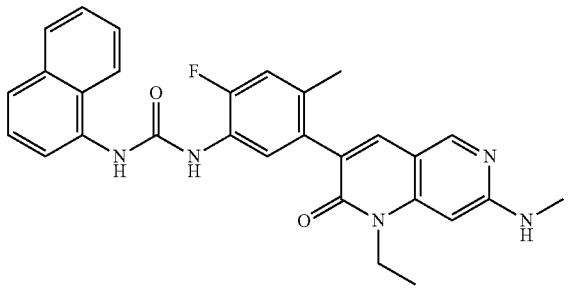

Example 1

Using general method B, 1-isocyanatonaphthalene (0.051 g, 0.3 mmol) and Example A2 (0.1 g, 0.3 mmol) were combined to afford 1-(5-(1-ethyl-7-(methylamino)-2-oxo-1,2-dihydro-1,6-naphthyridin-3-yl)-2-fluoro-4-methylphenyl)-3-(naphthalen-1-yl)urea as a white solid (0.115 g, 77% yield). $^1H$ NMR (400 MHz, DMSO-$d_6$): δ 9.16 (s, 1H), 9.05 (s, 1H), 8.45 (s, 1H), 8.19 (d, J=8.4 Hz, 1H), 8.08-8.04 (m, 2H), 7.96 (d, J=7.6 Hz, 1H), 7.72 (s, 1H), 7.67-7.58 (m, 3H), 7.47 (t, J=8.0 Hz, 1H), 7.21 (d, J=12.4 Hz, 1H), 7.05-7.02 (m, 1H), 6.28 (s, 1H), 4.21-4.16 (m, 2H), 2.89 (d, J=4.8 Hz, 3H), 2.12 (s, 3H), 1.25 (t, J=6.8 Hz, 3H); MS (ESI) m/z: 496.3 $[M+H]^+$.

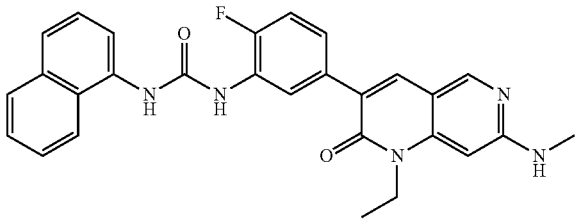

Example 2

Using general method B, 1-isocyanatonaphthalene (0.045 g, 0.26 mmol) and Example A39 (0.1 g, 0.3 mmol) were combined to afford 1-(5-(1-ethyl-7-(methylamino)-2-oxo-1,2-dihydro-1,6-naphthyridin-3-yl)-2-fluorophenyl)-3-(naphthalen-1-yl)urea as a white solid (0.062 g, 48% yield). $^1H$ NMR (400 MHz, DMSO-$d_6$): δ 9.23 (s, 1H), 9.14 (s, 1H), 8.56-8.54 (m, 1H), 8.52 (s, 1H), 8.23 (d, J=8.4 Hz, 1H), 8.11 (d, J=7.6 Hz, 1H), 8.09 (d, J=7.6 Hz, 1H), 7.93 (s, 1H), 7.71-7.59 (m, 3H), 7.53 (t, J=8.0 Hz, 1H), 7.36-7.34 (m, 2H), 7.10-7.07 (m 1H), 6.29 (s, 1H), 4.23 (q, J=6.8 Hz, 2H), 2.92 (d, J=4.8 Hz, 3H), 1.28 (t, J=7.2 Hz, 3H); MS (ESI) m/z: 482.0 $[M+H]^+$.

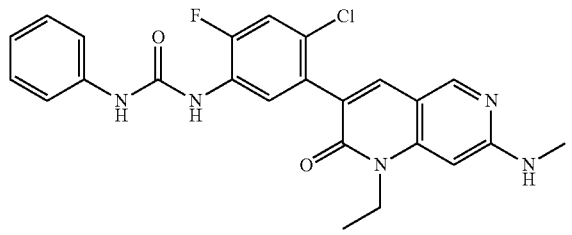

Example 3

Using general method B, 1-isocyanatobenzene (0.05 g, 0.420 mmol) and Example A5 (0.146 g, 0.420 mmol) were combined to provide 1-(4-chloro-5-(1-ethyl-7-(methylamino)-2-oxo-1,2-dihydro-1,6-naphthyridin-3-yl)-2-fluorophenyl)-3-phenylurea (0.180 g, 92% yield). $^1$H NMR (400 MHz, DMSO-$d_6$): δ δ 9.16 (s, 1H), 8.75 (s, 1H), 8.45 (s, 1H), 8.22 (d, J=9 Hz, 1H), 7.78 (s, 1H), 7.58 (d, J=10.5 Hz, 1H), 7.46 (s, 1H), 7.44 (s, 1H), 7.30 (m, 2H), 7.08 (m, 1H), 7.00 (s, 1H), 6.27 (s, 1H), 4.18 (q, J=5 Hz, 2H), 2.89 (d, J=5 Hz, 3H), 1.24 (t, J=6 Hz, 3H); MS (ESI) m/z: 466.0 [M+H]$^+$.

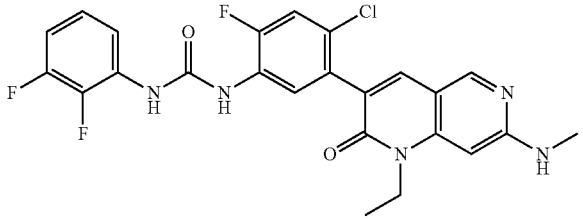

Example 4

Using general method A, 2,3-difluorobenzoic acid (0.100 g, 0.633 mmol) and Example A5 (0.219 g, 0.633 mmol) were combined to provide 1-(4-chloro-5-(1-ethyl-7-(methylamino)-2-oxo-1,2-dihydro-1,6-naphthyridin-3-yl)-2-fluorophenyl)-3-(2,3-difluorophenyl)urea (0.172 g, 54% yield). $^1$H NMR (400 MHz, DMSO-$d_6$): δ 9.27 (s, 1H), 9.24 (s, 1H), 8.45 (s, 1H), 8.22 (d, J=10 Hz, 1H), 7.96 (m, 1H), 7.77 (s, 1H), 7.58 (d, J=12 Hz, 1H), 7.18-7.00 (m, 3H), 6.27 (s, 1H), 4.17 (q, J=6 Hz, 2H), 2.90 (d, J=5.5 Hz, 3H), 1.24 (t, J=6 Hz, 3H); MS (ESI) m/z: 502.0 [M+H]$^+$.

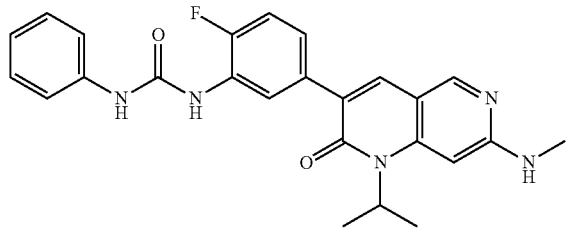

Example 5

Using general method B, phenyl isocyanate (0.036 g, 0.302 mmol) and Example A40 (0.1 g, 0.302 mmol) were combined to provide 1-(2-fluoro-5-(1-isopropyl-7-(methylamino)-2-oxo-1,2-dihydro-1,6-naphthyridin-3-yl)phenyl)-3-phenylurea (0.94 g, 70% yield). $^1$H NMR (400 MHz, DMSO-$d_6$): δ 9.03 (s, 1H), 8.62 (s, 1H), 8.49 (s, 1H), 8.42 (d, J=8 Hz, 1H), 7.86 (s, 1H), 7.52 (s, 1H), 7.50 (s, 1H), 7.32 (m, 4H), 7.03 (m, 2H), 6.50 (br s, 1H), 3.40 (s, 1H), 2.91 (d, J=6 Hz, 3H), 1.60 (d, J=6 Hz, 6H); MS (ESI) m/z: 446.3 [M+H]$^+$.

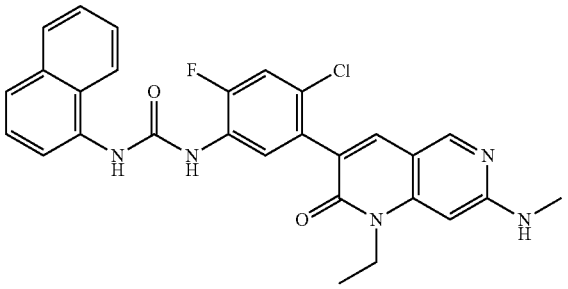

Example 6

Using general method B, 1-isocyanatonaphthalene (0.05 g, 0.29 mmol) and Example A5 (0.1 g, 0.29 mmol) were combined to afford 1-(4-chloro-5-(1-ethyl-7-(methylamino)-2-oxo-1,2-dihydro-1,6-naphthyridin-3-yl)-2-fluorophenyl)-3-(naphthalen-1-yl)urea as a white solid (0.121 g, 79% yield). $^1$H NMR (400 MHz, DMSO-$d_6$): δ 9.26 (b rs, 2H), 8.48 (s, 1H), 8.32 (d, J=8.8 Hz, 1H), 8.21 (d, J=8.8 Hz, 1H), 8.05 (dd, J=7.6 Hz, 0.8 Hz, 1H), 7.98 (d, J=8.4 Hz, 1H), 7.81 (s, 1H), 7.71-7.58 (m, 4H), 7.51 (t, J=8.0 Hz, 1H), 7.11 (q, J=4.8 Hz, 1H), 6.30 (s, 1H), 4.20 (q, J=6.8 Hz, 2H), 2.92 (d, J=4.8 Hz, 3H), 1.27 (t, J=6.8 Hz, 3H); MS (ESI) m/z: 516.0 [M+H]$^+$.

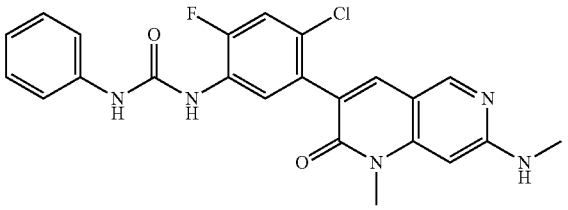

Example 7

Using general method B, phenyl isocyanate (0.050 g, 0.420 mmol) was reacted with Example A41 (0.070 g, 0.210 mmol) in EtOAc (2 mL) for 13 h to provide 1-(4-chloro-2-fluoro-5-(1-methyl-7-(methylamino)-2-oxo-1,2-dihydro-1,6-naphthyridin-3-yl)phenyl)-3-phenylurea (0.080 g, 84% yield). $^1$H NMR (400 MHz, DMSO-$d_6$): δ 9.08 (s, 1H), 8.68 (br s, 1H), 8.40 (s, 1H), 8.17 (d, J=9 Hz, 1H), 7.74 (s, 1H), 7.53 (d, J=11.5 Hz, 1H), 7.41 (m, 1H), 7.26 (m, 1H), 7.10 (m, 1H), 6.96 (m, 1H), 6.15 (s, 1H), 3.49 (s, 3H), 2.86 (d, J=5 Hz, 3H); MS (ESI) m/z: 452.0 [M+H]$^+$.

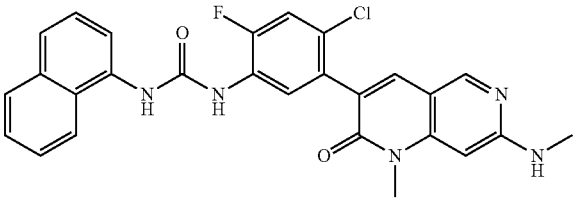

Example 8

Using general method B, 1-isocyanatonaphthalene (0.050 g, 0.296 mmol) was reacted with Example A41 (0.070 g, 0.210 mmol) in EtOAc (2 mL) at RT for 13 h to provide 1-(4-chloro-2-fluoro-5-(1-methyl-7-(methylamino)-2-oxo-1,2-dihydro-1,6-naphthyridin-3-yl)phenyl)-3-(naphthalen-1-yl)urea (0.07 g, 67% yield). $^1$H NMR (400 MHz, DMSO-$d_6$): δ 9.18 (s, 2H), 8.40 (s, 1H), 8.26 (d, J=9 Hz, 1H), 8.14 (d, J=9 Hz, 1H), 7.98 (d, J=7 Hz, 1H), 7.90 (d, J=8 Hz, 1H), 7.74 (s, 1H), 7.60 (m, 3H), 7.43 (t, J=8 Hz, 1H), 7.11 (m, 1H), 7.26 (m, 1H), 6.16 (s, 1H), 3.49 (s, 3H), 2.86 (d, J=5 Hz, 3H); MS (ESI) m/z: 502.0 [M+H]$^+$.

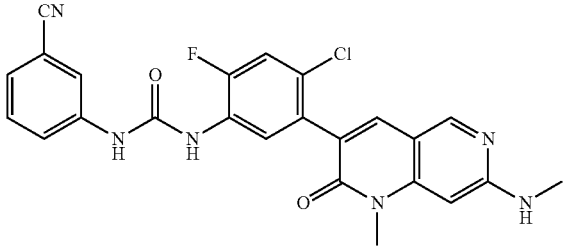

Example 9

Using general method B, 3-isocyanatobenzonitrile (0.050 g, 0.347 mmol) was reacted with Example A41 (0.070 g, 0.210 mmol) in EtOAc (2 mL) for 13 h to provide 1-(4-chloro-2-fluoro-5-(1-methyl-7-(methylamino)-2-oxo-1,2-dihydro-1,6-naphthyridin-3-yl)phenyl)-3-(3-cyanophenyl) urea (0.090 g, 90% yield). $^1$H NMR (400 MHz, DMSO-$d_6$): δ 9.42 (s, 1H), 8.86 (br s, 1H), 8.44 (s, 1H), 8.17 (d, J=9 Hz, 1H), 7.99 (m, 1H), 7.77 (s, 1H), 7.63 (m, 1H), 7.58 (d, J=11.5 Hz, 1H), 7.51 (t, J=7 Hz, 1H), 7.45 (m, 1H), 7.14 (m, 1H), 6.19 (s, 1H), 3.52 (s, 3H), 2.86 (d, J=5 Hz, 3H); MS (ESI) m/z: 477.0 [M+H]$^+$.

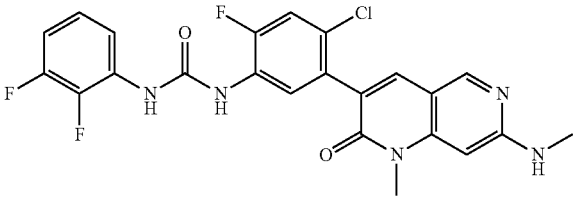

Example 10

Using general method A, 2,3-difluorobenzoic acid (0.071 g, 0.449 mmol), TEA (0.091 g, 0.898 mmol), DPPA (0.124 g, 0.449 mmol) and Example A41 (0.100 g, 0.299 mmol) were combined to provide 1-(4-chloro-2-fluoro-5-(1-methyl-7-(methylamino)-2-oxo-1,2-dihydro-1,6-naphthyridin-3-yl)phenyl)-3-(2,3-difluorophenyl)urea (0.070 g, 48% yield). $^1$H NMR (400 MHz, DMSO-$d_6$): δ 9.26 (br s, 1H), 9.22 (br s, 1H), 8.42 (s, 1H), 8.20 (d, J=10 Hz, 1H), 7.94 (m, 1H), 7.77 (s, 1H), 7.57 (d, J=12 Hz, 1H), 7.12 (m, 2H), 7.04 (m, 1H), 6.18 (s, 1H), 3.51 (s, 3H), 2.86 (d, J=5 Hz, 3H); MS (ESI) m/z: 488.0 [M+H]$^+$.

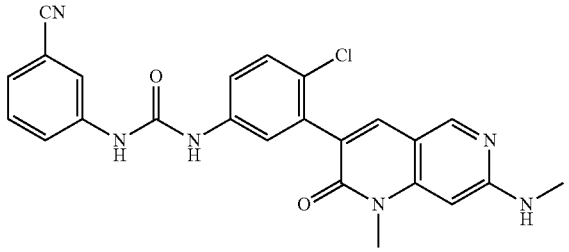

Example 11

Using general method B, 3-isocyanatobenzonitrile (0.070 g, 0.486 mmol) was reacted with Example A42 (0.070 g, 0.222 mmol) in EtOAc (2 mL) for 13 h to provide 1-(4-chloro-3-(1-methyl-7-(methylamino)-2-oxo-1,2-dihydro-1,6-naphthyridin-3-yl)phenyl)-3-(3-cyanophenyl)urea (55 mg, 54% yield). $^1$H NMR (400 MHz, DMSO-$d_6$): δ 9.13 (s, 1H), 9.07 (s, 1H), 8.45 (s, 1H), 8.00 (m, 1H), 7.79 (s, 1H), 7.69 (m, 1H), 7.59 (m, 1H), 7.52 (m, 1H), 7.47-7.44 (m, 3H), 7.17 (m, 1H), 6.22 (s, 1H), 3.55 (s, 3H), 290 (d, J=4.8 Hz, 3H); MS (ESI) m/z: 459.0 [M+H]$^+$.

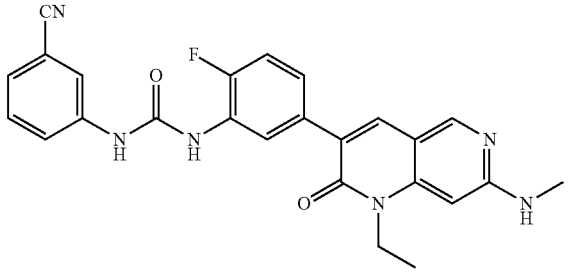

Example 12

Using general method B, 3-isocyanatobenzonitrile (0.032 g, 0.224 mmol) was reacted with Example A39 (0.070 g, 0.224 mmol) in EtOAc (5 mL) for 20 h to provide 1-(3-cyanophenyl)-3-(5-(1-ethyl-7-(methylamino)-2-oxo-1,2-dihydro-1,6-naphthyridin-3-yl)-2-fluorophenyl)urea (17 mg, 17% yield). $^1$H NMR (400 MHz, DMSO-$d_6$): δ 9.39 (s, 1H), 8.71 (d, J=2.3 Hz, 1H), 8.46 (s, 1H), 8.36 (dd, J=8.0, 2.2 Hz, 1H), 8.00 (t, J=1.8 Hz, 1H), 7.87 (s, 1H), 7.63 (ddd, J=8.2, 2.2, 1.2 Hz, 1H), 7.49 (t, J=7.9 Hz, 1H), 7.43 (dt, J=7.6, 1.4 Hz, 1H), 7.34-7.22 (m, 2H), 7.03 (m, 1H), 6.22 (s, 1H), 4.16 (q, J=7.0 Hz, 2H), 2.85 (d, J=4.8 Hz, 3H), 1.22 (t, J=7.0 Hz, 3H); MS (ESI) m/z: 457.2 [M+H]$^+$.

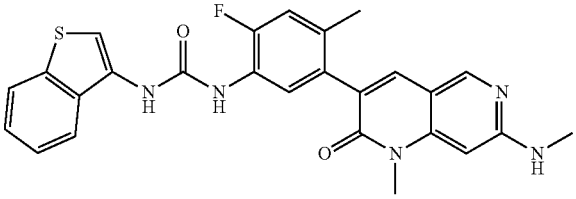

Example 13

Using general method A, benzothiophene-3-carboxylic acid (103 mg, 0.576 mmol), TEA (194 mg, 1.921 mmol), DPPA (165 mg, 0.600 mmol) and Example A43 (0.100 g, 0.299 mmol) were combined to provide 1-(benzo[b]thiophen-3-yl)-3-(2-fluoro-4-methyl-5-(1-methyl-7-(methylamino)-2-oxo-1,2-dihydro-1,6-naphthyridin-3-yl)phenyl) urea (140 mg, 59% yield). $^1$H NMR (400 MHz, DMSO-$d_6$): δ 9.42 (s, 1H), 8.85 (s, 1H), 8.40 (s, 1H), 8.03 (d, J=8.5 Hz, 1H), 7.95 (d, J=8.0 Hz, 1H), 7.88 (d, J=8.1 Hz, 1H), 7.68 (d, J=6.5 Hz, 2H), 7.48 (m, 1H), 7.41 (m, 1H), 7.16 (d, J=12.3 Hz, 1H), 7.03 (m, 1H), 6.18 (s, 1H), 3.51 (s, 3H), 2.86 (d, J=4.4 Hz, 3H), 2.08 (s, 3H); MS (ESI) m/z: 488.1 [M+H]$^+$.

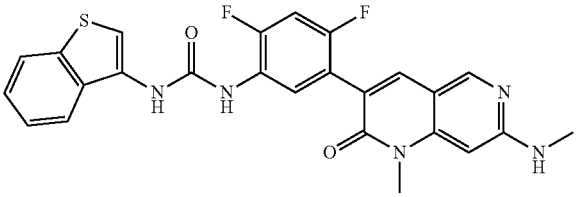

Example 14

Using general method A, benzo[b]thiophene-3-carboxylic acid (0.101 g, 0.569 mmol), TEA (0.144 g, 1.423 mmol), DPPA (0.196 g, 0.711 mmol) and Example A44 (0.150 g, 0.474 mmol) were combined to provide 1-(benzo[b]thiophen-3-yl)-3-(2,4-difluoro-5-(1-methyl-7-(methylamino)-2-oxo-1,2-dihydro-1,6-naphthyridin-3-yl)phenyl)urea (177 mg, 76% yield). $^1$H NMR (400 MHz, DMSO-$d_6$): δ 9.39 (s, 1H), 8.85 (s, 1H), 8.43 (s, 1H), 8.26 (t, J=8.5 Hz, 1H), 7.96 (d, J=8.1 Hz, 1H), 7.87 (d, J=8.0 Hz, 1H), 7.84 (s, 1H), 7.69 (s, 1H), 7.49 (t, J=7.6 Hz, 1H), 7.44-7.36 (m, 2H), 7.12-7.10 (m, 1H), 6.17 (s, 1H), 3.51 (s, 3H), 2.86 (d, J=4.8 Hz, 3H); MS (ESI) m/z: 492.0 [M+H]$^+$.

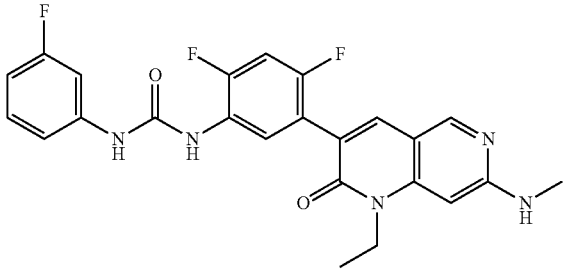

Example 15

3-Fluorophenyl isocyanate (81 mg, 0.444 mmol) was added to a solution of Example A7 (200 mg, 0.444 mmol) in THF (5 mL) and the mixture was stirred at RT overnight. The reaction was treated with additional isocyanate (10 mg) and stirred at RT for a further 4 h. The mixture was diluted with EtOAc, washed successively with water, satd. $NaHCO_3$, and brine, dried ($Na_2SO_4$), concentrated in vacuo, purified by reverse phase chromatography (MeCN/water with 0.1% TFA) and partially concentrated to give an aqueous solution. The solution was diluted with satd. $NaHCO_3$, extracted with EtOAc (2×) and the combined organics were washed with brine, dried ($Na_2SO_4$) and evaporated at reduced pressure to give 1-(5-(7-((4-methoxybenzyl)(methyl)amino)-1-ethyl-2-oxo-1,2-dihydro-1,6-naphthyridin-3-yl)-2,4-difluorophenyl)-3-(3-fluorophenyl) urea (207 mg, 79% yield, ~75% pure) as a light yellow solid, which was used without further purification. MS (ES-API) m/z: 588.2 [M+H]$^+$.

A solution of 1-(5-(7-((4-methoxybenzyl)(methyl)amino)-1-ethyl-2-oxo-1,2-dihydro-1,6-naphthyridin-3-yl)-2,4-difluorophenyl)-3-(3-fluorophenyl)urea (267 mg, 0.421 mmol) in TFA (3 mL) was stirred at RT for 40 min. The mixture was evaporated at reduced pressure, dissolved in EtOAc, washed with satd. $NaHCO_3$, then brine, dried ($Na_2SO_4$), concentrated in vacuo, purified by reverse phase chromatography (MeCN/water with 0.1% TFA) and partially concentrated to give an aqueous solution. The aqueous solution was diluted with satd. $NaHCO_3$ and allowed to precipitate. The white solid was collected by filtration, washed with water and dried in vacuo to give 1-(5-(1-ethyl-7-(methylamino)-2-oxo-1,2-dihydro-1,6-naphthyridin-3-yl)-2,4-difluorophenyl)-3-(3-fluorophenyl)urea (83 mg, 50% yield). $^1$H NMR (400 MHz, DMSO-$d_6$): δ 9.50 (br s, 1H), 8.80 (br s, 1H), 8.42 (s, 1H), 8.10-8.00 (m, 1H), 7.82 (s, 1H), 7.48 (d, 1H), 7.40-7.30 (m, 2H), 7.15-7.05 (m, 2H), 6.80-6.70 (m, 1H), 5.99 (s, 1H), 4.13 (m, 2H), 2.85 (s, 3H), 1.21 (m, 3H); MS (ES-API) m/z: 468.1 [M+H]$^+$.

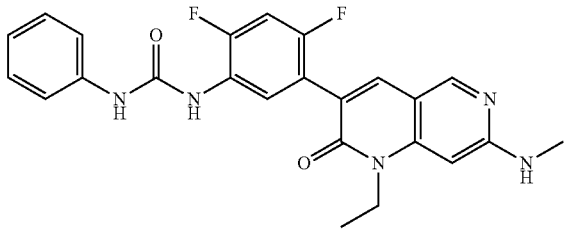

Example 16

Phenyl isocyanate (58 mg, 0.488 mmol) was added to a solution of Example A7 (200 mg, 0.444 mmol) and pyridine (140 mg, 1.776 mmol) in THF (5 mL) and the mixture was stirred at RT overnight. The mixture was diluted with EtOAc, water and satd. $NaHCO_3$; the resulting precipitate was collected by filtration, washed with EtOAc and dried in vacuo to give 1-(5-(7-((4-methoxybenzyl)(methyl)amino)-1-ethyl-2-oxo-1,2-dihydro-1,6-naphthyridin-3-yl)-2,4-difluorophenyl)-3-phenylurea (219 mg, 87% yield). MS (ES-API) m/z: 570.2 [M+H]$^+$.

A solution of 1-(5-(7-((4-methoxybenzyl)(methyl)amino)-1-ethyl-2-oxo-1,2-dihydro-1,6-naphthyridin-3-yl)-2,4-difluorophenyl)-3-phenylurea (219 mg, 0.384 mmol) in TFA (2.0 mL) was stirred at RT for 1 h. The mixture was concentrated in vacuo, dissolved in EtOAc, washed with satd. $NaHCO_3$ and brine, dried ($Na_2SO_4$), warmed to reflux in MeOH (5 mL) with the drying agent, filtered free of drying agent (while hot), concentrated in vacuo and treated with 4M HCl/dioxane (0.2 mL). The mixture was evaporated at reduced pressure and then triturated with $Et_2O$. The solid was collected by filtration, purified by reverse phase chromatography (MeCN/water with 0.1% TFA) and concentrated in vacuo to give an aqueous residue. The aqueous solution was treated with satd. $NaHCO_3$ and allowed to precipitate. The solid was collected by filtration, washed with water and dried in vacuo to give 1-(5-(1-ethyl-7-(methylamino)-2-oxo-1,2-dihydro-1,6-naphthyridin-3-yl)-2,4-difluorophenyl)-3-phenylurea (87 mg, 50% yield). $^1$H NMR (400 MHz, DMSO-$d_6$), δ 9.01 (s, 1H), 8.52 (s, 1H), 8.42 (s, 1H), 8.12 (m, 1H), 7.81 (s, 1H), 7.42-7.24 (m, 5H), 7.05-6.94 (m, 2H), 6.23 (s, 1H), 4.13 (m, 2H), 2.85 (s, 3H), 1.20 (m, 3H); MS (ES-API) m/z: 450.1 [M+H]$^+$.

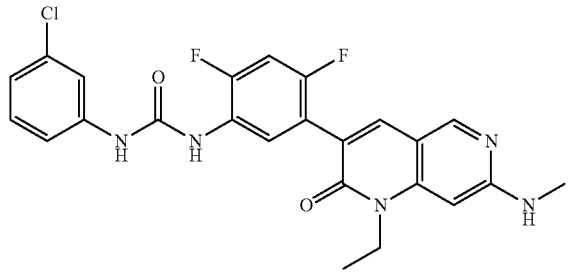

Example 17

Using a procedure analogous to Example 16, Example A7 (200 mg, 0.444 mmol) and 3-chlorophenyl isocyanate (58 mg, 0.488 mmol) were combined to give 1-(5-(7-((4-methoxybenzyl)(methyl)amino)-1-ethyl-2-oxo-1,2-dihydro-1,6-naphthyridin-3-yl)-2,4-difluorophenyl)-3-(3-chlorophenyl)urea (229 mg, 85% yield). MS (ES-API) m/z: 604.2 [M+H]$^+$.

Using a procedure analogous to Example 16, 1-(5-(7-((4-methoxybenzyl)(methyl)amino)-1-ethyl-2-oxo-1,2-dihydro-1,6-naphthyridin-3-yl)-2,4-difluorophenyl)-3-(3-chlorophenyl)urea (219 mg, 0.384 mmol) was converted to 1-(3-chlorophenyl)-3-(5-(1-ethyl-7-(methylamino)-2-oxo-1,2-dihydro-1,6-naphthyridin-3-yl)-2,4-difluorophenyl)urea (98 mg, 53% yield). $^1$H NMR (400 MHz, DMSO-$d_6$): δ 9.20 (br s, 1H), 8.65 (br s, 1H), 8.42 (s, 1H), 8.08 (t, 1H), 7.82 (s, 1H), 7.70 (s, 1H), 7.38-7.19 (m, 3H), 7.05 (s, 1H), 7.01-6.99 (m, 1H), 6.21 (s, 1H), 4.14 (q, 2H), 2.85 (s, 3H), 1.19 (t, 3H); MS (ES-API) m/z: 488.1 [M+H]$^+$.

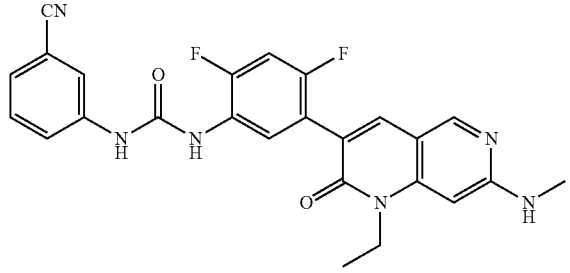

Example 18

Using a procedure analogous to Example 16, Example A7 (200 mg, 0.444 mmol) and 3-cyanophenyl isocyanate (70 mg, 0.488 mmol) were combined to give 1-(5-(7-((4-methoxybenzyl)(methyl)amino)-1-ethyl-2-oxo-1,2-dihydro-1,6-naphthyridin-3-yl)-2,4-difluorophenyl)-3-(3-cyanophenyl)urea (240 mg, 91% yield). MS (ES-API) m/z: 595.2 [M+H]$^+$.

Using a procedure analogous to Example 16, 1-(5-(7-((4-methoxybenzyl)(methyl)amino)-1-ethyl-2-oxo-1,2-dihydro-1,6-naphthyridin-3-yl)-2,4-difluorophenyl)-3-(3-cyanophenyl)urea (219 mg, 0.384 mmol) was converted to 1-(3-cyanophenyl)-3-(5-(1-ethyl-7-(methylamino)-2-oxo-1,2-dihydro-1,6-naphthyridin-3-yl)-2,4-difluorophenyl)urea (108 mg, 56% yield). $^1$H NMR (400 MHz, DMSO-$d_6$): δ 9.05 (br s, 2H), 8.42 (s, 1H), 8.06 (m, 1H), 7.96 (s, 1H), 7.81 (s, 1H), 7.63-7.60 (m, 1H), 7.49-7.33 (m, 3H), 7.05 (br s, 1H), 6.23 (s, 1H), 4.14 (q, 2H), 2.85 (s, 3H), 1.20 (t, 3H); MS (ES-API) m/z: 475.2 [M+H]$^+$.

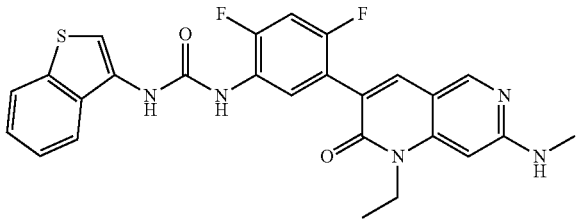

Example 19

Using general method A, benzo[b]thiophene-3-carboxylic acid (113 mg, 0.636 mmol), TEA (245 mg, 2.422 mmol), DPPA (200 mg, 0.727 mmol) and Example A8 (200 mg, 0.605 mmol) were combined and purified via precipitation to provide 1-(benzo[b]thiophen-3-yl)-3-(5-(1-ethyl-7-(methylamino)-2-oxo-1,2-dihydro-1,6-naphthyridin-3-yl)-2,4-difluorophenyl)urea (153 mg, 50% yield). $^1$H NMR (400 MHz, DMSO-$d_6$): δ 9.51 (s, 1H), 8.94 (s, 1H), 8.43 (s, 1H), 8.23 (t, 1H), 7.96-7.91 (m, 2H), 7.83 (s, 1H), 7.68 (s, 1H), 7.49-7.35 (m, 3H), 7.07-7.05 (m, 1H), 6.23 (s, 1H), 4.14 (q, 2H), 2.85 (s, 3H), 1.21 (t, 3H); MS (ES-API) m/z: 506.1 [M+H]$^+$.

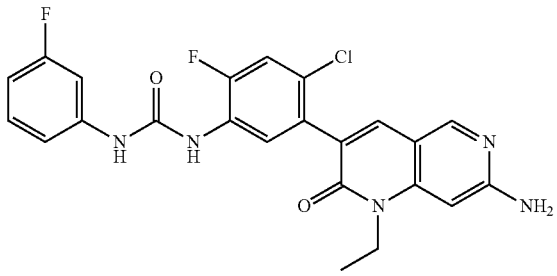

Example 20

DMF (0.2 mL) and 3-fluorophenyl isocyanate (67 mg, 0.486 mmol) were added to a slurry of Example A9 (200 mg, 0.442 mmol) and pyridine (140 mg, 1.766 mmol) in THF (5 mL) and the mixture was stirred at RT overnight. The mixture was diluted with EtOAc and water, warmed, then cooled to RT and the resulting solid collected via filtration. The solid was washed with EtOAc and dried in vacuo to give 1-(5-(7-(4-methoxybenzylamino)-1-ethyl-2-oxo-1,2-dihydro-1,6-naphthyridin-3-yl)-4-chloro-2-fluorophenyl)-3-(3-fluorophenyl)urea (206 mg, 79% yield). MS (ES-API) m/z: 590.2 $[M+H]^+$.

Using a procedure analogous to Example 15, 1-(5-(7-(4-methoxybenzylamino)-1-ethyl-2-oxo-1,2-dihydro-1,6-naphthyridin-3-yl)-4-chloro-2-fluorophenyl)-3-(3-fluorophenyl)urea (204 mg, 0.346 mmol) was converted to 1-(5-(7-amino-1-ethyl-2-oxo-1,2-dihydro-1,6-naphthyridin-3-yl)-4-chloro-2-fluorophenyl)-3-(3-fluorophenyl)urea (66 mg, 40% yield). $^1$H NMR (400 MHz, DMSO-$d_6$): δ 9.29 (s, 1H), 8.74 (s, 1H), 8.35 (s, 1H), 8.13 (d, 1H), 7.77 (s, 1H), 7.53 (d, 1H), 7.47-7.43 (m, 1H), 7.32-7.26 (m, 1H), 7.07-7.04 (m, 1H), 6.81-6.76 (m, 1H), 6.54 (s, 2H), 6.33 (s, 1H), 4.08 (q, 2H), 1.20 (t, 3H); MS (ES-API) m/z: 470.1 $[M+H]^+$.

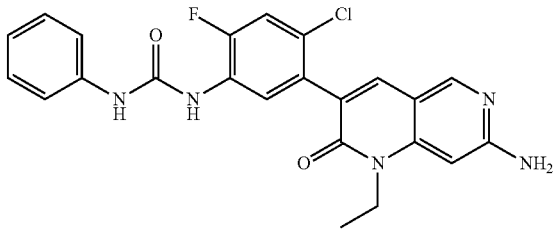

Example 21

DMF (0.2 mL) and phenyl isocyanate (58 mg, 0.486 mmol) were added to a slurry of Example A9 (200 mg, 0.442 mmol) and pyridine (140 mg, 1.766 mmol) in THF (5 mL) and the mixture stirred at RT overnight. The mixture was diluted with EtOAc and water and warmed. The organic phase was separated, washed with brine, dried ($Na_2SO_4$), concentrated in vacuo, purified by reverse phase chromatography (MeCN/water with 0.1% TFA) and concentrated to give an aqueous residue. The aqueous residue was treated with satd. $NaHCO_3$ and allowed to precipitate. The solid was collected by filtration, washed with water and dried in vacuo to provide 1-(5-(7-(4-methoxybenzylamino)-1-ethyl-2-oxo-1,2-dihydro-1,6-naphthyridin-3-yl)-4-chloro-2-fluorophenyl)-3-phenylurea (56 mg, 22% yield). MS (ES-API) m/z: 572.2 $[M+H]^+$.

Using a procedure analogous to Example 15, 1-(5-(7-(4-methoxybenzylamino)-1-ethyl-2-oxo-1,2-dihydro-1,6-naphthyridin-3-yl)-4-chloro-2-fluorophenyl)-3-phenylurea (109 mg, 0.191 mmol) was converted to 1-(5-(7-amino-1-ethyl-2-oxo-1,2-dihydro-1,6-naphthyridin-3-yl)-4-chloro-2-fluorophenyl)-3-phenylurea (45 mg, 53% yield). MS (ES-API) m/z: 452.1 $[M+H]^+$.

A 25 mg/mL solution of methanesulfonic acid in DCM (0.424 mL, 0.110 mmol) was added to a solution of 1-(5-(7-amino-1-ethyl-2-oxo-1,2-dihydro-1,6-naphthyridin-3-yl)-4-chloro-2-fluorophenyl)-3-phenylurea (45 mg, 0.100 mmol) in DCM (4 mL), the mixture stirred for 15 min. and then evaporated at reduced pressure to give a solid. The solid was dissolved in MeCN and water, frozen, and lyophilized to give 1-(5-(7-amino-1-ethyl-2-oxo-1,2-dihydro-1,6-naphthyridin-3-yl)-4-chloro-2-fluorophenyl)-3-phenylurea methanesulfonate (1.4 equiv.) (53 mg, 97% yield). $^1$H NMR (400 MHz, DMSO-$d_6$): δ 9.12 (s, 1H), 8.76 (s, 1H), 8.56 (s, 1H), 8.21 (d, 1H), 7.92 (s, 1H), 7.90 (br s, 2H), 7.60-7.56 (m, 1H), 7.42-7.40 (m, 2H), 7.28-7.24 (m, 2H), 6.98-6.95 (m, 1H), 6.74 (s, 1H), 4.12 (q, 2H), 2.34 (s, ~4H), 1.23 (t, 3H); MS (ES-API) m/z: 452.1 $[M+H]^+$.

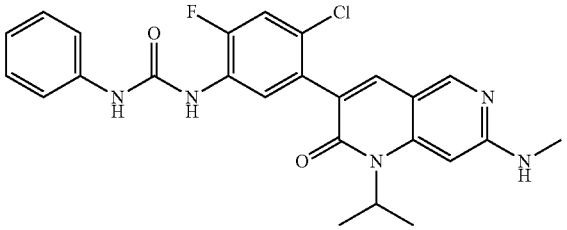

Example 22

Example A11 (0.12 g, 0.33 mmol), TEA (0.046 mL, 0.33 mmol) and phenyl isocyanate (0.044 g, 0.36 mmol) were combined in THF (4 mL), stirred at RT for 20 h, concentrated in vacuo and purified by silica gel chromatography (EtOAc/DCM) to afford 1-(4-chloro-2-fluoro-5-(1-isopropyl-7-(methylamino)-2-oxo-1,2-dihydro-1,6-naphthyridin-3-yl)phenyl)-3-phenylurea (97 mg, 61% yield) as a white solid. $^1$H NMR (400 MHz, DMSO-$d_6$): δ 9.07 (s, 1H), 8.67 (d, J=2.0 Hz, 1H), 8.37 (s, 1H), 8.16 (d, J=8.8 Hz, 1H), 7.67 (s, 1H), 7.51 (d, J=10.8 Hz, 1H), 7.41 (d, J=7.6 Hz, 2H), 7.28-7.24 (m, 2H), 6.98-6.94 (m, 2H), 6.44 (s, 1H), 5.31-4.82 (br s, 1H), 2.85 (d, J=4.8 Hz, 3H), 1.51 (d, J=7.2 Hz, 6H); MS (ESI) m/z: 480.2 $[M+H]^+$.

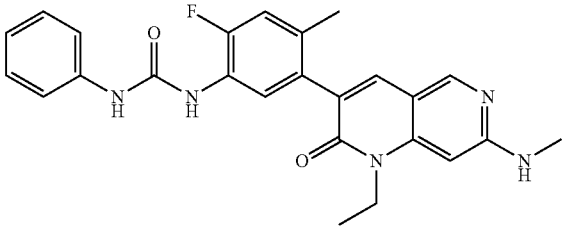

Example 23

A solution of pyridine (0.248 mL, 3.06 mmol) and phenyl isocyanate (0.100 mL, 0.919 mmol) in DMF (0.4 mL) was added to a solution of Example A2 (0.25 g, 0.766 mmol) in THF (5 mL) and the mixture was stirred at RT. After 14 h, the solid was filtered, washed with THF, and dried under vacuum to obtain 1-(5-(1-ethyl-7-(methylamino)-2-oxo-1,2-dihydro-1,6-naphthyridin-3-yl)-2-fluoro-4-methylphenyl)-3-phenylurea (280 mg, 79% yield). $^1$H NMR (400 MHz, DMSO-$d_6$): δ 9.00 (s, 1H), 8.46 (d, J=2.0 Hz, 1H), 8.40 (s, 1H), 7.93 (d, J=8.4 Hz, 1H), 7.66 (s, 1H), 7.40 (m, 2H), 7.25 (m, 2H), 7.12 (d, J=12.4 Hz, 1H), 6.96 (m, 2H), 6.24 (s, 1H), 4.14 (q, J=6.8 Hz, 2H), 2.85 (d, J=4.8 Hz, 3H), 2.06 (s, 3H), 1.21 (t, J=6.8 Hz, 3H); MS (ESI) m/z: 446.2 $[M+H]^+$.

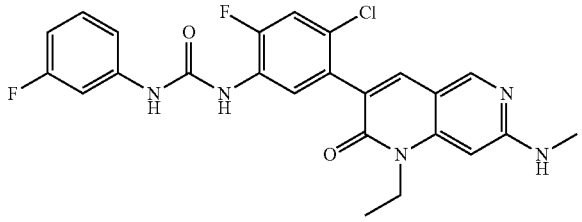

Example 24

A 0° C. solution of Example A5 (200 mg 0.58 mmol) and pyridine (68 mg, 0.87 mmol) in THF (20 mL) was treated with 1-fluoro-3-isocyanato-benzene (80 mg, 0.58 mmol), warmed to RT and stirred for 3 h. The mixture was concentrated in vacuo and purified by preparative HPLC to give 1-[4-chloro-5-(1-ethyl-7-methylamino-2-oxo-1,2-dihydro-[1,6]naphthyridin-3-yl)-2-fluoro-phenyl]-3-(3-fluoro-phenyl)-urea (193 mg, 69% yield). $^1$H NMR (400 MHz, DMSO-$d_6$): δ 9.34 (s, 1H), 8.78 (s, 1H), 8.51 (s, 1H), 8.19 (d, J=8.4 Hz, 1H), 7.85 (s, 1H), 7.87-7.49 (br. s, 1H), 7.59 (d, J=10.8 Hz, 1H), 7.48 (d, J=11.6 Hz, 1H), 7.33 (m, 1H), 7.08 (m, 1H), 6.83 (m, 1H), 6.44 (s, 1H), 4.18 (m, 2H), 2.94 (s, 3H), 1.24 (t, J=6.8 Hz, 3H); MS (ESI): m/z 484.1 [M+H]$^+$.

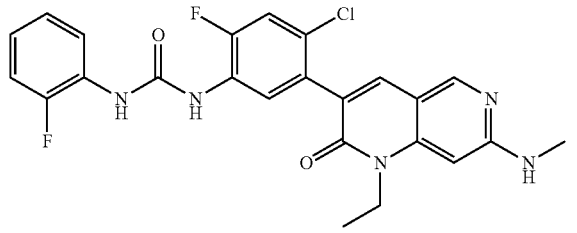

Example 25

Using a procedure analogous to Example 24, Example A5 (400 mg 1.16 mmol) and 1-fluoro-2-isocyanato-benzene (158 mg, 1.16 mmol) were converted to 1-[4-chloro-5-(1-ethyl-7-methylamino-2-oxo-1,2-dihydro-[1,6]naphthyridin-3-yl)-2-fluoro-phenyl]-3-(2-fluoro-phenyl)-urea (144 mg, 26% yield). $^1$H-NMR (400 MHz, DMSO-$d_6$): δ 9.22 (s, 1H), 9.10 (s, 1H), 8.52 (s, 1H), 8.25 (d, J=8.4 Hz, 1H), 8.12 (t, J=8 Hz, 1H), 7.87-7.57 (br. s, 1H), 7.86 (s, 1H), 7.59 (d, J=11.2 Hz, 1H), 7.26 (m, 1H), 7.13 (m, 1H), 7.04 (m, 1H), 6.47 (s, 1H), 4.18 (m, 2H), 2.95 (s, 3H), 1.24 (t, J=6.8 Hz, 3H); MS (ESI): m/z 484.1 [M+H]$^+$.

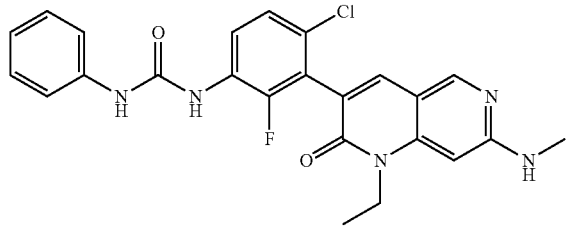

Example 26

A solution of Example A45 (0.09 g, 0.260 mmol) in THF (3 mL) was treated with TEA (0.036 mL, 0.260 mmol) and phenyl isocyanate (0.034 g, 0.285 mmol) and stirred at RT overnight. Additional phenyl isocyanate (0.034 g, 0.285 mmol) was added and the mixture heated at 60° C. for 5 h. The mixture was concentrated to dryness and purified via silica gel chromatography (MeOH/DCM) to afford 1-(4-chloro-3-(1-ethyl-7-(methylamino)-2-oxo-1,2-dihydro-1,6-naphthyridin-3-yl)-2-fluorophenyl)-3-phenylurea (101 mg, 84% yield) as a white solid. $^1$H NMR (500 MHz, DMSO-$d_6$): δ 9.08 (s, 1H), 8.65 (d, J=2.7 Hz, 1H), 8.44 (s, 1H), 8.20 (t, J=8.7 Hz, 1H), 7.86 (s, 1H), 7.46-7.45 (m, 2H), 7.35 (dd, J=9.0, 1.4 Hz, 1H), 7.30 (t, J=7.8 Hz, 2H), 7.13 (q, J=4.9 Hz, 1H), 7.00 (t, J=7.4 Hz, 1H), 6.28 (s, 1H), 4.16 (q, J=7.0 Hz, 2H), 2.88 (d, J=4.9 Hz, 3H), 1.23 (t, J=7.0 Hz, 3H); MS (ESI): m/z 466.1 [M+H]$^+$.

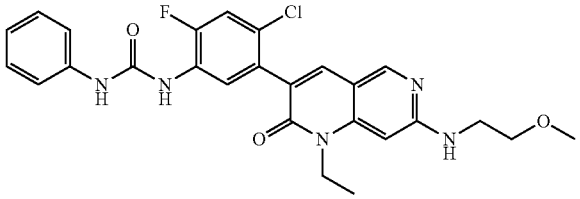

Example 27

A suspension of Example A12 (0.300 g, 0.768 mmol) in EtOAc (6 mL) was treated with phenyl isocyanate (0.091 g, 0.768 mmol), stirred at RT for 13 h and the resulting solid collected by suction filtration. The white solids were stirred in boiling MeCN for 20 minutes followed by stirring at RT for 1 h. The solids were collected by suction filtration, washed and dried to provide 1-(4-chloro-5-(1-ethyl-7-(2-methoxyethylamino)-2-oxo-1,2-dihydro-1,6-naphthyridin-3-yl)-2-fluorophenyl)-3-phenylurea (0.233 g, 60% yield) as a white solid. MS (ESI) m/z: 510.2 [M+H]$^+$.

A suspension of 1-(4-chloro-5-(1-ethyl-7-(2-methoxyethylamino)-2-oxo-1,2-dihydro-1,6-naphthyridin-3-yl)-2-fluorophenyl)-3-phenylurea, (0.233 g, 0.457 mmol) in MeCN (10 mL) was treated with methanesulfonic acid (0.044 g, 0.457 mmol). The crystallized solids were filtered, washed and dried to provide 1-(4-chloro-5-(1-ethyl-7-(2-methoxyethylamino)-2-oxo-1,2-dihydro-1,6-naphthyridin-3-yl)-2-fluorophenyl)-3-phenylurea methanesulfonate as a white solid (0.210 g, 76% yield). $^1$H NMR (400 MHz, DMSO-$d_6$): δ 9.13 (s, 1H), 8.70 (s, 1H), 8.54 (s, 1H), 8.22 (d, J=9 Hz, 2H), 7.90 (s, 1H), 7.58 (d, J=12 Hz, 1H), 7.42 (d, J=8 Hz, 2H), 7.26 (t, J=8 Hz 2H) 6.97 (t, J=8.5 Hz, 1H), 6.74 (s, 1H), 4.16 (m, 2H), 3.57 (m, 4H), 3.29 (s, 3H), 2.34 (s, 3H), 1.20 (t, J=6 Hz, 3H); MS (ESI) m/z: 510.2.2 [M+H]$^+$.

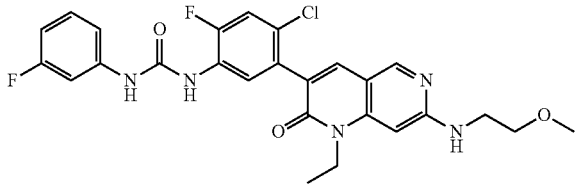

Example 28

To a suspension of Example A12 (0.300 g, 0.768 mmol) in EtOAc (6 mL) was added 3-fluorophenyl isocyanate (0.105 g, 0.768 mmol). The mixture was stirred at RT for 13 h and solids from the reaction mixture were collected by suction filtration. The white solids were stirred in refluxing MeCN for 20 minutes, followed by stirring at RT for 1 h. The solids were filtered, washed, and dried to provide 1-(4-chloro-5-(1-ethyl-7-(2-methoxyethylamino)-2-oxo-1,2-dihydro-1,6-naphthyridin-3-yl)-2-fluorophenyl)-3-(3-fluorophenyl)urea (0.300 g, 74% yield) as white solid. MS (ESI) m/z: 528.2 $[M+H]^+$.

To a suspension of 1-(4-chloro-5-(1-ethyl-7-(2-methoxyethylamino)-2-oxo-1,2-dihydro-1,6-naphthyridin-3-yl)-2-fluorophenyl)-3-(3-fluorophenyl)urea, (0.300 g, 0.568 mmol) in MeCN (10 mL) was added methanesulfonic acid (0.055 g, 0.568 mmol). After stirring at RT for 1 h, the solvent was completely evaporated and the residue was crystallized from EtOH to provide 1-(4-chloro-5-(1-ethyl-7-(2-methoxyethylamino)-2-oxo-1,2-dihydro-1,6-naphthyridin-3-yl)-2-fluorophenyl)-3-(3-fluorophenyl)urea methanesulfonate as a white solid (0.295 g, 83% yield). $^1$H NMR (400 MHz, DMSO-$d_6$): δ 9.37 (s, 1H), 8.84 (s, 1H), 8.55 (s, 1H), 8.30 (s, 1H), 8.18 (d, J=8 Hz, 1H), 7.91 (s, 1H), 7.59 (d, J=11 Hz, 1H), 7.47 (m, 1H), 7.29 (m, 1H), 7.07 (m, 1H), 6.77 (m, 2H), 4.15 (m, 2H), 3.56 (m, 4H), 3.30 (s, 3H), 2.37 (s, 3H), 1.20 (t, J=6 Hz, 3H); MS (ESI) m/z: 528.2 $[M+H]^+$.

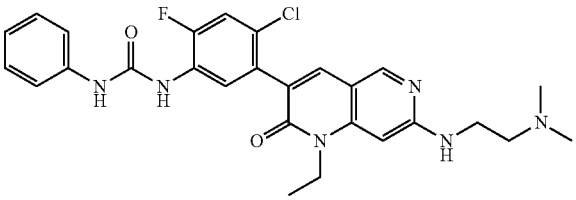

Example 29

To a suspension of Example A15 (0.300 g, 0.743 mmol) in EtOAc (6 mL) was added phenyl isocyanate (0.088 g, 0.743 mmol) and the mixture was stirred at RT for 13 h. The solids were filtered, washed and dried to provide 1-(4-chloro-5-(7-(2-(dimethylamino)ethylamino)-1-ethyl-2-oxo-1,2-dihydro-1,6-naphthyridin-3-yl)-2-fluorophenyl)-3-phenylurea (320 mg, 82% yield) as a white solid. MS (ESI) m/z: 524.2 $[M+H]^+$.

To a suspension of 1-(4-chloro-5-(7-(2-(dimethylamino)ethylamino)-1-ethyl-2-oxo-1,2-dihydro-1,6-naphthyridin-3-yl)-2-fluorophenyl)-3-phenylurea (0.260 g, 0.497 mmol) in MeOH (1 mL) was added HCl (1.25 M in MeOH) (0.875 mL, 1.094 mmol) and the mixture was stirred at RT for 1 h. The reaction mixture was diluted with EtOAc and the remaining solid was filtered, washed and dried to provide 1-(4-chloro-5-(7-(2-(dimethylamino)ethylamino)-1-ethyl-2-oxo-1,2-dihydro-1,6-naphthyridin-3-yl)-2-fluorophenyl)-3-phenylurea dihydrochloride (267 mg, 90% yield) as a white solid. $^1$H NMR (400 MHz, DMSO-$d_6$): δ 9.37 (s, 1H), 8.83 (s, 1H), 8.44 (s, 1H), 8.17 (d, J=9 Hz, 1H), 7.78 (m, 1H), 7.52 (d, J=11 Hz, 1H), 7.42 (m, 2H), 7.25 (m, 3H), 6.95 (t, J=8 Hz, 1H), 6.42 (s, 1H), 4.13 (m, 2H), 3.63 (m, 2H), 3.02 (s, 2H), 2.64 (s, 6), 1.20 (t, J=6 Hz, 3H); MS (ESI) m/z: 523.2 $[M+H]^+$.

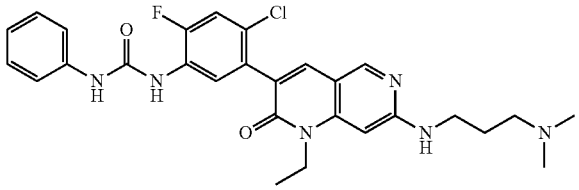

Example 30

To a suspension of Example A16 (0.320 g, 0.766 mmol) in EtOAc (6 mL) was added phenyl isocyanate (0.091 g, 0.766 mmol) and the mixture was stirred at RT for 13 h. The residue obtained after evaporation of the solvent was purified by silica gel chromatography (THF/EtOAc) to provide 1-(4-chloro-5-(7-(3-(dimethylamino)propylamino)-1-ethyl-2-oxo-1,2-dihydro-1,6-naphthyridin-3-yl)-2-fluorophenyl)-3-phenylurea (132 mg, 32% yield) as a white solid. MS (ESI) m/z: 537.2 $[M+H]^+$.

To a suspension of 1-(4-chloro-5-(7-(3-(dimethylamino)propylamino)-1-ethyl-2-oxo-1,2-dihydro-1,6-naphthyridin-3-yl)-2-fluorophenyl)-3-phenylurea (0.130 g, 0.242 mmol) in MeOH (1 mL) was added HCl (1.25 M in MeOH, 0.426 mL, 0.533 mmol) and the mixture stirred at RT for 1 h. The reaction mixture was diluted with EtOAc, filtered, washed and dried to provide 1-(4-chloro-5-(7-(3-(dimethylamino)propylamino)-1-ethyl-2-oxo-1,2-dihydro-1,6-naphthyridin-3-yl)-2-fluorophenyl)-3-phenylurea dihydrochloride (118 mg, 80% yield) as a white solid. $^1$H NMR (400 MHz, DMSO-$d_6$): δ 9.44 (s, 1H), 8.86 (s, 1H), 8.43 (s, 1H), 8.17 (d, J=9 Hz, 1H), 7.76 (s, 1H), 7.52 (d, J=9 Hz, 1H), 7.42 (m, 2H), 7.25 (m, 3H), 6.96 (t, J=7 Hz, 1H), 6.34 (s, 1H), 4.12 (m, 2H), 3.42 (m, 2H), 3.10 (m, 2H), 2.75 (s, 6H), 1.93 (m, 2H), 1.18 (t, J=6 Hz, 3H); MS (ESI) m/z: 537.2. $[M+H]^+$.

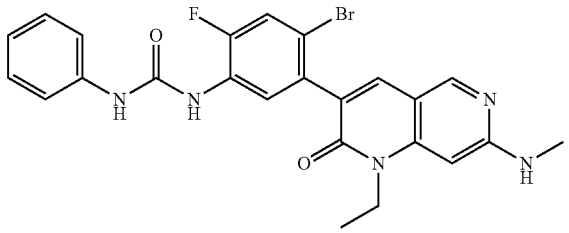

Example 31

A mixture of Example A14 (0.120 g, 0.307 mmol) and TEA (0.043 mL, 0.307 mmol) in THF (3.0 mL) was treated with phenyl isocyanate (0.040 g, 0.337 mmol) and stirred at RT for 4 h. Over the course of the next 4 days the mixture was treated with additional phenyl isocyanate (0.056 mL) and stirred at RT. The resulting solid was filtered, rinsed with THF, then triturated with MeOH to afford 1-(4-bromo-5-(1-ethyl-7-(methylamino)-2-oxo-1,2-dihydro-1,6-naphthyridin-3-yl)-2-fluorophenyl)-3-phenylurea (101 mg, 64.5% yield) as a bright white solid. $^1$H NMR (400 MHz, DMSO-$d_6$): δ 9.09 (s, 1H), 8.68 (s, 1H), 8.41 (s, 1H), 8.17 (d, 1H), 7.70 (s, 1H), 7.65 (d, 1H), 7.41 (d, 2H), 7.27 (m, 2H), 7.03 (m, 1H), 6.96 (t, 1H), 6.23 (s, 1H), 4.13 (q, 2H), 2.86 (d, 3H), 1.20 (t, 3H); MS (ESI) m/z: 510.1 $[M+H]^+$.

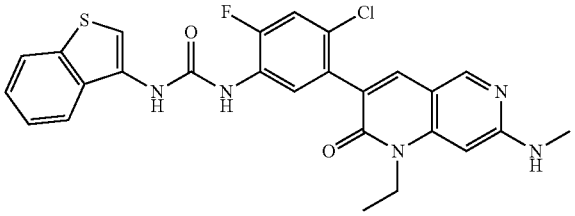

Example 32

Example A5 (0.2 g, 0.577 mmol), benzothiophene-3-carboxylic acid (0.134 g, 0.750 mmol) and TEA (0.322 mL, 2.307 mmol) were suspended in dioxane (5 mL), treated with DPPA (0.186 mL, 0.865 mmol) and heated to 100° C. for 3 h. The mixture was cooled to RT and the precipitate was filtered off and dried to yield 1-(benzo[b]thiophen-3-yl)-3-(4-chloro-5-(1-ethyl-7-(methylamino)-2-oxo-1,2,4a,8a-tetrahydro-1,6-naphthyridin-3-yl)-2-fluorophenyl)urea (215 mg, 71% yield), which was suspended in refluxing MeCN (6 mL). Methanesulfonic acid (0.027 mL, 0.412 mmol) was added, followed by the addition of MeOH (1 mL). The mixture was cooled to RT, allowed to stand for 2 h, treated with $Et_2O$ (3 mL) and sonicated for 5 min. The resulting solid was collected via filtration and dried to yield 1-(benzo[b]thiophen-3-yl)-3-(4-chloro-5-(1-ethyl-7-(methylamino)-2-oxo-1,2,4a,8a-tetrahydro-1,6-naphthyridin-3-yl)-2-fluorophenyl)urea mesylate (209 mg, 82% yield). $^1$H NMR (400 MHz, DMSO-$d_6$): δ 9.48 (s, 1H), 9.06 (s, 1H), 8.54 (s, 1H), 8.32 (d, 1H), 8.01 (br s, 1H), 7.96 (d, 1H), 7.91 (s, 1H), 7.86 (d, 1H), 7.68 (s, 1H), 7.62 (d, 1H), 7.49 (t, 1H), 7.42 (t, 1H), 6.55 (s, 1H), 4.17 (q, 2H), 2.96 (s, 3H), 2.30 (s, 3H), 1.22 (t, 3H); MS (ESI) m/z: 522.1 [M+H]$^+$.

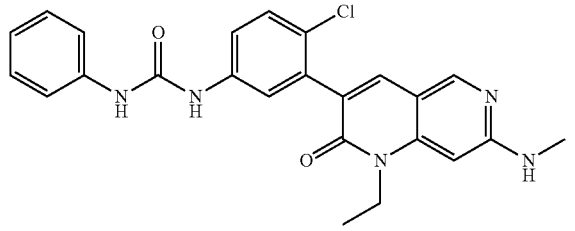

Example 33

A solution of Example A46 (0.12 g, 0.365 mmol) in pyridine (3 mL) was treated with phenyl isocyanate (0.044 mL, 0.401 mmol) and stirred at RT overnight. The mixture was concentrated to dryness, the residue treated with MeCN, sonicated and the resulting solid collected via filtration and dried to afford 1-(4-chloro-3-(1-ethyl-7-(methylamino)-2-oxo-1,2-dihydro-1,6-naphthyridin-3-yl)phenyl)-3-phenylurea (166 mg, 102% yield). MS (ESI) m/z: 448.1 [M+H]$^+$.

A suspension of 1-(4-chloro-3-(1-ethyl-7-(methylamino)-2-oxo-1,2-dihydro-1,6-naphthyridin-3-yl)phenyl)-3-phenylurea (0.166 g, 0.371 mmol) in refluxing MeCN (5 mL) was treated with methanesulfonic acid (0.026 mL, 0.408 mmol), cooled to RT, treated with water, frozen and lyophilized. The resulting material was treated with EtOAc, sonicated and collected via filtration to afford 1-(4-chloro-3-(1-ethyl-7-(methylamino)-2-oxo-1,2-dihydro-1,6-naphthyridin-3-yl)phenyl)-3-phenylurea methanesulfonate (172 mg, 85% yield). $^1$H NMR (400 MHz, DMSO-$d_6$): δ 8.96 (s, 1H), 8.81 (s, 1H), 8.54 (s, 1H), 8.08 (br s, 1H), 7.89 (s, 1H), 7.62 (t, J=1.4 Hz, 1H), 7.45-7.39 (m, 4H), 7.25 (t, J=7.8 Hz, 2H), 6.95 (t, J=7.3 Hz, 1H), 6.57 (s, 1H), 4.18 (q, J=7.1 Hz, 2H), 2.97 (s, 3H), 2.33 (s, 3H), 1.22 (t, J=7.0 Hz, 3H); MS (ESI) m/z: 448.1 [M+H]$^+$.

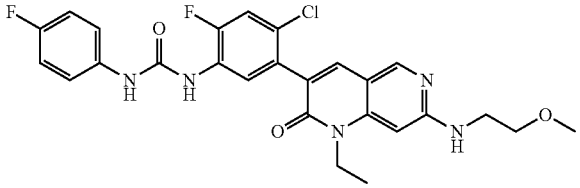

Example 34

To a suspension of Example A12 (0.200 g, 0.512 mmol) in EtOAc (5 mL) was added 1-fluoro-4-isocyanatobenzene (0.093 g, 0.681 mmol) and the mixture stirred at RT for 16 h. The solids were filtered, washed and dried to provide 1-(4-chloro-5-(1-ethyl-7-(2-methoxyethylamino)-2-oxo-1,2-dihydro-1,6-naphthyridin-3-yl)-2-fluorophenyl)-3-(4-fluorophenyl)urea (0.220 g, 81% yield) as a white solid. MS (ESI) m/z: 528.2 [M+H]$^+$.

A suspension of 1-(4-chloro-5-(1-ethyl-7-(2-methoxyethylamino)-2-oxo-1,2-dihydro-1,6-naphthyridin-3-yl)-2-fluorophenyl)-3-(4-fluorophenyl)urea, (0.220 g, 0.417 mmol) in MeCN (10 mL) was treated with methanesulfonic acid (0.044 g, 0.458 mmol) and stirred at RT for 20 h. The solids were filtered, washed and dried to provide 1-(4-chloro-5-(1-ethyl-7-(2-methoxyethylamino)-2-oxo-1,2-dihydro-1,6-naphthyridin-3-yl)-2-fluorophenyl)-3-(4-fluorophenyl)urea methanesulfonate (212 mg, 74% yield) as a white solid. $^1$H NMR (400 MHz, DMSO-$d_6$): δ 9.16 (s, 1H), 8.75 (s, 1H), 8.54 (s, 1H), 8.28 (b s, 1H), 8.19 (d, J=9 Hz, 1H), 7.89 (s, 1H), 7.58 (d, J=11 Hz, 1H), 7.43 (m, 2H), 7.10 (m, 2H), 6.74 (s, 1H), 4.14 (m, 2H), 3.56 (m, 4H), 3.30 (s, 3H), 2.34 (s, 3H), 1.20 (t, J=6 Hz, 3H); MS (ESI) m/z: 528.2 [M+H]$^+$.

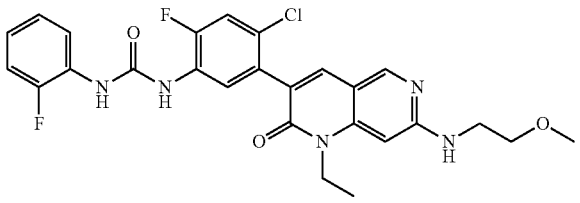

Example 35

To a suspension of Example A12 (0.200 g, 0.512 mmol) in EtOAc (5 mL) was added 1-fluoro-2-isocyanatobenzene (0.093 g, 0.681 mmol) and the mixture was stirred at RT for 16 h. The solids were filtered, washed and dried to provide 1-(4-chloro-5-(1-ethyl-7-(2-methoxyethylamino)-2-oxo-1,2-dihydro-1,6-naphthyridin-3-yl)-2-fluorophenyl)-3-(2-fluorophenyl)urea (0.220 g, 81% yield) as a white solid. MS (ESI) m/z: 528.1 [M+H]$^+$.

A suspension of 1-(4-chloro-5-(1-ethyl-7-(2-methoxyethylamino)-2-oxo-1,2-dihydro-1,6-naphthyridin-3-yl)-2-fluorophenyl)-3-(2-fluorophenyl)urea (0.220 g, 0.417 mmol) in MeCN (10 mL) was treated with methanesulfonic acid (0.040 g, 0.417 mmol) and stirred at RT for 20 h. The solids were filtered, washed and dried to provide 1-(4-chloro-5-(1-ethyl-7-(2-methoxyethylamino)-2-oxo-1,2-dihydro-1,6-naphthyridin-3-yl)-2-fluorophenyl)-3-(2-fluorophenyl)urea methanesulfonate (205 mg, 79% yield) as a white solid. $^1$H NMR (400 MHz, DMSO-$d_6$): δ 9.22 (s, 1H), 9.10 (s, 1H), 8.54 (s, 1H), 8.25 (d, J=9 Hz, 1H), 8.18 (br s, 1H), 8.10 (m, 1H), 7.89 (s, 1H), 7.60 (d, J=11 Hz, 1H), 7.23 (m, 1H), 7.10 (m, 1H), 7.00 (m, 1H), 6.72 (s, 1H), 4.14 (m, 2H), 3.56 (m, 4H), 3.30 (s, 3H), 2.31 (s, 3H), 1.20 (t, J=6 Hz, 3H); MS (ESI) m/z: 528.2 [M+H]$^+$.

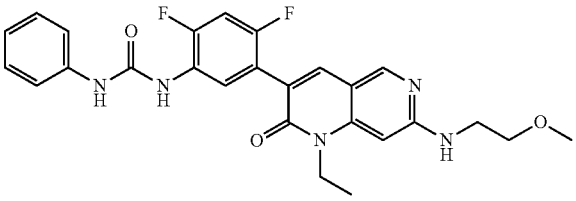

Example 36

To a suspension of Example A19 (0.200 g, 0.534 mmol) in EtOAc (5 mL) was added phenyl isocyanate (0.085 g, 0.710 mmol) and the mixture was stirred at RT for 16 h. The solids were filtered, washed and dried to provide 1-(5-(1-ethyl-7-(2-methoxyethylamino)-2-oxo-1,2-dihydro-1,6-naphthyridin-3-yl)-2,4-difluorophenyl)-3-phenylurea (201 mg, 76% yield) as a white solid. MS (ESI) m/z: 494.2 [M+H]$^+$.

To a suspension of 1-(5-(1-ethyl-7-(2-methoxyethylamino)-2-oxo-1,2-dihydro-1,6-naphthyridin-3-yl)-2,4-difluorophenyl)-3-phenylurea (0.200 g, 0.405 mmol) in MeCN (10 mL) was added methanesulfonic acid (0.039 g, 0.405 mmol) and the mixture stirred at RT for 1 h. The solvent was evaporated and the residue crystallized from MeCN to provide 1-(5-(1-ethyl-7-(2-methoxyethylamino)-2-oxo-1,2-dihydro-1,6-naphthyridin-3-yl)-2,4-difluorophenyl)-3-phenylurea methanesulfonate (190 mg, 80% yield) as a white solid. $^1$H NMR (400 MHz, DMSO-$d_6$): δ 9.22 (s, 1H), 9.10 (s, 1H), 8.64 (s, 1H), 8.56 (s, 1H), 8.15 (t, J=8 Hz, 1H), 8.00 (s, 1H), 7.42 (m, 3H), 7.26 (m, 2H), 6.96 (t, J=7 Hz, 1H), 6.73 (s, 1H), 4.14 (m, 2H), 3.56 (m, 4H), 3.30 (s, 3H), 2.35 (s, 3H), 1.20 (t, J=6 Hz, 3H); MS (ESI) m/z: 494.2 [M+H]$^+$.

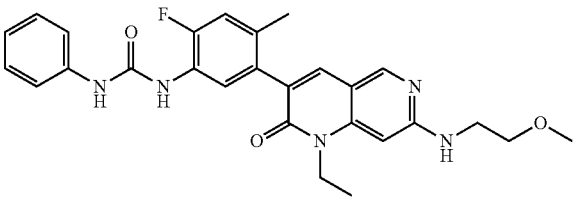

Example 37

To a suspension of Example A28 (0.400 g, 1.080 mmol) in EtOAc (10 mL) was added phenyl isocyanate (0.171 g, 1.436 mmol) and the mixture stirred at RT for 16 h. The solids were filtered, washed, and dried to provide 1-(5-(1-ethyl-7-(2-methoxyethylamino)-2-oxo-1,2-dihydro-1,6-naphthyridin-3-yl)-2-fluoro-4-methylphenyl)-3-phenylurea (500 mg, 95% yield) as a white solid. MS (ESI) m/z: 490.2 [M+H]$^+$.

To a suspension of 1-(5-(1-ethyl-7-(2-methoxyethylamino)-2-oxo-1,2-dihydro-1,6-naphthyridin-3-yl)-2-fluoro-4-methylphenyl)-3-phenylurea (0.500 g, 1.021 mmol) in MeCN (10 mL) was added methanesulfonic acid (0.098 g, 1.021 mmol) and the mixture stirred at RT for 1 h. The solids were filtered, washed, and dried to provide 1-(5-(1-ethyl-7-(2-methoxyethylamino)-2-oxo-1,2-dihydro-1,6-naphthyridin-3-yl)-2-fluoro-4-methylphenyl)-3-phenylurea methanesulfonate as a white solid (468 mg, 78% yield). $^1$H NMR (400 MHz, DMSO-$d_6$): δ 9.07 (s, 1H), 8.54 (m, 2H), 8.30 (br s, 1H), 7.98 (d, J=9 Hz, 1H), 7.83 (s, 1H), 7.42 (m, 2H), 7.25 (m, 2H), 7.16 (d, J=12 Hz, 1H), 6.94 (t, J=8 Hz, 1H), 6.77 (s, 1H), 4.18 (m, 2H), 3.60 (m, 4H),3.30 (s, 3H), 2.31 (s, 3H), 2.07 (s, 3H), 1.20 (t, J=6 Hz, 3H); MS (ESI) m/z: 490.2 [M+H]$^+$.

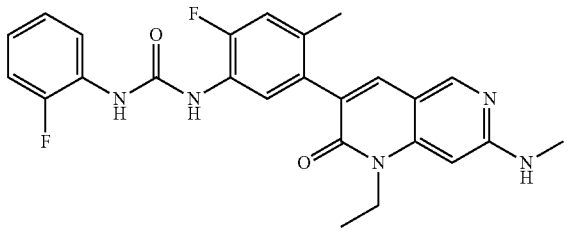

Example 38

To a suspension of Example A2 (0.09 g, 0.276 mmol) and TEA (0.038 mL, 0.276 mmol) in THF (3 mL) was added 2-fluorophenyl isocyanate (0.042 g, 0.303 mmol) and the mixture stirred at RT for 16 h. The solvent was removed and the resultant crude product was purified by silica gel chromatography (MeOH/DCM) to afford 1-(5-(1-ethyl-7-(methylamino)-2-oxo-1,2-dihydro-1,6-naphthyridin-3-yl)-2-fluoro-4-methylphenyl)-3-(2-fluorophenyl)urea (61 mg, 48% yield) as a white solid. $^1$H NMR (400 MHz, DMSO-$d_6$): δ 8.97 (br s, 2H), 8.40 (s, 1H), 8.10 (t d, J=8.0 Hz, 1.6 Hz, 1H), 7.95 (d, J=8.4 Hz, 1H), 7.66 (s, 1H), 7.24-7.18 (m, 1H), 7.14-7.07 (m, 2H), 7.00-6.95 (m, 2H), 6.23 (s, 1H), 4.14 (q, J=6.8 Hz, 2H), 2.85 (d, J=6.4 Hz, 3H), 2.06 (s, 3H), 1.20 (t, J=6.8 Hz, 3H); MS (ESI) m/z: 464.2 [M+H]$^+$.

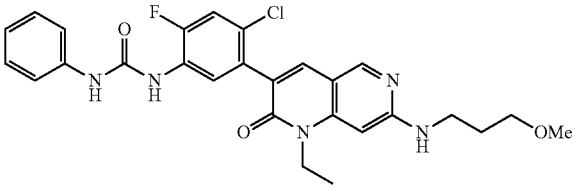

Example 39

To a solution of Example A23 (0.105 g, 0.26 mmol) and TEA (0.036 mL, 0.26 mmol) in THF (3 mL) was added phenyl isocyanate (0.04 g, 0.337 mmol) and the suspension was stirred at RT for 2 h. The suspension was filtered, washed with EtOAc and dried to afford 1-(4-chloro-5-(1-ethyl-7-(3-methoxypropylamino)-2-oxo-1,2-dihydro-1,6-naphthyridin-3-yl)-2-fluorophenyl)-3-phenylurea (0.12 g, 88% yield) as a white solid. $^1$H NMR (400 MHz, DMSO-$d_6$): δ 9.08 (s, 1H), 8.68 (d, J=2.0 Hz, 1H), 8.40 (s, 1H), 8.17 (d, J=8.8 Hz, 1H), 7.72 (s, 1H), 7.53 (d, J=11.2 Hz, 1H), 7.42-7.40 (m, 2H), 7.28-7.24 (m, 2H), 7.08 (t, J=5.6 Hz, 1H), 6.96 (t, J=7.2 Hz, 1H), 6.29 (s, 1H), 4.11 (q, J=6.8 Hz, 2H), 3.41-3.31 (m, 4H), 3.23 (s, 3H), 1.81-1.75 (m, 2H), 1.19 (t, J=6.8 Hz, 3H); MS (ESI) m/z: 524.2 [M+H]$^+$.

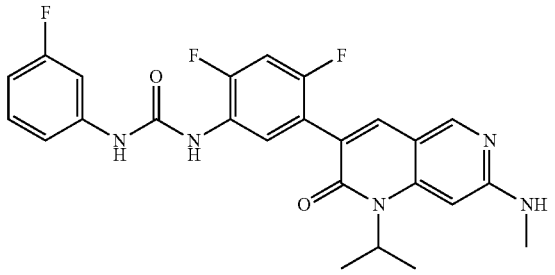

Example 40

To a suspension of Example A25 (0.300 g, 0.871 mmol) in EtOAc (5 mL) was added 3-fluorophenylisocyanate (0.119 g, 0.871 mmol) and the mixture stirred at RT for 2 h. The solids were filtered, washed and dried to provide 1-(2,4-difluoro-5-(1-isopropyl-7-(methylamino)-2-oxo-1,2-dihydro-1,6-naphthyridin-3-yl)phenyl)-3-(3-fluorophenyl) urea (0.364 g, 87% yield) as an off-white solid. $^1$H NMR (400 MHz, DMSO-$d_6$): δ 9.24 (s, 1H), 8.60 (s, 1H), 8.40 (s, 1H), 8.07 (t, J=8 Hz, 1H), 7.76 (s, 1H), 7.46 (m, 1H), 7.31 (m, 2H), 7.07 (m, 1H), 7.00 (m, 1H), 6.77 (m, 1H), 6.43 (s, 1H), 5.19 (br s, 1H), 2.84 (br s, 3H), 1.50 (d, J=6 Hz, 6H); MS (ESI) m/z: 482.2 [M+H]$^+$.

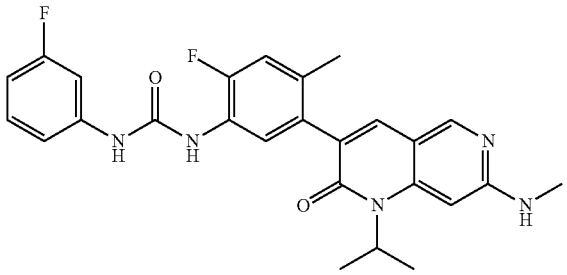

Example 41

Example A21 (0.20 g, 0.588 mmol) and 3-fluorophenyl isocyanate (0.081 g, 0.588 mmol) were combined in THF (5 mL), treated with TEA (0.163 mL, 1.175 mmol) and stirred at RT overnight. The solvent was removed and the residue was purified by reverse phase column chromatography (MeCN/$H_2O$ with 0.1% TFA). Pure fractions were combined and co-concentrated with MeOH and the remaining aqueous solution was treated with $NaHCO_3$ and extracted with EtOAc. The organics were washed with brine, dried ($Na_2SO_4$), filtered, concentrated, and dried under vacuum to obtain 1-(2-fluoro-5-(1-isopropyl-7-(methylamino)-2-oxo-1,2-dihydro-1,6-naphthyridin-3-yl)-4-methylphenyl)-3-(3-fluorophenyl)urea. The material was suspended in MeCN (3 mL), treated with methanesulfonic acid (1 M in DCM, 0.369 mL, 0.369 mmol), heated to reflux and allowed to cool to RT. The solvent was then removed, $Et_2O$ added, and the solid filtered and washed with $Et_2O$ to obtain 1-(2-fluoro-5-(1-isopropyl-7-(methylamino)-2-oxo-1,2-dihydro-1,6-naphthyridin-3-yl)-4-methylphenyl)-3-(3-fluorophenyl)urea methanesulfonate (190 mg, 57% yield). $^1$H NMR (400 MHz, DMSO-$d_6$): δ 9.26 (s, 1H), 8.60 (s, 1H), 8.49 (s, 1H), 8.11 (br s, 1H), 7.95 (d, J=8.4 Hz, 1H), 7.77 (s, 1H), 7.47 (m, 1H), 7.28 (m, 1H), 7.17 (d, J=12.4 Hz, 1H), 7.05 (m, 1H), 6.77 (m, 2H), 3.36 (m, 1H), 2.96 (s, 3H), 2.30 (s, 3H), 2.06 (s, 3H), 1.52 (d, J=6.8 Hz, 6H); MS (ESI) m/z: 478.2 [M+H]$^+$.

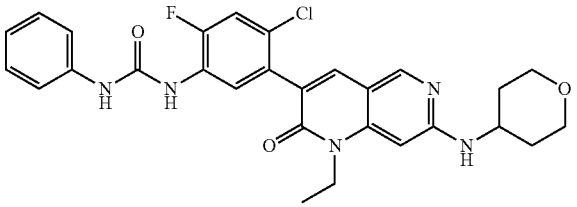

Example 42

Example A22 (0.15 g, 0.360 mmol) and phenyl isocyanate (0.051 g, 0.432 mmol) were combined in THF (5 mL), treated with TEA (0.100 mL, 0.720 mmol) and stirred at RT overnight. The solid was filtered, washed with EtOAc, and dried under vacuum to obtain 1-(4-chloro-5-(1-ethyl-2-oxo-7-(tetrahydro-2H-pyran-4-ylamino)-1,2-dihydro-1,6-naphthyridin-3-yl)-2-fluorophenyl)-3-phenylurea (0.135 g, 70% yield). $^1$H NMR (400 MHz, DMSO-$d_6$): δ 9.08 (s, 1H), 8.68 (s, 1H), 8.40 (s, 1H), 8.17 (d, J=8.8 Hz, 1H), 7.72 (s, 1H), 7.52 (d, J=10.8 Hz, 1H), 7.41 (d, J=8.0 Hz, 2H), 7.26 (m, 3H), 7.07 (d, J=7.6 Hz, 1H), 6.96 (t, J=7.2 Hz, 1H), 6.34 (s, 1H), 4.10 (q, J=6.8 Hz, 2H), 3.86 (m, 2H), 3.42 (m, 2H), 1.88 (m, 2H), 1.44 (m, 2H), 1.20 (t, J=6.8 Hz, 3H); MS (ESI) m/z: 536.2 [M+H]$^+$.

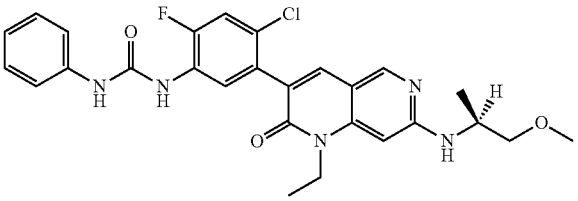

Example 43

Example A26 (0.13 g, 0.321 mmol) was dissolved in EtOAc (10 mL), treated with phenyl isocyanate (0.037 mL, 0.337 mmol) and stirred at RT overnight. Precipitated solids were collected by filtration, rinsed with EtOAc, and dried on the filter to afford (S)-1-(4-chloro-5-(1-ethyl-7-(1-methoxypropan-2-ylamino)-2-oxo-1,2-dihydro-1,6-naphthyridin-3-yl)-2-fluorophenyl)-3-phenylurea (0.138 g, 82% yield) as a white solid. $^1$H NMR (400 MHz, DMSO-$d_6$): δ 9.03 (s, 1H), 8.68 (br s, 1H), 8.39 (s, 1H), 8.17 (d, 1H, J=8.4 Hz), 7.72 (s, 1H), 7.52 (d, 1H, J=10.8 Hz), 7.42-7.40 (m, 2H), 7.28-7.24 (m, 2H), 6.98-6.92 (m, 2H), 6.39 (s, 1H), 4.26-4.20 (m, 1H), 4.09 (q, 2H, J=7.6 Hz), 3.40 (dd, 1H, J=4.0, 9.2 Hz), 3.34 (s, 3H), 3.34-3.28 (m, 1H), 1.19 (t, 3H, J=7.6 Hz), 1.15 (d, 3H, J=6.4 Hz); MS (ESI) m/z: 524.2 [M+H]$^+$.

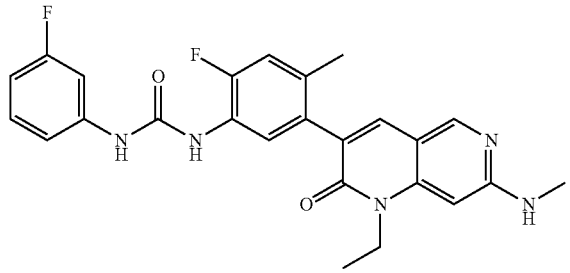

Example 44

A solution of Example A2 (300 mg, 0.919 mmol) in pyridine (5 mL) was treated drop-wise with 3-fluorophenyl isocyanate (139 mg, 1.011 mmol) and stirred at RT. The mixture was diluted with EtOAc and water and the remaining solid was collected via filtration, washed with water and EtOAc and purified by reverse phase chromatography (MeCN/water with 0.1% TFA). The organics were removed under reduced pressure and the aqueous residue was treated with satd. $NaHCO_3$ (10 mL) and allowed to precipitate. The solid was collected by filtration, washed with water and dried to yield 1-(5-(1-ethyl-7-(methylamino)-2-oxo-1,2-dihydro-1,6-naphthyridin-3-yl)-2-fluoro-4-methylphenyl)-3-(3-fluorophenyl)urea (214 mg, 50% yield). $^1$H NMR (400 MHz, DMSO-$d_6$): δ 9.23 (s, 1H), 8.54 (s, 1H), 8.41 (s, 1H), 7.90 (d, 1H), 7.67 (s, 1H), 7.45 (d, 1H), 7.30-7.24 (m, 1H), 7.14-7.03 (m, 3H), 6.78-6.74 (m, 1H), 6.28 (s, 1H), 4.17-4.12 (m, 2H), 2.85 (s, 3H), 2.05 (s, 3H), 1.20 (t, 3H); MS (ES-API) m/z: 463.9 $[M+H]^+$.

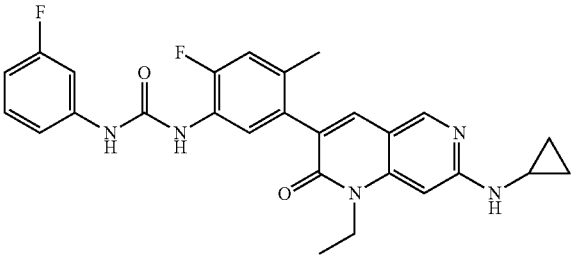

Example 45

A solution of Example A27 (124 mg, 0.352 mmol) in pyridine (4 mL) was treated drop-wise with 3-fluorophenyl isocyanate (51 mg, 0.369 mmol) and stirred at RT. The mixture was diluted with EtOAc and water, the remaining solid collected via filtration, washed with $Et_2O$, dried, and purified by reverse phase chromatography (MeCN/water with 0.1% TFA). The organics were removed under reduced pressure and the aqueous residue was treated with satd. $NaHCO_3$ and extracted with hot EtOAc (2×). The combined organics were dried hot over $Na_2SO_4$ and evaporated at reduced pressure to give a white solid which was dried under reduced pressure to yield 1-(5-(7-(cyclopropylamino)-1-ethyl-2-oxo-1,2-dihydro-1,6-naphthyridin-3-yl)-2-fluoro-4-methylphenyl)-3-(3-fluorophenyl)urea (75 mg, 43% yield). $^1$H NMR (400 MHz, DMSO-$d_6$): δ 9.22 (s, 1H), 8.53 (s, 1H), 8.40 (s, 1H), 7.91 (d, 1H), 7.68 (s, 1H), 7.47-7.44 (m, 1H), 7.34-7.26 (m, 2H), 7.15-7.11 (m, 1H), 7.06-7.03 (m, 1H), 6.80-6.72 (m, 1H), 6.41 (s, 1H), 4.21-4.15 (m, 2H), 2.20 (m, 1H), 2.06 (s, 3H), 1.23 (t, 3H), 0.79-0.74 (m, 2H), 0.50-0.47 (m, 2H); MS (ES-API) m/z: 490.2 $[M+H]^+$.

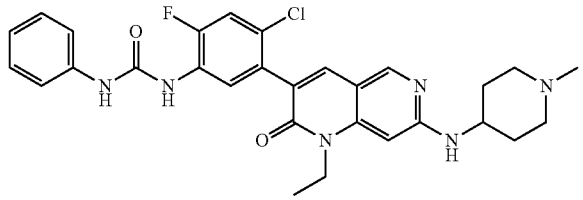

Example 46

To a solution of Example A3 (2.1 g, 5.96 mmol) in NMP (10 mL) was added 1-methyl-piperidin-4-ylamine (1.36 g, 11.9 mmol) and DBU (1.7 g, 11.4 mmol). Nitrogen was bubbled through the mixture for 5 min and then it was heated at 180° C. for 12 h. The reaction mixture was cooled to RT, poured into water and extracted with EtOAc (3×). The combined organics were washed with brine, dried over $Na_2SO_4$, concentrated under reduced pressure, and the residue was purified by silica gel chromatography to yield 3-(5-amino-2-chloro-4-fluorophenyl)-1-ethyl-7-(1-methylpiperidin-4-ylamino)-1,6-naphthyridin-2(1H)-one (0.50 g, 19.5% yield) which was 70% pure (30% de-methylated by-product) and used without further purification.

A solution of 3-(5-amino-2-chloro-4-fluorophenyl)-1-ethyl-7-(1-methylpiperidin-4-ylamino)-1,6-naphthyridin-2(1H)-one (200 mg, 0.465 mmol) and pyridine (70 mg, 0.95 mmol) in DCM (5 mL) was treated drop-wise with phenyl isocyanate (112 mg, 0.93 mmol) and stirred at RT under nitrogen overnight. The mixture was quenched with MeOH (5 mL), concentrated under reduced pressure and purified by prep-TLC separation to give 1-(4-chloro-5-(1-ethyl-7-(1-methylpiperidin-4-ylamino)-2-oxo-1,2-dihydro-1,6-naphthyridin-3-yl)-2-fluorophenyl)-3-phenylurea (120 mg, 47% yield). $^1$H NMR (400 MHz, DMSO-$d_6$): δ 9.16 (s, 1H), 8.72 (s, 1H), 8.39 (s, 1H), 8.17 (d, J=8.8 Hz, 1H), 7.71 (s, 1H), 7.51 (d, J=10.8 Hz, 1H), 7.42 (s, 1H), 7.40 (s, 1H), 7.26 (t, J=8.0 Hz, 2H), 7.02-6.94 (m, 2H), 6.33 (s, 1H), 4.11-4.05 (m, 2H), 3.81-3.78 (m, 1H), 2.78-2.75 (m, 2H), 2.20 (s, 3H), 2.12-2.05 (m, 2H), 1.90-1.88 (m, 2H), 1.52-1.47 (m, 2H), 1.21-1.18 (m, 3H); MS (ESI) m/z: 549.3 $[M+H]^+$.

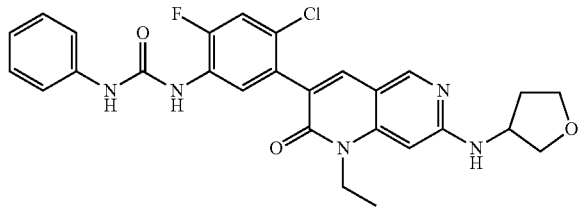

Example 47

A solution of Example A30 (150 mg, 0.37 mmol) and pyridine (59 mg, 0.74 mmol) in DCM (3 mL) was treated drop-wise with phenyl isocyanate (53 mg, 0.44 mmol) and stirred at RT under nitrogen overnight. The mixture was filtered and the filter cake was purified by prep-HPLC separation to give 1-(4-chloro-5-(1-ethyl-2-oxo-7-(THF-3-ylamino)-1,2-dihydro-1,6-naphthyridin-3-yl)-2-fluorophenyl)-3-phenylurea (49 mg, 25% yield). $^1$H NMR (400 MHz, $CDCl_3$): δ 8.36 (s, 1H), 8.21 (s, 1H), 7.94 (d, J=8.4 Hz, 1H), 7.77 (s, 1H), 7.68 (s, 1H), 7.40 (d, J=7.6 Hz, 2H), 7.22-7.18 (m, 2H), 6.97-6.91 (m, 2H), 6.14 (s, 1H), 5.08 (d, J=7.6 Hz, 1H), 4.46 (br s, 1H), 4.33 (q, J=6.4 Hz, 2H), 4.01-3.95 (m, 2H), 3.88-3.83 (m, 1H), 3.75 (dd, J=9.2 Hz, 2.8 Hz, 1H), 2.39-2.32 (m, 1H), 1.98-1.87 (m, 1H), 1.40 (t, J=6.4 Hz, 3H); MS (ESI) m/z: 522.1[M+H]$^+$.

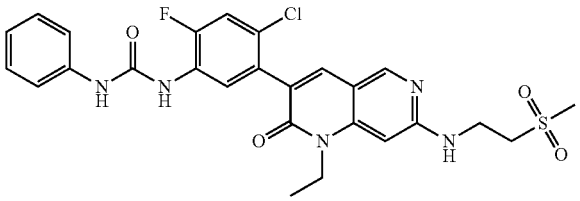

Example 48

2-Methylsulfanyl-ethylamine (5 mL) and Example A3 (500 mg, 1.42 mmol) were added to a sealed tube and the mixture was heated at 130° C. overnight. The reaction mixture was concentrated under vacuum, treated with water and extracted with EtOAc (3×). The combined organics were washed with brine, dried ($Na_2SO_4$), and concentrated to give 3-(5-amino-2-chloro-4-fluorophenyl)-1-ethyl-7-(2-(methylthio)ethylamino)-1,6-naphthyridin-2(1H)-one (400 mg, 69% yield) which was used directly without further purification.

To a solution of 3-(5-amino-2-chloro-4-fluorophenyl)-1-ethyl-7-(2-(methylthio)ethylamino)-1,6-naphthyridin-2(1H)-one (400 mg, 0.99 mmol) in DCM (20 mL) was added phenyl isocyanate (200 mg, 1.68 mmol) and the mixture was stirred overnight. The reaction mixture was quenched with MeOH and concentrated under reduced pressure. The residue was washed with $Et_2O$ to give 1-(4-chloro-5-(1-ethyl-7-(2-(methylthio)ethylamino)-2-oxo-1,2-dihydro-1,6-naphthyridin-3-yl)-2-fluorophenyl)-3-phenylurea (200 mg, 39% yield).

To a solution of 1-(4-chloro-5-(1-ethyl-7-(2-(methylthio)ethylamino)-2-oxo-1,2-dihydro-1,6-naphthyridin-3-yl)-2-fluorophenyl)-3-phenylurea (200 mg, 0.38 mmol) in DCM (20 mL) was added 85% mCPBA (169 mg, 0.84 mmol) at RT. The mixture was stirred for 2 h and then additional mCPBA (84 mg, 0.42 mmol) was added. The mixture was stirred for 1 h, washed successively with satd. $Na_2SO_3$, satd. $NaHCO_3$, and brine, dried ($Na_2SO_4$), and concentrated under reduced pressure. The residue was dissolved in MeOH and THF and $NH_4Cl$ (222 mg, 4.2 mmol) was added, followed by Zn powder (273 mg, 4.2 mmol), and the mixture stirred for 30 minutes. The mixture was filtered, the filtrate concentrated to dryness, treated with water, extracted with 10% MeOH/DCM and the organic layer was concentrated and purified by prep-HPLC to give 1-(4-chloro-5-(1-ethyl-7-(2-(methylsulfonyl)ethylamino)-2-oxo-1,2-dihydro-1,6-naphthyridin-3-yl)-2-fluorophenyl)-3-phenylurea (96 mg, 45% yield over two steps). $^1$H NMR (400 MHz, DMSO-$d_6$): δ 9.75 (s, 1H), 9.03 (s, 1H), 8.45 (s, 1H), 8.15 (d, J=8.4 Hz, 1H), 7.77 (s, 1H), 7.49 (d, J=10.8 Hz, 1H), 7.43 (d, J=8.0 Hz, 2H), 7.30 (m, 1H), 7.24 (m, 2H), 6.94 (m, 1H), 6.44 (s, 1H), 4.10 (q, J=7.2 Hz, 2H), 3.76 (m, 2H), 3.39 (t, J=6.4 Hz, 2H), 3.01 (s, 3H), 1.19 (t, J=6.8 Hz, 3H); MS (ESI): m/z 557.8 [M+H]$^+$.

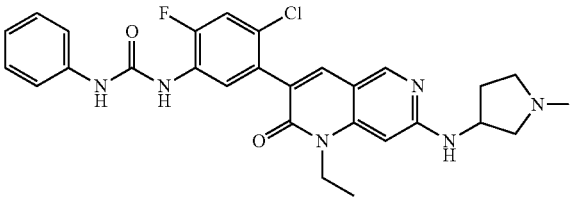

Example 49

A solution of Example A3 (500 mg, 1.42 mmol), 1-methyl-pyrrolidin-3-ylamine (170 mg, 1.7 mmol) and DBU (383 mg, 2.84 mmol) in NMP (5 mL) was heated with a microwave at 160° C. for 2 h. After cooling to RT, the mixture was purified by silica gel chromatography to yield 3-(5-amino-2-chloro-4-fluorophenyl)-1-ethyl-7-(1-methylpyrrolidin-3-ylamino)-1,6-naphthyridin-2(1H)-one (500 mg, 85% yield) as a yellow oil.

To a solution of 3-(5-amino-2-chloro-4-fluorophenyl)-1-ethyl-7-(1-methylpyrrolidin-3-ylamino)-1,6-naphthyridin-2(1H)-one (500 mg, 1.20 mmol) and pyridine (140 mg, 1.8 mmol) in DCM (20 mL) was added phenyl isocyanate (215 mg, 1.8 mmol). The mixture was stirred at RT overnight, concentrated, and purified by prep-HPLC separation to give 1-(4-chloro-5-(1-ethyl-7-(1-methylpyrrolidin-3-ylamino)-2-oxo-1,2-dihydro-1,6-naphthyridin-3-yl)-2-fluorophenyl)-3-phenylurea (53 mg, 8.4% yield) as a pale yellow solid. $^1$H NMR (400 MHz, DMSO-$d_6$): δ 9.08 (s, 1H), 8.67 (s, 1H), 8.40 (s, 1H), 8.17 (d, J=8.8 Hz, 1H), 7.73 (s, 1H), 7.53 (d, J=11.2 Hz, 1H), 7.41 (d, J=7.6 Hz, 2H), 7.28-7.23 (m, 3H), 6.98-6.95 (m, 1H), 6.35 (s, 1H), 4.39 (s, 1H), 4.11-4.09 (m, 2H), 2.77-2.71 (m, 1H), 2.65-2.61 (m, 1H), 2.44-2.36 (m, 2H), 2.26 (s, 3H), 2.23-2.20 (m, 1H), 1.68-1.62 (m, 1H), 1.64 (t, J=7.2 Hz, 3H).

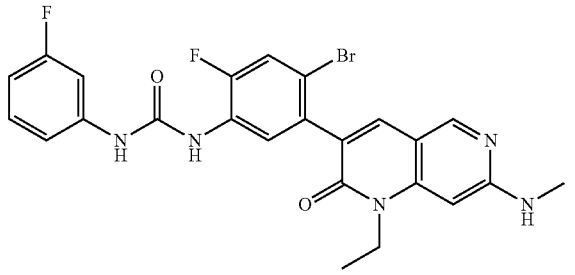

Example 50

A suspension of Example A14 (0.150 g, 0.383 mmol) and TEA (0.053 mL, 0.383 mmol) in THF (2.5 mL) was treated with 3-fluorophenyl isocyanate (0.048 mL, 0.422 mmol) and stirred at RT, under an Ar atmosphere, overnight. Additional 3-fluorophenyl isocyanate (0.024 mL, 0.55 eq.) was added, the mixture stirred at RT for 6 h, then treated again with 3-fluorophenyl isocyanate (1 drop) and the mixture stirred at RT overnight. The resulting solid was filtered, rinsed with a small amount of THF and dried to afford 1-(4-bromo-5-(1-ethyl-7-(methylamino)-2-oxo-1,2-dihydro-1,6-naphthyridin-3-yl)-2-fluorophenyl)-3-(3-fluorophenyl)urea (166 mg, 82% yield) as a white solid. $^1$H NMR (400 MHz, DMSO-$d_6$): δ 9.30 (s, 1H), 8.74 (s, 1H), 8.41 (s, 1H), 8.14 (d, 1H), 7.70 (s, 1H), 7.66 (d, 1H), 7.75 (m, 1H), 7.29 (q, 1H), 7.05 (m, 2H), 6.78 (m, 1H), 6.24 (s, 1H), 4.13 (q, 2H), 2.86 (d, 3H), 1.21 (t, 3H); MS (ESI) m/z: 528.1 $[M+H]^+$.

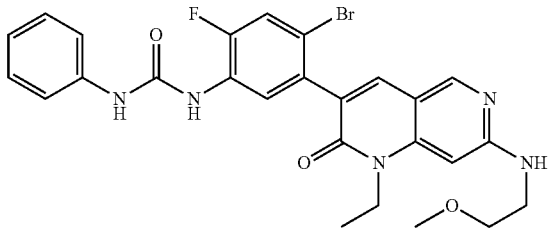

Example 51

To a solution of Example A29 (0.131 g, 1.103 mmol) in DCM (5 mL) was added phenyl isocyanate (0.480 g, 1.103 mmol) and the reaction mixture was stirred at RT. After 2 h the solvent was completely evaporated and the residue was crystallized from MeCN to provide 1-(4-bromo-5-(1-ethyl-7-(2-methoxyethylamino)-2-oxo-1,2-dihydro-1,6-naphthyridin-3-yl)-2-fluorophenyl)-3-phenylurea (0.433 g, 70.8% yield) as a white solid. MS (ESI) m/z: 554.1/556.1 $[M+H]^+$.

To a suspension of 1-(4-bromo-5-(1-ethyl-7-(2-methoxyethylamino)-2-oxo-1,2-dihydro-1,6-naphthyridin-3-yl)-2-fluorophenyl)-3-phenylurea (0.200 g, 0.361 mmol) in MeCN (4 mL) was added methanesulfonic acid (0.035 g, 0.361 mmol) and the mixture was stirred at RT for 30 minutes. The solvent was completely evaporated and the residue was crystallized from MeCN to provide 1-(4-bromo-5-(1-ethyl-7-(2-methoxyethylamino)-2-oxo-1,2-dihydro-1,6-naphthyridin-3-yl)-2-fluorophenyl)-3-phenylurea methanesulfonate (0.160 g, 67% yield) as a white solid. $^1$H NMR (400 MHz, DMSO-$d_6$): δ 9.23 (s, 1H), 9.04 (s. 1H), 8.53 (s, 1H), 8.22 (d, J=9 Hz, 2H), 7.87 (s, 1H), 7.70 (d, J=11 Hz, 1H), 7.41 (d, J=9 Hz, 2H), 7.26 (t, J=7 Hz, 2H), 6.96 (t, J=7 Hz, 1H), 6.72 (s, 1H), 4.13 (m, 2H), 3.56 (m, 4H), 3.30 (s, 3H), 2.33 (s, 3H), 1.21 (d, J=6 Hz, 3H); MS (ESI) m/z: 554.1/556.1 $[M+H]^+$.

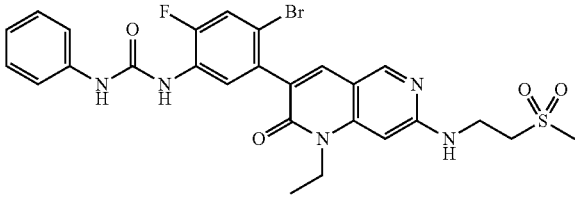

Example 52

Phenyl isocyanate (0.067 g, 0.56 mmol) was added to a solution of Example A31 (0.19 g, 0.43 mmol) and TEA (0.09 g, 0.87 mmol) in THF (3 mL) and stirred at RT for 1 h. The resultant suspension was diluted with MTBE (3 mL), filtered, washed with MTBE and dried to afford 1-(4-bromo-5-(1-ethyl-7-(2-(methylthio)ethylamino)-2-oxo-1,2-dihydro-1,6-naphthyridin-3-yl)-2-fluorophenyl)-3-phenylurea as a white solid (0.18 g, 74% yield). $^1$H NMR (400 MHz, DMSO-$d_6$): δ 9.08 (s, 1H), 8.68 (s, 1H), 8.41 (s, 1H), 8.17 (d, J=8.4 Hz, 1H), 7.70 (s, 1H), 7.65 (d, J=10.4 Hz, 1H), 7.41 (d, J=8.4 Hz, 2H), 7.28-7.17 (m, 3H), 6.96 (t, J=8.4 Hz, 1H), 6.35 (s, 1H), 4.11 (q, J=6.4 Hz, 2H), 3.55 (q, J=6.0 Hz, 2H), 2.66 (t, J=6.8 Hz, 2H), 2.10 (s, 3H), 1.20 (t, J=6.8 Hz, 3H); MS (ESI) m/z: 570.1 $[M+H]^+$.

To a suspension of 1-(4-bromo-5-(1-ethyl-7-(2-(methylthio)ethylamino)-2-oxo-1,2-dihydro-1,6-naphthyridin-3-yl)-2-fluorophenyl)-3-phenylurea (0.18 g, 0.31 mmol) in DCM (25 mL) was added 70-75% mCPBA (0.14 g, 0.63 mmol) and the suspension was stirred at RT for 15 minutes. The mixture was diluted with a 10% $Na_2SO_3$ solution (30 mL), the layers were separated, and the organic layer was washed with satd. $NaHCO_3$ solution, then brine, dried ($Na_2SO_4$), and concentrated. The crude product was purified by silica gel chromatography (MeOH/DCM) to afford 1-(4-bromo-5-(1-ethyl-7-(2-(methylsulfonyl)ethylamino)-2-oxo-1,2-dihydro-1,6-naphthyridin-3-yl)-2-fluorophenyl)-3-phenylurea (115 mg, 61% yield) as a white solid. $^1$H NMR (400 MHz, DMSO-$d_6$): δ 9.08 (s, 1H), 8.69 (s, 1H), 8.46 (s, 1H), 8.18 (d, J=8.4 Hz, 1H), 7.74 (s, 1H), 7.66 (d, J=10.8 Hz, 1H), 7.41 (d, J=7.6 Hz, 2H), 7.28-7.24 (m, 3H), 6.96 (t, J=7.6 Hz, 1H), 6.42 (s, 1H), 4.12 (q, J=6.8 Hz, 2H), 3.77 (q, J=6.4 Hz, 2H), 3.39 (t, J=6.8 Hz, 2H), 3.02 (s, 3H), 1.20 (t, J=6.8 Hz, 3H); MS (ESI) m/z: 602.1 $[M+H]^+$.

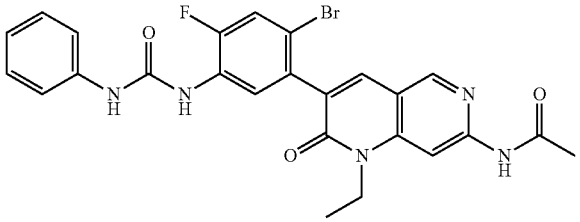

Example 53

A suspension of Example A32 (0.278 g, 0.559 mmol) in THF (6 mL) was treated with TEA (0.097 mL, 0.699 mmol) followed by phenyl isocyanate (0.061 mL, 0.559 mmol) and stirred at RT overnight. The resulting solids were collected by filtration, rinsed with THF and dried under vacuum to afford 1-(5-(7-(4-methoxybenzylamino)-1-ethyl-2-oxo-1,2-dihydro-1,6-naphthyridin-3-yl)-4-bromo-2-fluorophenyl)-3-phenylurea (0.256 g, 74% yield). $^1$H NMR (400 MHz, DMSO-$d_6$): δ 9.08 (s, 1H), 8.68 (d, 1H, J=2.4 Hz), 8.4 (s, 1H), 8.16 (d, 1H, J=8.8 Hz), 7.69 (s, 1H), 7.65 (d, 1H, J=10.8 Hz), 7.56-7.53 (m, 1H), 7.42-7.39 (m, 2H), 7.30-7.24 (m, 4H), 6.96 (m, 1H), 6.89-6.86 (m, 2H), 6.31 (br s, 1H), 4.49-4.47 (m, 2H), 4.07 (q, 2H, J=8.0 Hz), 3.70 (s, 3H), 1.12 (t, 3H, J=8.0 Hz); MS (ESI) m/z: 616.2 $(M+H^+)$, 618.2 $(M+2+H^+)$.

1-(5-(7-(4-methoxybenzylamino)-1-ethyl-2-oxo-1,2-dihydro-1,6-naphthyridin-3-yl)-4-bromo-2-fluorophenyl)-3-phenylurea (0.256 g, 0.415 mmol) was dissolved in TFA (4 mL, 51.9 mmol) and stirred at RT. After 4 h the reaction mixture was concentrated to dryness, the residue was diluted with MeOH, and the precipitated solids were removed by filtration. The filtrate was treated with satd. $NaHCO_3$ and the resulting solid collected by filtration, rinsed with $H_2O$, dried under vacuum, and purified by reverse phase chromatography (MeCN/$H_2O$ with 0.1% TFA). The organics were removed under reduced pressure, the aqueous residue treated with satd. $NaHCO_3$ and the resulting solids were collected by filtration, washed with $H_2O$ and dried to afford 1-(5-(7-amino-1-ethyl-2-oxo-1,2-dihydro-1,6-naphthyridin-3-yl)-4-bromo-2-fluorophenyl)-3-phenylurea (90 mg, 44% yield). $^1$H NMR (400 MHz, DMSO-$d_6$): δ 9.08 (s, 1H), 8.68 (d, 1H, J=2.4 Hz), 8.36 (s, 1H), 8.17 (d, 1H, J=8.8 Hz), 7.70 (s, 1H), 7.65 (d, 1H, J=10.8 Hz), 7.42-7.40 (m, 2H), 7.28-7.24 (m, 2H), 6.98-6.95 (m, 1H), 6.54 (br s, 2H), 6.34 (s, 1H), 4.08 (q, 2H, J=7.2 Hz), 1.20 (t, 3H, J=7.2 Hz); MS (ESI) m/z: 496.1 (M+H$^+$), 498.1 (M+2+H$^+$).

1-(5-(7-amino-1-ethyl-2-oxo-1,2-dihydro-1,6-naphthyridin-3-yl)-4-bromo-2-fluorophenyl)-3-phenylurea (90 mg, 0.181 mmol) was suspended in acetic anhydride (5 mL, 52.9 mmol) and heated at 110° C. for 4 h. The reaction was cooled to RT, poured onto ice (15 g), and stirred overnight. The solids were collected, rinsed well with $H_2O$, air dried, then suspended in MeCN (2-3 mL) and heated at 80° C. overnight. The solids were collected by filtration, rinsed with MeCN and dried under vacuum to afford 1-(5-(7-acetamido-1-ethyl-2-oxo-1,2-dihydro-1,6-naphthyridin-3-yl)-4-bromo-2-fluorophenyl)-3-phenylurea (56 mg, 57% yield). $^1$H NMR (400 MHz, DMSO-$d_6$): δ 10.84 (s, 1H), 9.10 (s, 1H), 8.73 (d, J=2.4 Hz, 1H), 8.71 (s, 1H), 8.26 (s, 1H), 8.22 (d, J=8.4 Hz, 1H), 7.95 (s, 1H), 7.7 (d, J=6.8 Hz, 1H), 7.42-7.40 (m, 2H), 7.28-7.24 (m, 2H), 6.98-6.95 (m, 1H), 4.19 (q, J=6.8 Hz, 2H), 2.15 (s, 3H), 1.25 (t, J=6.8 Hz, 3H); MS (ESI) m/z: 538.1 [M+H]$^+$.

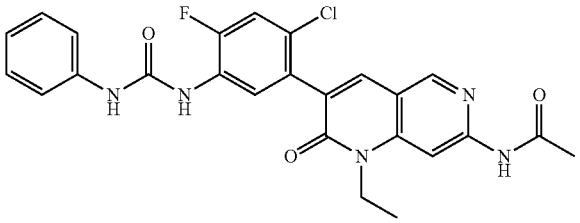

Example 54

Example A35 (0.200 g, 0.601 mmol) was dissolved in THF (6 mL) at RT and treated with TEA (0.109 mL, 0.781 mmol), followed by phenyl isocyanate (0.066 mL, 0.601 mmol). After 2 h, the precipitated solids were collected by filtration and rinsed with THF to obtain 1-(5-(7-amino-1-ethyl-2-oxo-1,2-dihydro-1,6-naphthyridin-3-yl)-4-chloro-2-fluorophenyl)-3-phenylurea (200 mg, 74% yield). $^1$H NMR (400 MHz, DMSO-$d_6$): δ 9.12 (s, 1H), 8.7 (s, 1H), 8.35 (s, 1H), 8.16 (d, J=8.4 Hz, 1H), 7.73 (s, 1H), 7.52 (d, J=11.8 Hz, 1H), 7.43-7.40 (m, 2H), 7.28-7.24 (m, 2H), 6.96-6.94 (m, 1H), 6.54 (br s, 2H), 6.34 (s, 1H), 4.08 (q, J=7.2 Hz, 2H), 1.20 (t, J=7.2 Hz, 3H); MS (ESI) m/z: 452.1 (M+H$^+$), 454.1 (M+2+H$^+$).

1-(5-(7-amino-1-ethyl-2-oxo-1,2-dihydro-1,6-naphthyridin-3-yl)-4-chloro-2-fluorophenyl)-3-phenylurea (0.100 g, 0.221 mmol) was suspended in acetic anhydride (5 mL, 53.0 mmol) and stirred with gradual heating to 110° C. After 5 h, the mixture was cooled to RT and diluted with MeCN (15 mL). The solids were collected by filtration, rinsed with MeCN and dried to afford 1-(5-(7-acetamido-1-ethyl-2-oxo-1,2-dihydro-1,6-naphthyridin-3-yl)-4-chloro-2-fluorophenyl)-3-phenylurea (107 mg, 98% yield). $^1$H NMR (400 MHz, DMSO-$d_6$): δ 10.84 (s, 1H), 9.13 (s, 1H), 8.74 (d, J=2.0 Hz, 1H), 8.71 (s, 1H), 8.26 (s, 1H), 8.22 (d, J=8.8 Hz, 1H), 7.97 (s, 1H), 7.57 (d, J=4.0 Hz, 1H) 7.42-7.40 (m, 2H), 7.28-7.24 (m, 2H), 6.98-6.95 (m, 1H), 4.19 (q, J=7.2 Hz, 2H), 2.14 (s, 3H), 1.25 (t, J=7.2 Hz, 3H); MS (ESI) m/z: 494.1 [M+H]$^+$.

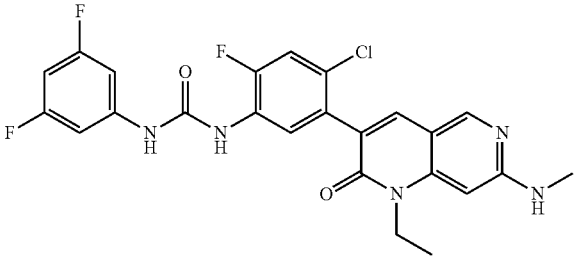

Example 55

A 0° C. solution of Example A5 (200 mg, 0.58 mmol) and pyridine (91 mg, 1.16 mmol) in DCM (4 mL) was treated drop-wise with 1,3-difluoro-5-isocyanato-benzene (98 mg, 0.64 mmol) and stirred at RT overnight as the cooling bath expired. The mixture was concentrated to dryness and purified by prep-HPLC. The resulting solution was treated with HCl (1 mL) and lyophilized to give 1-(4-chloro-5-(1-ethyl-7-(methylamino)-2-oxo-1,2-dihydro-1,6-naphthyridin-3-yl)-2-fluorophenyl)-3-(3,5-difluorophenyl)urea hydrochloride (74 mg, 26% yield). $^1$H NMR (400 MHz, DMSO-$d_6$): δ 9.94 (s, 1H), 9.03 (s, 1H), 8.54 (s, 1H), 8.14 (b s, 1H), 8.13 (d, J=8.8 Hz, 1H), 7.88 (s, 1H), 7.57 (d, J=11.2 Hz, 1H), 7.16-7.12 (m, 2H), 6.78 (t, J=8.8 Hz, 1H), 6.57 (s, 1H), 4.16-4.13 (m, 2H), 2.96 (s, 3H), 1.19 (t, J=6.8 Hz, 3H); MS (ESI) m/z: 502.3 [M+H]$^+$.

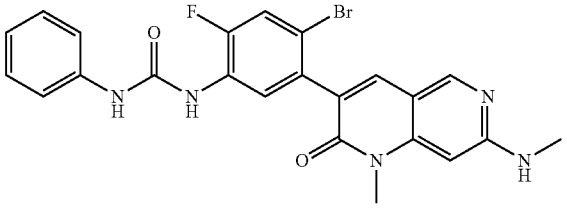

Example 56

A mixture of Example A37 (1.3 g, 3.4 mmol), methylamine (25%, 30 mL) and EtOH (5 mL) were heated at 120° C. in a pressure vessel for 1 day. The mixture was cooled to RT, the solids collected via filtration, washed with pet ether and dried to give 3-(5-amino-2-bromo-4-fluoro-phenyl)-1-methyl-7-methylamino-1H-[1,6]naphthyridin-2-one (1.06 g, 82.8% yield).

A solution of 3-(5-amino-2-bromo-4-fluoro-phenyl)-1-methyl-7-methylamino-1H-[1,6]naphthyridin-2-one (420 mg, 1.16 mmol) in DCM (25 mL) was treated with phenyl isocyanate (0.19 g, 1.62 mmol) and TEA (0.326 g, 3.23 mmol) and stirred at RT for 12 h. The mixture was concentrated under reduced pressure and washed with MTBE (1×). The crude product was purified by prep-HPLC separation (MeCN/$H_2O$ with 0.1% TFA) to give 1-(4-bromo-2-fluoro-5-(1-methyl-7-(methylamino)-2-oxo-1,2-dihydro-1,6-naphthyridin-3-yl)phenyl)-3-phenylurea (245 mg, 44% yield). $^1$H NMR (400 MHz, DMSO-$d_6$): δ 9.08 (s, 1H), 8.67 (s, 1H), 8.40 (s, 1H), 8.17 (d, J=8.8 Hz, 1H), 7.70 (s, 1H), 7.64 (d, J=10.8 Hz, 1H), 7.40 (d, J=7.6 Hz, 2H), 7.28-7.24 (t, J=7.6 Hz, 2H), 7.04-7.03 (m, 1H), 6.98-6.94 (t, J=8 Hz, 1H), 6.17 (s, 1H), 3.50 (s, 3H), 2.85 (d, J=4.8 Hz, 3H).

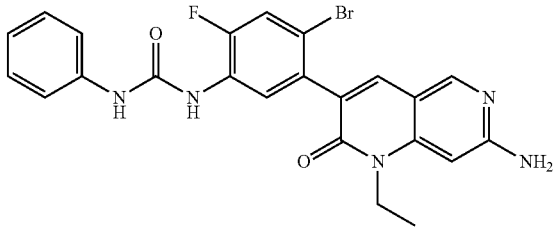

Example 57

To a solution of Example A33 (300 mg, 0.798 mmol) in DCM (20 mL) was added phenyl isocyanate (284 mg, 2.39 mmol) and TEA (241.7 mg, 2.39 mmol). The mixture was stirred at RT for 3 days and then concentrated and purified by HPLC separation (MeCN/$H_2O$ with 0.1% TFA) to give 1-(5-(7-amino-1-ethyl-2-oxo-1,2-dihydro-1,6-naphthyridin-3-yl)-4-bromo-2-fluorophenyl)-3-phenylurea (20 mg, 5% yield). $^1$H NMR (400 MHz, DMSO-$d_6$): δ 9.17 (s, 1H), 8.72 (s, 1H), 8.33 (s, 1H), 8.15 (d, J=8.4 Hz, 1H), 7.68 (s, 1H), 7.63 (d, J=10.8 Hz, 1H), 7.41 (s, 1H), 7.39 (s, 1H), 7.26-7.22 (t, J=8.0 Hz, 2H), 6.96-6.93 (t, J=7.2 Hz, 1H), 6.52 (s, 2H), 6.32 (s, 1H), 4.09-4.06 (q, J=5.2 Hz, 2H), 1.20-1.17 (t, J=5.2 Hz, 3H).

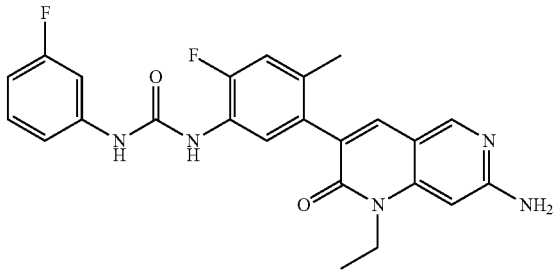

Example 58

To a biphasic solution of 3-fluoroaniline (0.3 mL, 3.12 mmol) in 1:1 EtOAc/water (10 mL) was added isopropenyl chloroformate (0.564 g, 4.68 mmol) and $NaHCO_3$ (1.31 g, 15.6 mmol) and the mixture stirred at RT overnight. The layers were separated and the aqueous layer was extracted with EtOAc. The combined organic layers were concentrated to dryness and purified by silica gel chromatography (EtOAc/Hex) to furnish prop-1-en-2-yl 3-fluorophenylcarbamate (125 mg, 21% yield) as a white solid. $^1$H NMR (400 MHz, DMSO-$d_6$): δ 10.14 (s, 1H), 7.35 (m, 1H), 7.31 (m, 1H), 7.21 (m, 1H), 6.83 (m, 1H), 4.74 (m, 2H), 1.92 (s, 3H).

A solution of prop-1-en-2-yl 3-fluorophenylcarbamate (0.094 g, 0.480 mmol) and Example A34 (0.100 g, 0.320 mmol) in THF (3 mL) was treated with a catalytic amount (1 drop) of 1-methylpyrrolidine and the mixture heated at 60° C. overnight. Additional 1-methylpyrrolidine (2 drops) was added and heating was continued at 60° C. for another 24 h. The mixture was cooled to RT, the solid collected via filtration, rinsed with THF and dried to afford 1-(5-(7-amino-1-ethyl-2-oxo-1,2-dihydro-1,6-naphthyridin-3-yl)-2-fluoro-4-methylphenyl)-3-(3-fluorophenyl)urea (123 mg, 85% yield) as a white solid. $^1$H NMR (400 MHz, DMSO-$d_6$): δ 9.22 (s, 1H), 8.53 (s, 1H), 8.34 (s, 1H), 7.89 (d, 1H), 7.65 (s, 1H), 7.46 (m, 1H), 7.27 (q, 1H), 7.13 (d, 1H), 7.04 (d, 1H), 6.76 (m, 1H), 6.47 (s, 2H), 6.34 (s, 1H), 4.09 (q, 2H), 2.06 (s, 3H), 1.20 (t, 3H); MS (ESI) m/z: 450.2 $[M+H]^+$.

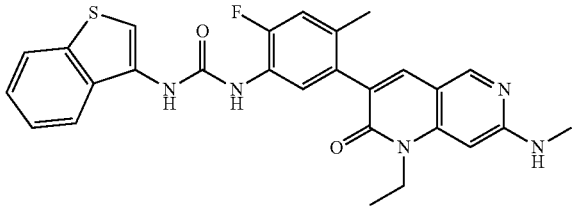

Example 59

A mixture of 1-benzothiophene carboxylic acid (0.131 g, 0.735 mmol)<autotext key="0C5A121E" name="[Reactants]" index="1" field="Reactants" type="field" length="54"/> and TEA (0.188 mL, 1.348 mmol)<autotext key="0C3956B0" name="[Reactants]" index="3" field="Reactants" type="field" length="26"/> in toluene (3.0 mL)<autotext key="0C3956B1" name="[Solvents]" index="1" field="Solvents" type="field" length="17"/> was treated with DPPA (0.198 mL, 0.919 mmol), <autotext key="0C3956B2" name="[Reactants]" index="4" field="Reactants" type="field" length="54"/> stirred at RT for 0.5 h, treated with Example A2 (0.200 g, 0.613 mmol) <autotext key="0C5A5BD9" name="[Reactants]" index="2" field="Reactants" type="field" length="31"/> and heated at 90° C. for 3 days. The mixture was cooled to RT, concentrated to dryness, treated with MeCN (5 mL) and heated at 70° C. for 5 minutes. The solid was collected via filtration, washed with MeCN, treated with MeOH, heated at 50° C. and collected via filtration. The material was purified via reverse-phase chromatography (MeCN/water with 0.1% TFA). Water and $NaHCO_3$ were added to the purified product and the resultant precipitate was filtered and dried to afford 1-(benzo[b]thiophen-3-yl)-3-(5-(1-ethyl-7-(methylamino)-2-oxo-1,2-dihydro-1,6-naphthyridin-3-yl)-2-fluoro-4-methylphenyl)urea (69 mg, 21% yield) as a white solid. $^1$H NMR (400 MHz, DMSO-$d_6$): δ 9.39 (s, 1H), 8.83 (s, 1H), 8.45 (s, 1H), 8.06 (d, 1H), 7.96 (d, 1H), 7.87 (d, 1H), 7.73 (s, 1H), 7.67 (s, 1H), 7.45 (m, 3H), 7.17 (d, 1H), 6.36 (s, 1H), 4.16 (m, 2H), 2.90 (d, 3H), 2.08 (s, 3H), 1.21 (t, 3H); MS (ESI) m/z: 502.2 $[M+H]^+$.

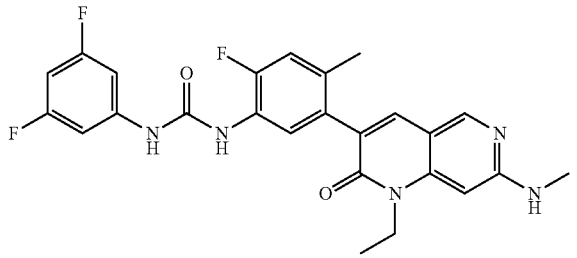

Example 60

A suspension of Example A2 (0.096 g, 0.29 mmol) in THF (3 mL) was treated with TEA (0.041 mL, 0.294 mmol) and 3,5-difluorophenyl isocyanate (0.114 g, 0.735 mmol)

and stirred at RT for 6 h. The mixture was treated with 60% EtOAc/Hex, stirred for 5 minutes and the resulting solid was collected via filtration and dried to afford 1-(3,5-difluorophenyl)-3-(5-(1-ethyl-7-(methylamino)-2-oxo-1,2-dihydro-1,6-naphthyridin-3-yl)-2-fluoro-4-methylphenyl)urea (0.11 g, 73% yield) as a white solid. $^1$H NMR (400 MHz, DMSO-$d_6$): δ 9.37 (s, 1H), 8.61 (s, 1H), 8.40 (s, 1H), 7.85 (d, J=8.4 Hz, 1H), 7.66 (s, 1H), 7.13 (dd, J=10.0 Hz, 2.4 Hz, 3H), 6.98 (q, J=4.8 Hz, 1H), 6.80-6.75 (m, 1H), 6.23 (s, 1H), 4.14 (q, J=6.8 Hz, 2H), 2.85 (d, J=4.8 Hz, 3H), 2.06 (s, 3H), 1.20 (t, J=6.8 Hz, 3H); MS (ESI) m/z: 482.2 [M+H]$^+$.

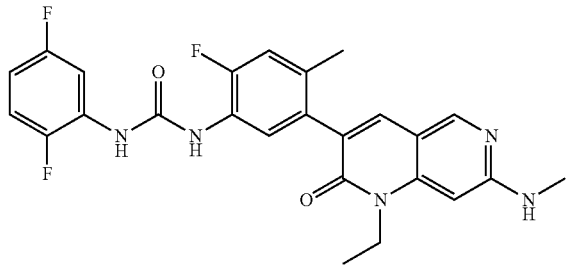

Example 61

A suspension of Example A2 (0.096 g, 0.29 mmol) in THF (3 mL) was treated with TEA (0.041 mL, 0.294 mmol) and 2,5-difluoro phenyl isocyanate (0.055 g, 0.353 mmol) and stirred at RT for 2 h. The mixture was treated with 60% EtOAc/Hex, stirred for 5 minutes and the resulting solid was collected via filtration and dried to afford 1-(2,5-difluorophenyl)-3-(5-(1-ethyl-7-(methylamino)-2-oxo-1,2-dihydro-1,6-naphthyridin-3-yl)-2-fluoro-4-methylphenyl)urea (0.12 g, 85% yield) as a white solid. $^1$H NMR (400 MHz, DMSO-$d_6$): δ 9.18 (s, 1H), 9.06 (s, 1H), 8.40 (s, 1H), 8.02-7.97 (m, 1H), 7.94 (d, J=8.4 Hz, 1H), 7.66 (s, 1H), 7.30-7.24 (m, 1H), 7.14 (d, J=12.4 Hz, 1H), 6.98 (q, J=4.8 Hz, 1H), 6.81-6.77 (m, 1H), 6.23 (s, 1H), 4.14 (q, J=6.8 Hz, 2H), 2.85 (d, J=4.8 Hz, 3H), 2.06 (s, 3H), 1.20 (t, J=6.8 Hz, 3H); MS (ESI) m/z: 482.2 [M+H]$^+$.

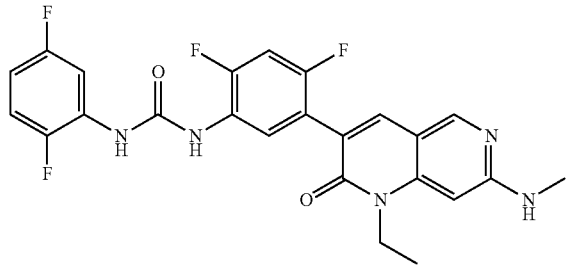

Example 62

A solution of Example A7 (0.12 g, 0.266 mmol) in dioxane (5 mL) was treated with 2,5-difluorophenyl isocyanate (0.034 mL, 0.293 mmol) and stirred at RT overnight. The resulting solid was collected via filtration and dried to yield 1-(5-(7-((4-methoxybenzyl)(methyl)amino)-1-ethyl-2-oxo-1,2,4a,8a-tetrahydro-1,6-naphthyridin-3-yl)-2,4-difluorophenyl)-3-(2,5-difluorophenyl)urea (129 mg, 80% yield). $^1$H NMR (400 MHz, DMSO-$d_6$): δ 9.19 (s, 1H), 9.10 (s, 1H), 8.52 (s, 1H), 8.16 (t, 1H), 8.01-7.98 (m, 1H), 7.86 (s, 1H), 7.38 (t, 1H), 7.31-7.27 (m, 1H), 7.18 (d, 2H), 6.87 (d, 2H), 6.82-6.80 (m, 1H), 6.32 (s, 1H), 4.85 (s, 2H), 4.19 (q, 2H), 3.70 (s, 3H), 3.13 (s, 3H), 1.13 (t, 3H); MS (ESI) m/z: 606.3 [M+H]$^+$.

A solution of 1-(5-(7-((4-methoxybenzyl)(methyl)amino)-1-ethyl-2-oxo-1,2,4a,8a-tetrahydro-1,6-naphthyridin-3-yl)-2,4-difluorophenyl)-3-(2,5-difluorophenyl)urea (0.129 g, 0.213 mmol) and anisole (0.233 mL, 2.130 mmol) in DCM (2 mL) was treated with TFA (2 mL, 26.0 mmol) and stirred at RT overnight. The mixture was concentrated to dryness, treated with EtOAc and satd. $NaHCO_3$, stirred for 1 h and the resulting solid collected via filtration and dried to afford 1-(2,5-difluorophenyl)-3-(5-(1-ethyl-7-(methylamino)-2-oxo-1,2,4a,8a-tetrahydro-1,6-naphthyridin-3-yl)-2,4-difluorophenyl)urea (84 mg, 81% yield). The material was suspended in MeCN (2 mL), treated with 0.5 N HCl (2.076 mL, 0.208 mmol), diluted with water (2 mL), frozen, lyophilized, triturated with $Et_2O$ and the resulting solid was collected via filtration and dried to yield 1-(2,5-difluorophenyl)-3-(5-(1-ethyl-7-(methylamino)-2-oxo-1,2,4a,8a-tetrahydro-1,6-naphthyridin-3-yl)-2,4-difluorophenyl)urea hydrochloride (85 mg, 94% yield). $^1$H NMR (400 MHz, DMSO-$d_6$): δ 9.24 (s, 1H), 9.18 (s, 1H), 8.53 (s, 1H), 8.18 (t, 1H), 8.02-7.97 (m, 1H), 7.94 (s, 1H), 7.90 (br s, 1H), 7.42 (t, 1H), 7.32-7.26 (m, 1H), 6.84-6.80 (m, 1H), 6.48 (s, 1H), 4.19 (q, 2H), 2.94 (s, 3H), 1.21 (t, 3H); MS (ESI) m/z: 486.2 [M+H]$^+$.

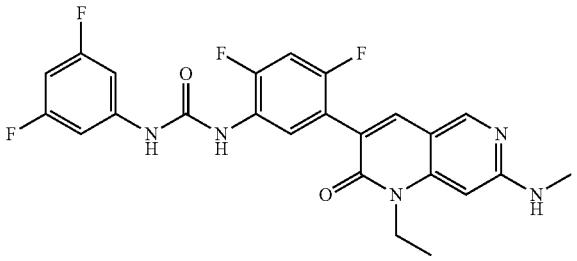

Example 63

A solution of Example A7 (0.12 g, 0.266 mmol) in dioxane (5 mL) was treated with 3,5-difluorophenyl isocyanate (0.038 mL, 0.320 mmol) and stirred at RT overnight. Additional 3,5-difluorophenyl isocyanate (0.038 mL, 0.320 mmol) was added and the mixture stirred for 4 h. The resulting precipitate was collected via filtration and dried to yield 1-(5-(7-((4-methoxybenzyl)(methyl)amino)-1-ethyl-2-oxo-1,2,4a,8a-tetrahydro-1,6-naphthyridin-3-yl)-2,4-difluorophenyl)-3-(3,5-difluorophenyl)urea (112 mg, 69% yield). $^1$H NMR (400 MHz, DMSO-$d_6$): δ 9.38 (s, 1H), 8.67 (s, 1H), 8.52 (s, 1H), 8.05 (t, 1H), 7.86 (s, 1H), 7.38 (t, 1H), 7.19-7.14 (m, 4H), 6.86 (d, 2H), 6.80-6.77 (m, 1H), 6.32 (s, 1H), 4.85 (s, 2H), 4.19 (q, 2H), 3.70 (s, 3H), 3.12 (s, 3H), 1.13 (t, 3H); MS (ESI) m/z: 606.3 [M+H]$^+$.

A solution of 1-(5-(7-((4-methoxybenzyl)(methyl)amino)-1-ethyl-2-oxo-1,2,4a,8a-tetrahydro-1,6-naphthyridin-3-yl)-2,4-difluorophenyl)-3-(3,5-difluorophenyl)urea (0.112 g, 0.185 mmol) and anisole (0.202 mL, 1.849 mmol) in DCM (2 mL) was treated with TFA (2 mL, 26.0 mmol) and stirred at RT overnight. The mixture was concentrated to dryness, treated with EtOAc and satd. $NaHCO_3$, stirred for 1 h and the resulting solid collected via filtration and dried to afford 1-(3,5-difluorophenyl)-3-(5-(1-ethyl-7-(methylamino)-2-oxo-1,2,4a,8a-tetrahydro-1,6-naphthyridin-3-yl)-2,4-difluorophenyl)urea (57 mg, 64% yield). The material was dissolved in MeCN (2 mL), treated with 0.1N HCl (1.17 mL, 0.117 mmol), diluted with water (3 mL), frozen, lyophilized, triturated with $Et_2O$ and the resulting solid was collected via filtration and dried to yield 1-(3,5-difluorophenyl)-3-(5-(1-ethyl-7-(methylamino)-2-oxo-1,2,4a,8a-tetrahydro-1,6-naphthyridin-3-yl)-2,4-difluorophenyl)urea hydrochloride (57 mg, 96% yield). $^1$H NMR (400 MHz, DMSO-$d_6$): δ 9.95 (s, 1H), 8.80 (s, 1H), 8.51 (s, 1H), 8.07 (t, 1H), 7.92 (s, 1H), 7.70 (br s, 1H), 7.40 (t, 1H), 7.15 (d, 2H), 6.82-6.77 (m, 1H), 6.43 (s, 1H), 4.15 (q, 2H), 2.91 (s, 3H), 1.21 (t, 3H); MS (ESI) m/z: 486.2 [M+H]$^+$.

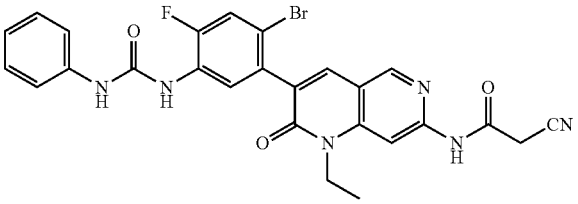

Example 64

A suspension of Example 57 (135 mg, 0.272 mmol) in ethyl cyanoacetate (2.307 g, 20.40 mmol) was heated at 105° C. for 4.5 h, then at 125° C. for 2 days. The mixture was treated with NMP (0.3 mL), heated at 125° C. for 5 h, then cooled to RT and purified via silica gel chromatography (EtOAc/Hex). The material was re-purified via silica gel chromatography (THF/Hex), dissolved in 4:1 MeCN/$H_2O$, frozen and lyophilized. The material was treated with MTBE, the resulting solid collected via filtration and dried to afford N-(3-(2-bromo-4-fluoro-5-(3-phenylureido)phenyl)-1-ethyl-2-oxo-1,2-dihydro-1,6-naphthyridin-7-yl)-2-cyanoacetamide (13 mg, 8.5% yield) as an off-white solid. $^1$H NMR (400 MHz, DMSO-$d_6$): δ 11.17 (s, 1H), 9.10 (s, 1H), 8.74 (m, 2H), 8.23 (d, J=8.5 Hz, 1H), 8.17 (s, 1H), 7.98 (s, 1H), 7.70 (d, J=10.7 Hz, 1H), 7.41 (d, J=8.1 Hz, 2H), 7.26 (t, J=7.8 Hz, 2H), 6.97 (t, J=7.4 Hz, 1H), 4.22 (q, J=7.2 Hz, 2H), 4.05 (s, 2H), 1.26 (t, J=6.8 Hz, 3H); MS (ESI) m/z: 565.1 [M+H]$^+$.

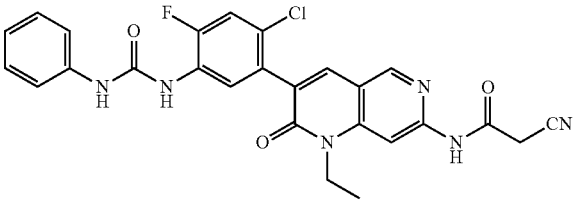

Example 65

A suspension of Example 21 (0.180 g, 0.398 mmol) in ethyl cyanoacetate (3 ml, 28.1 mmol) was heated at 125° C. overnight. The mixture was treated with NMP (0.3 mL), heated at 125° C. for 24 h, then cooled to RT and purified via silica gel chromatography (EtOAc/Hex). The material was re-purified via silica gel chromatography (THF/Hex), dissolved in 4:1 MeCN/$H_2O$, frozen and lyophilized, treated with MTBE and the resulting solid collected via filtration and dried to afford N-(3-(2-chloro-4-fluoro-5-(3-phenylureido)phenyl)-1-ethyl-2-oxo-1,2-dihydro-1,6-naphthyridin-7-yl)-2-cyanoacetamide (22 mg, 11% yield) as an off-white solid. $^1$H NMR (400 MHz, DMSO-$d_6$): δ 11.17 (s, 1H), 9.10 (s, 1H), 8.75 (s, 1H), 8.73 (s, 1H), 8.23 (d, J=8.6 Hz, 1H), 8.17 (s, 1H), 8.01 (s, 1H), 7.58 (d, J=11.0 Hz, 1H), 7.41 (d, J=8.0 Hz, 2H), 7.26 (t, J=7.8 Hz, 2H), 6.97 (t, J=7.0 Hz, 1H), 4.22 (q, J=7.1 Hz, 2H), 4.05 (s, 2H), 1.26 (t, J=7.0 Hz, 3H); MS (ESI) m/z: 519.1 [M+H]$^+$.

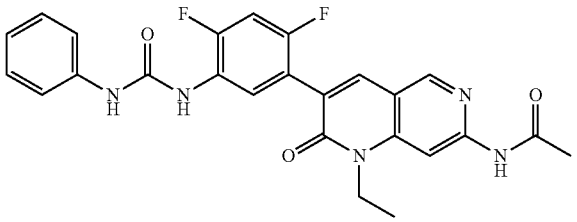

Example 66

A solution of Example A36 (1 g, 2.3 mmol) in TFA (10 mL) was stirred at 60° C. overnight. The solvent was removed and the crude product was treated with satd. $NaHCO_3$ and extracted with EtOAc (2×). The combined organic extracts were washed with brine, dried over $Na_2SO_4$, and evaporated to yield 7-amino-3-(5-amino-2,4-difluorophenyl)-1-ethyl-1,6-naphthyridin-2(1H)-one (600 mg, 83% yield), which was used in next step without purification.

A solution of 7-amino-3-(5-amino-2,4-difluorophenyl)-1-ethyl-1,6-naphthyridin-2(1H)-one (500 mg, 1.58 mmol) and TEA (638 mg, 6.32 mmol) in DCM (5 mL) was treated drop-wise with phenyl isocyanate (503 mg, 4.8 mmol) and stirred at RT overnight. The mixture was concentrated to dryness and purified by silica gel chromatography (EtOAc/pet ether) to afford 1-(5-(7-amino-1-ethyl-2-oxo-1,2-dihydro-1,6-naphthyridin-3-yl)-2,4-difluorophenyl)-3-phenylurea (500 mg, 73% yield). $^1$H NMR (400 MHz, DMSO-$d_6$): δ 9.03 (s, 1H), 8.55 (s, 1H), 8.38 (s, 1H), 8.13 (m, 1H), 7.83 (s, 1H), 7.43 (d, J=7.6 Hz, 2H), 7.39-7.34 (m, 1H), 7.29-7.25 (m, 2H), 6.99-6.95 (m, 1H), 6.58 (s, 2H), 6.34 (s, 1H), 4.13-4.08 (q, J=0.8 Hz, 2H), 1.22 (t, J=6.8 Hz, 3H).

A solution of 1-(5-(7-amino-1-ethyl-2-oxo-1,2-dihydro-1,6-naphthyridin-3-yl)-2,4-difluorophenyl)-3-phenylurea (150 mg, 0.344 mmol) and TEA (174.2 mg, 1.72 mmol) in THF (3 mL) was treated drop-wise with acetyl chloride (81 mg, 1.03 mmol) at RT. The resulting mixture was stirred for 2 h and the solvent was removed to give the crude product. It was diluted, washed with brine, dried over $Na_2SO_4$, concentrated under reduced pressure and purified by silica gel chromatography to give N-acetyl-N-{3-[2,4-difluoro-5-(3-phenyl-ureido)-phenyl]-1-ethyl-2-oxo-1,2-dihydro-[1,6]naphthyridin-7-yl}-acetamide (150 mg, 84% yield). $^1$H NMR (400 MHz, DMSO-$d_6$): δ 10.86 (s, 1H), 9.41 (s, 1H), 8.79 (s, 1H), 8.74 (s, 1H), 8.27 (s, 1H), 8.20-8.16 (m, 1H), 8.08 (s, 1H), 8.00 (s, 1H), 7.46-7.39 (m, 3H), 7.29-7.25 (m, 2H), 6.98-6.95 (m, 1H), 4.25-4.22 (t, J=7.2 Hz, 3H), 2.16 (s, 3H), 1.27 (s, 3H).

To a solution of N-acetyl-N-{3-[2,4-difluoro-5-(3-phenyl-ureido)-phenyl]-1-ethyl-2-oxo-1,2-dihydro-[1,6]naphthyridin-7-yl}-acetamide (100 mg, 0.19 mmol) in MeOH (2 mL) was added $K_2CO_3$ (79 mg, 0.57 mmol) and water (1 mL), and the mixture was stirred overnight at RT. MeOH was removed under reduced pressure and the residue was diluted with water (8 mL). The mixture was extracted with EtOAc to give a crude product which purified by prep-HPLC to give 1-(5-(7-acetamido-1-ethyl-2-oxo-1,2-dihydro-1,6-naphthyridin-3-yl)-2,4-difluorophenyl)-3-phenylurea (32 mg, 23% yield). $^1$H NMR (400 MHz, DMSO-$d_6$): δ 10.85 (s, 1H), 9.08 (s, 1H), 8.74 (s, 1H), 8.61 (s, 1H), 8.27 (s, 1H), 8.21-8.16 (m, 1H), 8.07 (s, 1H), 7.45-7.40 (m, 3H), 7.30-7.26 (m, 2H), 7.00-6.96 (m, 1H), 4.24-4.18 (q, J=6.8 Hz, 2H), 2.16 (s, 3H), 1.28-1.25 (t, J=6.8 Hz, 3H); MS (ESI) m/z: 478.3 [M+H]$^+$.

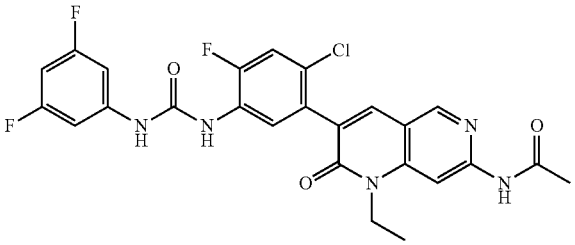

Example 67

A solution of Example A3 (0.20 g, 0.568 mmol) in THF (6 mL) was treated with TEA (0.098 mL, 0.710 mmol) followed by 3,5-difluorophenyl isocyanate (0.092 g, 0.596 mmol) and stirred at RT for 2 h. Additional 3,5-difluorophenyl isocyanate (0.14 g, 0.903 mmol) was added and the mixture stirred at RT overnight. More 3,5-difluorophenyl isocyanate (0.25 g, 1.61 mmol) was added and the mixture stirred at RT for 24 h. The mixture was cooled to 0° C. and the solids collected via filtration and dried. The filtrate was concentrated to dryness and purified via silica gel chromatography (THF/Hex) and combined with the isolated solid to afford 1-(4-chloro-5-(7-chloro-1-ethyl-2-oxo-1,2-dihydro-1,6-naphthyridin-3-yl)-2-fluorophenyl)-3-(3,5-difluorophenyl)urea (177 mg, 61% yield). $^1$H NMR (400 MHz, DMSO-$d_6$): δ 9.27 (br s, 2H), 8.79 (s, 1H), 8.15 (d, J=8.5 Hz, 1H), 8.08 (s, 1H), 7.74 (s, 1H), 7.57 (d, J=10.9 Hz, 1H), 7.16 (m, 2H), 6.77 (m, 1H), 4.27 (q, J=7.0 Hz, 2H), 1.20 (t, J=7.0 Hz, 3H); MS (ESI) m/z: 507.1 [M+H]$^+$.

A mixture of 1-(4-chloro-5-(7-chloro-1-ethyl-2-oxo-1,2-dihydro-1,6-naphthyridin-3-yl)-2-fluorophenyl)-3-(3,5-difluorophenyl)urea (178 mg, 0.351 mmol), Xantphos (20.30 mg, 0.035 mmol), $Cs_2CO_3$ (229 mg, 0.702 mmol) and acetamide (104 mg, 1.754 mmol) in dioxane (3.5 mL) was sparged with Ar for 10 min, treated with $Pd_2(dba)_3$ (16.07 mg, 0.018 mmol) and heated at 100° C. overnight. The mixture was cooled to RT, treated with THF, the solids removed via filtration through diatomaceous earth and rinsed well with THF. The filtrate was washed with brine (3×), dried over $MgSO_4$, concentrated to dryness and purified via silica gel chromatography (EtOAc/Hex). The material was suspended in 4:1 MeCN/$H_2O$, frozen and lyophilized; the resulting solid was triturated with MTBE, collected via filtration and dried to afford N-(3-(2-chloro-5-(3-(3,5-difluorophenyl)ureido)-4-fluorophenyl)-1-ethyl-2-oxo-1,2-dihydro-1,6-naphthyridin-7-yl)acetamide (9 mg, 4.8% yield). $^1$H NMR (500 MHz, DMSO-$d_6$): δ 10.86 (s, 1H), 9.48 (s, 1H), 8.89 (s, 1H), 8.74 (s, 1H), 8.29 (s, 1H), 8.17 (d, J=8.5 Hz, 1H), 8.01 (s, 1H), 7.63 (d, J=10.9 Hz, 1H), 7.17 (m, 2H), 6.84-6.83 (m, 1H), 4.22 (q, J=7.2 Hz, 2H), 2.17 (s, 3H), 1.27 (t, J=7.1 Hz, 3H); MS (ESI) m/z: 530.1 [M+H]$^+$.

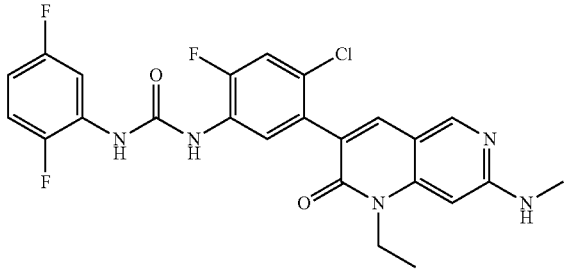

Example 68

A solution of Example A4 (250 mg, 0.535 mmol) in pyridine (2 mL) was treated with 2,5-difluorophenyl isocyanate (91 mg, 0.589 mmol) and stirred at RT overnight. Additional 2,5-difluorophenyl isocyanate (30 μL, 0.256 mmol) was added and stirred at RT for 4 h. The mixture was concentrated to near-dryness, treated with EtOAc and brine and the resulting solid was collected via filtration and dried to afford 1-(4-chloro-5-(1-ethyl-7-((4-methoxybenzyl)(methyl)amino)-2-oxo-1,2-dihydro-1,6-naphthyridin-3-yl)-2-fluorophenyl)-3-(2,5-difluorophenyl)urea (314 mg, 94% yield). $^1$H NMR (400 MHz, DMSO-$d_6$): δ 9.31 (s, 2H), 8.51 (s, 1H), 8.19 (d, J=8.6 Hz, 1H), 7.98 (m, 1H), 7.78 (s, 1H), 7.56 (d, J=10.9 Hz, 1H), 7.29 (m, 1H), 7.18 (d, J=8.4 Hz, 2H), 6.89-6.78 (m, 3H), 6.33 (s, 1H), 4.85 (s, 2H), 4.19 (q, J=7.1 Hz, 2H), 3.70 (s, 3H), 3.13 (s, 3H), 1.13 (t, J=7.0 Hz, 3H); MS (ESI) m/z: 622.2 [M+H]$^+$.

A mixture of 1-(4-chloro-5-(1-ethyl-7-((4-methoxybenzyl)(methyl)amino)-2-oxo-1,2-dihydro-1,6-naphthyridin-3-yl)-2-fluorophenyl)-3-(2,5-difluorophenyl)urea (314 mg, 0.505 mmol) and anisole (273 mg, 2.52 mmol) was treated with TFA (3.0 mL, 51.9 mmol) and stirred at RT for 2.5 h. The mixture was concentrated to near-dryness, treated with EtOAc and satd. $NaHCO_3$ and the resulting solid collected via filtration and dried to afford 1-(4-chloro-5-(1-ethyl-7-(methylamino)-2-oxo-1,2-dihydro-1,6-naphthyridin-3-yl)-2-fluorophenyl)-3-(2,5-difluorophenyl)urea (233 mg, 92% yield). $^1$H NMR (400 MHz, DMSO-$d_6$): δ 9.24 (m, 2H), 8.40 (s, 1H), 8.17 (d, J=8.7 Hz, 1H), 7.97 (m, 1H), 7.73 (s, 1H), 7.54 (d, J=11.0 Hz, 1H), 7.27 (m, 1H), 7.02 (m, 1H), 6.80 (m, 1H), 6.23 (s, 1H), 4.12 (q, J=7.1 Hz, 2H), 2.85 (d, J=4.9 Hz, 3H), 1.19 (t, J=7.0 Hz, 3H); MS (ESI) m/z: 502.2 [M+H]$^+$.

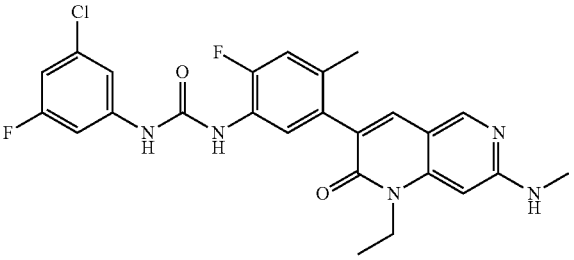

Example 69

A bi-phasic solution of Example A1 (0.15 g, 0.336 mmol) in EtOAc (5 mL) and satd. $NaHCO_3$ (4.2 mL) was treated with isopropenyl chloroformate (0.061 g, 0.504 mmol) and stirred at RT for 2 h. The layers were separated, the aqueous layer extracted with EtOAc (1×) and the combined organics were washed with brine, dried over $Na_2SO_4$ and concentrated to dryness. The solid was dissolved in THF (2 mL), treated with 1-methylpyrrolidine (0.011 g, 0.134 mmol) and 3-chloro-5-fluoro aniline (0.098 g, 0.672 mmol) and heated at 55° C. for 20 h. The mixture was cooled to RT, concentrated to dryness and purified via silica gel chromatography (EtOAc/Hex) to afford 1-(3-chloro-5-fluorophenyl)-3-(5-(1-ethyl-7-((4-methoxybenzyl)(methyl)amino)-2-oxo-1,2-dihydro-1,6-naphthyridin-3-yl)-2-fluoro-4-methylphenyl)urea (105 mg, 51% yield). MS (ESI) m/z: 618.2 $[M+H]^+$.

A solution of 1-(3-chloro-5-fluorophenyl)-3-(5-(1-ethyl-7-((4-methoxybenzyl)(methyl)amino)-2-oxo-1,2-dihydro-1,6-naphthyridin-3-yl)-2-fluoro-4-methylphenyl)urea (0.105 g, 0.170 mmol) in TFA (3 mL) was treated with anisole (0.093 ml, 0.849 mmol) and stirred at RT for 4 h. The mixture was concentrated to dryness and purified via reverse-phase chromatography (MeCN/$H_2O$ with 0.1% TFA). The combined fractions were neutralized with satd. $NaHCO_3$, extracted with EtOAc (2×) and the combined organics were washed with water, then brine, dried over $Na_2SO_4$ and concentrated to dryness to afford 1-(3-chloro-5-fluorophenyl)-3-(5-(1-ethyl-7-(methylamino)-2-oxo-1,2-dihydro-1,6-naphthyridin-3-yl)-2-fluoro-4-methylphenyl) urea (62 mg, 73% yield). $^1H$ NMR (400 MHz, DMSO-$d_6$): δ 9.54 (s, 1H), 8.69 (s, 1H), 8.40 (s, 1H), 7.85 (d, J=8.4 Hz, 1H), 7.66 (s, 1H), 7.35 (s, 1H), 7.27 (dt, J=11.3, 2.1 Hz, 1H), 7.14 (d, J=12.1 Hz, 1H), 7.00-6.95 (m, 2H), 6.24 (s, 1H), 4.14 (q, J=7.1 Hz, 2H), 2.85 (d, J=4.9 Hz, 3H), 2.07 (s, 3H), 1.21 (t, J=7.0 Hz, 3H); MS (ESI) m/z: 498.2 $[M+H]^+$.

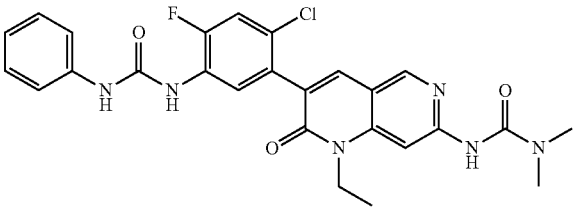

Example 70

A solution of Example A50 (0.105 g, 0.196 mmol) in dioxane (4 mL) was treated with dimethylamine (2M in THF, 4 mL, 8.0 mmol) and stirred at RT overnight. 1-Methylpyrrolidine (0.1 ml) was added and the mixture was stirred at RT for 24 h. Additional 1-methylpyrrolidine (0.1 ml) and dimethylamine (2M in THF, 2 mL, 4.0 mmol) were added and the mixture was stirred at RT for 3 days, then heated at 40° C. for 24 h. The mixture was cooled to RT, the solid collected via filtration and dried to afford 3-(3-(2-chloro-4-fluoro-5-(3-phenylureido)phenyl)-1-ethyl-2-oxo-1,2-dihydro-1,6-naphthyridin-7-yl)-1,1-dimethylurea (80 mg, 73% yield). $^1H$ NMR (400 MHz, DMSO-$d_6$): δ 9.19 (s, 1H), 9.08 (s, 1H), 8.70 (m, 1H), 8.65 (s, 1H), 8.21 (d, J=8.6 Hz, 1H), 8.01 (s, 1H), 7.94 (s, 1H), 7.56 (d, J=11.0 Hz, 1H), 7.43-7.41 (m, 2H), 7.26 (m, 2H), 6.97 (t, J=7.4 Hz, 1H), 4.17 (q, J=7.0 Hz, 2H), 2.97 (s, 6H), 1.24 (t, J=7.0 Hz, 3H); MS (ESI) m/z: 523.2 $[M+H]^+$.

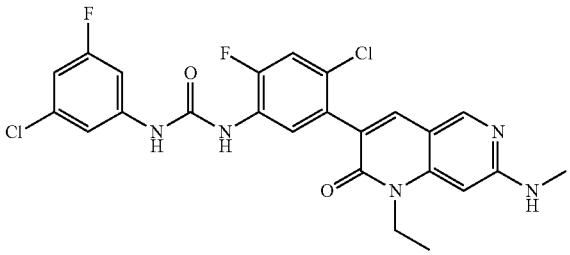

Example 71

A mixture of Example A47 (200 mg, 0.363 mmol), DIEA (188 mg, 1.452 mmol) and 3-chloro-5-fluoroaniline (211 mg, 1.452 mmol) in dioxane (5 mL) was heated at 80° C. overnight. The mixture was cooled to RT, treated with EtOAc and satd. $NaHCO_3$ and the resulting solid collected via filtration and dried to afford crude 1-(4-chloro-5-(1-ethyl-7-((4-methoxybenzyl)(methyl)amino)-2-oxo-1,2-dihydro-1,6-naphthyridin-3-yl)-2-fluorophenyl)-3-(3-chloro-5-fluorophenyl)urea (91 mg, 39% yield) which was carried on to the next step without further purification. MS (ESI) m/z: 638.2 $[M+H]^+$.

A mixture of 1-(4-chloro-5-(1-ethyl-7-((4-methoxybenzyl)(methyl)amino)-2-oxo-1,2-dihydro-1,6-naphthyridin-3-yl)-2-fluorophenyl)-3-(3-chloro-5-fluorophenyl)urea (91 mg, 0.143 mmol) and anisole (77 mg, 0.713 mmol) was stirred in TFA (3 mL) at RT for 3 h. The mixture was concentrated to near-dryness, dissolved in EtOAc and treated with satd. $NaHCO_3$. The layers were separated, the organic layer washed with brine and dried over $Na_2SO_4$. Solids precipitated, so THF, MeOH and DMF were added and the mixture was warmed to afford a clear solution, then filtered to remove salts. The filtrate was concentrated to dryness and purified via reverse-phase chromatography (MeCN/$H_2O$ with 0.1% TFA). The organics were removed under reduced pressure, the aqueous residue neutralized with satd. $NaHCO_3$, extracted with warm EtOAc (2×) and the combined organics were washed with brine, dried over $Na_2SO_4$ and concentrated to dryness to afford 1-(4-chloro-5-(1-ethyl-7-(methylamino)-2-oxo-1,2-dihydro-1,6-naphthyridin-3-yl)-2-fluorophenyl)-3-(3-chloro-5-fluorophenyl) urea (55 mg, 74% yield). $^1H$ NMR (400 MHz, DMSO-$d_6$): δ 9.43 (s, 1H), 8.83 (s, 1H), 8.41 (s, 1H), 8.09 (d, J=8.6 Hz, 1H), 7.74 (s, 1H), 7.55 (d, J=10.9 Hz, 1H), 7.36 (s, 1H), 7.27 (dt, J=11.2, 2.1 Hz, 1H), 7.06-6.98 (m, 2H), 6.24 (s, 1H), 4.14 (q, J=7.1 Hz, 2H), 2.86 (d, J=4.8 Hz, 3H), 1.20 (t, J=7.0 Hz, 3H); MS (ESI) m/z: 518.1 $[M+H]^+$.

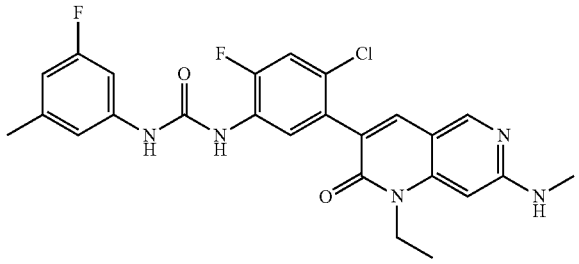

Example 72

A mixture of Example A47 (200 mg, 0.363 mmol), DIEA (188 mg, 1.452 mmol) and 3-chloro-5-methylaniline (182 mg, 1.452 mmol) in dioxane (5 mL) was heated at 80° C. overnight. The mixture was cooled to RT, treated with EtOAc and satd. $NaHCO_3$ and the resulting solid collected via filtration and dried to afford crude 1-(4-chloro-5-(1-ethyl-7-((4-methoxybenzyl)(methyl)amino)-2-oxo-1,2-dihydro-1,6-naphthyridin-3-yl)-2-fluorophenyl)-3-(3-fluoro-5-methylphenyl)urea (197 mg, 88% yield). MS (ESI) m/z: 618.2 $[M+H]^+$.

A mixture of 1-(4-chloro-5-(1-ethyl-7-((4-methoxybenzyl)(methyl)amino)-2-oxo-1,2-dihydro-1,6-naphthyridin-3-yl)-2-fluorophenyl)-3-(3-fluoro-5-methylphenyl)urea (197 mg, 0.319 mmol) and anisole (172 mg, 1.594 mmol) was stirred in TFA (4 mL) at RT for 3 h. The mixture was concentrated to near-dryness, treated with EtOAc and satd. $NaHCO_3$ and the resulting solid collected via filtration and dried to afford 1-(4-chloro-5-(1-ethyl-7-(methylamino)-2-oxo-1,2-dihydro-1,6-naphthyridin-3-yl)-2-fluorophenyl)-3-(3-fluoro-5-methylphenyl)urea (113 mg, 71% yield). $^1H$ NMR (400 MHz, DMSO-$d_6$): δ 9.18 (br s, 1H), 8.80 (br s, 1H), 8.41 (s, 1H), 8.14 (d, J=8.5 Hz, 1H), 7.73 (s, 1H), 7.52 (d, J=10.8 Hz, 1H), 7.22 (d, J=11.5 Hz, 1H), 7.03 (br s, 1H), 6.92 (s, 1H), 6.67-6.59 (m, 1H), 6.24 (s, 1H), 4.14 (q, J=7.1 Hz, 2H), 2.86 (s, 3H), 2.25 (s, 3H), 1.21 (t, J=7.3 Hz, 3H); MS (ESI) m/z: 498.1 $[M+H]^+$.

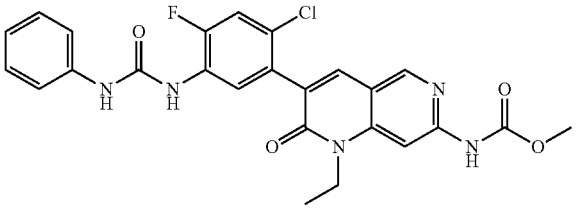

Example 73

A mixture of Example 21 (100 mg, 0.221 mmol) in pyridine (3 mL) was treated drop-wise with methylchloroformate (23 mg, 0.243 mmol) and stirred at RT for 4 h. Additional methylchloroformate (50 mL) was added and the mixture stirred overnight. The mixture was treated with additional methylchloroformate (100 mL) and stirred for another 2 days. The mixture was concentrated to dryness, treated with EtOAc and water and the resulting solid collected via filtration. The material was purified via reverse-phase chromatography (MeCN/$H_2O$ with 0.1% TFA); the organics were removed under reduced pressure and the aqueous mixture was neutralized with satd. $NaHCO_3$. The resulting solid was collected via filtration, washed with water and dried to afford methyl (3-(2-chloro-4-fluoro-5-(3-phenylureido)phenyl)-1-ethyl-2-oxo-1,2-dihydro-1,6-naphthyridin-7-yl)carbamate (101 mg, 87% yield). $^1H$ NMR (400 MHz, DMSO-$d_6$): δ 10.56 (br s, 1H), 9.31-8.78 (m, 2H), 8.67 (s, 1H), 8.20 (d, J=8.6 Hz, 1H), 7.96 (s, 2H), 7.56 (d, J=11.0 Hz, 1H), 7.42 (d, J=8.0 Hz, 2H), 7.26 (t, J=7.8 Hz, 2H), 6.96 (t, J=7.4 Hz, 1H), 4.20 (q, J=7.2 Hz, 2H), 3.71 (s, 3H), 1.25 (t, J=7.1 Hz, 3H); MS (ESI) m/z: 510.1 $[M+H]^+$.

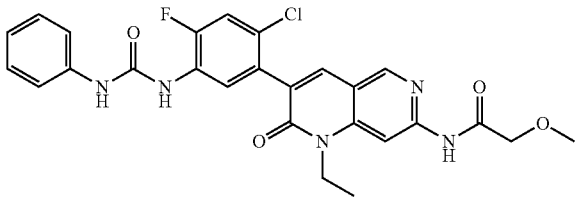

Example 74

A mixture of Example 21 (90 mg, 0.199 mmol) and pyridine (79 mg, 0.996 mmol) in THF (4 mL) was treated drop-wise with methoxy acetyl chloride (27 mg, 0.249 mmol) and stirred at RT for 22 h. Additional methoxy acetyl chloride (30 μL, 0.328 mmol) was added, the mixture heated at 40° C. for 6 h, then cooled to RT and stirred overnight. The mixture was treated with EtOAc and water, stirred for 1 h, the resulting solid collected via filtration and dried to afford N-(3-(2-chloro-4-fluoro-5-(3-phenylureido)phenyl)-1-ethyl-2-oxo-1,2-dihydro-1,6-naphthyridin-7-yl)-2-methoxyacetamide (76 mg, 72% yield). $^1H$ NMR (400 MHz, DMSO-$d_6$): δ 10.39 (s, 1H), 9.09 (s, 1H), 8.73 (m, 2H), 8.27-8.20 (m, 2H), 8.00 (s, 1H), 7.58 (d, J=10.9 Hz, 1H), 7.41 (d, J=8.0 Hz, 2H), 7.26 (t, J=7.7 Hz, 2H), 6.97 (t, J=7.3 Hz, 1H), 4.21 (q, J=7.1 Hz, 2H), 4.12 (s, 2H), 3.38 (s, 3H), 1.26 (t, J=7.1 Hz, 3H); MS (ESI) m/z: 524.2 $[M+H]^+$.

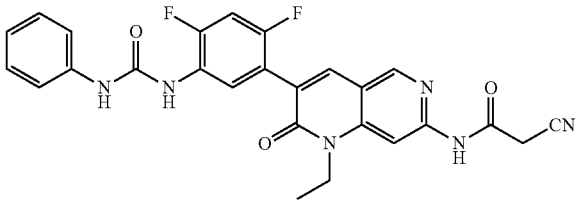

Example 75

A mixture of Example A18 (752 mg, 9.0 mmol), $Cs_2CO_3$ (2.0 g, 6.0 mmol) and Xantphos (173 mg, 0.3 mmol) in dioxane (10 mL) was sparged with $N_2$, treated with $Pd_2(dba)_3$ (165 mg, 0.18 mmol), sparged again with $N_2$ and heated at 100° C. overnight. The mixture was cooled to RT, poured into water and extracted with EtOAc (3×). The combined organics were washed with brine, dried over $Na_2SO_4$, concentrated to dryness and purified via silica gel chromatography to afford N-(3-(5-amino-2,4-difluorophenyl)-1-ethyl-2-oxo-1,2-dihydro-1,6-naphthyridin-7-yl)-2-cyanoacetamide (500 mg, 44% yield). $^1H$ NMR (400 MHz, DMSO-$d_6$): δ 11.15 (s, 1H), 8.71 (s, 1H), 8.14 (s, 1H), 7.98 (s, 1H), 7.06-7.11 (m, 1H), 6.80-6.85 (m, 1H), 5.06 (s, 2H) 4.22-4.18 (m, 2H), 4.08 (s, 2H), 1.25-1.22 (t, J=7.2 Hz, 3H).

A solution of N-(3-(5-amino-2,4-difluorophenyl)-1-ethyl-2-oxo-1,2-dihydro-1,6-naphthyridin-7-yl)-2-cyanoacetamide (0.5 g, 1.3 mmol) and $K_2CO_3$ (448 mg, 3.25 mmol) in THF (4 mL) was treated drop-wise with phenyl chloroformate (408 mg, 2.6 mmol) and heated at 60° C. overnight. The mixture was cooled to RT, concentrated to dryness, treated with water and extracted with EtOAc (2×). The combined organics were washed with brine, dried over $Na_2SO_4$, concentrated and purified via silica gel chromatography to afford phenyl (5-(7-(2-cyanoacetamido)-1-ethyl-2-oxo-1,2-dihydro-1,6-naphthyridin-3-yl)-2,4-difluorophenyl)carbamate (400 mg, 61% yield).

A solution of phenyl (5-(7-(2-cyanoacetamido)-1-ethyl-2-oxo-1,2-dihydro-1,6-naphthyridin-3-yl)-2,4-difluorophenyl)carbamate (400 mg, 0.80 mmol) and aniline (158 mg, 1.6 mmol) in DMSO (3 mL) was heated at 60° C. overnight and purified via reverse-phase chromatography (MeCN/$H_2O$ with 0.1% TFA) to afford 2-cyano-N-(3-(2,4-difluoro-5-(3-phenylureido)phenyl)-1-ethyl-2-oxo-1,2-dihydro-1,6-naphthyridin-7-yl)acetamide (50 mg, 13% yield). $^1$H NMR (400 MHz, DMSO-$d_6$): δ 11.23 (s, 1H), 8.92 (s, 1H), 8.78 (s, 1H), 8.20-8.16 (m, 2H), 8.11 (s, 1H),7.49-7.39 (m, 4H), 7.29-7.25 (m, 2H), 6.96 (t, J=7.2 Hz, 1H) 4.26-4.21 (q, J=6.8 Hz, 2H), 4.09 (s, 2H),1.30-1.26 (t, J=6.8 Hz, 3H); MS (ESI) m/z: 503.2 [M+H]$^+$.

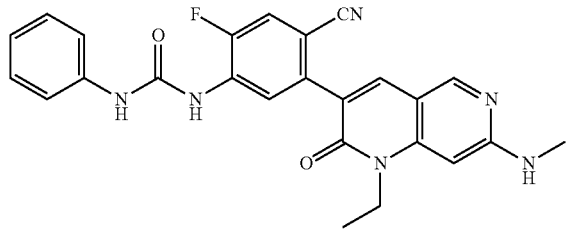

Example 76

A solution of Example C5 (3 g, 10.9 mmol) in DMF (50 mL) was treated with $ZnCN_2$ (1.7 g, 16.4 mmol) and $Pd(PPh_3)_4$ (1.26 g, 1.09 mmol), sparged with $N_2$ and heated at 100° C. for 12 h. The mixture was cooled to RT, treated with water and extracted with EtOAc (3×). The combined organics were washed with brine (3×), dried over $Na_2SO_4$, concentrated to dryness and purified via silica gel chromatography (EtOAc/pet ether) to afford ethyl 2-(5-amino-2-cyano-4-fluorophenyl)acetate (600 mg, 25% yield). $^1$H NMR (400 MHz, $CDCl_3$): δ 7.19 (d, J=2.4 Hz, 1H), 6.67 (d, J=8.4 Hz, 1H), 4.13-4.11 (q, J=6.8 Hz, 2H), 3.66 (s, 2H), 1.23-1.19 (t, J=6.8 Hz, 3H).

A solution of ethyl 2-(5-amino-2-cyano-4-fluorophenyl) acetate (400 mg, 1.80 mmol) and Example B1 (281 mg, 1.80 mmol) in DMF (20 mL) was treated with $Cs_2CO_3$ (1.17 g, 3.60 mmol) and stirred at RT for 1 h. The resulting solid was collected via filtration, washed with water and dried to afford 4-amino-2-(7-chloro-1-ethyl-2-oxo-1,2-dihydro-1,6-naphthyridin-3-yl)-5-fluorobenzonitrile (420 mg, 68% yield). $^1$H NMR (400 MHz, DMSO-$d_6$): δ 8.88 (s, 1H), 8.26 (s, 1H), 7.83 (s, 1H), 7.69 (d, J=11.6 Hz, 1H), 6.92 (d, J=8.8 Hz, 1H), 6.43 (s, 2H), 4.38-4.33 (q, J=6.4 Hz, 2H), 1.30-1.26 (t, J=6.4 Hz, 3H).

A mixture of 4-amino-2-(7-chloro-1-ethyl-2-oxo-1,2-dihydro-1,6-naphthyridin-3-yl)-5-fluorobenzonitrile (420 mg, 1.23 mmol) and methylamine (25%, 50 mL) was heated at 120° C. in a pressure vessel for 1 day. The mixture was cooled to RT, the solid collected via filtration and purified via silica gel chromatography (EtOAc/pet ether) to afford 4-amino-2-(1-ethyl-7-(methylamino)-2-oxo-1,2-dihydro-1,6-naphthyridin-3-yl)-5-fluorobenzonitrile (250 mg, 61% yield). $^1$H NMR (400 MHz, DMSO-$d_6$): δ 8.42 (s, 1H), 7.81 (s, 1H), 7.72 (s, 1H), 7.53 (d, J=11.6 Hz, 1H), 7.09-7.08 (m, 1H), 6.81 (d, J=8.4 Hz, 1H), 6.23 (s, 2H), 4.16-4.11 (q, J=6.8 Hz, 2H), 2.85 (d, J=4.8 Hz, 3H), 1.22-1.18 (t, J=6.8 Hz, 3H).

A −70° C. solution of 4-amino-2-(1-ethyl-7-(methylamino)-2-oxo-1,2-dihydro-1,6-naphthyridin-3-yl)-5-fluorobenzonitrile (100 mg, 0.296 mmol) in DCM was treated drop-wise with n-BuLi (0.47 mL, 1.17 mmol), stirred at −60° C. for 40 min, treated with phenyl isocyanate (70.6 mg, 0.593 mmol), warmed to RT and stirred for 12 h. The mixture was concentrated and purified by HPLC to afford 1-(4-cyano-5-(1-ethyl-7-(methylamino)-2-oxo-1,2-dihydro-1,6-naphthyridin-3-yl)-2-fluorophenyl)-3-phenylurea (22 mg, 16% yield). $^1$H NMR (400 MHz, DMSO-$d_6$): δ 9.28 (s, 1H), 9.08 (s, 1H), 8.46 (s, 1H), 8.42 (d, J=8.0 Hz, 1H), 7.94 (s, 1H), 7.91 (s, 1H), 7.45-7.43 (m, 2H), 7.31-7.27 (m, 2H), 7.18-7.13 (q, J=4.8 Hz, 1H), 7.02-6.98 (m, 1H), 6.26 (s, 1H), 4.16 (q, J=7.2 Hz, 2H), 2.87 (d, J=4.8 Hz, 3H), 1.22 (t, J=7.2 Hz, 3H); MS (ESI) m/z: 457.3 [M+H]$^+$.

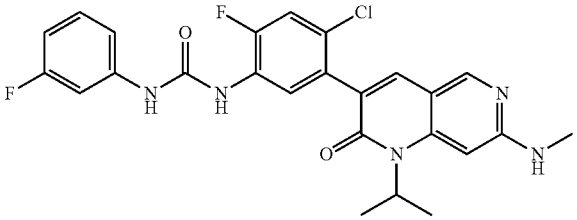

Example 77

A mixture of Example A52 (153 mg, 0.304 mmol), t-butyl X-phos (6.45 mg, 0.015 mmol), $Cs_2CO_3$ (198 mg, 0.608 mmol), $Pd_2(dba)_3$ (28 mg, 0.030 mmol) and methylamine (2.0N in THF, 2.0 mL, 4.0 mmol) in dioxane (3 mL) was sparged with Ar and heated at 80° C. for 4.5 h. The mixture was cooled to RT, treated with EtOAc and DCM and the solids removed via filtration through diatomaceous earth. The filtrate was concentrated to dryness and purified via reverse-phase chromatography (MeCN/$H_2O$ with 0.1% TFA). The organics were removed under reduced pressure and the aqueous layer was neutralized with satd. $NaHCO_3$. The mixture was extracted with EtOAc (2×) and the combined organics were washed with brine, dried over $Na_2SO_4$ and concentrated to dryness to afford 1-(4-chloro-2-fluoro-5-(1-isopropyl-7-(methylamino)-2-oxo-1,2-dihydro-1,6-naphthyridin-3-yl)phenyl)-3-(3-fluorophenyl)urea (22 mg, 14% yield). MS (ESI) m/z: 498.1 [M+H]$^+$.

A mixture of 1-(4-chloro-2-fluoro-5-(1-isopropyl-7-(methylamino)-2-oxo-1,2-dihydro-1,6-naphthyridin-3-yl) phenyl)-3-(3-fluorophenyl)urea (22 mg, 0.042 mmol) in MeCN (1.5 mL) was treated with 0.1N HCl (464 μL, 0.046 mmol), frozen and lyophilized to afford 1-(4-chloro-2-fluoro-5-(1-isopropyl-7-(methylamino)-2-oxo-1,2-dihydro-1,6-naphthyridin-3-yl)phenyl)-3-(3-fluorophenyl)urea hydrochloride (19 mg, 84% yield). $^1$H NMR (400 MHz, DMSO-$d_6$): δ 9.58 (s, 1H), 8.90 (s, 1H), 8.50 (s, 1H), 8.18 (d, J=8.6 Hz, 1H), 7.83 (s, 1H), 7.56 (d, J=10.9 Hz, 1H), 7.50-7.38 (m, 2H), 7.32-7.25 (m, 1H), 7.07 (dd, J=8.2, 1.9 Hz, 1H), 6.82-6.73 (m, 2H), 5.12 (m, 1H), 2.96 (s, 3H), 1.52 (d, J=6.9 Hz, 6H); MS (ESI) m/z: 498.2 [M+H]$^+$.

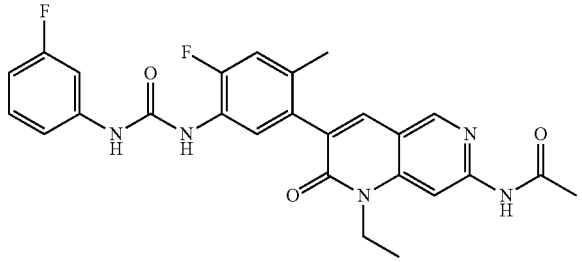

Example 78

A mixture of Example A56 (88 mg, 0.188 mmol), $Cs_2CO_3$ (122 mg, 0.375 mmol) and acetamide (55.4 mg, 0.938 mmol) in dioxane (2 mL) was sparged with Ar for 15 minutes, treated with $Pd_2(dba)_3$ (8.59 mg, 9.38 μmol) and Xantphos (10.86 mg, 0.019 mmol), sparged again with Ar and heated to 100° C. for 2.5 h. The mixture was cooled to RT, treated with 10% MeOH/DCM and the solids removed via filtration through diatomaceous earth. The filtrate was concentrated to dryness and purified via silica gel chromatography (EtOAc/Hex). The material was re-purified via reverse-phase chromatography (MeCN/$H_2O$ with 0.1% TFA); the organics were removed under reduced pressure and the aqueous residue was frozen and lyophilized. The resulting material was treated with MTBE, the solid collected via filtration and dried to afford N-(1-ethyl-3-(4-fluoro-5-(3-(3-fluorophenyl)ureido)-2-methylphenyl)-2-oxo-1,2-dihydro-1,6-naphthyridin-7-yl)acetamide (12 mg, 13% yield). $^1$H NMR (400 MHz, DMSO-$d_6$): δ 10.80 (s, 1H), 9.23 (s, 1H), 8.70 (s, 1H), 8.57 (s, 1H), 8.26 (s, 1H), 7.95 (d, J=8.4 Hz, 1H), 7.89 (s, 1H), 7.46 (dt, J=12.0, 2.3 Hz, 1H), 7.28 (m, 1H), 7.17 (d, J=12.2 Hz, 1H), 7.05 (d, J=8.3 Hz, 1H), 6.77 (td, J=8.5, 2.6 Hz, 1H), 4.20 (q, J=7.0 Hz, 2H), 2.14 (s, 3H), 2.08 (s, 3H), 1.25 (t, J=7.1 Hz, 3H); MS (ESI) m/z: 492.2 $[M+H]^+$.

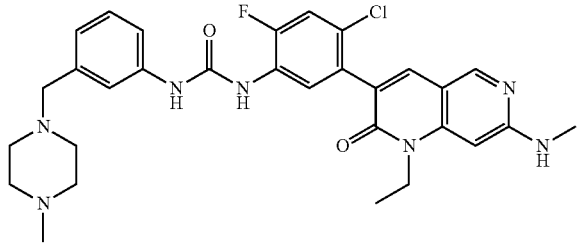

Example 79

A mixture of Example D1 (155 mg, 0.493 mmol), DIEA (146 mg, 1.126 mmol), 1-methylpyrrolidine (24 mg, 0.281 mmol) and Example A47 (155 mg, 0.281 mmol) in dioxane (4 mL) was heated at 80° C. for 20 h. The mixture was cooled to RT, treated with EtOAc, washed with satd. $NaHCO_3$, then brine, dried over $Na_2SO_4$, concentrated to dryness and purified via reverse-phase chromatography (MeCN/$H_2O$ with 0.1% TFA). The organics were removed under reduced pressure and the aqueous residue treated with satd. $NaHCO_3$ and allowed to stand at RT. The resulting solid was collected via filtration, washed with water and dried to afford 1-(4-chloro-5-(1-ethyl-7-((4-methoxybenzyl)(methyl)amino)-2-oxo-1,2-dihydro-1,6-naphthyridin-3-yl)-2-fluorophenyl)-3-(3-((4-methylpiperazin-1-yl)methyl)phenyl)urea (79 mg, 40% yield). $^1$H NMR (400 MHz, DMSO-$d_6$): δ 9.16 (s, 1H), 8.73 (s, 1H), 8.51 (s, 1H), 8.17 (d, J=8.6 Hz, 1H), 7.78 (s, 1H), 7.52 (d, J=10.9 Hz, 1H), 7.39 (s, 1H), 7.27 (m, 1H), 7.20-7.15 (m, 3H), 6.91-6.84 (m, 3H), 6.32 (s, 1H), 4.85 (s, 2H), 4.19 (q, J=7.0 Hz, 2H), 3.70 (s, 3H), 3.37 (s, 2H), 3.13 (s, 3H), 2.40-2.19 (m, 8H), 2.11 (s, 3H), 1.13 (t, J=6.9 Hz, 3H); MS (ESI) m/z: 698.3 $[M+H]^+$.

A mixture of 1-(4-chloro-5-(1-ethyl-7-((4-methoxybenzyl)(methyl)amino)-2-oxo-1,2-dihydro-1,6-naphthyridin-3-yl)-2-fluorophenyl)-3-(3-((4-methylpiperazin-1-yl)methyl)phenyl)urea (78 mg, 0.112 mmol) and anisole (60 mg, 0.559 mmol) was stirred in TFA (2 mL) at RT for 2 h. The mixture was concentrated to dryness and purified via reverse-phase chromatography (MeCN/$H_2O$ with 0.1% TFA). The organics were removed under reduced pressure and the aqueous residue was treated with satd. $NaHCO_3$. The mixture was extracted with EtOAc (2×) and the combined organics were washed with brine, dried over $Na_2SO_4$ and concentrated to dryness to afford 1-(4-chloro-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea (50 mg, 76% yield). MS (ESI) m/z: 578.2 $[M+H]^+$.

A mixture of 1-(4-chloro-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea in MeCN (4 mL) was treated with 0.1N HCl (1.77 mL, 0.177 mmol), frozen and lyophilized to afford 1-(4-chloro-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea dihydrochloride (53 mg, 91% yield). $^1$H NMR (400 MHz, DMSO-$d_6$): δ 9.46 (s, 1H), 8.89 (s, 1H), 8.42 (s, 1H), 8.14 (d, J=8.6 Hz, 1H), 7.75 (s, 1H), 7.50 (m, 2H), 7.35-7.19 (m, 3H), 6.96 (s, 1H), 6.33 (s, 1H), 4.10 (q, J=7.0 Hz, 2H), 3.66-3.21 (m, 8H), 3.09-2.94 (br s, 2H), 2.86 (s, 3H), 2.68 (s, 3H), 1.16 (t, J=7.0 Hz, 3H); MS (ESI) m/z: 578.3 $[M+H]^+$.

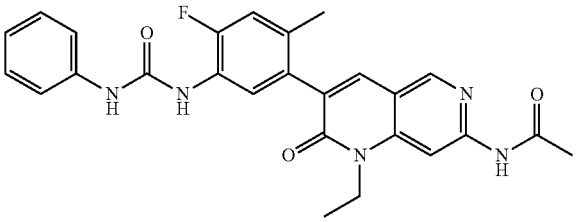

Example 80

A mixture of Example A54 (0.211 g, 0.468 mmol), Bippyphos (0.024 g, 0.047 mmol), acetamide (0.332 g, 5.62 mmol) and $K_3PO_4$ (0.397 g, 1.872 mmol) in dioxane (5 mL) was sparged with Ar for 15 min, treated with $Pd_2(dba)_3$ (0.021 g, 0.023 mmol) and heated at 80° C. overnight. The mixture was cooled to RT, diluted with EtOAc and the solids were removed via filtration. The filtrate was concentrated to dryness, dissolved in EtOAc/THF, washed with brine (2×), dried over $MgSO_4$ and concentrated to dryness. The material was treated with acetone, the solid collected via filtration and dried. The filtrate was concentrated to dryness, purified via silica gel chromatography (MeOH/DCM) and combined with the isolated solid. The material was re-purified via reverse-phase chromatography (MeCN/$H_2O$ with 0.1%

TFA); the combined fractions were partially concentrated, then frozen and lyophilized to afford N-(1-ethyl-3-(4-fluoro-2-methyl-5-(3-phenylureido)phenyl)-2-oxo-1,2-dihydro-1,6-naphthyridin-7-yl)acetamide (24 mg, 11% yield). $^1$H NMR (400 MHz, DMSO-$d_6$): δ 10.79 (s, 1H), 9.01 (s, 1H), 8.70 (s, 1H), 8.50 (s, 1H), 8.26 (s, 1H), 7.98 (d, J=8.2 Hz, 1H), 7.89 (s, 1H), 7.41 (d, J=7.8 Hz, 2H), 7.25 (t, J=7.5 Hz, 2H), 7.16 (dd, J=12.3 Hz, 1H), 6.99-6.89 (m, 1H), 4.25-4.14 (m, 2H), 2.14 (s, 3H), 2.08 (s, 3H), 1.30-1.20 (m, 3H); MS (ESI) m/z: 474.2 [M+H]$^+$.

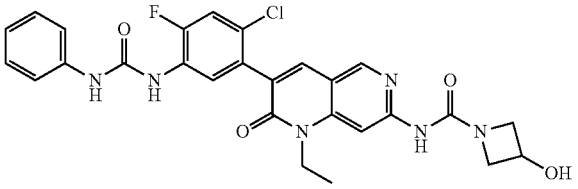

Example 81

A suspension of Example A50 (0.202 g, 0.377 mmol) and 3-hydroxyazetidine hydrochloride (0.045 g, 0.415 mmol) in THF (4 mL) was treated with 1-methylpyrrolidine (0.050 ml, 0.471 mmol) and heated at 55° C. overnight. Additional 3-hydroxyazetidine hydrochloride (0.150 g) and 1-methylpyrrolidine (0.30 mL) were added and the mixture was heated at 55° C. for another 24 h. The mixture was cooled to RT, diluted with water and the remaining solid collected via filtration, rinsed with THF and dried. The solid was purified via reverse-phase chromatography (MeCN/$H_2O$ with 0.1% TFA); the organics were removed under reduced pressure, the aqueous residue neutralized with satd. $NaHCO_3$, then azeotroped with IPA to dryness. The residue was suspended in water, the solid collected via filtration and dried to afford N-(3-(2-chloro-4-fluoro-5-(3-phenylureido)phenyl)-1-ethyl-2-oxo-1,2-dihydro-1,6-naphthyridin-7-yl)-3-hydroxyazetidine-1-carboxamide (26 mg, 13% yield). $^1$H NMR (400 MHz, DMSO-$d_6$): δ 9.47 (s, 1H), 9.10 (s, 1H), 8.72 (s, 1H), 8.64 (s, 1H), 8.21 (d, J=8.6 Hz, 1H), 8.11 (s, 1H), 7.94 (s, 1H), 7.56 (d, J=11.0 Hz, 1H), 7.41 (d, J=8.0 Hz, 2H), 7.26 (t, J=7.7 Hz, 2H), 6.97 (t, J=6.9 Hz, 1H), 5.64 (d, J=6.3 Hz, 1H), 4.47-4.37 (m, 1H), 4.26-4.09 (m, 4H), 3.81-3.72 (m, 2H), 1.25-1.23 (m, 3H); MS (ESI) m/z: 551.2 [M+H]$^+$.

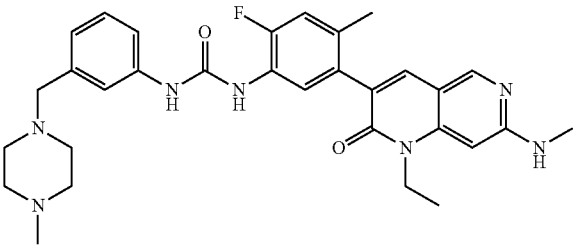

Example 82

A mixture of Example D1 (250 mg, 0.794 mmol), DIEA (252 mg, 1.949 mmol) and 1-methylpyrrolidine (41 mg, 0.487 mmol) in dioxane (4 mL) was treated with Example A48: (200 mg, 0.487 mmol), heated at 80° C. for 4 h, then cooled to RT for 3 days. The mixture was diluted with EtOAc, washed with 50% satd. $NaHCO_3$, then brine, dried over $Na_2SO_4$, concentrated to dryness and purified via reverse-phase chromatography (MeCN/$H_2O$ with 0.1% TFA). The organics were removed under reduced pressure and the aqueous residue was treated with satd. $NaHCO_3$ and allowed to stand at RT. The resulting solid was collected via filtration, washed with water and dried to afford 1-(5-(1-ethyl-7-(methylamino)-2-oxo-1,2-dihydro-1,6-naphthyridin-3-yl)-2-fluoro-4-methylphenyl)-3-(3-((4-methylpiperazin-1-yl)methyl)phenyl)urea (62 mg, 22% yield). $^1$H NMR (400 MHz, DMSO-$d_6$): δ 9.03 (s, 1H), 8.45-8.41 (m, 2H), 7.93 (d, J=8.5 Hz, 1H), 7.66 (s, 1H), 7.41 (s, 1H), 7.28-7.16 (m, 2H), 7.12 (d, J=12.6 Hz, 1H), 6.97 (m, 1H), 6.87 (m, 1H), 6.24 (s, 1H), 4.14 (m, 2H), 3.39 (s, 2H), 2.86 (d, J=5.2 Hz, 3H), 2.43-2.26 (br m, 8H), 2. (s, 3H), 2.06 (s, 3H), 1.21 (t, J=7.9 Hz, 3H); MS (ESI) m/z: 558.3 [M+H]$^+$.

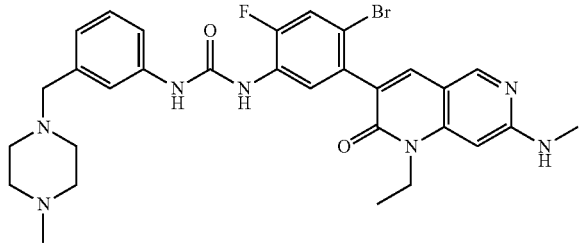

Example 83

A mixture of Example D1 (250 mg, 0.794 mmol), DIEA (218 mg, 1.683 mmol) and 1-methylpyrrolidine (36 mg, 0.421 mmol) in dioxane (4 mL) was treated with Example A49 (200 mg, 0.421 mmol), heated at 80° C. for 4 h, then cooled to RT for 3 days. The mixture was treated with EtOAc and DCM, washed with 50% satd. $NaHCO_3$, then brine, dried over $Na_2SO_4$, concentrated to dryness and purified via reverse-phase chromatography (MeCN/$H_2O$ with 0.1% TFA). The organics were removed under reduced pressure, the aqueous residue treated with satd. $NaHCO_3$ and extracted with EtOAc (2×). The combined organics were washed with brine, dried over $Na_2SO_4$ and concentrated to dryness to afford 1-(4-bromo-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea (57 mg, 21% yield). MS (ESI) m/z: 622.2 [M+H]$^+$.

A suspension of 1-(4-bromo-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea (55 mg, 0.088 mmol) in MeCN (4 mL) was treated with 0.1N HCl (1.81 mL, 0.181 mmol), frozen and lyophilized to afford 1-(4-bromo-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea dihydrochloride (60 mg, 93% yield). MS (ESI) m/z: 622.2 [M+H]$^+$.

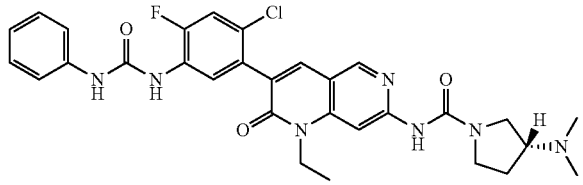

Example 84

A solution of Example A50 (0.098 g, 0.183 mmol) in THF (3 mL) was treated with (3R)-(+)-3-(dimethylamino)pyrrolidine (0.047 g, 0.549 mmol) and 1-methylpyrrolidine (2.088 mg, 0.018 mmol) and heated at 55° C. for 16 h. The mixture was concentrated to dryness and purified via silica gel chromatography (MeOH/DCM) to afford (R)—N-(3-(2-chloro-4-fluoro-5-(3-phenylureido)phenyl)-1-ethyl-2-oxo-1,2-dihydro-1,6-naphthyridin-7-yl)-3-(dimethylamino)pyrrolidine-1-carboxamide (48 mg, 45% yield). $^1$H NMR (400 MHz, DMSO-$d_6$): δ 9.10 (s, 1H), 9.08 (s, 1H), 8.72 (s, 1H), 8.65 (s, 1H), 8.21 (d, J=8.6 Hz, 1H), 8.11 (s, 1H), 7.94 (s, 1H), 7.57 (d, J=11.0 Hz, 1H), 7.41 (dd, J=8.3, 1.2 Hz, 2H), 7.26 (t, J=7.8 Hz, 2H), 6.97 (t, J=7.4 Hz, 1H), 4.18 (q, J=7.2 Hz, 2H), 3.68 (m, 2H), 3.39 (m, 1H), 3.20 (m, 1H), 2.19 (br s, 6H), 2.07 (m, 2H), 1.72 (m, 1H), 1.24 (t, J=7.1 Hz, 3H); MS (ESI) m/z: 592.2 [M+H]$^+$.

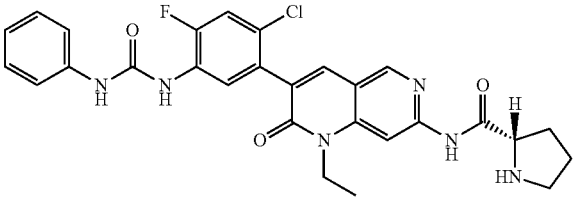

Example 85

A solution of Example A3 (500 mg, 1.420 mmol) and pyridine (449 mg, 5.68 mmol) in THF (20 mL) was treated with phenyl isocyanate (186 mg, 1.562 mmol) and stirred at RT for 20 h. The mixture was accidentally treated with a few drops of $SOCl_2$; EtOAc, water and satd. $NaHCO_3$ were added and the mixture stirred at RT for 2 h. The resulting solid was collected via filtration and dried. The layers of the filtrate were separated, the organic layer washed with brine, dried over $Na_2SO_4$ and concentrated to dryness. The material was treated with EtOAc, sonicated for 2 minutes, collected via filtration and combined with the above-isolated solid to afford 1-(4-chloro-5-(7-chloro-1-ethyl-2-oxo-1,2-dihydro-1,6-naphthyridin-3-yl)-2-fluorophenyl)-3-phenylurea (366 mg, 54% yield). $^1$H NMR (400 MHz, DMSO-$d_6$): δ 9.10 (s, 1H), 8.79 (s, 1H), 8.74 (s, 1H), 8.24 (d, J=8.6 Hz, 1H), 8.09 (s, 1H), 7.75 (s, 1H), 7.60 (d, J=11.0 Hz, 1H), 7.41 (d, J=8.0 Hz, 2H), 7.26 (t, J=7.8 Hz, 2H), 6.97 (t, J=7.3 Hz, 1H), 4.27 (q, J=7.1 Hz, 2H), 1.20 (t, J=7.0 Hz, 3H).

A mixture of 1-(4-chloro-5-(7-chloro-1-ethyl-2-oxo-1,2-dihydro-1,6-naphthyridin-3-yl)-2-fluorophenyl)-3-phenylurea (185 mg, 0.393 mmol), $Pd_2(dba)_3$ (18 mg, 0.020 mmol), Bippyphos (20 mg, 0.039 mmol), $K_3PO_4$ (333 mg, 1.570 mmol) and L-N-1-BOC-prolinamide (673 mg, 3.14 mmol) in dioxane (9 mL) was sparged with Ar, heated at 90° C. for 4 h, then cooled to RT and stirred overnight. The mixture was cooled to RT, treated with EtOAc, water and DMF, and the solids removed via filtration through diatomaceous earth. The layers of the filtrate were separated, the organic layer washed with brine, dried over $Na_2SO_4$, concentrated to dryness and purified via reverse-phase chromatography (MeCN/$H_2O$ with 0.1% TFA). The organics were removed under reduced pressure and the aqueous residue treated with satd. $NaHCO_3$ and extracted with EtOAc (2×). The combined organics were washed with brine, dried over $Na_2SO_4$ and concentrated to dryness to afford (S)-tert-butyl 2-((3-(2-chloro-4-fluoro-5-(3-phenylureido)phenyl)-1-ethyl-2-oxo-1,2-dihydro-1,6-naphthyridin-7-yl)carbamoyl)pyrrolidine-1-carboxylate (105 mg, 41% yield). MS (ESI) m/z: 648.9 [M+H]$^+$.

A mixture of (S)-tert-butyl 2-((3-(2-chloro-4-fluoro-5-(3-phenylureido)phenyl)-1-ethyl-2-oxo-1,2-dihydro-1,6-naphthyridin-7-yl)carbamoyl)pyrrolidine-1-carboxylate (115 mg, 0.177 mmol) in dioxane (3 mL) was treated with 1.25 N HCl in MeOH (2.8 mL, 3.5 mmol) and heated at 50° C. for 2 h. The mixture was concentrated to dryness, treated with satd. $NaHCO_3$ and extracted with EtOAc (2×). The combined organics were washed with brine, dried over $Na_2SO_4$, concentrated to dryness and purified via reverse-phase chromatography (MeCN/$H_2O$ with 0.1% TFA). The organics were removed under reduced pressure and the aqueous residue treated with satd. $NaHCO_3$ and extracted with EtOAc (2×). The combined organics were washed with brine, dried over $Na_2SO_4$ and concentrated to dryness to afford (S)—N-(3-(2-chloro-4-fluoro-5-(3-phenylureido)phenyl)-1-ethyl-2-oxo-1,2-dihydro-1,6-naphthyridin-7-yl)pyrrolidine-2-carboxamide (27 mg, 30% yield). MS (ESI) m/z: 549.2 [M+H]$^+$.

A mixture of (S)—N-(3-(2-chloro-4-fluoro-5-(3-phenylureido)phenyl)-1-ethyl-2-oxo-1,2-dihydro-1,6-naphthyridin-7-yl)pyrrolidine-2-carboxamide (43 mg, 0.078 mmol) in MeCN (3 mL) was treated with 0.1N HCl (aq.) (1.56 mL, 0.156 mmol), frozen and lyophilized. The material was treated with MTBE, sonicated, the solid collected via filtration and dried to afford (S)—N-(3-(2-chloro-4-fluoro-5-(3-phenylureido)phenyl)-1-ethyl-2-oxo-1,2-dihydro-1,6-naphthyridin-7-yl)pyrrolidine-2-carboxamide dihydrochloride (31 mg, 63% yield). MS (ESI) m/z: 549.2 [M+H]$^+$.

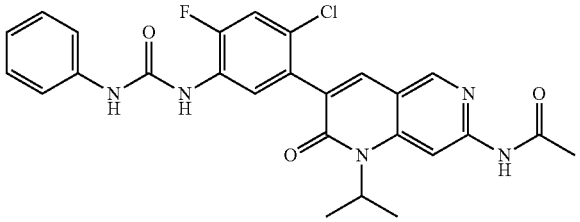

Example 86

A mixture of Example A55 (320 mg, 0.659 mmol), $Pd_2(dba)_3$ (30 mg, 0.033 mmol), Bippyphos (33 mg, 0.066 mmol), $K_3PO_4$ (560 mg, 2.64 mmol) and acetamide (389 mg, 6.59 mmol) in dioxane (8 mL) was sparged with Ar and heated to 90° C. for 22 h. The mixture was cooled to RT, diluted with DMF, stirred for 1 h and the solids were removed via filtration through diatomaceous earth. The filtrate was concentrated to dryness and purified via reverse-phase chromatography (MeCN/$H_2O$ with 0.1% TFA). The organics were removed under reduced pressure, the aqueous residue treated with satd. $NaHCO_3$ and extracted with EtOAc (2×). The combined organics were washed with brine, dried over $Na_2SO_4$ and concentrated to dryness. The material was re-purified via silica gel chromatography (EtOAc/Hex) to afford N-(3-(2-chloro-4-fluoro-5-(3-phenylureido)phenyl)-1-isopropyl-2-oxo-1,2-dihydro-1,6-naphthyridin-7-yl)acetamide (33 mg, 9.8% yield). MS (ESI) m/z: 508.2 [M+H]$^+$.

A mixture of N-(3-(2-chloro-4-fluoro-5-(3-phenylureido)phenyl)-1-isopropyl-2-oxo-1,2-dihydro-1,6-naphthyridin-7-yl)acetamide (33 mg, 0.065 mmol) in MeCN (3 mL) was treated with 0.1N HCl (0.650 mL, 0.065 mmol), frozen and lyophilized. The material was treated with $Et_2O$, the solid collected via filtration and dried to afford N-(3-(2-chloro-4-fluoro-5-(3-phenylureido)phenyl)-1-isopropyl-2-oxo-1,2-dihydro-1,6-naphthyridin-7-yl)acetamide hydrochloride (17 mg, 47% yield). $^1$H NMR (400 MHz, DMSO-$d_6$): δ 10.82 (s, 1H), 9.16 (s, 1H), 8.75 (s, 1H), 8.69 (s, 1H), 8.53 (s, 1H), 8.22 (d, J=8.6 Hz, 1H), 7.93 (s, 1H), 7.56 (d, J=11.0 Hz, 1H), 7.42 (d, J=8.0 Hz, 2H), 7.26 (t, J=7.7 Hz, 2H), 6.97 (t, J=7.3 Hz, 1H), 3.71 (m, 1H), 2.15 (s, 3H), 1.56 (d, J=7.0 Hz, 6H); MS (ESI) m/z: 508.2 [M+H]$^+$.

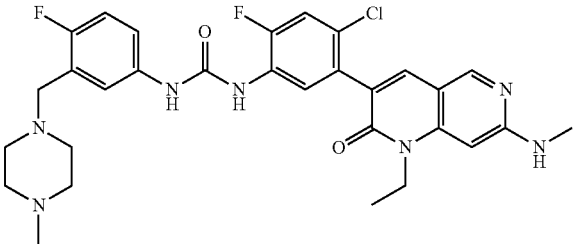

Example 87

A mixture of Example A51 (0.138 g, 0.320 mmol) and Example D2 (0.100 g, 0.448 mmol) in dioxane (4 mL) was treated with 1-methylpyrrolidine (6.73 μL, 0.064 mmol) and heated to 80° C. overnight. The mixture was cooled to RT, treated with a small amount of additional dioxane and the solids collected via filtration and dried to afford 1-(4-chloro-5-(1-ethyl-7-(methylamino)-2-oxo-1,2-dihydro-1,6-naphthyridin-3-yl)-2-fluorophenyl)-3-(4-fluoro-3-((4-methyl)piperazin-1-yl)methyl)phenyl)urea (141 mg, 74% yield). $^1$H NMR (400 MHz, $CD_3OD$): δ 8.38 (s, 1H), 8.14 (d, J=8.5 Hz, 1H), 7.75 (s, 1H), 7.68 (dd, J=6.5, 2.8 Hz, 1H), 7.35 (d, J=10.8 Hz, 1H), 7.18 (m, 1H), 7.04 (t, J=9.2 Hz, 1H), 6.35 (s, 1H), 4.29 (q, J=7.2 Hz, 2H), 3.68 (s, 2H), 2.98 (s, 3H), 3.46-2.95 (br m, 8H), 2.83 (s, 3H), 1.34 (t, J=7.1 Hz, 3H); MS (ESI) m/z: 596.2 [M+H]$^+$.

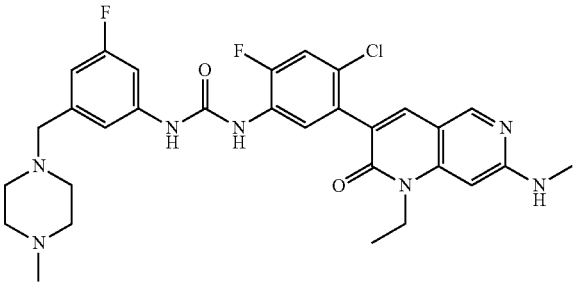

Example 88

A solution of 3-fluoro-5-nitrotoluene (1.0 g, 6.45 mmol) in trifluorotoluene (15 ml) was treated with NBS (1.721 g, 9.67 mmol) and AIBN (0.212 g, 1.289 mmol) and heated at 105° C. overnight. The mixture was cooled to RT, the solids removed via filtration and the filtrate concentrated to dryness to afford 1-(bromomethyl)-3-fluoro-5-nitrobenzene (95 mg, 63% yield).

A −20° C. solution of 1-(bromomethyl)-3-fluoro-5-nitrobenzene (0.95 g, 4.06 mmol) and DIEA (1.418 ml, 8.12 mmol) in THF (20 mL) was treated drop-wise with a solution of 1-methylpiperazine (0.488 g, 4.87 mmol) in THF (10 mL) and stirred at RT overnight as the cooling bath expired. The solid was removed via filtration and the filtrate concentrated to dryness and purified via silica gel chromatography (MeOH/DCM) to afford 1-(3-fluoro-5-nitrobenzyl)-4-methylpiperazine (820 mg, 80% yield). $^1$H NMR (400 MHz, DMSO-$d_6$): δ 8.01 (s, 1H), 7.97 (dt, J=8.6, 2.3 Hz, 1H), 7.64 (dd, J=9.2, 2.2 Hz, 1H), 3.60 (s, 2H), 2.41 (s, 8H), 2.21 (s, 3H); MS (ESI) m/z: 254.1 [M+H]$^+$.

A solution of 1-(3-fluoro-5-nitrobenzyl)-4-methylpiperazine (0.15 g, 0.592 mmol) in MeOH (5 mL) was treated with 10% Pd—C (dry) (0.063 g, 0.059 mmol) and hydrogenated (1 atm) for 3 h. The solids were removed via filtration, rinsed with MeOH and the filtrate concentrated to dryness to afford 3-fluoro-5-((4-methylpiperazin-1-yl)methyl)aniline (100% yield assumed). MS (ESI) m/z: 224.1 [M+H]$^+$.

A mixture of 3-fluoro-5-((4-methylpiperazin-1-yl)methyl)aniline (0.13 g, 0.582 mmol), Example A51 (0.167 g, 0.388 mmol) and 1-methylpyrrolidine (4.08 L, 0.039 mmol) in dioxane (5 mL) was heated at 60° C. for 2 days. The mixture was cooled to RT, concentrated to dryness and the residue treated with $Et_2O$. The solid was collected via filtration, treated with EtOAc, stirred at RT for 2 h, then collected via filtration. The resulting solid was treated with dioxane, stirred at RT overnight, collected via filtration and dried to afford 1-(4-chloro-5-(1-ethyl-7-(methylamino)-2-oxo-1,2-dihydro-1,6-naphthyridin-3-yl)-2-fluorophenyl)-3-(3-fluoro-5-((4-methylpiperazin-1-yl)methyl)phenyl)urea (84 mg, 36% yield). $^1$H NMR (400 MHz, pyridine): δ 10.20 (s, 1H), 9.16 (s, 1H), 8.85 (d, J=8.6 Hz, 1H), 8.61 (s, 1H), 7.91 (d, J=11.3 Hz, 1H), 7.71 (s, 1H), 7.55 (s, 1H), 7.48 (s, 1H), 7.36 (d, J=10.8 Hz, 1H), 6.87 (d, J=9.3 Hz, 1H), 6.26 (s, 1H), 4.21 (q, J=7.0 Hz, 2H), 3.36 (s, 2H), 3.08 (s, 3H), 2.70-2.50 (m, 8H), 2.35 (s, 3H), 1.19 (t, J=7.0 Hz, 3H); MS (ESI) m/z: 596.3 [M+H]$^+$.

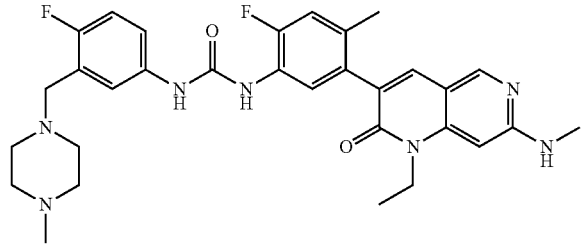

Example 89

A mixture of Example D2 (0.060 g, 0.269 mmol) and Example A48 (0.085 g, 0.207 mmol) in dioxane (2 mL) was treated with 1-methylpyrrolidine (2 drops) and heated to 80° C. overnight. The mixture was concentrated to dryness, treated with EtOAc and the resulting solid collected via filtration and purified via reverse-phase chromatography (MeCN/$H_2O$ with 0.1% TFA). The organics were removed under reduced pressure, the aqueous residue treated with satd. $NaHCO_3$, extracted with EtOAc (2×) and the combined organics were washed with brine, dried over $MgSO_4$ and concentrated to dryness to afford 1-(5-(1-ethyl-7-(methylamino)-2-oxo-1,2-dihydro-1,6-naphthyridin-3-yl)-2-fluoro-4-methylphenyl)-3-(4-fluoro-3-((4-methyl)piperazin-1-yl)

methyl)phenyl)urea (39 mg, 33% yield). $^1$H NMR (400 MHz, DMSO-$d_6$): δ 9.84 (s, 1H), 8.87 (s, 1H), 8.73 (d, J=8.43 Hz, 1H), 8.62 (s, 1H), 7.96 (dd, J=6.5, 2.8 Hz, 1H), 7.79 (ddd, J=8.9, 4.5, 2.8 Hz, 1H), 7.65 (s, 1H), 7.58 (s, 1H), 7.15 (t, J=9.2 Hz, 1H), 7.08 (d, J=12.0 Hz, 1H), 6.32 (s, 1H), 4.26 (q, J=7.1 Hz, 2H), 3.58 (s, 2H), 3.13 (d, J=4.8 Hz, 3H), 2.53 (br m, 4H), 2.31 (m, 7H), 2.13 (s, 3H), 1.24 (t, J=7.0 Hz, 3H); MS (ESI) m/z: 576.2 [M+H]$^+$.

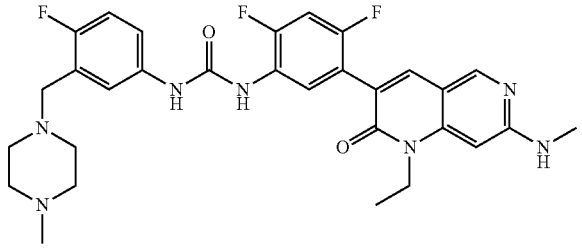

Example 90

A suspension of Example A8 (0.078 g, 0.236 mmol) in EtOAc (1.5 mL) was treated with satd. $NaHCO_3$ (1.5 mL) followed by isopropenyl chloroformate (0.036 mL, 0.331 mmol) and the bi-phasic mixture stirred vigorously at RT overnight. The layers were separated, the organic layer washed with brine, dried over $MgSO_4$ and concentrated to dryness to afford prop-1-en-2-yl (5-(1-ethyl-7-(methylamino)-2-oxo-1,2-dihydro-1,6-naphthyridin-3-yl)-2,4-difluorophenyl)carbamate (86 mg, 88% yield). $^1$H NMR (400 MHz, DMSO-$d_6$): δ 9.64 (s, 1H), 8.41 (s, 1H), 7.83 (s, 1H), 7.61 (s, 1H), 7.36 (t, J=10.2 Hz, 1H), 7.06 (m, 1H), 6.23 (s, 1H), 4.71 (d, J=7.9 Hz, 2H), 4.13 (q, J=7.1 Hz, 2H), 2.85 (d, J=4.9 Hz, 3H), 1.91 (s, 3H), 1.20 (t, J=7.1 Hz, 3H); MS (ESI) m/z: 415.1 [M+H]$^+$.

A mixture of Example D2 (0.060 g, 0.269 mmol) and prop-1-en-2-yl (5-(1-ethyl-7-(methylamino)-2-oxo-1,2-dihydro-1,6-naphthyridin-3-yl)-2,4-difluorophenyl)carbamate (0.086 g, 0.208 mmol) in dioxane (2 mL) was treated with 1-methylpyrrolidine (2 drops) and heated at 80° C. overnight. The mixture was concentrated to dryness, treated with EtOAc and the resulting solid collected via filtration and purified via reverse-phase chromatography (MeCN/$H_2O$ with 0.1% TFA). The organics were removed under reduced pressure, the aqueous residue treated with satd. $NaHCO_3$, extracted with EtOAc (2×) and the combined organics were washed with brine, dried over $MgSO_4$ and concentrated to dryness to afford 1-(5-(1-ethyl-7-(methylamino)-2-oxo-1,2-dihydro-1,6-naphthyridin-3-yl)-2,4-difluorophenyl)-3-(4-fluoro-3-((4-methylpiperazin-1-yl)methyl)phenyl)urea (37 mg, 31% yield). $^1$H NMR (400 MHz, DMSO-$d_6$): δ 9.82 (s, 1H), 8.94 (s, 1H), 8.86 (t, J=8.5 Hz, 1H), 8.59 (s, 1H), 7.93 (dd, J=6.5, 2.8 Hz, 1H), 7.76 (m, 2H), 7.62 (s, 1H), 7.13 (t, J=9.5 Hz, 2H), 6.25 (s, 1H), 4.19 (q, J=7.1 Hz, 2H), 3.55 (s, 2H), 3.08 (d, J=4.9 Hz, 3H), 2.50 (br s, 4H), 2.30 (br s, 4H), 2.10 (s, 3H), 1.18 (t, J=7.1 Hz, 3H); MS (ESI) m/z: 580.2 [M+H]$^+$.

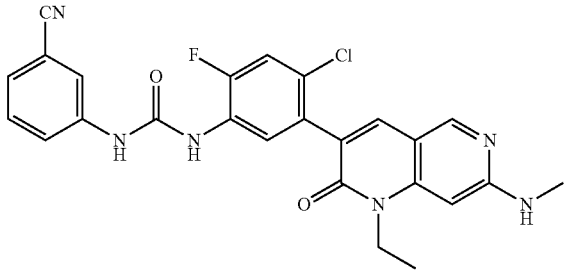

Example 91

A suspension of Example A3 (0.250 g, 0.710 mmol) in THF (10 mL) was treated with 3-cyanophenyl isocyanate (0.102 g, 0.710 mmol) followed by pyridine (0.011 g, 0.142 mmol) and stirred at RT for 2 days. The mixture was concentrated to dryness and the residue treated with MeCN. The solid was collected via filtration, treated with MeOH and the resulting solid collected via filtration and dried to afford 1-(4-chloro-5-(7-chloro-1-ethyl-2-oxo-1,2-dihydro-1,6-naphthyridin-3-yl)-2-fluorophenyl)-3-(3-cyanophenyl)urea (212 mg, 60% yield). $^1$H NMR (400 MHz, DMSO-$d_6$): δ 9.39 (s, 1H), 8.89 (s, 1H), 8.79 (s, 1H), 8.20 (d, J=8.5 Hz, 1H), 8.09 (s, 1H), 7.97 (t, J=1.8 Hz, 1H), 7.75 (s, 1H), 7.61 (d, J=10.6 Hz, 2H), 7.44 (m, 2H), 4.27 (q, J=7.1 Hz, 2H), 1.20 (t, J=7.0 Hz, 3H); MS (ESI) m/z: 496.1 [M+H]$^+$.

A mixture of 1-(4-chloro-5-(7-chloro-1-ethyl-2-oxo-1,2-dihydro-1,6-naphthyridin-3-yl)-2-fluorophenyl)-3-(3-cyanophenyl)urea (0.210 g, 0.423 mmol), t-butyl X-Phos (0.020 g, 0.047 mmol), $Pd_2(dba)_3$ (0.020 g, 0.022 mmol), $Cs_2CO_3$ (0.400 g, 1.228 mmol) and methylamine (2.0M in THF, 4.0 mL, 8.0 mmol) in dioxane (5 mL) was heated at 90° C. for 5 h, then cooled to RT stirred overnight. The solids were removed via filtration, washed with DCM, then MeCN and the filtrate concentrated to dryness and purified via silica gel chromatography (EtOAc/DCM) to afford 1-(4-chloro-5-(1-ethyl-7-(methylamino)-2-oxo-1,2-dihydro-1,6-naphthyridin-3-yl)-2-fluorophenyl)-3-(3-cyanophenyl)urea (33 mg, 15% yield). $^1$H NMR (400 MHz, DMSO-$d_6$): δ 9.40 (s, 1H), 8.83 (s, 1H), 8.41 (s, 1H), 8.13 (d, J=8.6 Hz, 1H), 7.97 (t, J=1.8 Hz, 1H), 7.74 (s, 1H), 7.61-7.45 (m, 4H), 7.05 (d, J=5.1 Hz, 1H), 6.24 (s, 1H), 4.14 (d, J=7.4 Hz, 2H), 2.86 (d, J=4.9 Hz, 3H), 1.21 (t, J=7.0 Hz, 3H); MS (ESI) m/z: 491.1 [M+H]$^+$.

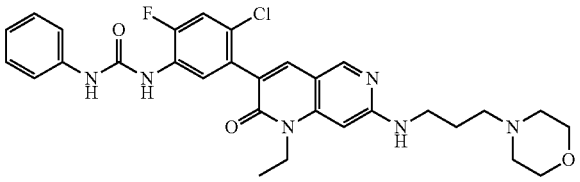

Example 92

A suspension of Example A3 (0.200 g, 0.568 mmol) in 3-morpholinopropan-1-amine (1 mL) was subjected to microwave irradiation at 160° C. for 30 minutes. The mixture was cooled to RT, treated with water and the aqueous liquid decanted. The material was treated with MTBE and the resulting solid collected via filtration to afford 3-(5-amino-2-chloro-4-fluorophenyl)-1-ethyl-7-((3-morpholinopropyl)amino)-1,6-naphthyridin-2(1H)-one (150 mg, 57% yield). MS (ESI) m/z: 460.1 $[M+H]^+$.

A solution of 3-(5-amino-2-chloro-4-fluorophenyl)-1-ethyl-7-((3-morpholinopropyl)amino)-1,6-naphthyridin-2(1H)-one (0.140 g, 0.304 mmol) in pyridine (4 mL) was treated with phenyl isocyanate (0.040 g, 0.336 mmol) and stirred at RT for 1 h. The mixture was concentrated to dryness, treated with MeOH and the resulting solid was collected via filtration to afford 1-(4-chloro-5-(1-ethyl-7-((3-morpholinopropyl)amino)-2-oxo-1,2-dihydro-1,6-naphthyridin-3-yl)-2-fluorophenyl)-3-phenylurea (120 mg, 61% yield). $^1$H NMR (400 MHz, DMSO-$d_6$): δ 9.08 (s, 1H), 8.68 (s, 1H), 8.40 (s, 1H), 8.17 (d, J=8.7 Hz, 1H), 7.72 (s, 1H), 7.52 (d, J=11.0 Hz, 1H), 7.41 (d, J=8.0 Hz, 2H), 7.26 (t, J=7.8 Hz, 2H), 7.10 (t, J=5.6 Hz, 1H), 6.97 (t, J=7.4 Hz, 1H), 6.28 (s, 1H), 4.06 (m, 2H), 3.56 (t, J=4.5 Hz, 4H), 3.34 (m, 2H), 2.34 (d, J=6.8 Hz, 6H), 1.70 (t, J=7.0 Hz, 2H), 1.20 (t, J=7.0 Hz, 3H); MS (ESI) m/z: 579.2 $[M+H]^+$.

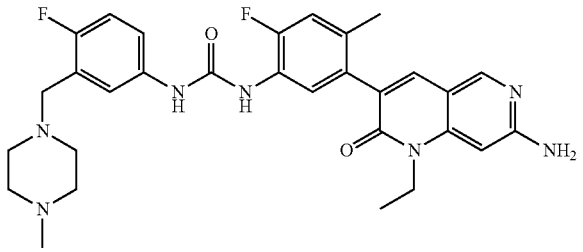

Example 93

A solution of Example A34 (0.200 g, 0.640 mmol) in pyridine (0.5 mL) was cooled to 0° C. and treated slowly with isopropenyl chloroformate (0.073 mL, 0.672 mmol). The mixture was stirred at 0° C. for 0.5 h, warmed to RT, concentrated to dryness and purified via silica gel chromatography (EtOAc/Hex) to afford prop-1-en-2-yl (5-(7-amino-1-ethyl-2-oxo-1,2-dihydro-1,6-naphthyridin-3-yl)-2-fluoro-4-methylphenyl)carbamate (244 mg, 96% yield). $^1$H NMR (400 MHz, DMSO-$d_6$): δ 9.54 (s, 1H), 8.33 (s, 1H), 7.66 (s, 1H), 7.35 (m, 1H), 7.13 (d, J=11.7 Hz, 1H), 6.48 (s, 2H), 6.33 (s, 1H), 4.69 (d, J=8.4 Hz, 2H), 4.08 (q, J=7.3 Hz, 2H), 2.08 (s, 3H), 1.90 (s, 3H), 0.84 (t, J=7.0 Hz, 3H); MS (ESI) m/z: 397.1 $[M+H]^+$.

A mixture of Example D2 (0.100 g, 0.448 mmol) and prop-1-en-2-yl (5-(7-amino-1-ethyl-2-oxo-1,2-dihydro-1,6-naphthyridin-3-yl)-2-fluoro-4-methylphenyl)carbamate (0.142 g, 0.358 mmol) in dioxane (3 mL) was treated with 1-methylpyrrolidine (3 drops) and heated at 80° C. overnight. The mixture was treated with DMSO (2 drops) and heated at 80° C. for an additional 24 h. The mixture was cooled to RT, concentrated to dryness and purified via reverse-phase chromatography (MeCN/$H_2O$ with 0.1% TFA). The organics were removed under reduced pressure, the aqueous residue treated with satd. $NaHCO_3$, extracted with EtOAc (2×) and the combined organics were washed with brine, dried over $MgSO_4$ and concentrated to dryness to afford 1-(5-(7-amino-1-ethyl-2-oxo-1,2-dihydro-1,6-naphthyridin-3-yl)-2-fluoro-4-methylphenyl)-3-(4-fluoro-3-((4-methylpiperazin-1-yl)methyl)phenyl)urea (44 mg, 22% yield). $^1$H NMR (400 MHz, pyridine-$d_5$): δ 9.87 (s, 1H), 8.89 (s, 1H), 8.71 (m, 1H), 8.60 (s, 1H), 7.97 (dd, J=6.5, 2.8 Hz, 1H), 7.79 (dt, J=8.7, 3.6 Hz, 1H), 7.64 (s, 1H), 7.26 (s, 2H), 7.15 (t, J=9.2 Hz, 1H), 7.07 (d, J=12.0 Hz, 1H), 6.56 (s, 1H), 4.17 (q, J=7.1 Hz, 2H), 3.58 (s, 2H), 2.53 (s, 4H), 2.30 (m, 7H), 2.13 (s, 3H), 1.16 (t, J=7.1 Hz, 3H); MS (ESI) m/z: 562.2 $[M+H]^+$.

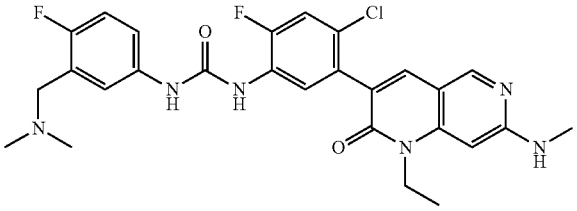

Example 94

A mixture of 1-fluoro-2-methyl-4-nitrobenzene (2.5 g, 16.12 mmol) NBS (5.02 g, 28.2 mmol) and AIBN (265 mg, 1.612 mmol) in trifluorotoluene (45 mL) was heated to reflux overnight. The mixture was cooled to RT, filtered to remove solids and the filtrate concentrated to dryness. The residue was dissolved in $Et_2O$, washed with water, then brine, dried over $Na_2SO_4$, concentrated to dryness and purified via silica gel chromatography (EtOAc/Hex) to afford 2-(bromomethyl)-1-fluoro-4-nitrobenzene (698 mg, 18% yield). $^1$H NMR (400 MHz, DMSO-$d_6$): δ 8.53 (dd, J=6.4, 3.0 Hz, 1H), 8.28 (ddd, J=9.1, 4.4, 3.0 Hz, 1H), 7.55 (t, J=9.2 Hz, 1H), 4.80 (s, 2H).

A −20° C. solution of DIEA (771 mg, 5.97 mmol) and dimethylamine (2.0M in THF, 1.94 mL, 3.88 mmol) in THF (5 mL) was treated drop-wise with a solution of 2-(bromomethyl)-1-fluoro-4-nitrobenzene (698 mg 2.98 mmol) in THF (5 mL) and stirred at RT overnight as the cooling bath expired. The mixture was treated with EtOAc, washed with water, then brine, dried over $Na_2SO_4$ and concentrated to dryness to afford 1-(2-fluoro-5-nitrophenyl)-N,N-dimethylmethanamine (494 mg, 84% yield). MS (ESI) m/z: 199.1 $[M+H]^+$.

A mix of satd. $NH_4Cl$ (5.19 mL) in EtOH (8 mL) was treated with 1-(2-fluoro-5-nitrophenyl)-N,N-dimethylmethanamine (494 mg, 2.49 mmol), followed by iron powder (1.39 g, 24.93 mmol) and heated at 55° C. overnight. The mixture was cooled to RT, the solids removed via filtration through diatomaceous earth and washed with 10% MeOH/DCM. The filtrate was concentrated to dryness, the residue treated with DCM, sonicated and the resulting solid collected via filtration, washed with THF and dried to afford 3-((dimethylamino)methyl)-4-fluoroaniline (305 mg, 72% yield). MS (ESI) m/z: 169.1 $[M+H]^+$.

A mixture of Example A47 (200 mg, 0.363 mmol), 3-((dimethylamino)methyl)-4-fluoroaniline (300 mg, 1.815 mmol) and 1-methylpyrrolidine (31 mg, 0.363 mmol) in dioxane (4 mL) was heated at 80° C. overnight. The mixture was cooled to RT, treated EtOAc and satd. $NaHCO_3$, warmed to near reflux and the resulting solid collected via filtration and dried to afford 1-(4-chloro-5-(1-ethyl-7-((4-methoxybenzyl)(methyl)amino)-2-oxo-1,2-dihydro-1,6-naphthyridin-3-yl)-2-fluorophenyl)-3-(3-((dimethylamino)methyl)-4-fluorophenyl)urea (174 mg, 72% yield). $^1$H NMR (400 MHz, DMSO-$d_6$): δ 9.21 (br s, 1H), 8.80 (br s, 1H), 8.50 (s, 1H), 8.14 (d, J=9.1 Hz, 1H), 7.77 (s, 1H), 7.56-7.48 (m, 2H), 7.25 (m, 1H), 7.18 (d, J=8.3 Hz, 2H), 7.04 (m, 1H), 6.86 (d, J=8.4 Hz, 2H), 6.32 (s, 1H), 4.85 (s, 2H), 4.18 (q, J=7.0 Hz, 2H), 3.70 (s, 3H), 3.36 (s, 2H), 3.13 (s, 3H), 2.13 (s, 6H), 1.13 (t, J=7.0 Hz, 3H); MS (ESI) m/z: 661.2 $[M+H]^+$.

A mixture of 1-(4-chloro-5-(1-ethyl-7-((4-methoxybenzyl)(methyl)amino)-2-oxo-1,2-dihydro-1,6-naphthyridin-3-yl)-2-fluorophenyl)-3-(3-((dimethylamino)methyl)-4-fluorophenyl)urea (174 mg, 0.263 mmol) in TFA (2.0 mL) was stirred at RT for 2.5 h. The mixture was concentrated to dryness, treated with EtOAc and satd. $NaHCO_3$, stirred for 0.5 h and the resulting solid collected via filtration and dried to afford 1-(4-chloro-5-(1-ethyl-7-(methylamino)-2-oxo-1,2-dihydro-1,6-naphthyridin-3-yl)-2-fluorophenyl)-3-(3-((dimethylamino)methyl)-4-fluorophenyl)urea (111 mg, 78% yield). $^1H$ NMR (400 MHz, DMSO-$d_6$): δ 9.12 (s, 1H), 8.63 (s, 1H), 8.41 (s, 1H), 8.15 (d, J=8.7 Hz, 1H), 7.74 (s, 1H), 7.54-7.50 (m, 2H), 7.23 (m, 1H), 7.09-7.01 (m, 2H), 6.23 (s, 1H), 4.13 (q, J=6.8 Hz, 2H), 3.37 (s, 2H), 2.86 (d, J=4.4 Hz, 3H), 2.13 (s, 6H), 1.20 (t, J=7.0 Hz, 3H); MS (ESI) m/z: 541.1 $[M+H]^+$.

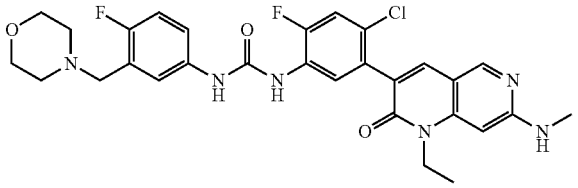

Example 95

A mixture of Example A47 (200 mg, 0.363 mmol) and Example D3 (95 mg, 0.454 mmol) in dioxane (5 mL) was treated with 1-methylpyrrolidine (31 mg, 0.363 mmol) and heated at 70° C. overnight. The mixture was cooled to RT, treated with EtOAc and 50% satd. $NaHCO_3$ and stirred for 0.5 h. The resulting solid was collected via filtration and dried to afford 1-(4-chloro-5-(1-ethyl-7-((4-methoxybenzyl)(methyl)amino)-2-oxo-1,2-dihydro-1,6-naphthyridin-3-yl)-2-fluorophenyl)-3-(4-fluoro-3-(morpholinomethyl)phenyl)urea (152 mg, 60% yield). $^1H$ NMR (400 MHz, DMSO-$d_6$): δ 9.12 (s, 1H), 8.62 (m, 1H), 8.50 (s, 1H), 8.16 (d, J=8.7 Hz, 1H), 7.77 (s, 1H), 7.53 (d, J=11.0 Hz, 1H), 7.47 (m, 1H), 7.30 (m, 1H), 7.18 (m, 2H), 7.07 (t, J=9.2 Hz, 1H), 6.87 (m, 2H), 6.32 (s, 1H), 4.85 (s, 2H), 4.19 (q, J=7.0 Hz, 2H), 3.70 (s, 3H), 3.54-3.53 (m, 4H), 3.45 (s, 2H), 3.13 (s, 3H), 2.35 (m, 4H), 1.13 (t, J=7.0 Hz, 3H); MS (ESI) m/z: 703.2 $[M+H]^+$.

A mixture of 1-(4-chloro-5-(1-ethyl-7-((4-methoxybenzyl)(methyl)amino)-2-oxo-1,2-dihydro-1,6-naphthyridin-3-yl)-2-fluorophenyl)-3-(4-fluoro-3-(morpholinomethyl)phenyl)urea (152 mg, 0.216 mmol) in TFA (3 mL) was stirred under Ar for 3 h. The mixture was concentrated to dryness, treated with EtOAc and satd. $NaHCO_3$ and stirred for 0.5 h. The resulting solid was collected via filtration and dried to afford 1-(4-chloro-5-(1-ethyl-7-(methylamino)-2-oxo-1,2-dihydro-1,6-naphthyridin-3-yl)-2-fluorophenyl)-3-(4-fluoro-3-(morpholinomethyl)phenyl)urea (111 mg, 76% yield). $^1H$ NMR (400 MHz, DMSO-$d_6$): δ 9.12 (s, 1H), 8.63 (d, J=2.5 Hz, 1H), 8.41 (s, 1H), 8.15 (d, J=8.7 Hz, 1H), 7.73 (s, 1H), 7.53 (d, J=11.0 Hz, 1H), 7.47 (dd, J=6.5, 2.8 Hz, 1H), 7.30 (ddd, J=8.9, 4.5, 2.8 Hz, 1H), 7.10-7.01 (m, 2H), 6.24 (s, 1H), 4.14 (q, J=7.1 Hz, 2H), 3.53 (t, J=4.4 Hz, 4H), 3.44 (s, 2H), 2.86 (d, J=4.9 Hz, 3H), 2.35 (m, 4H), 1.20 (t, J=7.0 Hz, 3H); MS (ESI) m/z: 583.2 $[M+H]^+$.

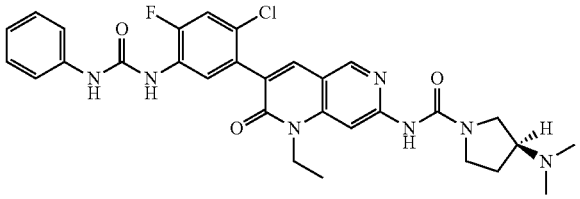

Example 96

A mixture of Example A50 (0.12 g, 0.224 mmol), (3S)-(+)-3-(dimethylamino)pyrrolidine (0.077 g, 0.672 mmol) and 1-methylpyrrolidine (9.53 mg, 0.112 mmol) in THF (3 mL) was heated at 60° C. overnight. The mixture was cooled to RT, concentrated to dryness and purified via silica gel chromatography (MeOH/DCM) to afford (S)—N-(3-(2-chloro-4-fluoro-5-(3-phenylureido)phenyl)-1-ethyl-2-oxo-1,2-dihydro-1,6-naphthyridin-7-yl)-3-(dimethylamino)pyrrolidine-1-carboxamide (67 mg, 51% yield). $^1H$ NMR (400 MHz, DMSO-d6): δ 9.05 (s, 2H); 8.67 (s, 1H); 8.61 (s, 1H); 8.17 (d, J=8.6 Hz, 1H); 8.06 (s, 1H); 7.90 (s, 1H); 7.52 (d, J=11.0 Hz, 1H); 7.37 (d, J=8.1 Hz, 2H); 7.21 (t, J=7.8 Hz, 3H); 6.92 (m, 1H); 4.13 (q, J=6.9 Hz, 2H); 3.65 (m, 2H), 3.38 (m, 1H); 2.15 (m, 3H); 1.19 (t, J=6.9 Hz, 3H); MS (ESI) m/z: 592.2 $[M+H]^+$.

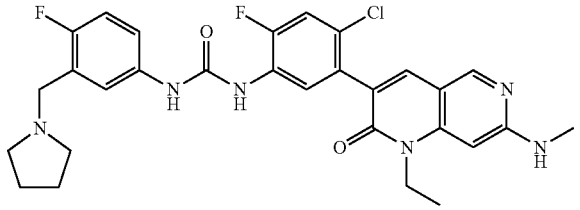

Example 97

A −20° C. mixture of DIEA (552 mg, 4.27 mmol) and pyrrolidine (152 mg, 2.137 mmol) in THF (5 mL) was treated drop-wise with a solution of 2-(bromomethyl)-1-fluoro-4-nitrobenzene (500 mg, 2.137 mmol) in THF (5 mL), allowed to warm to RT and stirred for 6 h. The mixture was treated with EtOAc, washed with water, then brine, dried over $Na_2SO_4$ and concentrated to dryness to afford 1-(2-fluoro-5-nitrobenzyl)pyrrolidine (450 mg, 94% yield). MS (ESI) m/z: 225.1 $[M+H]^+$.

A mixture of 1-(2-fluoro-5-nitrobenzyl)pyrrolidine (450 mg, 2.007 mmol) in EtOAc (15 mL) was treated with 10% Pd/C (107 mg) and hydrogenated (1 atm) for 3 h. Additional 10% Pd/C (100 mg) was added and the mixture hydrogenated (1 atm) overnight. The solids were removed via filtration through diatomaceous earth, washed with EtOAc and the filtrate washed with water, then brine, dried over $Na_2SO_4$ and concentrated to dryness to afford 4-fluoro-3-(pyrrolidin-1-ylmethyl)aniline (282 mg, 72% yield). $^1H$ NMR (400 MHz, DMSO-$d_6$): δ 6.75 (dd, J=10.0, 8.7 Hz, 1H), 6.56 (dd, J=6.4, 2.9 Hz, 1H), 6.39 (ddd, J=8.7, 4.3, 2.9 Hz, 1H), 4.85 (s, 2H), 3.44 (d, J=1.5 Hz, 2H), 2.40 (m, 4H), 1.66 (m, 4H); MS (ESI) m/z: 195.1 $[M+H]^+$.

A mixture of Example A47 (200 mg, 0.363 mmol) and 4-fluoro-3-(pyrrolidin-1-ylmethyl)aniline (88 mg, 0.454 mmol) in dioxane (5 mL) was treated with 1-methylpyrrolidine (31 mg, 0.363 mmol) and heated at 70° C. overnight. The mixture was cooled to RT, treated with EtOAc and 50% satd. $NaHCO_3$ and stirred for 0.5 h. The resulting solid was collected via filtration and dried to afford 1-(4-chloro-5-(1-ethyl-7-((4-methoxybenzyl)(methyl)amino)-2-oxo-1,2-dihydro-1,6-naphthyridin-3-yl)-2-fluorophenyl)-3-(4-fluoro-3-(pyrrolidin-1-ylmethyl)phenyl)urea (135 mg, 54% yield). $^1$H NMR (400 MHz, DMSO-$d_6$): δ 9.11 (s, 1H), 8.61 (d, J=2.5 Hz, 1H), 8.50 (s, 1H), 8.16 (d, J=8.7 Hz, 1H), 7.78 (s, 1H), 7.53 (d, J=11.0 Hz, 1H), 7.49 (dd, J=6.5, 2.8 Hz, 1H), 7.27 (m, 1H), 7.18 (d, J=8.5 Hz, 2H), 7.05 (t, J=9.3 Hz, 1H), 6.87 (d, J=8.6 Hz, 2H), 6.32 (s, 1H), 4.85 (s, 2H), 4.19 (q, J=7.1 Hz, 2H), 3.70 (s, 3H), 3.55 (s, 2H), 3.13 (s, 3H), 2.43 (m, 4H), 1.66 (m, 4H), 1.13 (t, J=7.0 Hz, 3H); MS (ESI) m/z: 687.2 $[M+H]^+$.

A mixture of 1-(4-chloro-5-(1-ethyl-7-((4-methoxybenzyl)(methyl)amino)-2-oxo-1,2-dihydro-1,6-naphthyridin-3-yl)-2-fluorophenyl)-3-(4-fluoro-3-(pyrrolidin-1-ylmethyl)phenyl)urea (135 mg, 0.196 mmol) in TFA (3 mL) was stirred at RT for 3 h. The mixture was concentrated to dryness, treated with EtOAc and satd. $NaHCO_3$ and stirred for 15 min. The resulting solid was collected via filtration and dried to afford 1-(4-chloro-5-(1-ethyl-7-(methylamino)-2-oxo-1,2-dihydro-1,6-naphthyridin-3-yl)-2-fluorophenyl)-3-(4-fluoro-3-(pyrrolidin-1-ylmethyl)phenyl)urea (98 mg, 88% yield). $^1$H NMR (400 MHz, DMSO-$d_6$): δ 9.19 (br s, 1H), 8.71 (br s, 1H), 8.41 (s, 1H), 8.13 (m, 1H), 7.73 (s, 1H), 7.54-7.48 (m, 2H), 7.27 (m, 1H), 7.04 (m, 2H), 6.23 (s, 1H), 4.13 (q, J=7.2 Hz, 2H), 3.54 (s, 2H), 2.86 (s, 3H), 2.42 (m, 4H), 1.66 (m, 4H), 1.20 (t, J=6.9 Hz, 3H); MS (ESI) m/z: 567.2 $[M+H]^+$.

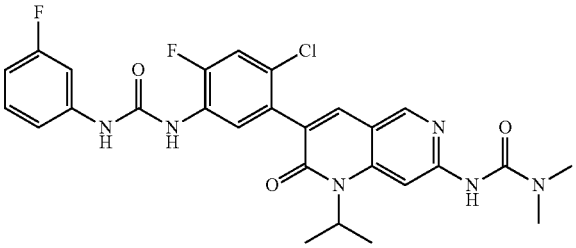

Example 98

A mixture of Example A52 (0.27 g, 0.536 mmol), $Cs_2CO_3$ (0.524 g, 1.609 mmol), N,N-dimethylurea (0.236 g, 2.68 mmol) and Xantphos (0.093 g, 0.161 mmol) in dioxane (10 mL) was sparged with Ar, treated with $Pd_2(dba)_3$ (0.074 g, 0.080 mmol), sparged again with Ar and heated at 100° C. overnight. The mixture was cooled to RT, the solid removed via filtration and washed with EtOAc. The filtrate was washed with brine (2×), dried over $Na_2SO_4$, concentrated to dryness and purified via silica gel chromatography (EtOAc/Hex). The material was re-purified via reverse-phase chromatography (MeCN/$H_2O$ with 0.1% TFA); the organics were removed under reduced pressure and the aqueous residue was treated satd. $NaHCO_3$. The mixture was extracted with EtOAc (3×) and the combined organics were washed with brine, dried over $Na_2SO_4$ and concentrated to dryness to afford 3-(3-(2-chloro-4-fluoro-5-(3-(3-fluorophenyl)ureido)phenyl)-1-isopropyl-2-oxo-1,2-dihydro-1,6-naphthyridin-7-yl)-1,1-dimethylurea (65 mg, 22% yield). $^1$H NMR (400 MHz, DMSO-$d_6$): δ 9.31 (s, 1H), 9.17 (s, 1H), 8.77 (s, 1H), 8.62 (s, 1H), 8.30 (s, 1H), 8.17 (d, J=8.6 Hz, 1H), 7.89 (s, 1H), 7.58 (m, 1H), 7.48 (m, 1H), 7.30 (m, 1H), 7.07 (d, J=8.3 Hz, 1H), 6.79 (m, 1H), 2.97 (s, 6H), 1.55 (d, J=7.0 Hz, 6H); MS (ESI) m/z: 555.1 $[M+H]^+$.

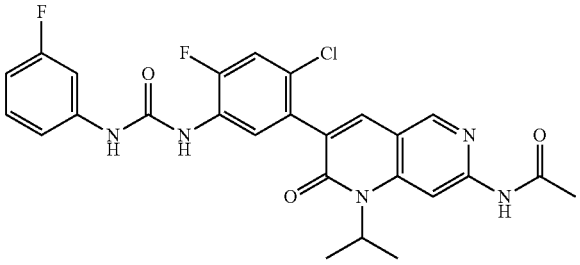

Example 99

A solution of Example A10 (0.16 g, 0.437 mmol) in NMP (3 mL) was treated with DBU (0.079 mL, 0.524 mmol) and 4-methoxybenzylamine (0.150 g, 1.092 mmol) and heated at 150° C. overnight. Additional 4-methoxybenzylamine (0.05 mL) was added and the mixture heated at 150° C. for 24 h. The mixture was cooled to RT, treated with brine and extracted with EtOAc (3×). The combined organics were dried over $Na_2SO_4$, concentrated to dryness and purified via silica gel chromatography (EtOAc/Hex) to afford 3-(5-amino-2-chloro-4-fluorophenyl)-1-isopropyl-7-((4-methoxybenzyl)amino)-1,6-naphthyridin-2(1H)-one (110 mg, 54% yield). MS (ESI) m/z: 467.1 $[M+H]^+$.

A solution of 3-(5-amino-2-chloro-4-fluorophenyl)-1-isopropyl-7-((4-methoxybenzyl)amino)-1,6-naphthyridin-2(1H)-one (0.11 g, 0.236 mmol) in THF (5 mL) was treated with TEA (0.1 mL) and 3-fluorophenyl isocyanate (0.032 mL, 0.259 mmol) and stirred at RT for 5 h. The mixture was concentrated to dryness, treated with DCM and the solid collected via filtration and dried to afford 1-(4-chloro-2-fluoro-5-(1-isopropyl-7-((4-methoxybenzyl)amino)-2-oxo-1,2-dihydro-1,6-naphthyridin-3-yl)phenyl)-3-(3-fluorophenyl)urea (94 mg, 66% yield). MS (ESI) m/z: 604.1 $[M+H]^+$.

A mixture of 1-(4-chloro-2-fluoro-5-(1-isopropyl-7-((4-methoxybenzyl)amino)-2-oxo-1,2-dihydro-1,6-naphthyridin-3-yl)phenyl)-3-(3-fluorophenyl)urea (0.094 g, 0.156 mmol) and anisole (0.085 mL, 0.778 mmol) was stirred in TFA (1 mL) at RT for 3 h. The mixture was concentrated to dryness, treated with EtOAc and satd. $NaHCO_3$ and stirred for 1 h. The resulting solid was collected via filtration and dried to afford 1-(5-(7-amino-1-isopropyl-2-oxo-1,2-dihydro-1,6-naphthyridin-3-yl)-4-chloro-2-fluorophenyl)-3-(3-fluorophenyl)urea (70 mg, 93% yield). MS (ESI) m/z: 484.1 $[M+H]^+$.

A solution of 1-(5-(7-amino-1-isopropyl-2-oxo-1,2-dihydro-1,6-naphthyridin-3-yl)-4-chloro-2-fluorophenyl)-3-(3-fluorophenyl)urea (0.07 g, 0.145 mmol) in pyridine (2 mL) was treated with acetyl chloride (0.011 mL, 0.159 mmol) and stirred at RT for 2 h. The mixture was concentrated to dryness, treated with EtOAc, washed with brine, dried over $Na_2SO_4$ and concentrated to dryness. The material was treated with $Et_2O$ and the solid collected via filtration to afford N-(3-(2-chloro-4-fluoro-5-(3-(3-fluorophenyl)ureido)phenyl)-1-isopropyl-2-oxo-1,2-dihydro-1,6-naphthyridin-7-yl)acetamide (65 mg, 84% yield). $^1$H NMR (400 MHz, DMSO-$d_6$): δ 10.81 (s, 1H), 9.31 (s, 1H), 8.78 (s, 1H), 8.68 (s, 1H), 8.54 (s, 1H), 8.18 (d, J=8.6 Hz, 1H), 7.93 (s, 1H), 7.58 (d, J=11.0 Hz, 1H), 7.46 (dt, J=11.9, 2.3 Hz, 1H), 7.29 (m, 1H), 7.06 (m, 1H), 6.79 (td, J=8.5, 2.6 Hz, 1H), 5.36 (m, 1H), 2.14 (s, 3H), 1.56 (d, J=7.0 Hz, 6H); MS (ESI) m/z: 526.1 $[M+H]^+$.

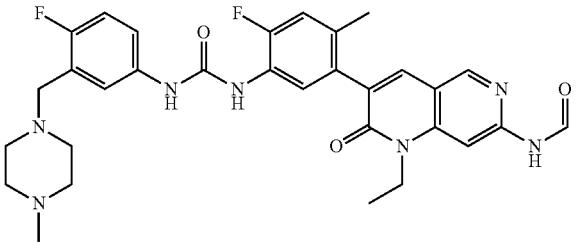

Example 100

A solution of Example D2 (0.117 g, 0.524 mmol) and Example A53 (0.182 g, 0.437 mmol) in dioxane (4.5 mL) was treated with catalytic 1-methylpyrrolidine (2 drops) and the mixture heated at 80° C. overnight. The mixture was cooled to RT, concentrated to dryness and purified via silica gel chromatography (MeOH/DCM) to afford 1-(5-(7-chloro-1-ethyl-2-oxo-1,2-dihydro-1,6-naphthyridin-3-yl)-2-fluoro-4-methylphenyl)-3-(4-fluoro-3-((4-methyl)piperazin-1-yl)methyl)phenyl)urea (123 mg, 49% yield). $^1$H NMR (400 MHz, DMSO-$d_6$): δ 9.06 (s, 1H), 8.77 (s, 1H), 8.47 (s, 1H), 8.00-7.95 (m, 2H), 7.73 (s, 1H), 7.45 (m, 1H), 7.31-7.26 (m, 1H), 7.17 (d, J=12.2 Hz, 1H), 7.05 (t, J=9.2 Hz, 1H), 4.27 (q, J=7.1 Hz, 2H), 3.44 (s, 2H), 2.38 (br s, 8H), 2.17 (s, 3H), 2.07 (s, 3H), 1.20 (t, J=7.0 Hz, 3H); MS (ESI) m/z: 581.2 $[M+H]^+$.

A mixture of 1-(5-(7-chloro-1-ethyl-2-oxo-1,2-dihydro-1,6-naphthyridin-3-yl)-2-fluoro-4-methylphenyl)-3-(4-fluoro-3-((4-methyl)piperazin-1-yl)methyl)phenyl)urea (0.120 g, 0.207 mmol), formamide (0.041 ml, 1.033 mmol) and $K_2CO_3$ (0.057 g, 0.413 mmol) in dioxane (3 mL) was sparged with Ar, treated with BrettPhos Palladacycle (8.05 mg, 10.33 μmol), sparged again with Ar, and heated to 100° C. for 1 h. The mixture was cooled to RT, treated with EtOAc and satd. $NaHCO_3$, filtered to remove insoluble material and the layers separated. The organic layer was washed with brine, dried over $MgSO_4$ and concentrated to dryness. The material was treated with a small amount of DCM, allowed to stand at RT, and the resulting solid collected via filtration and dried. The filtrate was concentrated to dryness, layered with a small amount of DCM and allowed to stand at RT overnight. The resulting solid was collected via filtration and combined with the above-isolated solid to afford N-(1-ethyl-3-(4-fluoro-5-(3-(4-fluoro-3-((4-methylpiperazin-1-yl)methyl)phenyl)ureido)-2-methylphenyl)-2-oxo-1,2-dihydro-1,6-naphthyridin-7-yl)formamide (53 mg, 44% yield). $^1$H NMR (400 MHz, DMSO-$d_6$): δ 9.38 (m, 1H), 9.05 (s, 1H), 8.69 (d, J=18.4 Hz, 1H), 8.44 (s, 1H), 8.21 (s, 1H), 7.96 (d, J=8.4 Hz, 1H), 7.90 (s, 1H), 7.43 (dd, J=6.5, 2.8 Hz, 1H), 7.30 (ddd, J=8.9, 4.4, 2.8 Hz, 1H), 7.16 (d, J=12.2 Hz, 1H), 7.05 (t, J=9.3 Hz, 1H), 6.96 (s, 1H), 4.19 (m, 2H), 3.42 (s, 2H), 2.41-2.19 (m, 8H), 2.10 (s, 3H), 2.07 (s, 3H), 1.24 (m, 3H); MS (ESI) m/z: 590.2 $[M+H]^+$.

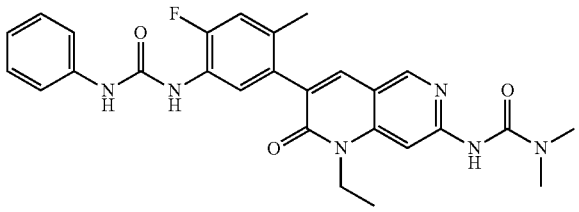

Example 101

A mixture of Example A54 (308 mg, 0.665 mmol), $Cs_2CO_3$ (650 mg, 1.996 mmol), N,N-dimethylurea (293 mg, 3.33 mmol) and Xantphos (115 mg, 0.20 mmol) in dioxane (10 mL) was sparged with Ar, treated with $Pd_2(dba)_3$ (91 mg, 0.100 mmol) and heated at 100° C. overnight. The mixture was cooled to RT, treated with EtOAc and DMF, the solids removed via filtration through diatomaceous earth and washed with water and EtOAc. The layers of the filtrate were separated, the organic layer washed with satd. NaHCO3, then brine, dried over $Na_2SO_4$, concentrated to dryness and purified via reverse-phase chromatography ($MeCN/H_2O$ with 0.1% TFA). The organics were removed under reduced pressure and the aqueous residue treated with satd. $NaHCO_3$. The resulting solid was collected via filtration and dried to afford 3-(1-ethyl-3-(4-fluoro-2-methyl-5-(3-phenylureido)phenyl)-2-oxo-1,2-dihydro-1,6-naphthyridin-7-yl)-1,1-dimethylurea (35 mg, 10% yield). $^1$H NMR (400 MHz, DMSO-$d_6$): δ 9.18 (s, 1H), 9.01 (s, 1H), 8.64 (s, 1H), 8.50 (s, 1H), 8.01 (s, 1H), 7.98 (d, J=8.4 Hz, 1H), 7.86 (s, 1H), 7.41 (d, J=8.0 Hz, 2H), 7.25 (t, J=7.7 Hz, 2H), 7.15 (d, J=12.2 Hz, 1H), 6.95 (t, J=7.3 Hz, 1H), 4.18 (q, J=7.2 Hz, 2H), 2.97 (s, 6H), 2.08 (s, 3H), 1.24 (t, J=7.1 Hz, 3H); MS (ESI) m/z: 503.2 $[M+H]^+$.

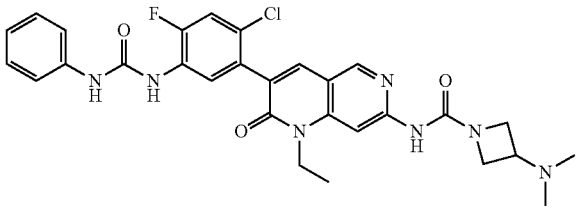

Example 102

A suspension of N,N-dimethylazetidin-3-amine dihydrochloride (0.071 g, 0.410 mmol) and N-methylpyrrolidine (0.070 g, 0.821 mmol) in dioxane (4 mL) was heated at 55° C. for 10 minutes, treated with Example A50 (0.11 g, 0.205 mmol) and heated at 55° C. for 16 h. The mixture was concentrated to dryness and purified via silica gel chromatography (MeOH/DCM) to afford N-(3-(2-chloro-4-fluoro-5-(3-phenylureido)phenyl)-1-ethyl-2-oxo-1,2-dihydro-1,6-naphthyridin-7-yl)-3-(dimethylamino)azetidine-1-carboxamide (68 mg, 57% yield). $^1$H NMR (400 MHz, DMSO-$d_6$): δ 9.49 (s, 1H), 9.09 (s, 1H), 8.71 (d, J=2.6 Hz, 1H), 8.65 (s, 1H), 8.21 (d, J=8.6 Hz, 1H), 8.09 (s, 1H), 7.94 (s, 1H), 7.57 (d, J=11.0 Hz, 1H), 7.41 (dd, J=8.2, 1.2 Hz, 2H), 7.26 (t, J=7.8 Hz, 2H), 6.97 (t, J=7.3 Hz, 1H), 4.17 (q, J=7.3 Hz, 2H), 4.06-4.01 (m, 2H), 3.86-3.77 (m, 2H), 3.04 (m, 1H), 2.09 (s, 6H), 1.24 (t, J=7.0 Hz, 3H); MS (ESI) m/z: 578.2 $[M+H]^+$.

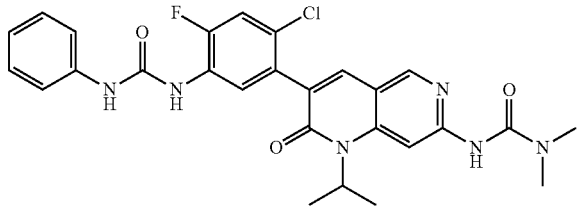

Example 103

A mixture of Example A55 (0.2 g, 0.412 mmol), $Cs_2CO_3$ (0.403 g, 1.236 mmol), N,N-dimethylurea (0.182 g, 2.060 mmol) and Xantphos (0.072 g, 0.124 mmol) in dioxane (10 mL) was sparged with Ar, treated with $Pd_2(dba)_3$ (0.057 g, 0.062 mmol), sparged again with Ar and heated at 100° C. overnight. The mixture was cooled to RT, the solids removed via filtration and washed with water and EtOAc. The layers of the filtrate were separated, the organic layer washed with brine, dried over $Na_2SO_4$, concentrated to dryness and purified via silica gel chromatography (EtOAc/Hex). The material was re-purified via reverse-phase chromatography (MeCN/$H_2O$ with 0.1% TFA). The organics were removed under reduced pressure and the aqueous residue treated with satd. $NaHCO_3$. The resulting solid was collected via filtration and dried to afford 3-(3-(2-chloro-4-fluoro-5-(3-phenylureido)phenyl)-1-isopropyl-2-oxo-1,2-dihydro-1,6-naphthyridin-7-yl)-1,1-dimethylurea (25 mg, 6% yield). $^1$H NMR (400 MHz, DMSO-$d_6$): δ 9.16 (s, 1H), 9.11 (s, 1H), 8.73 (s, 1H), 8.62 (s, 1H), 8.30 (s, 1H), 8.20 (d, J=8.6 Hz, 1H), 7.89 (s, 1H), 7.55 (d, J=11.0 Hz, 1H), 7.42 (m, 2H), 7.26 (t, J=7.8 Hz, 2H), 6.97 (t, J=7.3 Hz, 1H), 5.32 (m, 1H), 2.97 (s, 6H), 1.55 (d, J=7.0 Hz, 6H); MS (ESI) m/z: 537.1 $[M+H]^+$.

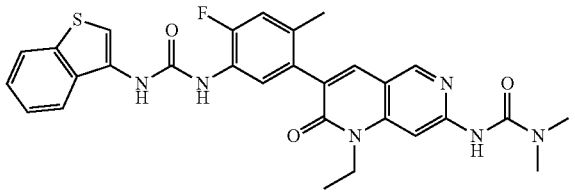

Example 104

A solution of benzo[b]thiophene-3-carboxylic acid (0.129 g, 0.723 mmol) in toluene (5 mL) was treated with TEA (0.167 mL, 1.206 mmol) and DPPA (0.195 ml, 0.904 mmol), stirred at RT for 5 min, treated with Example A6 (0.20 g, 0.603 mmol) and heated at 100° C. for 2 h. The mixture was cooled to RT and the resulting solid collected via filtration to afford 1-(benzo[b]thiophen-3-yl)-3-(5-(7-chloro-1-ethyl-2-oxo-1,2-dihydro-1,6-naphthyridin-3-yl)-2-fluoro-4-methylphenyl)urea (230 mg, 75% yield). $^1$H NMR (400 MHz, DMSO-$d_6$): δ 9.40 (s, 1H), 8.86 (s, 1H), 8.78 (s, 1H), 8.11 (d, J=8.4 Hz, 1H), 8.02 (s, 1H), 7.96 (d, J=8.0 Hz, 1H), 7.87 (d, J=8.1 Hz, 1H), 7.74 (s, 1H), 7.67 (s, 1H), 7.48 (m, 1H), 7.41 (m, 1H), 7.20 (m, 1H), 4.28 (q, J=7.1 Hz, 2H), 2.08 (s, 3H), 1.21 (t, J=7.0 Hz, 3H); MS (ESI) m/z: 507.1 $[M+H]^+$.

A mixture of 1-(benzo[b]thiophen-3-yl)-3-(5-(7-chloro-1-ethyl-2-oxo-1,2-dihydro-1,6-naphthyridin-3-yl)-2-fluoro-4-methylphenyl)urea (0.23 g, 0.454 mmol), $Cs_2CO_3$ (0.443 g, 1.361 mmol), N,N-dimethylurea (0.200 g, 2.268 mmol) and Xantphos (0.079 g, 0.136 mmol) in dioxane (10 mL) was sparged with Ar, treated with $Pd_2(dba)_3$ (0.062 g, 0.068 mmol), sparged again with Ar and heated at 100° C. overnight. The mixture was cooled to RT, the solids removed via filtration and rinsed with water and EtOAc. The layers of the filtrate were separated, the organic layer washed with brine, dried over $Na_2SO_4$ and concentrated to dryness. The material was treated with DCM, the solid removed via filtration and the filtrate purified via silica gel chromatography (EtOAc/Hex) to afford 3-(3-(5-(3-(benzo[b]thiophen-3-yl)ureido)-4-fluoro-2-methylphenyl)-1-ethyl-2-oxo-1,2-dihydro-1,6-naphthyridin-7-yl)-1,1-dimethylurea (25 mg, 9% yield). $^1$H NMR (400 MHz, DMSO-$d_6$): δ 9.34 (s, 1H), 9.13 (s, 1H), 8.79 (s, 1H), 8.60 (s, 1H), 8.03 (d, J=8.4 Hz, 1H), 7.97 (s, 1H), 7.91 (d, J=8.0 Hz, 1H), 7.83 (m, 2H), 7.62 (s, 1H), 7.45-7.40 (m, 1H), 7.36 (t, J=7.5 Hz, 1H), 7.15 (d, J=12.3 Hz, 1H), 4.14 (d, J=8.0 Hz, 2H), 2.93 (s, 3H), 1.20 (m, 3H); MS (ESI) m/z: 559.2 $[M+H]^+$.

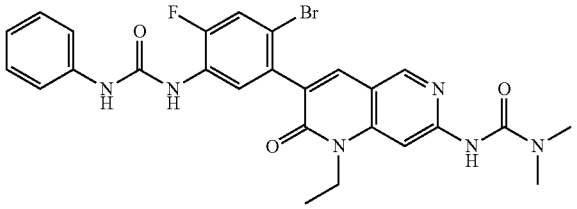

Example 105

A solution of Example A13 (0.300 g, 0.756 mmol) in pyridine (8 mL) was cooled to 0° C., treated slowly with phenyl isocyanate (0.086 mL, 0.794 mmol), stirred at 0° C. for 20 min then warmed to RT for 45 min. The solids were collected via filtration, rinsed with a small amount of DCM and dried; the filtrate was treated with satd. $NaHCO_3$ and extracted with DCM. The organic layer was washed with brine, dried over $MgSO_4$, concentrated to dryness, triturated with DCM, the solid collected via filtration and combined with the above-isolated solid to afford 1-(4-bromo-5-(7-chloro-1-ethyl-2-oxo-1,2-dihydro-1,6-naphthyridin-3-yl)-2-fluorophenyl)-3-phenylurea (170 mg, 44% yield). $^1$H NMR (400 MHz, DMSO-$d_6$): δ 9.11 (s, 1H), 8.79 (s, 1H), 8.75 (d, J=2.5 Hz, 1H), 8.24 (d, J=8.5 Hz, 1H), 8.06 (s, 1H), 7.75 (s, 1H), 7.71 (d, J=10.8 Hz, 1H), 7.41 (dd, J=8.2, 1.2 Hz, 2H), 7.26 (t, J=7.8 Hz, 2H), 6.97 (t, J=7.4 Hz, 1H), 4.27 (q, J=7.1 Hz, 2H), 1.20 (t, J=7.0 Hz, 3H); MS (ESI) m/z: 515.0 $[M+H]^+$.

A suspension of 1-(4-bromo-5-(7-chloro-1-ethyl-2-oxo-1,2-dihydro-1,6-naphthyridin-3-yl)-2-fluorophenyl)-3-phenylurea (0.360 g, 0.698 mmol), N,N-dimethylurea (0.307 g, 3.49 mmol) and $Cs_2CO_3$ (0.682 g, 2.094 mmol) in dioxane (8 mL) was sparged with Ar, treated with XantPhos (0.121 g, 0.209 mmol) and $Pd_2(dba)_3$ (0.096 g, 0.105 mmol), sparged again with Ar and heated at 100° C. overnight. The mixture was cooled to RT, the solids removed via filtration and rinsed with EtOAc. The filtrate was treated with brine, filtered again to remove solids and the layers separated. The organic layer was washed a second time with brine, dried over $MgSO_4$, concentrated to dryness and purified via reverse-phase chromatography (MeCN/$H_2O$ with 0.1% TFA). The organics were removed under reduced pressure, the aqueous residue treated with satd. $NaHCO_3$ and stirred for 1 h. The resulting solid was collected via filtration and dried to afford 3-(3-(2-bromo-4-fluoro-5-(3-phenylureido)

phenyl)-1-ethyl-2-oxo-1,2-dihydro-1,6-naphthyridin-7-yl)-1,1-dimethylurea (37 mg, 9% yield). $^1$H NMR (400 MHz, DMSO-$d_6$): δ 9.21 (s, 1H), 9.10 (s, 1H), 8.72 (s, 1H), 8.65 (s, 1H), 8.21 (d, J=8.5 Hz, 1H), 8.01 (s, 1H), 7.91 (s, 1H), 7.69 (d, J=10.8 Hz, 1H), 7.42 (m, 2H), 7.26 (m, 2H), 6.97 (t, J=7.4 Hz, 1H), 4.18 (q, J=7.1 Hz, 2H), 2.97 (s, 6H), 1.24 (t, J=7.1 Hz, 3H); MS (ESI) m/z: 567.1 [M+H]$^+$.

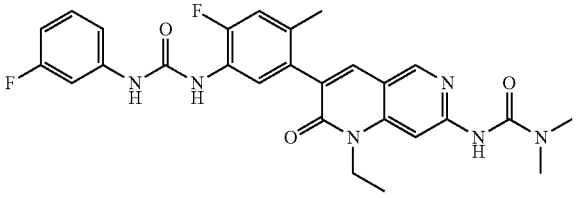

Example 106

A mixture of Example A56 (320 mg, 0.682 mmol), $Cs_2CO_3$ (667 mg, 2.047 mmol), N,N-dimethylurea (301 mg, 3.41 mmol) and Xantphos (118 mg, 0.205 mmol) in dioxane (5 mL) was sparged with Ar, treated with $Pd_2(dba)_3$ (94 mg, 0.102 mmol) and heated at 100° C. overnight. The mixture was cooled to RT, treated with EtOAc and DMF, the solids removed via filtration through diatomaceous earth and washed with water and EtOAc. The layers of the filtrate were separated, the organic layer washed with satd. $NaHCO_3$, then brine, dried over $Na_2SO_4$, concentrated to dryness and purified via reverse-phase chromatography (MeCN/$H_2O$ with 0.1% TFA). The organics were removed under reduced pressure, the aqueous residue treated with satd. $NaHCO_3$ and stirred for 1 h. The resulting solid was collected via filtration and dried to afford 3-(1-ethyl-3-(4-fluoro-5-(3-(3-fluorophenyl)ureido)-2-methylphenyl)-2-oxo-1,2-dihydro-1,6-naphthyridin-7-yl)-1,1-dimethylurea (30 mg, 8% yield). $^1$H NMR (400 MHz, DMSO-$d_6$): δ 9.27 (s, 1H), 9.17 (s, 1H), 8.66-8.58 (m, 2H), 8.01 (s, 1H), 7.93 (m, 1H), 7.86 (s, 1H), 7.47 (m, 1H), 7.29 (m, 1H), 7.17 (m, 1H), 7.06 (m, 1H), 6.76 (m, 1H), 4.18 (q, 2H), 2.97 (s, 6H), 2.08 (s, 3H), 1.24 (t, 3H); MS (ESI) m/z: 521.2 [M+H]$^+$.

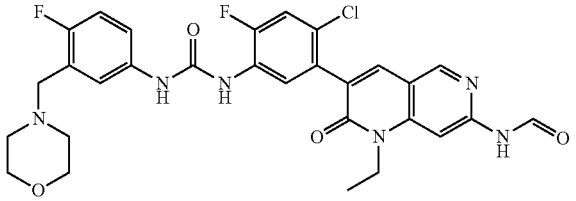

Example 107

A bi-phasic mixture of Example A3 (250 mg, 0.710 mmol) in EtOAc (10 mL) and satd. $NaHCO_3$ (15 mL) was treated with isopropenyl chloroformate 9120 mg, 0.984 mmol) and stirred at RT for 2 h. The layers were separated, the organic layer washed with water, then brine, dried over $Na_2SO_4$ and concentrated to dryness to afford prop-1-en-2-yl (4-chloro-5-(7-chloro-1-ethyl-2-oxo-1,2-dihydro-1,6-naphthyridin-3-yl)-2-fluorophenyl)carbamate (292 mg, 94% yield). MS (ESI) m/z: 436.0 [M+H]$^+$.

A mixture of prop-1-en-2-yl (4-chloro-5-(7-chloro-1-ethyl-2-oxo-1,2-dihydro-1,6-naphthyridin-3-yl)-2-fluorophenyl)carbamate (182 mg, 0.416 mmol) and Example D3 (105 mg, 0.454 mmol) in dioxane (5 mL) was treated with 1-methylpyrrolidine (35 mg, 0.416 mmol) and heated at 70° C. overnight. The mixture was cooled to RT, treated with EtOAc and 50% satd. $NaHCO_3$ and stirred for 0.5 h. The resulting solid was collected via filtration and dried. The layers of the filtrate were separated, the organics layer washed with brine, dried over $Na_2SO_4$, concentrated to dryness and purified via reverse-phase chromatography (MeCN/$H_2O$ with 0.1% TFA). The organics were removed under reduced pressure, the aqueous residue treated with satd. $NaHCO_3$ and stirred for 1 h. The resulting solid was collected via filtration and combined with the above-isolated solid to afford 1-(4-chloro-5-(7-chloro-1-ethyl-2-oxo-1,2-dihydro-1,6-naphthyridin-3-yl)-2-fluorophenyl)-3-(4-fluoro-3-(morpholinomethyl)phenyl)urea (155 mg, 63% yield). $^1$H NMR (400 MHz, DMSO-$d_6$): δ 9.14 (s, 1H), 8.79 (s, 1H), 8.68 (s, 1H), 8.22 (d, J=8.6 Hz, 1H), 8.09 (s, 1H), 7.75 (s, 1H), 7.59 (d, J=11.0 Hz, 1H), 7.48 (dd, J=6.5, 2.8 Hz, 1H), 7.30 (m, 1H), 7.07 (t, J=9.2 Hz, 1H), 4.27 (q, J=7.1 Hz, 2H), 3.56-3.51 (m, 4H), 3.44 (s, 2H), 2.35 (m, 4H), 1.20 (t, J=7.0 Hz, 3H); MS (ESI) m/z: 588.1 [M+H]$^+$.

A mixture of 1-(4-chloro-5-(7-chloro-1-ethyl-2-oxo-1,2-dihydro-1,6-naphthyridin-3-yl)-2-fluorophenyl)-3-(4-fluoro-3-(morpholinomethyl)phenyl)urea (155 mg, 0.263 mmol), $K_2CO_3$ (73 mg, 0.570 mmol) and formamide (59 mg, 1.317 mmol) in dioxane (3 mL) was sparged with Ar, treated with BrettPhos Palladacycle (10 mg, 13 μmol) and heated at 100° C. for 2 h. The mixture was cooled to RT, treated with EtOAc, DMF and 50% satd. $NaHCO_3$ and the solid collected via filtration. The layers of the filtrate were separated, the organics layer washed with brine, dried over $Na_2SO_4$, concentrated to dryness, combined with the isolated solid and purified via reverse-phase chromatography (MeCN/$H_2O$ with 0.1% TFA). The organics were removed under reduced pressure, the aqueous residue treated with satd. $NaHCO_3$ and stirred for 1 h. The resulting solid was collected via filtration, dried and re-purified via reverse-phase chromatography (MeCN/$H_2O$ with 0.1% TFA). The organics were removed under reduced pressure, the aqueous residue treated with satd. $NaHCO_3$ and extracted with EtOAc (3×). The combined organics were dried over $Na_2SO_4$ and concentrated to dryness to afford N-(3-(2-chloro-4-fluoro-5-(3-(4-fluoro-3-(morpholinomethyl)phenyl)ureido)phenyl)-1-ethyl-2-oxo-1,2-dihydro-1,6-naphthyridin-7-yl)formamide (33 mg, 20% yield). MS (ESI) m/z: 597.2 [M+H]$^+$.

A suspension of N-(3-(2-chloro-4-fluoro-5-(3-(4-fluoro-3-(morpholinomethyl)phenyl)ureido)phenyl)-1-ethyl-2-oxo-1,2-dihydro-1,6-naphthyridin-7-yl)formamide (33 mg, 0.055 mmol) in MeCN (2 mL) was treated with 0.1N HCl (580 μL, 0.058 mmol), frozen and lyophilized to afford N-(3-(2-chloro-4-fluoro-5-(3-(4-fluoro-3-(morpholinomethyl)phenyl)ureido)phenyl)-1-ethyl-2-oxo-1,2-dihydro-1,6-naphthyridin-7-yl)formamide hydrochloride (34 mg, 91% yield). MS (ESI) m/z: 597.2 [M+H]$^+$.

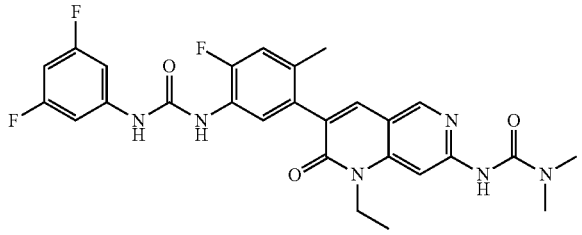

Example 108

A mixture of Example A53 (400 mg, 0.962 mmol) and 3,5-difluoroaniline (186 mg, 1.443 mmol) in dioxane (5 mL) was treated with 1-methylpyrrolidine (123 mg, 1.443 mmol) and heated at 70° C. for 20 h. The mixture was cooled to RT, treated with EtOAc and 50% satd. $NaHCO_3$ and stirred for 1 h. The resulting solid was collected via filtration and dried to afford 1-(5-(7-chloro-1-ethyl-2-oxo-1,2-dihydro-1,6-naphthyridin-3-yl)-2-fluoro-4-methylphenyl)-3-(3,5-difluorophenyl)urea (287 mg, 61% yield). MS (ESI) m/z: 487.1 $[M+H]^+$.

A mixture of 1-(5-(7-chloro-1-ethyl-2-oxo-1,2-dihydro-1,6-naphthyridin-3-yl)-2-fluoro-4-methylphenyl)-3-(3,5-difluorophenyl)urea (287 mg, 0.589 mmol), $Cs_2CO_3$ (576 mg, 1.768 mmol), N,N-dimethylurea (260 mg, 2.95 mmol) and Xantphos (102 mg, 0.177 mmol) in dioxane (5 mL) was sparged with Ar, treated with $Pd_2(dba)_3$ (81 mg, 0.088 mmol) and heated at 100° C. overnight. The mixture was cooled to RT, treated with water, EtOAc and DMF and the solids removed via filtration through diatomaceous earth. The layers of the filtrate were separated, the organic layer washed with brine, dried over $Na_2SO_4$, concentrated to dryness and purified via reverse-phase chromatography ($MeCN/H_2O$ with 0.1% TFA). The organics were removed under reduced pressure, the aqueous residue treated with satd. $NaHCO_3$ and stirred overnight. The resulting solid was collected via filtration and dried to afford 3-(3-(5-(3-(3,5-difluorophenyl)ureido)-4-fluoro-2-methylphenyl)-1-ethyl-2-oxo-1,2-dihydro-1,6-naphthyridin-7-yl)-1,1-dimethylurea (18 mg, 5% yield). $^1H$ NMR (400 MHz, DMSO-$d_6$): δ 9.41 (s, 1H), 9.17 (s, 1H), 8.65 (m, 2H), 8.01 (s, 1H), 7.90 (d, J=8.3 Hz, 1H), 7.86 (s, 1H), 7.20-7.11 (m, 3H), 6.78 (m, 1H), 4.18 (q, J=7.1 Hz, 2H), 2.97 (s, 6H), 2.08 (s, 3H), 1.24 (t, J=7.1 Hz, 3H); MS (ESI) m/z: 539.2 $[M+H]^+$.

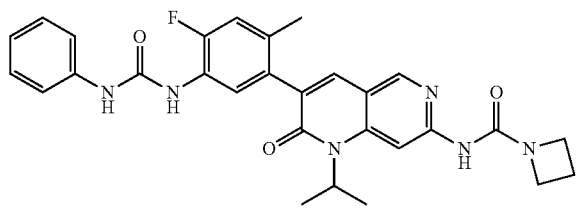

Example 109

A mixture of Example A20 (0.345 g, 0.998 mmol), phenyl isocyanate (0.143 g, 1.197 mmol) and TEA (0.138 ml, 0.998 mmol) in THF (5 mL) was stirred at RT for 3 h. The mixture was treated with 30% EtOAc/Hex, stirred for several minutes and the resulting solid was collected via filtration and dried to afford 1-(5-(7-chloro-1-isopropyl-2-oxo-1,2-dihydro-1,6-naphthyridin-3-yl)-2-fluoro-4-methylphenyl)-3-phenylurea (350 mg, 75% yield). MS (ESI) m/z: 465.1 $[M+H]^+$.

A solution of 1-(5-(7-chloro-1-isopropyl-2-oxo-1,2-dihydro-1,6-naphthyridin-3-yl)-2-fluoro-4-methylphenyl)-3-phenylurea (0.35 g, 0.753 mmol) in dioxane (4 mL) and DMF (1 mL) was sparged with Ar, treated with N-t-butylcarbamate (0.441 g, 3.76 mmol), $Cs_2CO_3$ (0.368 g, 1.129 mmol), X-Phos (0.036 g, 0.075 mmol) and $Pd_2(dba)_3$ (0.034 g, 0.038 mmol) and the mixture heated at 80° C. for 16 h. The mixture was cooled to RT, treated with THF and the solids removed via filtration through diatomaceous earth. The filtrate was washed with brine, dried over $Na_2SO_4$ and concentrated to dryness. The residue was suspended in 1:1 EtOAc/Hex, sonicated and the solid collected via filtration to afford tert-butyl (3-(4-fluoro-2-methyl-5-(3-phenylureido)phenyl)-1-isopropyl-2-oxo-1,2-dihydro-1,6-naphthyridin-7-yl)carbamate (205 mg, 50% yield). $^1H$ NMR (400 MHz, DMSO-$d_6$): δ 10.10 (s, 1H), 9.02 (s, 1H), 8.61 (s, 1H), 8.50 (s, 1H), 8.13 (s, 1H), 7.97 (d, J=8.4 Hz, 1H), 7.82 (s, 1H), 7.41 (d, J=8.0 Hz, 2H), 7.25 (t, J=7.8 Hz, 2H), 7.15 (d, J=12.2 Hz, 1H), 6.95 (t, J=7.4 Hz, 1H), 5.28 (m, 1H), 2.07 (s, 3H), 1.57 (d, J=7.0 Hz, 6H), 1.49 (s, 9H); MS (ESI) m/z: 546.2 $[M+H]^+$.

A solution of tert-butyl (3-(4-fluoro-2-methyl-5-(3-phenylureido)phenyl)-1-isopropyl-2-oxo-1,2-dihydro-1,6-naphthyridin-7-yl)carbamate (0.2 g, 0.367 mmol) in MeOH (3 mL) was treated with HCl in dioxane (4 M, 0.916 mL, 3.67 mmol) and stirred at RT for 16 h. The mixture was concentrated to dryness, treated with pyridine (3 mL) and isopropenyl chloroformate (0.066 g, 0.550 mmol) and stirred at RT for 1 h. Water was added, the mixture stirred for several minutes, extracted with 20% THF/EtOAc (2×) and the combined organics were washed with brine, dried over $Na_2SO_4$ and concentrated to dryness. The residue was treated with 30% EtOAc/Hex, sonicated and the resulting solid collected via filtration to afford prop-1-en-2-yl (3-(4-fluoro-2-methyl-5-(3-phenylureido)phenyl)-1-isopropyl-2-oxo-1,2-dihydro-1,6-naphthyridin-7-yl)carbamate (175 mg, 90% yield). $^1H$ NMR (400 MHz, DMSO-$d_6$): δ 10.77 (s, 1H), 9.02 (s, 1H), 8.66 (s, 1H), 8.50 (s, 1H), 8.15 (s, 1H), 7.98 (d, J=8.5 Hz, 1H), 7.85 (s, 1H), 7.41 (d, J=8.0 Hz, 2H), 7.25 (t, J=7.8 Hz, 2H), 7.15 (d, J=12.2 Hz, 1H), 6.95 (t, J=7.3 Hz, 1H), 5.33 (m, 1H), 4.81 (s, 1H), 4.77 (s, 1H), 2.07 (s, 3H), 1.96 (s, 3H), 1.56 (d, J=7.0 Hz, 6H); MS (ESI) m/z: 530.2 $[M+H]^+$.

A suspension of prop-1-en-2-yl (3-(4-fluoro-2-methyl-5-(3-phenylureido)phenyl)-1-isopropyl-2-oxo-1,2-dihydro-1,6-naphthyridin-7-yl)carbamate (0.1 g, 0.189 mmol) in dioxane (3 mL) was treated with azetidine hydrochloride (0.071 g, 0.755 mmol) and 1-methylpyrrolidine (0.129 g, 1.511 mmol) and heated at 70° C. for 16 h, then cooled to RT and stirred for 24 h. The mixture was concentrated to dryness and purified via reverse-phase chromatography ($MeCN/H_2O$ with 0.1% TFA). The fractions were neutralized with satd. $NaHCO_3$, extracted with EtOAc (2×) and the combined organics were washed with brine, dried over $Na_2SO_4$ and concentrated to dryness to afford N-(3-(4-fluoro-2-methyl-5-(3-phenylureido)phenyl)-1-isopropyl-2-oxo-1,2-dihydro-1,6-naphthyridin-7-yl)azetidine-1-carboxamide (43 mg, 43% yield). $^1H$ NMR (400 MHz, DMSO-$d_6$): δ 9.34 (s, 1H), 9.01 (s, 1H), 8.60 (s, 1H), 8.49 (s, 1H), 8.38 (s, 1H), 7.97 (d, J=8.4 Hz, 1H), 7.80 (s, 1H), 7.41 (d, J=8.0 Hz, 2H), 7.25 (t, J=7.8 Hz, 2H), 7.14 (d, J=12.2 Hz, 1H), 6.95 (t, J=7.4 Hz, 1H), 5.35 (m, 1H), 4.02 (t, J=7.5 Hz, 4H), 2.17 (t, J=7.7 Hz, 2H), 2.07 (s, 3H), 1.55 (d, J=7.0 Hz, 6H); MS (ESI) m/z: 529.2 $[M+H]^+$.

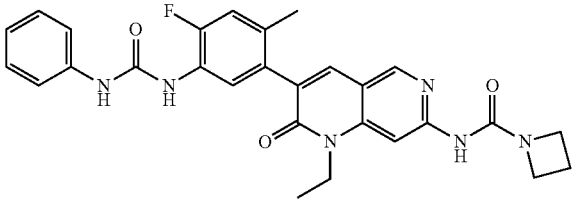

Example 110

A suspension of Example A57 (0.15 g, 0.291 mmol) in THF (4 mL) was treated with azetidine hydrochloride (0.109 g, 1.164 mmol) and 1-methylpyrrolidine (0.248 g, 2.91 mmol) and heated at 60° C. for 16 h. The mixture was concentrated to dryness and purified via reverse-phase chromatography (MeCN/$H_2O$ with 0.1% TFA). The fractions were neutralized with satd. $NaHCO_3$, extracted with EtOAc (2×) and the combined organics were washed with brine, dried over $Na_2SO_4$ and concentrated to dryness to afford N-(1-ethyl-3-(4-fluoro-2-methyl-5-(3-phenylureido)phenyl)-2-oxo-1,2-dihydro-1,6-naphthyridin-7-yl)azetidine-1-carboxamide (53 mg, 35% yield). $^1$H NMR (400 MHz, DMSO-$d_6$): δ 9.37 (s, 1H), 9.05 (s, 1H), 8.63 (s, 1H), 8.52 (s, 1H), 8.10 (s, 1H), 7.97 (d, J=8.4 Hz, 1H), 7.85 (s, 1H), 7.41 (d, J=8.1 Hz, 2H), 7.25 (t, J=7.8 Hz, 2H), 7.15 (d, J=12.2 Hz, 1H), 6.95 (t, J=7.4 Hz, 1H), 4.17 (q, J=7.5 Hz, 2H), 4.02 (t, J=7.5 Hz, 4H), 2.17 (t, J=7.7 Hz, 2H), 2.07 (s, 3H), 1.24 (t, J=7.0 Hz, 3H); MS (ESI) m/z: 515.2 [M+H]$^+$.

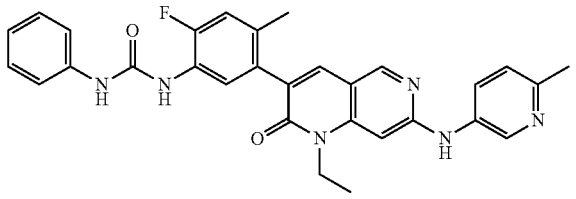

Example 111

A mixture of Example A54 (222 mg, 0.492 mmol), $Pd(OAc)_2$ (6 mg, 0.026 mmol), Xantphos (31 mg, 0.053 mmol), $K_2CO_3$ (73 mg, 0.527 mmol) and 3-amino-6-methylpyridine (171 mg, 1.582 mmol) in dioxane (4 mL) was sparged with Ar and heated at 90° C. for 4 h. The mixture was cooled to RT, treated with EtOAc and 50% satd. $NaHCO_3$ and the solids removed via filtration through diatomaceous earth. The layers of the filtrate were separated, the organics layer washed with brine, dried over $Na_2SO_4$, concentrated to dryness and purified via reverse-phase chromatography (MeCN/$H_2O$ with 0.1% TFA). The organics were removed under reduced pressure, the aqueous residue treated with satd. $NaHCO_3$ and stirred. The resulting solid was collected via filtration and dried to afford 1-(5-(1-ethyl-7-((6-methylpyridin-3-yl)amino)-2-oxo-1,2-dihydro-1,6-naphthyridin-3-yl)-2-fluoro-4-methylphenyl)-3-phenylurea (87 mg, 33% yield). $^1$H NMR (400 MHz, DMSO-$d_6$): δ 9.47 (s, 1H), 9.08 (s, 1H), 8.64 (d, J=2.7 Hz, 1H), 8.57 (s, 1H), 8.55 (s, 1H), 8.07 (dd, J=8.4, 2.7 Hz, 1H), 7.96 (d, J=8.4 Hz, 1H), 7.79 (s, 1H), 7.41 (dd, J=8.2, 1.2 Hz, 2H), 7.25 (t, J=7.8 Hz, 2H), 7.16 (t, J=8.7 Hz, 2H), 6.94 (t, J=7.3 Hz, 1H), 6.73 (s, 1H), 4.16 (q, J=7.1 Hz, 2H), 2.40 (s, 3H), 2.08 (s, 3H), 1.25 (t, J=7.0 Hz, 3H); MS (ESI) m/z: 523.2 [M+H]$^+$.

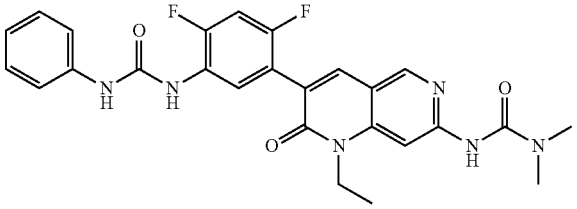

Example 112

A mixture of Example A18 (400 mg, 1.191 mmol) and pyridine (471 mg, 5.96 mmol) in THF (10 mL) was treated drop-wise with phenyl isocyanate (170 mg, 1.43 mmol) and stirred at RT overnight. The mixture was treated with EtOAc and 50% satd. $NaHCO_3$ and stirred for 2 h. The resulting solid was collected via filtration and dried to afford 1-(5-(7-chloro-1-ethyl-2-oxo-1,2-dihydro-1,6-naphthyridin-3-yl)-2,4-difluorophenyl)-3-phenylurea (211 mg, 38% yield). $^1$H NMR (400 MHz, DMSO-$d_6$): δ 9.07 (br s, 1H), 8.80 (s, 1H), 8.64 (br s, 1H), 8.22-8.15 (m, 2H), 7.74 (s, 1H), 7.46-7.39 (m, 3H), 7.26 (t, J=7.8 Hz, 2H), 6.96 (t, J=7.3 Hz, 1H), 4.27 (q, J=7.1 Hz, 2H), 1.20 (t, J=7.0 Hz, 3H); MS (ESI) m/z: 455.1 [M+H]$^+$.

A mixture of 1-(5-(7-chloro-1-ethyl-2-oxo-1,2-dihydro-1,6-naphthyridin-3-yl)-2,4-difluorophenyl)-3-phenylurea (211 mg, 0.464 mmol), $Cs_2CO_3$ (453 mg, 1.392 mmol), N,N-dimethylurea (204 mg, 2.319 mmol) and Xantphos (81 mg, 0.139 mmol) in dioxane (5 mL) was sparged with Ar, treated with $Pd_2(dba)_3$ (64 mg, 0.070 mmol) and heated at 100° C. for 4 h. The mixture was cooled to RT, treated with EtOAc, DMF and 50% satd. $NaHCO_3$ and the solids removed via filtration through diatomaceous earth. The layers of the filtrate were separated, the organic layer washed with brine, dried over $Na_2SO_4$, concentrated to dryness and purified via reverse-phase chromatography (MeCN/$H_2O$ with 0.1% TFA). The organics were removed under reduced pressure, the aqueous residue treated with satd. $NaHCO_3$ and stirred. The resulting solid was collected via filtration and dried to afford 3-(3-(2,4-difluoro-5-(3-phenylureido)phenyl)-1-ethyl-2-oxo-1,2-dihydro-1,6-naphthyridin-7-yl)-1,1-dimethylurea (47 mg, 33% yield). $^1$H NMR (400 MHz, DMSO-$d_6$): δ 9.21 (s, 1H), 9.03 (s, 1H), 8.66 (s, 1H), 8.57 (s, 1H), 8.17 (dd, J=9.1, 7.8 Hz, 1H), 8.01 (d, J=2.1 Hz, 2H), 7.45-7.38 (m, 3H), 7.26 (t, J=7.8 Hz, 2H), 6.96 (t, J=7.4 Hz, 1H), 4.18 (q, J=7.3 Hz, 2H), 2.97 (s, 6H), 1.24 (t, J=7.1 Hz, 3H); MS (ESI) m/z: 507.2 [M+H]$^+$.

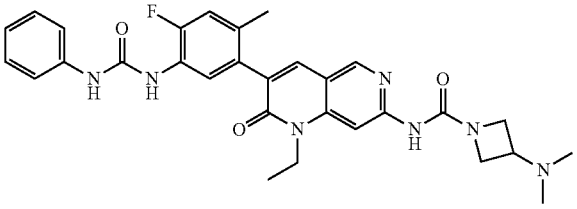

Example 113

A suspension of Example A57 (0.210 g, 0.407 mmol) in MeCN (8 mL) was treated with N,N-dimethylazetidin-3-amine dihydrochloride (0.300 g, 1.733 mmol) followed by 1-methylpyrrolidine (0.150 g, 1.762 mmol) and heated at 70° C. for 3 h. The mixture was cooled to RT, concentrated to dryness and purified via silica gel chromatography (MeOH/DCM) to afford 3-(dimethylamino)-N-(1-ethyl-3-(4-fluoro-2-methyl-5-(3-phenylureido)phenyl)-2-oxo-1,2-dihydro-1,6-naphthyridin-7-yl)azetidine-1-carboxamide (160 mg, 70% yield). $^1$H NMR (400 MHz, DMSO-$d_6$): δ 9.56 (s, 1H), 9.48 (s, 1H), 8.72 (s, 1H), 8.64 (s, 1H), 8.08 (s, 1H), 7.96 (d, J=8.4 Hz, 1H), 7.86 (s, 1H), 7.42 (dd, J=8.2, 1.2 Hz, 2H), 7.24 (t, J=7.8 Hz, 2H), 7.14 (d, J=12.2 Hz, 1H), 6.93 (t, J=7.4 Hz, 1H), 4.21-3.91 (m, 6H), 3.32 (m, 1H), 2.73 (s, 6H), 2.07 (s, 3H), 1.24 (t, J=7.1 Hz, 3H); MS (ESI) m/z: 558.3 [M+H]$^+$.

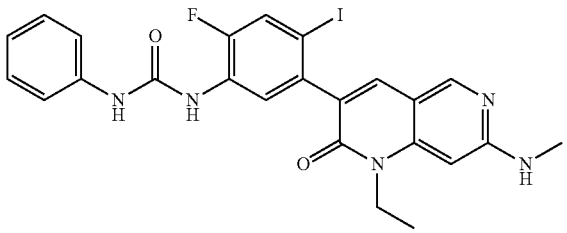

Example 114

A solution of Example A39 (0.600 g, 1.921 mmol) in dioxane (4 mL) and pyridine (4 mL) was treated with iodine (1.463 g, 5.76 mmol) and stirred at RT for 2 days. The mixture was treated with satd. $Na_2S_2O_3$, stirred for several minutes and extracted with DCM (4×). The combined organics were washed with brine, dried over $Na_2SO_4$ and concentrated to dryness. The residue was treated with MeOH and the resulting solid was collected via filtration and dried to afford 3-(5-amino-4-fluoro-2-iodophenyl)-1-ethyl-7-(methylamino)-1,6-naphthyridin-2(1H)-one (312 mg, 37% yield). MS (ESI) m/z: 439.0 [M+H]$^+$.

A suspension of 3-(5-amino-4-fluoro-2-iodophenyl)-1-ethyl-7-(methylamino)-1,6-naphthyridin-2(1H)-one (0.310 g, 0.707 mmol) in DCM (10 mL) was treated with phenyl isocyanate (0.100 g, 0.839 mmol) followed by pyridine (0.060 g, 0.759 mmol) and stirred at RT for 3 h. The mixture was concentrated to dryness and purified via silica gel chromatography (EtOAc/Hex) to afford 1-(5-(1-ethyl-7-(methylamino)-2-oxo-1,2-dihydro-1,6-naphthyridin-3-yl)-2-fluoro-4-iodophenyl)-3-phenylurea (120 mg, 29% yield). $^1$H NMR (400 MHz, DMSO-$d_6$): δ 9.08 (s, 1H), 8.66 (s, 1H), 8.41 (s, 1H), 8.14 (d, J=8.3 Hz, 1H), 7.77 (d, J=10.6 Hz, 1H), 7.64 (s, 1H), 7.41 (d, J=8.0 Hz, 2H), 7.26 (t, J=7.7 Hz, 2H), 7.05 (m, 2H), 6.24 (s, 1H), 4.14 (d, J=8.1 Hz, 2H), 2.86 (d, J=4.8 Hz, 3H), 1.22 (t, J=7.0 Hz, 3H); MS (ESI) m/z: 558.1 [M+H]$^+$.

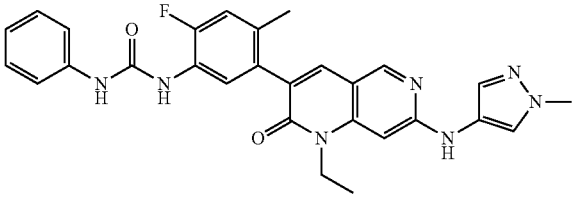

Example 115

A mixture of Example A54 (255 mg, 0.566 mmol), $Pd(OAc)_2$ (6.4 mg, 0.028 mmol), Xantphos (33 mg, 0.057 mmol), $K_2CO_3$ (117 mg, 0.848 mmol) and 4-amino-1-methylpyrazole (60 mg, 0.622 mmol) in dioxane (4 mL) was sparged with Ar and heated at 99° C. overnight. The mixture was cooled to RT, treated with EtOAc and DMF and the solids removed via filtration through diatomaceous earth. The filtrate was concentrated to dryness and purified via reverse-phase chromatography (MeCN/$H_2O$ with 0.1% TFA). The organics were removed under reduced pressure, the aqueous residue treated with satd. $NaHCO_3$ and extracted with EtOAc (2×). The combined organics were washed with brine, dried over $Na_2SO_4$ and concentrated to dryness to afford 1-(5-(1-ethyl-7-((1-methyl-1H-pyrazol-4-yl)amino)-2-oxo-1,2-dihydro-1,6-naphthyridin-3-yl)-2-fluoro-4-methylphenyl)-3-phenylurea (14 mg, 4% yield). $^1$H NMR (400 MHz, DMSO-$d_6$): δ 9.11 (s, 1H), 8.96 (s, 1H), 8.47 (s, 1H), 8.43 (s, 1H), 7.92-7.88 (m, 2H), 7.69 (s, 1H), 7.41 (s, 1H), 7.36 (d, J=8.0 Hz, 2H), 7.20 (t, J=7.8 Hz, 2H), 7.08 (d, J=12.3 Hz, 1H), 6.90 (t, J=7.3 Hz, 1H), 6.46 (s, 1H), 4.07 (q, J=7.1 Hz, 2H), 3.76 (s, 3H), 2.02 (s, 3H), 1.17 (t, J=7.0 Hz, 3H); MS (ESI) m/z: 512.2 [M+H]$^+$.

The following assays demonstrate that certain compounds of Formula Ia inhibit c-KIT kinase, and mutants thereof, in enzymatic assays and also inhibit cKIT kinase in GIST cell lines.

c-KIT Kinase Assay

Activity of c-KIT kinase (Seq ID no. 1) was determined by following the production of ADP from the kinase reaction through coupling with the pyruvate kinase/lactate dehydrogenase system (e.g., Schindler et al. Science (2000) 289: 1938-1942). In this assay, the oxidation of NADH (measured by decrease in absorbance at 340 nm) was continuously monitored spectrophotometrically. The reaction mixture (100 μL) contained c-KIT (cKIT residues T544-V976, 6 nM, polyE4Y (1 mg/mL), $MgCl_2$ (10 mM), pyruvate kinase (4 units), lactate dehydrogenase (0.7 units), phosphoenol pyruvate (1 mM), and NADH (0.28 mM) in 90 mM Tris buffer containing 0.2% octyl-glucoside and 1% DMSO, pH 7.5. Test compounds were incubated with c-Kit (Seq ID no. 1) and other reaction reagents at 22° C. for ~30 min before ATP (200 μM) was added to start the reaction. The absorption at 340 nm was monitored continuously for 2 hours at 30° C. on Synergy 2 (BioTeK). The reaction rate was calculated using the 0 to 1 h time frame. Percent inhibition was obtained by comparison of reaction rate with that of a control (i.e. with no test compound). $IC_{50}$ values were calculated from a series of percent inhibition values determined at a range of inhibitor concentrations using software routines as implemented in the GraphPad Prism software package.

c-KIT Protein Sequence (Seq ID no. 1)

The protein construct was prepared by deCODE Biostructures using procedures known in the art. The construct contains residues T544-V976 of cKit, an N-terminal tag, a GST-fusion sequence and a TEV cleavage site.

```
MEHHHHHHHH EYMPMEMAPI LGYWKIKGLV QPTRLLLEYL
EEKYEEHLYE RDEGDKWRNK KFELGLEFPN LPYYIDGDVK
LTQSMAIIRY IADKHNMLGG CPKERAEISM LEGAVLDIRY
GVSRIAYSKD FETLKVDFLS KLPEMLKMFE DRLCHKTYLN
```

-continued

```
GDHVTHPDFM LYDALDVVLY MDPMCLDAFP KLVCFKKRIE
AIPQIDKYLK SSKYIAWPLQ GWQATFGGGD HPPKSDLVPR
HNQTSLYKKA GSAAAVLEEN LYFQGTYKYL QKPMYEVQWK
VVEEINGNNY VYIDPTQLPY DHKWEFPRNR LSFGKTLGAG
AFGKVVEATA YGLIKSDAAM TVAVKMLKPS AHLTEREALM
SELKVLSYLG NHMNIVNLLG ACTIGGPTLV ITEYCCYGDL
LNFLRRKRDS FICSKQEDHA EAALYKNLLH SKESSCSDST
NEYMDMKPGV SYVVPTKADK RRSVRIGSYI ERDVTPAIME
DDELALDLED LLSFSYQVAK GMAFLASKNC IHRDLAARNI
LLTHGRITKI CDFGLARDIK NDSNYVVKGN ARLPVKWMAP
ESIFNCVYTF ESDVWSYGIF LWELFSLGSS PYPGMPVDSK
FYKMIKEGFR MLSPEHAPAE MYDIMKTCWD ADPLKRPTFK
QIVQLIEKQI SESTNHIYSN LANCSPNRQK PVVDHSVRIN
SVGSTASSSQ PLLVHDDV
```

c-KIT V654A Kinase Assay

Activity of c-KIT V654A kinase (Seq ID no. 2) was determined by following the production of ADP from the kinase reaction through coupling with the pyruvate kinase/lactate dehydrogenase system (e.g., Schindler et al. Science (2000) 289: 1938-1942). In this assay, the oxidation of NADH (measured by decrease in absorbance at 340 nm) was continuously monitored spectrophotometrically. The reaction mixture (100 μl) contained V654A c-Kit (residues T544-V976 with N-terminal GST fusion, 47 nM), polyE4Y (1 mg/ml), MgCl2 (10 mM), pyruvate kinase (4 units), lactate dehydrogenase (0.7 units), phosphoenol pyruvate (1 mM), and NADH (0.28 mM) and ATP (200 μM) in 90 mM Tris buffer containing 0.2% octyl-glucoside and 1% DMSO, pH 7.5. The inhibition reaction was started by mixing serial diluted test compound with the above reaction mixture. The absorption at 340 nm was monitored continuously for 6 hours at 30° C. on Synergy 2 plate reader (BioTech). Reaction rates around 3 to 5 h time frame were used to calculate % inhibitions, from which $IC_{50}$ values were generated using GraphPad Prism.

c-KIT (V654A) Protein Sequence (Seq ID No. 2)

The protein construct was prepared by deCODE Biostructures using procedures known in the art. The construct contains residues T544-V976 of cKit, an N-terminal tag, a GST-fusion sequence and a TEV cleavage site. This construct is identical to Seq ID no. 1 except for the V654A mutation.

```
MEHHHHHHHH EYMPMEMAPI LGYWKIKGLV QPTRLLLEYL
EEKYEEHLYE RDEGDKWRNK KFELGLEFPN LPYYIDGDVK
LTQSMAIIRY IADKHNMLGG CPKERAEISM LEGAVLDIRY
GVSRIAYSKD FETLKVDFLS KLPEMLKMFE DRLCHKTYLN
GDHVTHPDFM LYDALDVVLY MDPMCLDAFP KLVCFKKRIE
AIPQIDKYLK SSKYIAWPLQ GWQATFGGGD HPPKSDLVPR
HNQTSLYKKA GSAAAVLEEN LYFQGTYKYL QKPMYEVQWK
```

-continued

```
VVEEINGNNY VYIDPTQLPY DHKWEFPRNR LSFGKTLGAG
AFGKVVEATA YGLIKSDAAM TVAVKMLKPS AHLTEREALM
SELKVLSYLG NHMNIANLLG ACTIGGPTLV ITEYCCYGDL
LNFLRRKRDS FICSKQEDHA EAALYKNLLH SKESSCSDST
NEYMDMKPGV SYVVPTKADK RRSVRIGSYI ERDVTPAIME
DDELALDLED LLSFSYQVAK GMAFLASKNC IHRDLAARNI
LLTHGRITKI CDFGLARDIK NDSNYVVKGN ARLPVKWMAP
ESIFNCVYTF ESDVWSYGIF LWELFSLGSS PYPGMPVDSK
FYKMIKEGFR MLSPEHAPAE MYDIMKTCWD ADPLKRPTFK
QIVQLIEKQI SESTNHIYSN LANCSPNRQK PVVDHSVRIN
SVGSTASSSQ PLLVHDDV
```

c-KIT D816H Kinase Assay

The kinase assay for c-KIT D816H kinase (Seq ID no. 3) was performed using the conditions described above for c-KIT V654A assay except that 10 nM of c-KIT D816H was used.

c-KIT (D816H) Protein Sequence (Seq ID no. 3)

The protein construct was prepared by deCODE Biostructures using procedures known in the art. The construct contains residues T544-V976 of cKit, an N-terminal tag, a GST-fusion sequence and a TEV cleavage site. This construct is identical to Seq ID no. 1 except for the D816H mutation.

```
MEHHHHHHHH EYMPMEMAPI LGYWKIKGLV QPTRLLLEYL
EEKYEEHLYE RDEGDKWRNK KFELGLEFPN LPYYIDGDVK
LTQSMAIIRY IADKHNMLGG CPKERAEISM LEGAVLDIRY
GVSRIAYSKD FETLKVDFLS KLPEMLKMFE DRLCHKTYLN
GDHVTHPDFM LYDALDVVLY MDPMCLDAFP KLVCFKKRIE
AIPQIDKYLK SSKYIAWPLQ GWQATFGGGD HPPKSDLVPR
HNQTSLYKKA GSAAAVLEEN LYFQGTYKYL QKPMYEVQWK
VVEEINGNNY VYIDPTQLPY DHKWEFPRNR LSFGKTLGAG
AFGKVVEATA YGLIKSDAAM TVAVKMLKPS AHLTEREALM
SELKVLSYLG NHMNIVNLLG ACTIGGPTLV ITEYCCYGDL
LNFLRRKRDS FICSKQEDHA EAALYKNLLH SKESSCSDST
NEYMDMKPGV SYVVPTKADK RRSVRIGSYI ERDVTPAIME
DDELALDLED LLSFSYQVAK GMAFLASKNC IHRDLAARNI
LLTHGRITKI CDFGLARHIK NDSNYVVKGN ARLPVKWMAP
ESIFNCVYTF ESDVWSYGIF LWELFSLGSS PYPGMPVDSK
FYKMIKEGFR MLSPEHAPAE MYDIMKTCWD ADPLKRPTFK
QIVQLIEKQI SESTNHIYSN LANCSPNRQK PVVDHSVRIN
SVGSTASSSQ PLLVHDDV
```

c-KIT D816V kinase Assay

Activity of c-KIT D816V kinase (Seq ID no. 4) was determined by following the production of ADP from the kinase reaction through coupling with the pyruvate kinase/lactate dehydrogenase system (e.g., Schindler et al. Science (2000) 289: 1938-1942). In this assay, the oxidation of NADH (measured by decrease in absorbance at 340 nm) was continuously monitored spectrophotometrically. The reaction mixture (100 μL) contained D816V c-KIT (residues T544-V976 with N-terminal GST fusion, 16 nM), polyE4Y (1 mg/mL), ATP (200 uM), $MgCl_2$ (10 mM), pyruvate kinase (4 units), lactate dehydrogenase (0.7 units), phosphoenol pyruvate (1 mM), NADH (0.28 mM) in 90 mM Tris buffer containing 0.001% Triton-X100 and 1% DMSO, pH 7.5. The inhibition reaction was started by mixing serial diluted test compound with the above reaction mixture. The absorption at 340 nm was monitored continuously for 5 hours at 30° C. on Synergy 2 plate reader (BioTech). Reaction rates around 3 to 4 h time frame were used to calculate % inhibitions, from which $IC_{50}$ values are generated using GraphPad Prism.

c-KIT (D816V) Protein Sequence (Seq ID no. 4)

The protein construct was prepared by deCODE Biostructures using procedures known in the art. The construct contains residues T544-V976 of cKit, an N-terminal tag, a GST-fusion sequence and a TEV cleavage site. This construct is identical to Seq ID no. 1 except for the D816V mutation.

```
MEHHHHHHHH EYMPMEMAPI LGYWKIKGLV QPTRLLLEYL
EEKYEEHLYE RDEGDKWRNK KFELGLEFPN LPYYIDGDVK
LTQSMAIIRY IADKHNMLGG CPKERAEISM LEGAVLDIRY
GVSRIAYSKD FETLKVDFLS KLPEMLKMFE DRLCHKTYLN
GDHVTHPDFM LYDALDVVLY MDPMCLDAFP KLVCFKKRIE
AIPQIDKYLK SSKYIAWPLQ GWQATFGGGD HPPKSDLVPR
HNQTSLYKKA GSAAAVLEEN LYFQGTYKYL QKPMYEVQWK
VVEEINGNNY VYIDPTQLPY DHKWEFPRNR LSFGKTLGAG
AFGKVVEATA YGLIKSDAAM TVAVKMLKPS AHLTEREALM
SELKVLSYLG NHMNIVNLLG ACTIGGPTLV ITEYCCYGDL
LNFLRRKRDS FICSKQEDHA EAALYKNLLH SKESSCSDST
NEYMDMKPGV SYVVPTKADK RRSVRIGSYI ERDVTPAIME
DDELALDLED LLSFSYQVAK GMAFLASKNC IHRDLAARNI
LLTHGRITKI CDFGLARVIK NDSNYVVKGN ARLPVKWMAP
ESIFNCVYTF ESDVWSYGIF LWELFSLGSS PYPGMPVDSK
FYKMIKEGFR MLSPEHAPAE MYDIMKTCWD ADPLKRPTFK
QIVQLIEKQI SESTNHIYSN LANCSPNRQK PVVDHSVRIN
SVGSTASSSQ PLLVHDDV
```

cKIT-VVDV Kinase Assay c-KIT-VVDV is a mutant of c-KIT with V559 and V560 deleted and D816V mutation. The kinase assay for c-KIT VVDV kinase (Seq ID no. 5) was performed using the conditions described above for the KIT-D816V assay except that 16 nM of c-KIT-VVDV was used.

c-KIT VVDV Protein Sequence (Seq ID no. 5)

The protein construct was prepared by deCODE Biostructures using procedures known in the art. This construct contains residues T544-V976 of cKit (except for the D816V mutation and the deletion of residues V559 and V560), an N-terminal tag, a GST-fusion sequence and a TEV cleavage site. This construct is identical to Seq ID no. 1 except for the D816V mutation and the deletion of residues V559 and V560.

```
MEHHHHHHHH EYMPMEMAPI LGYWKIKGLV QPTRLLLEYL
EEKYEEHLYE RDEGDKWRNK KFELGLEFPN LPYYIDGDVK
LTQSMAIIRY IADKHNMLGG CPKERAEISM LEGAVLDIRY
GVSRIAYSKD FETLKVDFLS KLPEMLKMFE DRLCHKTYLN
GDHVTHPDFM LYDALDVVLY MDPMCLDAFP KLVCFKKRIE
AIPQIDKYLK SSKYIAWPLQ GWQATFGGGD HPPKSDLVPR
HNQTSLYKKA GSAAAVLEEN LYFQGTYKYL QKPMYEVQWK
EEINGNNYVY IDPTQLPYDH KWEFPRNRLS FGKTLGAGAF
GKVVEATAYG LIKSDAAMTV AVKMLKPSAH LTEREALMSE
LKVLSYLGNH MNIVNLLGAC TIGGPTLVIT EYCCYGDLLN
FLRRKRDSFI CSKQEDHAEA ALYKNLLHSK ESSCSDSTNE
YMDMKPGVSY VVPTKADKRR SVRIGSYIER DVTPAIMEDD
ELALDLEDLL SFSYQVAKGM AFLASKNCIH RDLAARNILL
THGRITKICD FGLARVIKND SNYVVKGNAR LPVKWMAPES
IFNCVYTFES DVWSYGIFLW ELFSLGSSPY PGMPVDSKFY
KMIKEGFRML SPEHAPAEMY DIMKTCWDAD PLKRPTFKQI
VQLIEKQISE STNHIYSNLA NCSPNRQKPV VDHSVRINSV
GSTASSSQPL LVHDDV
```

c-KIT T670I Kinase Assay

The kinase assay for c-KIT T670I kinase (Seq ID no. 6) was performed using the conditions described above for the KIT-D816V assay except that 25 nM Kit T670I was used in the assay.

cKIT-T670I Protein Sequence (Seq ID no. 6)

The protein construct was prepared by deCODE Biostructures using procedures known in the art. The construct contains residues T544-V976 of cKit, an N-terminal tag, a GST-fusion sequence and a TEV cleavage site. This construct is identical to Seq ID no. 1 except for the T670I mutation.

```
MEHHHHHHHH EYMPMEMAPI LGYWKIKGLV QPTRLLLEYL
EEKYEEHLYE RDEGDKWRNK KFELGLEFPN LPYYIDGDVK
LTQSMAIIRY IADKHNMLGG CPKERAEISM LEGAVLDIRY
GVSRIAYSKD FETLKVDFLS KLPEMLKMFE DRLCHKTYLN
GDHVTHPDFM LYDALDVVLY MDPMCLDAFP KLVCFKKRIE
AIPQIDKYLK SSKYIAWPLQ GWQATFGGGD HPPKSDLVPR
HNQTSLYKKA GSAAAVLEEN LYFQGTYKYL QKPMYEVQWK
VVEEINGNNY VYIDPTQLPY DHKWEFPRNR LSFGKTLGAG
AFGKVVEATA YGLIKSDAAM TVAVKMLKPS AHLTEREALM
SELKVLSYLG NHMNIVNLLG ACTIGGPTLV IIEYCCYGDL
LNFLRRKRDS FICSKQEDHA EAALYKNLLH SKESSCSDST
NEYMDMKPGV SYVVPTKADK RRSVRIGSYI ERDVTPAIME
DDELALDLED LLSFSYQVAK GMAFLASKNC IHRDLAARNI
LLTHGRITKI CDFGLARDIK NDSNYVVKGN ARLPVKWMAP
```

-continued

```
ESIFNCVYTF ESDVWSYGIF LWELFSLGSS PYPGMPVDSK

FYKMIKEGFR MLSPEHAPAE MYDIMKTCWD ADPLKRPTFK

QIVQLIEKQI SESTNHIYSN LANCSPNRQK PVVDHSVRIN

SVGSTASSSQ PLLVHDDV
```

Using the enzymatic protocols described above, compounds of Formula Ia are shown to be inhibitors in assays measuring the kinase activity of KIT kinase, V654A KIT kinase, D816H KIT kinase, D816V KIT kinase, a KIT kinase mutant containing V559+V560 deletions in addition to a D816V mutation (KIT-VVDV), and T670I KIT kinase, as indicated below in Table 1.

TABLE 1

Activity of Compounds of Formula Ia in Enyzmatic Assays of KIT kinase and mutant forms of KIT kinase.

| Ex No | KIT (wt) | KIT-V654A | KIT-D816H | KIT-D816V | KIT-VVDV | KIT-T670I |
|---|---|---|---|---|---|---|
| 1 | ++++ | NT | +++ | +++ | +++ | ++++ |
| 2 | NT | NT | NT | ++ | ++ | ++++ |
| 3 | ++++ | ++++ | ++++ | +++ | ++++ | +++ |
| 4 | ++++ | ++++ | ++++ | +++ | ++++ | +++ |
| 5 | NT | NT | NT | ++ | ++ | NT |
| 6 | ++++ | +++ | +++ | +++ | ++++ | ++++ |
| 7 | NT | NT | NT | +++ | +++ | +++ |
| 8 | NT | NT | NT | +++ | ++ | +++ |
| 9 | ++++ | NT | NT | +++ | +++ | +++ |
| 10 | NT | NT | NT | +++ | +++ | +++ |
| 11 | NT | NT | NT | + | NT | NT |
| 12 | NT | NT | NT | + | ++ | NT |
| 13 | NT | NT | NT | +++ | ++++ | +++ |
| 14 | NT | NT | NT | +++ | +++ | ++++ |
| 15 | ++++ | ++++ | +++ | +++ | +++ | +++ |
| 16 | ++++ | ++++ | +++ | +++ | +++ | +++ |
| 17 | NT | NT | NT | +++ | ++ | NT |
| 18 | ++++ | NT | NT | ++ | +++ | +++ |
| 19 | ++++ | NT | NT | ++++ | +++ | NT |
| 20 | ++++ | +++ | ++++ | ++++ | ++++ | ++++ |
| 21 | ++++ | ++++ | ++++ | +++ | ++++ | ++++ |
| 22 | ++++ | +++ | +++ | ++++ | ++++ | ++ |
| 23 | ++++ | ++++ | +++ | +++ | +++ | +++ |
| 24 | ++++ | ++++ | ++++ | ++++ | ++++ | ++++ |
| 25 | ++++ | ++++ | +++ | +++ | ++++ | ++++ |
| 26 | +++ | NT | NT | + | + | NT |
| 27 | ++++ | +++ | +++ | +++ | +++ | +++ |
| 28 | +++ | ++++ | +++ | +++ | +++ | +++ |
| 29 | +++ | NT | NT | ++ | NT | ++ |
| 30 | ++++ | +++ | ++ | +++ | +++ | +++ |
| 31 | ++++ | ++++ | ++++ | +++ | ++++ | +++ |
| 32 | ++++ | +++ | ++++ | ++++ | ++++ | +++ |
| 33 | ++++ | ++++ | +++ | +++ | ++ | ++ |
| 34 | ++++ | +++ | +++ | +++ | NT | +++ |
| 35 | ++++ | +++ | +++ | +++ | NT | ++ |
| 36 | ++++ | +++ | +++ | +++ | +++ | ++ |
| 37 | ++++ | +++ | +++ | +++ | NT | ++ |
| 38 | ++++ | NT | +++ | +++ | NT | ++ |
| 39 | ++++ | NT | NT | +++ | NT | +++ |
| 40 | ++++ | +++ | +++ | +++ | ++ | ++ |
| 41 | ++++ | +++ | ++++ | +++ | NT | + |
| 42 | +++ | NT | NT | +++ | NT | ++ |
| 43 | +++ | NT | NT | ++ | NT | ++ |
| 44 | ++++ | +++ | ++++ | +++ | +++ | +++ |
| 45 | ++++ | +++ | +++ | +++ | + | +++ |
| 46 | +++ | NT | NT | ++ | NT | + |
| 47 | ++++ | NT | NT | +++ | NT | + |
| 48 | +++ | NT | NT | ++ | NT | + |
| 49 | +++ | NT | NT | ++ | NT | ++ |
| 50 | ++++ | +++ | +++ | +++ | ++ | +++ |
| 51 | +++ | +++ | NT | ++ | ++ | + |
| 52 | ++++ | NT | ++ | NT | NT | NT |
| 53 | ++++ | +++ | NT | ++++ | ++++ | +++ |
| 54 | ++++ | +++ | ++++ | ++++ | ++++ | +++ |
| 55 | +++ | +++ | ++++ | +++ | +++ | +++ |

TABLE 1-continued

Activity of Compounds of Formula Ia in Enyzmatic Assays of KIT kinase and mutant forms of KIT kinase.

| Ex No | KIT (wt) | KIT-V654A | KIT-D816H | KIT-D816V | KIT-VVDV | KIT-T670I |
|---|---|---|---|---|---|---|
| 56 | ++++ | NT | NT | +++ | NT | ++ |
| 57 | ++++ | +++ | +++ | ++ | NT | ++++ |
| 58 | ++++ | ++++ | ++++ | +++ | NT | +++ |
| 59 | +++ | +++ | +++ | +++ | +++ | +++ |
| 60 | ++++ | +++ | +++ | +++ | +++ | ++ |
| 61 | ++++ | +++ | ++ | +++ | ++++ | ++++ |
| 62 | ++++ | NT | NT | ++ | NT | ++++ |
| 63 | ++++ | ++++ | NT | +++ | NT | +++ |
| 64 | +++ | NT | NT | ++ | NT | ++ |
| 65 | ++++ | NT | NT | +++ | NT | +++ |
| 66 | ++++ | NT | NT | +++ | NT | +++ |
| 67 | +++ | +++ | ++++ | ++++ | NT | ++++ |
| 68 | ++++ | +++ | NT | +++ | NT | +++ |
| 69 | +++ | +++ | NT | ++ | NT | +++ |
| 70 | ++++ | +++ | +++ | ++++ | ++++ | ++++ |
| 71 | +++ | +++ | NT | ++ | NT | +++ |
| 72 | ++++ | ++ | NT | +++ | NT | ++++ |
| 73 | +++ | +++ | +++ | ++++ | ++++ | +++ |
| 74 | ++++ | NT | NT | ++++ | NT | +++ |
| 75 | ++++ | NT | ++ | ++ | NT | +++ |
| 76 | ++++ | NT | NT | +++ | NT | ++ |
| 77 | ++++ | +++ | +++ | ++++ | NT | ++ |
| 78 | ++++ | NT | NT | +++ | NT | +++ |
| 79 | ++++ | ++ | +++ | ++ | + | +++ |
| 80 | ++++ | NT | ++++ | +++ | NT | +++ |
| 81 | ++++ | +++ | ++++ | +++ | NT | +++ |
| 82 | +++ | NT | NT | ++ | NT | ++ |
| 83 | ++++ | NT | NT | ++ | NT | ++ |
| 84 | ++++ | ++ | +++ | +++ | NT | +++ |
| 85 | +++ | NT | NT | +++ | NT | ++ |
| 86 | ++++ | +++ | NT | ++++ | NT | +++ |
| 87 | ++++ | ++ | +++ | ++ | NT | +++ |
| 88 | ++++ | +++ | +++ | ++ | NT | +++ |
| 89 | +++ | ++ | +++ | ++ | NT | +++ |
| 90 | ++++ | NT | +++ | + | NT | +++ |
| 91 | ++++ | +++ | +++ | +++ | NT | +++ |
| 92 | ++++ | ++++ | +++ | +++ | NT | +++ |
| 93 | +++ | ++ | +++ | ++ | NT | +++ |
| 94 | ++++ | NT | NT | + | NT | +++ |
| 95 | ++++ | NT | NT | ++ | NT | +++ |
| 96 | ++++ | +++ | +++ | +++ | NT | +++ |
| 97 | ++++ | NT | +++ | + | NT | +++ |
| 98 | +++ | +++ | +++ | ++++ | NT | +++ |
| 99 | ++++ | +++ | +++ | ++++ | NT | +++ |
| 100 | +++ | ++ | ++ | ++ | NT | ++ |
| 101 | +++ | +++ | +++ | +++ | NT | +++ |
| 102 | ++++ | +++ | +++ | +++ | NT | +++ |
| 103 | +++ | +++ | +++ | ++++ | NT | +++ |
| 104 | +++ | ++ | +++ | +++ | NT | +++ |
| 105 | +++ | +++ | +++ | +++ | NT | +++ |
| 106 | +++ | +++ | ++++ | +++ | NT | +++ |
| 107 | +++ | NT | NT | + | NT | +++ |
| 108 | +++ | ++ | +++ | +++ | NT | +++ |
| 109 | +++ | +++ | +++ | +++ | NT | +++ |
| 110 | +++ | +++ | +++ | +++ | NT | +++ |
| 111 | +++ | NT | NT | +++ | NT | ++ |
| 112 | ++++ | NT | ++++ | +++ | NT | ++++ |
| 113 | +++ | ++ | ++++ | +++ | NT | +++ |
| 114 | +++ | NT | NT | ++ | NT | + |
| 115 | ++++ | +++ | ++++ | ++++ | NT | +++ |

NT: Not Tested; +: $IC_{50} > 1$ uM; ++: 0.1 uM $< IC_{50} \leq 1$ uM; +++: 0.01 uM $< IC_{50} \leq 0.1$ uM; ++++: $IC_{50} \leq 0.01$ uM GIST Cell Culture GIST48, GIST430, and GIST882 cells were obtained from J. Fletcher (Brigham and Women's Hospital, Boston, Mass.). GIST T1 cells were obtained from B. Rubin (Cleveland Clinic, Cleveland, Ohio) and Professor Takahiro Taguchi (Kochi Medical School, Nankoku, Kochi, Japan). Briefly, GIST48 and GIST 882 cells were grown in RPMI 1640 medium supplemented with 15% characterized fetal bovine serum (Invitrogen, Carlsbad, Calif.), 1 unit/mL penicillin G, 1 μg/ml streptomycin, and 0.29 mg/mL L-glutamine at 37° C., 5% $CO_2$, and 95% humidity. GIST430 cells were grown in Ham's F10 medium supplemented with 15% characterized fetal bovine serum (Invitrogen, Carlsbad, Calif.), 30 mg/L bovine pituitary extract (BD Biosciences, San Jose, Calif.), 0.5% Mito+ serum extender (BD Biosciences, San Jose, Calif.), 1 unit/mL penicillin G, 1 μg/ml streptomycin, and 0.29 mg/mL L-glutamine at 37° C., 5% $CO_2$, 95% humidity. GIST T1 cells were grown in DMEM medium supplemented with 10% characterized fetal bovine serum (Invitrogen, Carlsbad, Calif.), 1 unit/mL penicillin G, 1 ng/ml streptomycin, and 0.29 mg/mL L-glutamine at 37° C., 5% $CO_2$, and 95% humidity. Cells were allowed to expand until reaching 70-95% confluence at which point they were subcultured or harvested for assay use.

GIST48 KIT Western Blot

Two hundred fifty thousand cells were added per well in a 24-well tissue-culture treated plate. Cells were then incubated overnight at 37° C., 5% $CO_2$, 95% humidity. Medium was aspirated, cells were washed with PBS, and serum-free RPMI1640 medium was added. A serial dilution of test compound was added to plates containing cells and plates were incubated for 4 hours at 37° C., 5% $CO_2$, 95% humidity. Cells were washed with PBS, then lysed. Cell lysates were separated by SDS-PAGE and transferred to PVDF. Phospho-KIT (Tyr719) was detected using an antibody from Cell Signaling Technology (Beverly, Mass.), ECL Plus detection reagent (GE Healthcare, Piscataway, N.J.) and a Molecular Devices Storm 840 phosphorimager in fluorescence mode. Blots were stripped and probed for total KIT using an antibody from Santa Cruz Biotech (Santa Cruz, Calif.). $IC_{50}$ values were calculated using Prism software (Graphpad, San Diego, Calif.).

GIST430 KIT Western Blot

One hundred fifty thousand cells were added per well in a 24-well tissue-culture treated plate. Cells were then incubated overnight at 37° C., 5% $CO_2$, 95% humidity. Medium was aspirated, cells were washed with PBS, and serum-free Ham's F10 medium was added. A serial dilution of test compound was added to plates containing cells and plates were incubated for 4 hours at 37° C., 5% $CO_2$, 95% humidity. Cells were washed with PBS, then lysed. Cell lysates were separated by SDS-PAGE and transferred to PVDF. Phospho-KIT (Tyr719) was detected using an antibody from Cell Signaling Technology (Beverly, Mass.), ECL Plus detection reagent (GE Healthcare, Piscataway, N.J.) and a Molecular Devices Storm 840 phosphorimager in fluorescence mode. Blots were stripped and probed for total KIT using an antibody from Santa Cruz Biotech (Santa Cruz, Calif.). $IC_{50}$ values were calculated using Prism software (Graphpad, San Diego, Calif.).

GIST 430 Cell Proliferation Assay

A serial dilution of test compound was dispensed into a 384-well black clear bottom plate (Corning, Corning, N.Y.). Two thousand five-hundred cells were added per well in 50 μL complete growth medium. Plates were incubated for 115 hours at 37° C., 5% $CO_2$, 95% humidity. At the end of the incubation period 10 μL of a 440 μM solution of resazurin (Sigma, St. Louis, Mo.) in PBS was added to each well and incubated for an additional 5 hours at 37° C., 5% $CO_2$, 95% humidity. Plates were read on a Synergy2 reader (Biotek, Winooski, Vt.) using an excitation of 540 nM and an emission of 600 nM. Data was analyzed using Prism software (Graphpad, San Diego, Calif.) to calculate $IC_{50}$ values.

GIST882 KIT Western Blot

Two hundred fifty thousand cells were added per well in a 24-well tissue-culture treated plate. Cells were then incubated overnight at 37° C., 5% $CO_2$, 95% humidity. Medium was aspirated, cells were washed with PBS, and serum-free RPMI1640 medium was added. A serial dilution of test compound was added to plates containing cells and plates were incubated for 4 hours at 37° C., 5% $CO_2$, 95% humidity. Cells were washed with PBS, then lysed. Cell lysates were separated by SDS-PAGE and transferred to PVDF. Phospho-KIT (Tyr719) was detected using an antibody from Cell Signaling Technology (Beverly, Mass.), ECL Plus detection reagent (GE Healthcare, Piscataway, N.J.) and a Molecular Devices Storm 840 phosphorimager in fluorescence mode. Blots were stripped and probed for total KIT using an antibody from Santa Cruz Biotech (Santa Cruz, Calif.). $IC_{50}$ values were calculated using Prism software (Graphpad, San Diego, Calif.).

GIST T1 KIT Western Blot

One hundred twenty-five thousand cells were added per well in a 24-well tissue-culture treated plate. Cells were then incubated overnight at 37° C., 5% $CO_2$, 95% humidity. Medium was aspirated, cells were washed with PBS, and serum-free DMEM medium was added. A serial dilution of test compound was added to plates containing cells and plates were incubated for 4 hours at 37° C., 5% $CO_2$, 95% humidity. Cells were washed with PBS, then lysed. Cell lysates were separated by SDS-PAGE and transferred to PVDF. Phospho-KIT (Tyr719) was detected using an antibody from Cell Signaling Technology (Beverly, Mass.), ECL Plus detection reagent (GE Healthcare, Piscataway, N.J.) and a Molecular Devices Storm 840 phosphorimager in fluorescence mode. Blots were stripped and probed for total KIT using an antibody from Santa Cruz Biotech (Santa Cruz, Calif.). $IC_{50}$ values were calculated using Prism software (Graphpad, San Diego, Calif.).

GIST T1 Cell Proliferation Assay

A serial dilution of test compound was dispensed into a 384-well black clear bottom plate (Corning, Corning, N.Y.). One thousand two-hundred fifty cells were added per well in 50 μL complete growth medium. Plates were incubated for 68 hours at 37° C., 5% $CO_2$, 95% humidity. At the end of the incubation period 10 μL of a 440 μM solution of resazurin (Sigma, St. Louis, Mo.) in PBS was added to each well and incubated for an additional 4 hours at 37° C., 5% $CO_2$, 95% humidity. Plates were read on a Synergy2 reader (Biotek, Winooski, Vt.) using an excitation of 540 nM and an emission of 600 nM. Data was analyzed using Prism software (Graphpad, San Diego, Calif.) to calculate $IC_{50}$ values.

In the cellular assays described above, the compounds of formula Ia are demonstrated to suppress levels of phospho-KIT (autophosphrorylation) in one or more GIST cell lines by western blot analysis, as indicated in Table 2. Additionally or alternately, compounds of formula Ia show antiproliferative effects in GIST cell lines, as measured by reduction of cellular proliferation in Table 2.

TABLE 2

Inhibitory effects of compounds of formula Ia versus GIST cell lines

| | pKIT suppression by western blot analysi | | | | Cell Proliferation | |
|---|---|---|---|---|---|---|
| Ex No | GIST430 | GIST48 | GIST T1 | GIST 882 | GIST430 | GIST T1 |
| 1 | ++++ | +++ | NT | ++ | NT | NT |
| 3 | +++ | ++ | ++++ | +++ | +++ | ++++ |
| 4 | +++ | +++ | NT | ++++ | NT | ++++ |
| 6 | ++++ | ++++ | +++ | +++ | NT | +++ |
| 14 | +++ | ++++ | NT | ++++ | NT | NT |
| 15 | +++ | +++ | NT | +++ | NT | NT |

TABLE 2-continued

| Inhibitory effects of compounds of formula Ia versus GIST cell lines | | | | | | |
|---|---|---|---|---|---|---|
| | pKIT suppression by western blot analysi | | | | Cell Proliferation | |
| Ex No | GIST430 | GIST48 | GIST T1 | GIST 882 | GIST430 | GIST T1 |
| 16 | ++ | ++ | NT | +++ | NT | NT |
| 17 | +++ | +++ | NT | NT | NT | NT |
| 20 | +++ | ++ | ++++ | +++ | NT | NT |
| 21 | ++++ | +++ | ++++ | +++ | NT | ++++ |
| 22 | +++ | +++ | ++++ | +++ | NT | ++++ |
| 23 | +++ | ++ | ++++ | +++ | +++ | ++++ |
| 24 | ++++ | +++ | ++++ | +++ | NT | ++++ |
| 25 | +++ | +++ | NT | +++ | NT | ++++ |
| 27 | +++ | +++ | NT | ++ | ++ | NT |
| 28 | +++ | ++ | ++++ | +++ | NT | +++ |
| 30 | +++ | ++ | ++++ | NT | NT | NT |
| 31 | ++++ | +++ | ++++ | ++ | +++ | ++++ |
| 32 | ++++ | ++++ | ++++ | +++ | +++ | ++++ |
| 33 | +++ | NT | NT | NT | NT | NT |
| 36 | ++ | ++ | NT | NT | NT | NT |
| 38 | +++ | + | NT | NT | +++ | ++++ |
| 39 | NT | NT | NT | NT | +++ | NT |
| 40 | NT | NT | NT | NT | ++ | ++++ |
| 41 | +++ | ++ | NT | NT | NT | NT |
| 44 | ++++ | +++ | ++++ | +++ | +++ | ++++ |
| 50 | ++++ | ++ | ++++ | +++ | NT | +++ |
| 51 | +++ | ++ | NT | +++ | NT | ++++ |
| 53 | ++++ | ++ | NT | +++ | NT | ++++ |
| 54 | +++ | +++ | ++++ | +++ | NT | ++++ |
| 55 | +++ | + | NT | +++ | NT | ++++ |
| 57 | +++ | ++ | ++++ | ++ | NT | ++++ |
| 58 | +++ | ++ | NT | ++ | NT | ++++ |
| 59 | +++ | +++ | ++++ | +++ | NT | +++ |
| 60 | +++ | + | NT | NT | NT | +++ |
| 61 | +++ | + | NT | NT | NT | ++++ |
| 63 | +++ | ++ | NT | NT | NT | ++++ |
| 66 | +++ | ++ | NT | NT | NT | ++++ |
| 67 | ++++ | ++++ | NT | +++ | NT | ++++ |
| 68 | +++ | ++ | NT | NT | NT | ++++ |
| 70 | ++++ | +++ | ++++ | +++ | NT | ++++ |
| 73 | +++ | +++ | NT | +++ | NT | +++ |
| 77 | +++ | +++ | NT | +++ | NT | ++++ |
| 79 | +++ | +++ | NT | + | NT | ++++ |
| 81 | +++ | +++ | NT | +++ | NT | ++++ |
| 84 | +++ | +++ | NT | +++ | NT | NT |
| 86 | +++ | ++++ | NT | ++++ | NT | ++++ |
| 87 | ++ | +++ | NT | ++ | NT | +++ |
| 88 | +++ | +++ | ++++ | ++ | NT | ++++ |
| 92 | NT | NT | NT | NT | NT | ++++ |
| 93 | NT | NT | NT | NT | NT | +++ |
| 95 | NT | NT | NT | NT | NT | ++++ |
| 96 | NT | NT | NT | NT | NT | ++++ |
| 97 | NT | NT | NT | NT | NT | ++++ |
| 98 | NT | NT | NT | NT | NT | ++++ |
| 99 | NT | NT | NT | NT | NT | ++++ |
| 100 | NT | NT | NT | NT | NT | +++ |
| 101 | +++ | + | NT | ++ | NT | ++++ |
| 102 | +++ | +++ | NT | NT | NT | ++++ |
| 103 | NT | NT | NT | NT | NT | +++ |
| 104 | NT | NT | NT | NT | NT | +++ |
| 105 | NT | NT | NT | NT | NT | ++++ |
| 106 | NT | NT | NT | NT | NT | ++++ |
| 107 | NT | NT | NT | NT | NT | +++ |
| 108 | +++ | ++ | NT | NT | NT | NT |
| 109 | NT | +++ | NT | NT | NT | NT |
| 110 | NT | ++++ | NT | NT | NT | NT |

NT: Not Tested; +: $IC_{50} > 1$ uM; ++: 0.1 uM $< IC_{50} \leq 1$ uM; +++: 0.01 uM $< IC_{50} \leq 0.1$ uM; ++++: $IC_{50} \leq 0.01$ uM CHO K1 Cell Culture CHO K1 cells (catalog #CCL-61) were obtained from the American Type Culture Collection, Manassas, Va. Briefly, cells were grown in RPMI 1640 supplemented with 10% characterized fetal bovine serum and 1% Penicillin-streptomycin-L-glutamine solution (Invitrogen, Carlsbad, Calif.) at 37 degrees Celsius, 5% $CO_2$, 95% RH. Cells were allowed to expand until reaching 70-95% confluency at which point they were subcultured or harvested for assay use.

CHO K1 Phospoho-KIT ELISA

Forty thousand cells in RPMI 1640 supplemented with 10% characterized fetal bovine serum and 1% MEM Non-essential amino acids (Invitrogen, Carlsbad, Calif.) were added to each well of a 24-well tissue-culture treated plate (Nunc, Rochester, N.Y.). Cells were then incubated overnight at 37° C., 5% $CO_2$, 95% RH. Transfection-grade pcDNA3.2 V5 DEST expression vector containing KIT variant, Lipofectamine LTX Reagent, and PLUS reagent (Invitrogen, Carlsbad, Calif.) were diluted into Opti-MEM® I medium (Invitrogen, Carlsbad, Calif.). The tube was incubated at room temperature to allow formation of DNA-Lipofectamine LTX complexes. The DNA-lipofectamine LTX complex mix was added directly to each well and mixed gently. Eighteen hours post-transfection, medium was replaced with serum-free RPMI medium. A serial dilution of test compound was added, and plates were incubated for 4 hours at 37° C., 5% $CO_2$, 95% RH. Cell lysates were prepared, then phospho-c-KIT (Tyr719) was measured by using a Human phospho-c-KIT ELISA kit (Cell Signaling, Beverly, Mass.). Data was analyzed using Prism software (Graphpad, San Diego, Calif.) to calculate $IC_{50}$ values.

Plasmid DNA Constructs (pcDNA 3.2 V5 DEST Expression Vector)

AY502 duplication/N882K KIT

AY502 duplication/D820E KIT

AY502 duplication/D816G KIT

AY502 duplication/D820G KIT

AY502 duplication/N822Y KIT

AY502 duplication/N822H KIT

WKV557-559 deletion/C557insertion/D820Y

WKV557-559 deletion/C557insertion/D820A

V560D/N822K

V560D/Y823D

CHO K1 Phospho-KIT Western

One-hundred thousand cells in RPMI 1640 supplemented with 10% characterized fetal bovine serum and 1% MEM Non-essential amino acids (Invitrogen, Carlsbad, Calif.) were added to each well of a 24-well tissue-culture treated plate (Nunc, Rochester, N.Y.). Cells were then incubated overnight at 37° C., 5% $CO_2$, 95% RH. Transfection-grade pcDNA3.2 V5 DEST expression vector containing KIT variant and Lipofectamine LTX Reagent (Invitrogen, Carlsbad, Calif.) were diluted into Opti-MEM® I medium (Invitrogen, Carlsbad, Calif.). The tube was incubated at room temperature to allow formation of DNA-Lipofectamine LTX complexes. The DNA-lipofectamine LTX complex mix was added directly to each well and mixed gently. Eighteen hours post-transfection, medium was replaced with serum-free RPMI medium. A serial dilution of test compound was added, and plates were incubated for 4 hours at 37° C., 5% $CO_2$, 95% RH. Cells were washed with PBS, then lysed. Cell lysates were separated by SDS-PAGE and transferred to PVDF. Phospho-KIT (Tyr719) was detected using an antibody from Cell Signaling Technology (Beverly, Mass.), ECL Plus detection reagent (GE Healthcare, Piscataway, N.J.) and a Molecular Devices Storm 840 phosphorimager in fluorescence mode. Blots were stripped and probed for total KIT using an antibody from Santa Cruz Biotech (Santa Cruz, Calif.). $IC_{50}$ values were calculated using Prism software (Graphpad, San Diego, Calif.).

Plasmid DNA Constructs (pcDNA 3.2 V5 DEST Expression Vector)
D816V KIT
D820A KIT
VV559-560 deletion/D816V KIT GIST most often become Gleevec® (imatinib) resistant, and molecularly targeted small molecule therapies that target c-KIT secondary mutations remain elusive. GIST patients who relapse after treatment with Gleevec® (imatinib) or Sutent® (sunitinib) have disease still driven by c-KIT mutations. These secondary mutations occur on the same alleles as the primary JM-region mutation, and thus represent even more aggressive activated forms of c-KIT than the original primary mutation. The CHO K1 cellular assays described above demonstrate that certain compounds of the present invention inhibit many mutant forms of cKIT kinase that have been detected in GIST patients that have acquired resistance to imatinib or sunitinib treatment (Table 3).

TABLE 3

Activity of compounds against KIT Exon 17 primary or secondary mutations in transient transfected CHO K1 cells

| KIT kinase domain mutations (primary/ secondary) | Compound | | | | |
|---|---|---|---|---|---|
| | Imatinib | Sunitinib | Ex 23 | Ex 31 | Ex 59 |
| D816V | + | + | + | ++ | ++++ |
| D820A | + | + | +++ | +++ | +++ |
| VV559-560 deletion/D816V | + | + | ++ | ++ | +++ |
| V560D/N822K | + | + | +++ | +++ | ++++ |
| V560D/Y823D | + | ++ | ++++ | +++ | ++++ |
| AY502 duplication/D816G | + | NT | +++ | +++ | NT |
| AY502 duplication/D820E | + | NT | NT | +++ | NT |
| AY502 duplication/D820G | + | NT | NT | +++ | NT |
| AY502 duplication/N822H | + | NT | NT | +++ | NT |
| AY502 duplication/N822K | + | NT | NT | +++ | NT |
| AY502 duplication/N822Y | + | NT | NT | +++ | NT |
| WKV557-559 deletion; C557insertion/D820A | + | + | +++ | ++++ | ++++ |

TABLE 3-continued

Activity of compounds against KIT Exon 17 primary or secondary mutations in transient transfected CHO K1 cells

| KIT kinase domain mutations (primary/ secondary) | Compound | | | | |
|---|---|---|---|---|---|
| | Imatinib | Sunitinib | Ex 23 | Ex 31 | Ex 59 |
| WKV557-559 deletion; C557insertion/D820Y | + | NT | NT | ++++ | NT |

NT: Not Tested;
+: IC50 > 1 uM;
++: 0.1 uM < IC50 ≤ 1 uM;
+++: 0.01 uM < IC50 ≤ 0.1 uM;
++++: IC50 ≤ 0.01 uM The compounds described in the present invention useful for the treatment of c-KIT kinase-mediated diseases are structurally related to compounds previously disclosed in WO2008/034008 as inhibitors of the RAF-MEK-ERK pathway, more specifically as inhibitors of RAF kinases. The use of the compounds of WO2008/034008 as inhibitors of c-KIT kinase, however, was unexpected, and hence not contemplated in WO2008/034008. Thus, the unanticipated ability of the compounds to inhibit c-KIT, and more importantly the oncogenic mutant forms of c-KIT kinase described herein, constitutes a novel invention. Furthermore, it is not obvious that inhibitors of RAF kinases should also potently inhibit c-KIT kinase, as evidenced by the data below illustrating the differential kinase inhibitory profile of marketed cKIT inhibitors Imatinib® and Sunitinib® and marketed BRAF inhibitor Vemurafenib®.

| | BRAF(V600E) kinase $IC_{50}$ (nM) | c-KIT kinase $IC_{50}$ (nM) |
|---|---|---|
| Imatinib ® | >50,000 | 14 |
| Sunitinib ® | 5,000 | 6 |
| Vemurafenib ® | 6 | 1,600 |

SEQUENCE LISTING

```
<160> NUMBER OF SEQ ID NOS: 6

<210> SEQ ID NO 1
<211> LENGTH: 676
<212> TYPE: PRT
<213> ORGANISM: Artificial Sequence
<220> FEATURE:
<223> OTHER INFORMATION: c-KIT with N-terminal GST fusion

<400> SEQUENCE: 1

Leu Gly Tyr Trp Lys Ile Lys Gly Leu Val Gln Pro Thr Arg Leu Leu
1               5                   10                  15

Leu Glu Tyr Leu Glu Glu Lys Tyr Glu Glu His Leu Tyr Glu Arg Asp
            20                  25                  30

Glu Gly Asp Lys Trp Arg Asn Lys Lys Phe Glu Leu Gly Leu Glu Phe
        35                  40                  45

Pro Asn Leu Pro Tyr Tyr Ile Asp Gly Asp Val Lys Leu Thr Gln Ser
    50                  55                  60

Met Ala Ile Ile Arg Tyr Ile Ala Asp Lys His Asn Met Leu Gly Gly
65                  70                  75                  80

Cys Pro Lys Glu Arg Ala Glu Ile Ser Met Leu Glu Gly Ala Val Asp
```

```
                85                  90                  95

Ile Arg Tyr Gly Val Ser Arg Ile Ala Tyr Ser Lys Asp Phe Glu Thr
            100                 105                 110

Leu Lys Val Asp Phe Leu Ser Lys Leu Pro Glu Met Leu Lys Met Phe
        115                 120                 125

Glu Asp Arg Leu Cys His Lys Thr Tyr Leu Asn Gly Asp His Val Thr
    130                 135                 140

His Pro Asp Phe Met Leu Tyr Asp Ala Leu Asp Val Val Leu Tyr Met
145                 150                 155                 160

Asp Pro Met Cys Leu Asp Ala Phe Pro Lys Leu Val Cys Phe Lys Lys
                165                 170                 175

Arg Ile Glu Ala Ile Pro Gln Ile Asp Lys Tyr Leu Lys Ser Ser Lys
            180                 185                 190

Tyr Ile Trp Pro Leu Gln Gly Trp Gln Ala Thr Phe Gly Gly Gly Asp
        195                 200                 205

His Pro Pro Lys Ser Asp Leu Val Pro Arg His Asn Gln Thr Ser Leu
    210                 215                 220

Tyr Lys Lys Ala Gly Ser Ala Ala Ala Val Leu Glu Glu Asn Leu Tyr
225                 230                 235                 240

Phe Gln Gly Thr Tyr Lys Tyr Leu Gln Lys Pro Met Tyr Glu Val Gln
                245                 250                 255

Trp Lys Val Val Glu Glu Ile Asn Gly Asn Asn Tyr Val Tyr Ile Asp
            260                 265                 270

Pro Thr Gln Leu Pro Tyr Asp His Lys Trp Glu Phe Pro Arg Asn Arg
        275                 280                 285

Leu Ser Phe Gly Lys Thr Leu Gly Ala Gly Ala Phe Gly Lys Val Val
    290                 295                 300

Glu Ala Thr Ala Tyr Gly Leu Ile Lys Ser Asp Ala Ala Met Thr Val
305                 310                 315                 320

Ala Val Lys Met Leu Lys Pro Ser Ala His Leu Thr Glu Arg Glu Ala
                325                 330                 335

Leu Met Ser Glu Leu Lys Val Leu Ser Tyr Leu Gly Asn His Met Asn
            340                 345                 350

Ile Val Asn Leu Leu Gly Ala Cys Thr Ile Gly Gly Pro Thr Leu Val
        355                 360                 365

Ile Thr Glu Tyr Cys Cys Tyr Gly Asp Leu Leu Asn Phe Leu Arg Arg
    370                 375                 380

Lys Arg Asp Ser Phe Ile Cys Ser Lys Gln Glu Asp His Ala Glu Ala
385                 390                 395                 400

Ala Leu Tyr Lys Asn Leu Leu His Ser Lys Glu Ser Ser Cys Ser Asp
                405                 410                 415

Ser Thr Asn Glu Tyr Met Asp Met Lys Pro Gly Val Ser Tyr Val Val
            420                 425                 430

Pro Thr Lys Ala Asp Lys Arg Arg Ser Val Arg Ile Gly Ser Tyr Ile
        435                 440                 445

Glu Arg Asp Val Thr Pro Ala Ile Met Glu Asp Asp Glu Leu Ala Leu
    450                 455                 460

Asp Leu Glu Asp Leu Leu Ser Phe Ser Tyr Gln Val Ala Lys Gly Met
465                 470                 475                 480

Ala Phe Leu Ala Ser Lys Asn Cys Ile His Arg Asp Leu Ala Ala Arg
                485                 490                 495

Asn Ile Leu Leu Thr His Gly Arg Ile Thr Lys Ile Cys Asp Phe Gly
            500                 505                 510
```

```
Leu Ala Arg Asp Ile Lys Asn Asp Ser Asn Tyr Val Val Lys Gly Asn
        515                 520                 525

Ala Arg Leu Pro Val Lys Trp Met Ala Pro Glu Ser Ile Phe Asn Cys
    530                 535                 540

Val Tyr Thr Phe Glu Ser Asp Val Trp Ser Tyr Gly Ile Phe Leu Trp
545                 550                 555                 560

Glu Leu Phe Ser Leu Gly Ser Ser Pro Tyr Pro Gly Met Pro Val Asp
                565                 570                 575

Ser Lys Phe Tyr Lys Met Ile Lys Glu Gly Phe Arg Met Leu Ser Pro
            580                 585                 590

Glu His Ala Pro Ala Glu Met Tyr Asp Ile Met Lys Thr Cys Trp Asp
        595                 600                 605

Ala Asp Pro Leu Lys Arg Pro Thr Phe Lys Gln Ile Val Gln Leu Ile
    610                 615                 620

Glu Lys Gln Ile Ser Glu Ser Thr Asn His Ile Tyr Ser Asn Leu Ala
625                 630                 635                 640

Asn Cys Ser Pro Asn Arg Gln Lys Pro Val Val Asp His Ser Val Arg
                645                 650                 655

Ile Asn Ser Val Gly Ser Thr Ala Ser Ser Ser Gln Pro Leu Leu Val
            660                 665                 670

His Asp Asp Val
        675


<210> SEQ ID NO 2
<211> LENGTH: 469
<212> TYPE: PRT
<213> ORGANISM: Artificial Sequence
<220> FEATURE:
<223> OTHER INFORMATION: c-KIT (V654A)

<400> SEQUENCE: 2

Met Ser Tyr Tyr His His His His His His Asp Tyr Asp Ile Pro Thr
1               5                   10                  15

Thr Glu Asn Leu Tyr Phe Gln Gly Ala Met Leu Val Pro Arg Gly Ser
            20                  25                  30

Pro Trp Gly Ser Thr Tyr Lys Tyr Leu Gln Lys Pro Met Tyr Glu Val
        35                  40                  45

Gln Trp Lys Val Val Glu Glu Ile Asn Gly Asn Asn Tyr Val Tyr Ile
    50                  55                  60

Asp Pro Thr Gln Leu Pro Tyr Asp His Lys Trp Glu Phe Pro Arg Asn
65                  70                  75                  80

Arg Leu Ser Phe Gly Lys Thr Leu Gly Ala Gly Ala Phe Gly Lys Val
                85                  90                  95

Val Glu Ala Thr Ala Tyr Gly Leu Ile Lys Ser Asp Ala Ala Met Thr
            100                 105                 110

Val Ala Val Lys Met Leu Lys Pro Ser Ala His Leu Thr Glu Arg Glu
        115                 120                 125

Ala Leu Met Ser Glu Leu Lys Val Leu Ser Tyr Leu Gly Asn His Met
    130                 135                 140

Asn Ile Ala Asn Leu Leu Gly Ala Cys Thr Ile Gly Gly Pro Thr Leu
145                 150                 155                 160

Val Ile Thr Glu Tyr Cys Cys Tyr Gly Asp Leu Leu Asn Phe Leu Arg
                165                 170                 175

Arg Lys Arg Asp Ser Phe Ile Cys Ser Lys Gln Glu Asp His Ala Glu
            180                 185                 190
```

```
Ala Ala Leu Tyr Lys Asn Leu Leu His Ser Lys Glu Ser Ser Cys Ser
        195                 200                 205

Asp Ser Thr Asn Glu Tyr Met Asp Met Lys Pro Gly Val Ser Tyr Val
    210                 215                 220

Val Pro Thr Lys Ala Asp Lys Arg Arg Ser Val Arg Ile Gly Ser Tyr
225                 230                 235                 240

Ile Glu Arg Asp Val Thr Pro Ala Ile Met Glu Asp Asp Glu Leu Ala
                245                 250                 255

Leu Asp Leu Glu Asp Leu Leu Ser Phe Ser Tyr Gln Val Ala Lys Gly
            260                 265                 270

Met Ala Phe Leu Ala Ser Lys Asn Cys Ile His Arg Asp Leu Ala Ala
        275                 280                 285

Arg Asn Ile Leu Leu Thr His Gly Arg Ile Thr Lys Ile Cys Asp Phe
    290                 295                 300

Gly Leu Ala Arg Asp Ile Lys Asn Asp Ser Asn Tyr Val Val Lys Gly
305                 310                 315                 320

Asn Ala Arg Leu Pro Val Lys Trp Met Ala Pro Glu Ser Ile Phe Asn
                325                 330                 335

Cys Val Tyr Thr Phe Glu Ser Asp Val Trp Ser Tyr Gly Ile Phe Leu
            340                 345                 350

Trp Glu Leu Phe Ser Leu Gly Ser Ser Pro Tyr Pro Gly Met Pro Val
        355                 360                 365

Asp Ser Lys Phe Tyr Lys Met Ile Lys Glu Gly Phe Arg Met Leu Ser
    370                 375                 380

Pro Glu His Ala Pro Ala Glu Met Tyr Asp Ile Met Lys Thr Cys Trp
385                 390                 395                 400

Asp Ala Asp Pro Leu Lys Arg Pro Thr Phe Lys Gln Ile Val Gln Leu
                405                 410                 415

Ile Glu Lys Gln Ile Ser Glu Ser Thr Asn His Ile Tyr Ser Asn Leu
            420                 425                 430

Ala Asn Cys Ser Pro Asn Arg Gln Lys Pro Val Val Asp His Ser Val
        435                 440                 445

Arg Ile Asn Ser Val Gly Ser Thr Ala Ser Ser Ser Gln Pro Leu Leu
    450                 455                 460

Val His Asp Asp Val
465


<210> SEQ ID NO 3
<211> LENGTH: 620
<212> TYPE: PRT
<213> ORGANISM: Artificial Sequence
<220> FEATURE:
<223> OTHER INFORMATION: c-KIT (D816H)

<400> SEQUENCE: 3

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80
```

```
Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Leu Glu Val Leu
    210                 215                 220

Phe Gln Gly Pro Glu Phe Lys Gly Leu Arg Arg Gln Thr Tyr Lys Tyr
225                 230                 235                 240

Leu Gln Lys Pro Met Tyr Glu Val Gln Trp Lys Val Val Glu Glu Ile
                245                 250                 255

Asn Gly Asn Asn Tyr Val Tyr Ile Asp Pro Thr Gln Leu Pro Tyr Asp
            260                 265                 270

His Lys Trp Glu Phe Pro Arg Asn Arg Leu Ser Phe Gly Lys Thr Leu
        275                 280                 285

Gly Ala Gly Ala Phe Gly Lys Val Val Glu Ala Thr Ala Tyr Gly Leu
    290                 295                 300

Ile Lys Ser Asp Ala Ala Met Thr Val Ala Val Lys Met Leu Lys Pro
305                 310                 315                 320

Ser Ala His Leu Thr Glu Arg Glu Ala Leu Met Ser Glu Leu Lys Val
                325                 330                 335

Leu Ser Tyr Leu Gly Asn His Met Asn Ile Val Asn Leu Leu Gly Ala
            340                 345                 350

Cys Thr Ile Gly Gly Pro Thr Leu Val Ile Thr Glu Tyr Cys Cys Tyr
        355                 360                 365

Gly Asp Leu Leu Asn Phe Leu Arg Arg Lys Arg Asp Ser Phe Ile Cys
    370                 375                 380

Ser Lys Gln Glu Asp His Ala Glu Ala Ala Leu Tyr Lys Asn Leu Leu
385                 390                 395                 400

His Ser Lys Glu Ser Ser Cys Ser Asp Ser Thr Asn Glu Tyr Met Asp
                405                 410                 415

Met Lys Pro Gly Val Ser Tyr Val Val Pro Thr Lys Ala Asp Lys Arg
            420                 425                 430

Arg Ser Val Arg Ile Gly Ser Tyr Ile Glu Arg Asp Val Thr Pro Ala
        435                 440                 445

Ile Met Glu Asp Asp Glu Leu Ala Leu Asp Leu Glu Asp Leu Leu Ser
    450                 455                 460

Phe Ser Tyr Gln Val Ala Lys Gly Met Ala Phe Leu Ala Ser Lys Asn
465                 470                 475                 480

Cys Ile His Arg Asp Leu Ala Ala Arg Asn Ile Leu Leu Thr His Gly
                485                 490                 495
```

```
Arg Ile Thr Lys Ile Cys Asp Phe Gly Leu Ala Arg His Ile Lys Asn
            500                 505                 510

Asp Ser Asn Tyr Val Val Lys Gly Asn Ala Arg Leu Pro Val Lys Trp
        515                 520                 525

Met Ala Pro Glu Ser Ile Phe Asn Cys Val Tyr Thr Phe Glu Ser Asp
    530                 535                 540

Val Trp Ser Tyr Gly Ile Phe Leu Trp Glu Leu Phe Ser Leu Gly Ser
545                 550                 555                 560

Ser Pro Tyr Pro Gly Met Pro Val Asp Ser Lys Phe Tyr Lys Met Ile
                565                 570                 575

Lys Glu Gly Phe Arg Met Leu Ser Pro Glu His Ala Pro Ala Glu Met
            580                 585                 590

Tyr Asp Ile Met Lys Thr Cys Trp Asp Ala Asp Pro Leu Lys Arg Pro
        595                 600                 605

Thr Phe Lys Gln Ile Val Gln Leu Ile Glu Lys Gln
    610                 615                 620


<210> SEQ ID NO 4
<211> LENGTH: 698
<212> TYPE: PRT
<213> ORGANISM: Artificial Sequence
<220> FEATURE:
<223> OTHER INFORMATION: c-KIT (D816V)

<400> SEQUENCE: 4

Met Glu His His His His His His His His Glu Tyr Met Pro Met Glu
1               5                   10                  15

Met Ala Pro Ile Leu Gly Tyr Trp Lys Ile Lys Gly Leu Val Gln Pro
            20                  25                  30

Thr Arg Leu Leu Leu Glu Tyr Leu Glu Glu Lys Tyr Glu Glu His Leu
        35                  40                  45

Tyr Glu Arg Asp Glu Gly Asp Lys Trp Arg Asn Lys Lys Phe Glu Leu
    50                  55                  60

Gly Leu Glu Phe Pro Asn Leu Pro Tyr Tyr Ile Asp Gly Asp Val Lys
65                  70                  75                  80

Leu Thr Gln Ser Met Ala Ile Ile Arg Tyr Ile Ala Asp Lys His Asn
                85                  90                  95

Met Leu Gly Gly Cys Pro Lys Glu Arg Ala Glu Ile Ser Met Leu Glu
            100                 105                 110

Gly Ala Val Leu Asp Ile Arg Tyr Gly Val Ser Arg Ile Ala Tyr Ser
        115                 120                 125

Lys Asp Phe Glu Thr Leu Lys Val Asp Phe Leu Ser Lys Leu Pro Glu
    130                 135                 140

Met Leu Lys Met Phe Glu Asp Arg Leu Cys His Lys Thr Tyr Leu Asn
145                 150                 155                 160

Gly Asp His Val Thr His Pro Asp Phe Met Leu Tyr Asp Ala Leu Asp
                165                 170                 175

Val Val Leu Tyr Met Asp Pro Met Cys Leu Asp Ala Phe Pro Lys Leu
            180                 185                 190

Val Cys Phe Lys Lys Arg Ile Glu Ala Ile Pro Gln Ile Asp Lys Tyr
        195                 200                 205

Leu Lys Ser Ser Lys Tyr Ile Ala Trp Pro Leu Gln Gly Trp Gln Ala
    210                 215                 220

Thr Phe Gly Gly Gly Asp His Pro Pro Lys Ser Asp Leu Val Pro Arg
225                 230                 235                 240
```

```
His Asn Gln Thr Ser Leu Tyr Lys Lys Ala Gly Ser Ala Ala Ala Val
                245                 250                 255

Leu Glu Glu Asn Leu Tyr Phe Gln Gly Thr Tyr Lys Tyr Leu Gln Lys
            260                 265                 270

Pro Met Tyr Glu Val Gln Trp Lys Val Val Glu Glu Ile Asn Gly Asn
        275                 280                 285

Asn Tyr Val Tyr Ile Asp Pro Thr Gln Leu Pro Tyr Asp His Lys Trp
    290                 295                 300

Glu Phe Pro Arg Asn Arg Leu Ser Phe Gly Lys Thr Leu Gly Ala Gly
305                 310                 315                 320

Ala Phe Gly Lys Val Val Glu Ala Thr Ala Tyr Gly Leu Ile Lys Ser
                325                 330                 335

Asp Ala Ala Met Thr Val Ala Val Lys Met Leu Lys Pro Ser Ala His
            340                 345                 350

Leu Thr Glu Arg Glu Ala Leu Met Ser Glu Leu Lys Val Leu Ser Tyr
        355                 360                 365

Leu Gly Asn His Met Asn Ile Val Asn Leu Leu Gly Ala Cys Thr Ile
    370                 375                 380

Gly Gly Pro Thr Leu Val Ile Thr Glu Tyr Cys Cys Tyr Gly Asp Leu
385                 390                 395                 400

Leu Asn Phe Leu Arg Arg Lys Arg Asp Ser Phe Ile Cys Ser Lys Gln
                405                 410                 415

Glu Asp His Ala Glu Ala Ala Leu Tyr Lys Asn Leu Leu His Ser Lys
            420                 425                 430

Glu Ser Ser Cys Ser Asp Ser Thr Asn Glu Tyr Met Asp Met Lys Pro
        435                 440                 445

Gly Val Ser Tyr Val Val Pro Thr Lys Ala Asp Lys Arg Arg Ser Val
    450                 455                 460

Arg Ile Gly Ser Tyr Ile Glu Arg Asp Val Thr Pro Ala Ile Met Glu
465                 470                 475                 480

Asp Asp Glu Leu Ala Leu Asp Leu Glu Asp Leu Leu Ser Phe Ser Tyr
                485                 490                 495

Gln Val Ala Lys Gly Met Ala Phe Leu Ala Ser Lys Asn Cys Ile His
            500                 505                 510

Arg Asp Leu Ala Ala Arg Asn Ile Leu Leu Thr His Gly Arg Ile Thr
        515                 520                 525

Lys Ile Cys Asp Phe Gly Leu Ala Arg Val Ile Lys Asn Asp Ser Asn
    530                 535                 540

Tyr Val Val Lys Gly Asn Ala Arg Leu Pro Val Lys Trp Met Ala Pro
545                 550                 555                 560

Glu Ser Ile Phe Asn Cys Val Tyr Thr Phe Glu Ser Asp Val Trp Ser
                565                 570                 575

Tyr Gly Ile Phe Leu Trp Glu Leu Phe Ser Leu Gly Ser Ser Pro Tyr
            580                 585                 590

Pro Gly Met Pro Val Asp Ser Lys Phe Tyr Lys Met Ile Lys Glu Gly
        595                 600                 605

Phe Arg Met Leu Ser Pro Glu His Ala Pro Ala Glu Met Tyr Asp Ile
    610                 615                 620

Met Lys Thr Cys Trp Asp Ala Asp Pro Leu Lys Arg Pro Thr Phe Lys
625                 630                 635                 640

Gln Ile Val Gln Leu Ile Glu Lys Gln Ile Ser Glu Ser Thr Asn His
                645                 650                 655

Ile Tyr Ser Asn Leu Ala Asn Cys Ser Pro Asn Arg Gln Lys Pro Val
```

```
            660                 665                 670

Val Asp His Ser Val Arg Ile Asn Ser Val Gly Ser Thr Ala Ser Ser
        675                 680                 685

Ser Gln Pro Leu Leu Val His Asp Asp Val
    690                 695


<210> SEQ ID NO 5
<211> LENGTH: 696
<212> TYPE: PRT
<213> ORGANISM: Artificial Sequence
<220> FEATURE:
<223> OTHER INFORMATION: cKIT-VVDV

<400> SEQUENCE: 5

Met Glu His His His His His His His His Glu Tyr Met Pro Met Glu
1               5                   10                  15

Met Ala Pro Ile Leu Gly Tyr Trp Lys Ile Lys Gly Leu Val Gln Pro
            20                  25                  30

Thr Arg Leu Leu Leu Glu Tyr Leu Glu Glu Lys Tyr Glu Glu His Leu
        35                  40                  45

Tyr Glu Arg Asp Glu Gly Asp Lys Trp Arg Asn Lys Lys Phe Glu Leu
    50                  55                  60

Gly Leu Glu Phe Pro Asn Leu Pro Tyr Tyr Ile Asp Gly Asp Val Lys
65                  70                  75                  80

Leu Thr Gln Ser Met Ala Ile Ile Arg Tyr Ile Ala Asp Lys His Asn
                85                  90                  95

Met Leu Gly Gly Cys Pro Lys Glu Arg Ala Glu Ile Ser Met Leu Glu
            100                 105                 110

Gly Ala Val Leu Asp Ile Arg Tyr Gly Val Ser Arg Ile Ala Tyr Ser
        115                 120                 125

Lys Asp Phe Glu Thr Leu Lys Val Asp Phe Leu Ser Lys Leu Pro Glu
    130                 135                 140

Met Leu Lys Met Phe Glu Asp Arg Leu Cys His Lys Thr Tyr Leu Asn
145                 150                 155                 160

Gly Asp His Val Thr His Pro Asp Phe Met Leu Tyr Asp Ala Leu Asp
                165                 170                 175

Val Val Leu Tyr Met Asp Pro Met Cys Leu Asp Ala Phe Pro Lys Leu
            180                 185                 190

Val Cys Phe Lys Lys Arg Ile Glu Ala Ile Pro Gln Ile Asp Lys Tyr
        195                 200                 205

Leu Lys Ser Ser Lys Tyr Ile Ala Trp Pro Leu Gln Gly Trp Gln Ala
    210                 215                 220

Thr Phe Gly Gly Gly Asp His Pro Pro Lys Ser Asp Leu Val Pro Arg
225                 230                 235                 240

His Asn Gln Thr Ser Leu Tyr Lys Lys Ala Gly Ser Ala Ala Ala Val
                245                 250                 255

Leu Glu Glu Asn Leu Tyr Phe Gln Gly Thr Tyr Lys Tyr Leu Gln Lys
            260                 265                 270

Pro Met Tyr Glu Val Gln Trp Lys Glu Glu Ile Asn Gly Asn Asn Tyr
        275                 280                 285

Val Tyr Ile Asp Pro Thr Gln Leu Pro Tyr Asp His Lys Trp Glu Phe
    290                 295                 300

Pro Arg Asn Arg Leu Ser Phe Gly Lys Thr Leu Gly Ala Gly Ala Phe
305                 310                 315                 320

Gly Lys Val Val Glu Ala Thr Ala Tyr Gly Leu Ile Lys Ser Asp Ala
```

```
                325                 330                 335

Ala Met Thr Val Ala Val Lys Met Leu Lys Pro Ser Ala His Leu Thr
            340                 345                 350

Glu Arg Glu Ala Leu Met Ser Glu Leu Lys Val Leu Ser Tyr Leu Gly
        355                 360                 365

Asn His Met Asn Ile Val Asn Leu Leu Gly Ala Cys Thr Ile Gly Gly
    370                 375                 380

Pro Thr Leu Val Ile Thr Glu Tyr Cys Cys Tyr Gly Asp Leu Leu Asn
385                 390                 395                 400

Phe Leu Arg Arg Lys Arg Asp Ser Phe Ile Cys Ser Lys Gln Glu Asp
                405                 410                 415

His Ala Glu Ala Ala Leu Tyr Lys Asn Leu Leu His Ser Lys Glu Ser
            420                 425                 430

Ser Cys Ser Asp Ser Thr Asn Glu Tyr Met Asp Met Lys Pro Gly Val
        435                 440                 445

Ser Tyr Val Val Pro Thr Lys Ala Asp Lys Arg Arg Ser Val Arg Ile
    450                 455                 460

Gly Ser Tyr Ile Glu Arg Asp Val Thr Pro Ala Ile Met Glu Asp Asp
465                 470                 475                 480

Glu Leu Ala Leu Asp Leu Glu Asp Leu Leu Ser Phe Ser Tyr Gln Val
                485                 490                 495

Ala Lys Gly Met Ala Phe Leu Ala Ser Lys Asn Cys Ile His Arg Asp
            500                 505                 510

Leu Ala Ala Arg Asn Ile Leu Leu Thr His Gly Arg Ile Thr Lys Ile
        515                 520                 525

Cys Asp Phe Gly Leu Ala Arg Val Ile Lys Asn Asp Ser Asn Tyr Val
    530                 535                 540

Val Lys Gly Asn Ala Arg Leu Pro Val Lys Trp Met Ala Pro Glu Ser
545                 550                 555                 560

Ile Phe Asn Cys Val Tyr Thr Phe Glu Ser Asp Val Trp Ser Tyr Gly
                565                 570                 575

Ile Phe Leu Trp Glu Leu Phe Ser Leu Gly Ser Ser Pro Tyr Pro Gly
            580                 585                 590

Met Pro Val Asp Ser Lys Phe Tyr Lys Met Ile Lys Glu Gly Phe Arg
        595                 600                 605

Met Leu Ser Pro Glu His Ala Pro Ala Glu Met Tyr Asp Ile Met Lys
    610                 615                 620

Thr Cys Trp Asp Ala Asp Pro Leu Lys Arg Pro Thr Phe Lys Gln Ile
625                 630                 635                 640

Val Gln Leu Ile Glu Lys Gln Ile Ser Glu Ser Thr Asn His Ile Tyr
                645                 650                 655

Ser Asn Leu Ala Asn Cys Ser Pro Asn Arg Gln Lys Pro Val Val Asp
            660                 665                 670

His Ser Val Arg Ile Asn Ser Val Gly Ser Thr Ala Ser Ser Ser Gln
        675                 680                 685

Pro Leu Leu Val His Asp Asp Val
    690                 695


<210> SEQ ID NO 6
<211> LENGTH: 469
<212> TYPE: PRT
<213> ORGANISM: Artificial Sequence
<220> FEATURE:
<223> OTHER INFORMATION: cKIT-T670I
```

<400> SEQUENCE: 6

Met Ser Tyr Tyr His His His His His His Asp Tyr Asp Ile Pro Thr
1 5 10 15

Thr Glu Asn Leu Tyr Phe Gln Gly Ala Met Leu Val Pro Arg Gly Ser
20 25 30

Pro Trp Gly Ser Thr Tyr Lys Tyr Leu Gln Lys Pro Met Tyr Glu Val
35 40 45

Gln Trp Lys Val Val Glu Glu Ile Asn Gly Asn Asn Tyr Val Tyr Ile
50 55 60

Asp Pro Thr Gln Leu Pro Tyr Asp His Lys Trp Glu Phe Pro Arg Asn
65 70 75 80

Arg Leu Ser Phe Gly Lys Thr Leu Gly Ala Gly Ala Phe Gly Lys Val
85 90 95

Val Glu Ala Thr Ala Tyr Gly Leu Ile Lys Ser Asp Ala Ala Met Thr
100 105 110

Val Ala Val Lys Met Leu Lys Pro Ser Ala His Leu Thr Glu Arg Glu
115 120 125

Ala Leu Met Ser Glu Leu Lys Val Leu Ser Tyr Leu Gly Asn His Met
130 135 140

Asn Ile Val Asn Leu Leu Gly Ala Cys Thr Ile Gly Gly Pro Thr Leu
145 150 155 160

Val Ile Ile Glu Tyr Cys Cys Tyr Gly Asp Leu Leu Asn Phe Leu Arg
165 170 175

Arg Lys Arg Asp Ser Phe Ile Cys Ser Lys Gln Glu Asp His Ala Glu
180 185 190

Ala Ala Leu Tyr Lys Asn Leu Leu His Ser Lys Glu Ser Ser Cys Ser
195 200 205

Asp Ser Thr Asn Glu Tyr Met Asp Met Lys Pro Gly Val Ser Tyr Val
210 215 220

Val Pro Thr Lys Ala Asp Lys Arg Arg Ser Val Arg Ile Gly Ser Tyr
225 230 235 240

Ile Glu Arg Asp Val Thr Pro Ala Ile Met Glu Asp Asp Glu Leu Ala
245 250 255

Leu Asp Leu Glu Asp Leu Leu Ser Phe Ser Tyr Gln Val Ala Lys Gly
260 265 270

Met Ala Phe Leu Ala Ser Lys Asn Cys Ile His Arg Asp Leu Ala Ala
275 280 285

Arg Asn Ile Leu Leu Thr His Gly Arg Ile Thr Lys Ile Cys Asp Phe
290 295 300

Gly Leu Ala Arg Asp Ile Lys Asn Asp Ser Asn Tyr Val Val Lys Gly
305 310 315 320

Asn Ala Arg Leu Pro Val Lys Trp Met Ala Pro Glu Ser Ile Phe Asn
325 330 335

Cys Val Tyr Thr Phe Glu Ser Asp Val Trp Ser Tyr Gly Ile Phe Leu
340 345 350

Trp Glu Leu Phe Ser Leu Gly Ser Ser Pro Tyr Pro Gly Met Pro Val
355 360 365

Asp Ser Lys Phe Tyr Lys Met Ile Lys Glu Gly Phe Arg Met Leu Ser
370 375 380

Pro Glu His Ala Pro Ala Glu Met Tyr Asp Ile Met Lys Thr Cys Trp
385 390 395 400

Asp Ala Asp Pro Leu Lys Arg Pro Thr Phe Lys Gln Ile Val Gln Leu
405 410 415

-continued

```
Ile Glu Lys Gln Ile Ser Glu Ser Thr Asn His Ile Tyr Ser Asn Leu
            420                 425                 430

Ala Asn Cys Ser Pro Asn Arg Gln Lys Pro Val Val Asp His Ser Val
        435                 440                 445

Arg Ile Asn Ser Val Gly Ser Thr Ala Ser Ser Ser Gln Pro Leu Leu
    450                 455                 460

Val His Asp Asp Val
465
```

The invention claimed is:

1. A method of treating a disease caused by the kinase activity of c-KIT, oncogenic forms thereof, or polymorphs thereof, *in a patient in need thereof,* wherein the disease is [selected from the group consisting of] gastrointestinal stromal tumors, [ovarian cancer, melanoma, acute myeloid leukemia, germ cell tumors of the seminoma or dysgerminoma, mastocytosis, and mast cell leukemia,] *and wherein the c-KIT contains a missense mutation, insertion mutation, or a deletion mutation and is encoded by exons selected from the group consisting of Exon 9, Exon 11, Exon 13, Exon 14, Exon 17, and Exon 18, presenting either individually or in combination,* comprising [the administration of] *administering to the patient a therapeutically effective amouont of* a compound *selected from the group consisting* of [formula Ia Ia

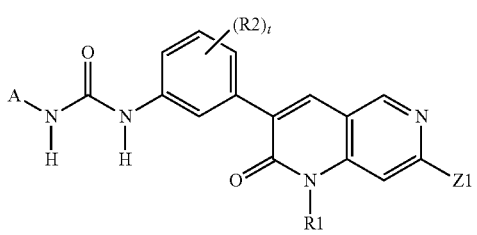

]

*1-(4-bromo-5-(1-ethyl-7-(methylamino)-2-oxo-1,2-dihydro-1,6-naphthyridin-3-yl)-2-fluorophenyl)-3-phenylurea;*

*1-(benzo[b]thiophen-3-yl)-3-(5-(1-ethyl-7-(methylamino)-2-oxo-1,2-dihydro-1,6-naphthyridin-3-yl)-2-fluoro-4-methylphenyl)urea; and*

*1-(5-(7-amino-1-ethyl-2-oxo-1,2-dihydro-1,6-naphthyridin-3-yl)-4-bromo-2-fluorophenyl)-3-phenylurea;* or a pharmaceutically acceptable salt thereof[, wherein:

A is selected from the group consisting of phenyl, naphthyl, and benzothienyl;

G1 is a heteroaryl taken from the group consisting of pyrrolyl, furyl, thienyl, oxazolyl, thiazolyl, isoxazolyl, isothiazolyl, imidazolyl, pyrazolyl, oxadiazolyl, thiadiazolyl, triazolyl, tetrazolyl, pyrazinyl, pyridazinyl, triazinyl, pyridinyl, and pyrimidinyl;

G4 is a heterocyclyl taken from the group consisting of oxetanyl, azetadinyl, tetrahydrofuranyl, pyrrolidinyl, oxazolinyl, oxazolidinyl, imidazolonyl, pyranyl, tetrahydropyranyl, dioxalinyl, piperidinyl, and morpholinyl;

when A has one or more substitutable sp2-hybridized carbon atom, each respective sp2 hybridized carbon atom may be optionally substituted with a Z3 substituent;

Z1 is selected from the group consisting of —NH(R4), and —NHCOR8;

in the event that Z1 contains an alkyl or alkylene moiety, such moieties may be further substituted with one or more C1-C6alkyls;

each Z2 is independently and individually selected from the group consisting of hydrogen, C1-C6alkyl, C3-C8-carbocyclyl, C1-C6 alkoxy, hydroxyl, hydroxyC1-C6alkyl-, cyano, $(R3)_2N$—, and —$(CH_2)_nR5$;

in the event that Z2 contains an alkyl or alkylene moiety, such moieties may be further substituted with one or more C1-C6alkyls;

each Z3 is independently and individually selected from the group consisting of H, methyl, ethyl, isopropyl, C3-C4 carbocyclyl, halogen, cyano, —$(CH_2)_k$—$N(R3)_2$, and —$(CH_2)_k$—R5;

R1 is selected from the group consisting of C1-C4alkyl, branched C3-C5alkyl, and C3-C5carbocyclyl;

each R2 is independently and individually selected from the group consisting of hydrogen, methyl, ethyl, halogen, fluoroalkyl wherein the alkyl moiety can be partially or fully fluorinated, cyano, and C2-C3alkynyl;

each R3 is independently and individually selected from the group consisting of H, C1-C6alkyl, branched C3-C7alkyl, and C3-C8carbocyclyl;

each R4 is independently and individually selected from the group consisting of H, C1-C6alkyl, hydroxyC2-C6alkyl, C1-C6alkoxyC2-C6alkyl, branched C3-C7alkyl, branched hydroxyC2-C6alkyl, branched C1-C6alkoxyC2-C6alkyl, —$(CH_2)_q$—$N(R7)_2$, —$(CH_2)_q$—R5, —$(CH_2)_n$C(O)R5, C3-C8carbocyclyl, hydroxyl substituted C3-C8carbocyclyl, alkoxy substituted C3-C8carbocyclyl, and —$(CH_2)_n$—R17;

each R5 is independently and individually selected from the group consisting of

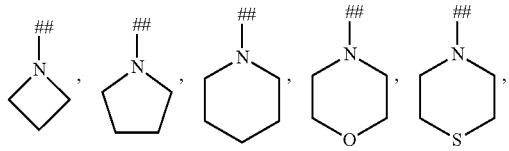

-continued

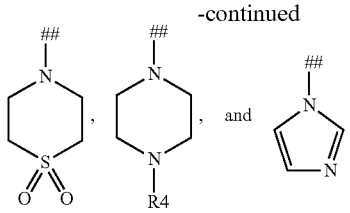

and wherein the symbol (##) is the point of attachment of the R5 moiety;

each R5 may be optionally substituted with one or two R10 substituents;

each R7 is independently and individually selected from the group consisting of H, C1-C6alkyl, hydroxyC2-C6alkyl, C1-C6alkoxyC2-C6alkyl, branched C3-C7alkyl, branched hydroxyC2-C6 alkyl, branched C1-C6alkoxyC2-C6alkyl, —$(CH_2)_q$—R5, —$(CH_2)$—C(O)R5, —$(CH_2)$—C(O)OR3, C3-C8carbocyclyl, hydroxyl substituted C3-C8carbocyclyl, alkoxy substituted C3-C8carbocyclyl, and —$(CH_2)_n$—R17;

each R8 is independently and individually selected from the group consisting of hydrogen, C1-C6alkyl, branched C3-C7alkyl, fluoroalkyl wherein the alkyl moiety is partially or fully fluorinated, C3-C8carbocyclyl, Z3-substituted phenyl, Z3-substituted G1, Z3-substituted G1-C1-C6alkyl, Z2-substituted G4, Z2-substituted G4-C1-C6alkyl, C1-C6alkoxy, C1-C6alkoxyC1-C6alkyl, cyanoC1-C6alkyl, —$N(R4)_2$, and R5;

each R10 is independently and individually selected from the group consisting of $CO_2H$, $CO_2$C1-C6alkyl, CO—$N(R4)_2$, OH, C1-C6alkoxy, C1-C6alkyl, and —$N(R4)_2$;

each R17 is taken from the group comprising phenyl, naphthyl, pyrrolyl, furyl, thienyl, oxazolyl, thiazolyl, isoxazolyl, imidazolyl, pyrazolyl, oxadiazolyl, thiadiazolyl, triazolyl, tetrazolyl, pyrazinyl, pyridazinyl, triazinyl, oxetanyl, azetadinyl, tetrahydrofuranyl, oxazolinyl, oxazolidinyl, pyranyl, thiopyranyl, tetrahydropyranyl, dioxalinyl, pyrrolidinyl, and piperidinyl;

wherein R17 can be further substituted with one or more Z2 or Z3 moieties;

wherein two R3 or R4 moieties are independently and individually taken from the group consisting of C1-C6alkyl and branched C3-C6alkyl, hydroxyalkyl, and alkoxyalkyl and are attached to the same nitrogen atom, said moieties may cyclize to form a C3-C7 heterocyclyl ring;

and k is 1 or 2; n is 0-6; p is 1-4; q is 2-6; r is 0 or 1; t is 1-3].

[2. The method of claim 1 wherein the compound of Formula Ia is a compound of Formula Ib Ib

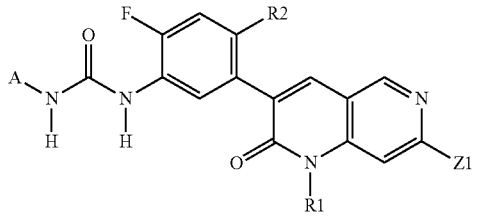

or a pharmaceutically acceptable salt thereof, wherein:

A is phenyl, R1 is linear or branched C1-C4alkyl, R2 is methyl or halogen, Z1 is —NH(R4) or —NHCOR8.]

[3. The method of claim 1 wherein the kinase activity of c-KIT, oncogenic forms thereof, or polymorphs thereof, wherein c-KIT contains a missense mutation, insertion mutation, or a deletion mutation encoded by exons comprising Exon 9, Exon 11, Exon 13, Exon 14, Exon 17, or Exon 18, presenting either individually or in combination, comprising the administration of a compound of formula Ia or a pharmaceutically acceptable salt thereof.]

[4. The method of claim 1 wherein the compound is selected from the group consisting of 1-(5-(1-ethyl-7-(methylamino)-2-oxo-1,2-dihydro-1,6-naphthyridin-3-yl)-2-fluoro-4-methylphenyl)-3-(naphthalen-1-yl)urea, 1-(5-(1-ethyl-7-(methylamino)-2-oxo-1,2-dihydro-1,6-naphthyridin-3-yl)-2-fluorophenyl)-3-(naphthalen-1-yl)urea, 1-(4-chloro-5-(1-ethyl-7-(methylamino)-2-oxo-1,2-dihydro-1,6-naphthyridin-3-yl)-2-fluorophenyl)-3-phenylurea, 1-(4-chloro-5-(1-ethyl-7-(methylamino)-2-oxo-1,2-dihydro-1,6-naphthyridin-3-yl)-2-fluorophenyl)-3-(2,3-difluorophenyl)urea, 1-(2-fluoro-5-(1-isopropyl-7-(methylamino)-2-oxo-1,2-dihydro-1,6-naphthyridin-3-yl)phenyl)-3-phenylurea, 1-(4-chloro-5-(1-ethyl-7-(methylamino)-2-oxo-1,2-dihydro-1,6-naphthyridin-3-yl)-2-fluorophenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-phenylurea, 1-(4-chloro-2-fluoro-5-(1-methyl-7-(methylamino)-2-oxo-1,2-dihydro-1,6-naphthyridin-3-yl)phenyl)-3-(naphthalen-1-yl)urea, 1-(4-chloro-2-fluoro-5-(1-methyl-7-(methylamino)-2-oxo-1,2-dihydro-1,6-naphthyridin-3-yl)phenyl)-3-(3-cyanophenyl)urea, 1-(4-chloro-2-fluoro-5-(1-methyl-7-(methylamino)-2-oxo-1,2-dihydro-1,6-naphthyridin-3-yl)phenyl)-3-(2,3-difluorophenyl)urea, 1-(4-chloro-3-(1-methyl-7-(methylamino)-2-oxo-1,2-dihydro-1,6-naphthyridin-3-yl)phenyl)-3-(3-cyanophenyl)urea, 1-(3-cyanophenyl)-3-(5-(1-ethyl-7-(methylamino)-2-oxo-1,2-dihydro-1,6-naphthyridin-3-yl)-2-fluorophenyl)urea, 1-(benzo[b]thiophen-3-yl)-3-(2-fluoro-4-methyl-5-(1-methyl-7-(methylamino)-2-oxo-1,2-dihydro-1,6-naphthyridin-3-yl)phenyl)urea, 1-(benzo[b]thiophen-3-yl)-3-(2,4-difluoro-5-(1-methyl-7-(methylamino)-2-oxo-1,2-dihydro-1,6-naphthyridin-3-yl)phenyl)urea, 1-(5-(1-ethyl-7-(methylamino)-2-oxo-1,2-dihydro-1,6-naphthyridin-3-yl)-2,4-difluorophenyl)-3-(3-fluorophenyl)urea, 1-(5-(1-ethyl-7-(methylamino)-2-oxo-1,2-dihydro-1,6-naphthyridin-3-yl)-2,4-difluorophenyl)-3-phenylurea, 1-(3-chlorophenyl)-3-(5-(1-ethyl-7-(methylamino)-2-oxo-1,2-dihydro-1,6-naphthyridin-3-yl)-2,4-difluorophenyl)urea, 1-(3-cyanophenyl)-3-(5-(1-ethyl-7-(methylamino)-2-oxo-1,2-dihydro-1,6-naphthyridin-3-yl)-2,4-difluorophenyl)urea, 1-(benzo[b]thiophen-3-yl)-3-(5-(1-ethyl-7-(methylamino)-2-oxo-1,2-dihydro-1,6-naphthyridin-3-yl)-2,4-difluorophenyl)urea, 1-(5-(7-amino-1-ethyl-2-oxo-1,2-dihydro-1,6-naphthyridin-3-yl)-4-chloro-2-fluorophenyl)-3-(3-fluorophenyl)urea, 1-(5-(7-amino-1-ethyl-2-oxo-1,2-dihydro-1,6-naphthyridin-3-yl)-4-chloro-2-fluorophenyl)-3-phenylurea, 1-(4-chloro-2-fluoro-5-(1-isopropyl-7-(methylamino)-2-oxo-1,2-dihydro-1,6-naphthyridin-3-yl)phenyl)-3-phenylurea, 1-(5-(1-ethyl-7-(methylamino)-2-oxo-1,2-dihydro-1,6-naphthyridin-3-yl)-2-fluoro-4-methylphenyl)-3-phenylurea, 1-[4-chloro-5-(1-ethyl-7-methylamino-2-oxo-1,2-dihydro-[1,6]naphthyridin-3-yl)-2-fluoro-phenyl]-3-(3-fluoro-phenyl)-urea, 1-[4-chloro-5-(1-ethyl-7-methylamino-2-oxo-1,2-dihydro-[1,6]naphthyridin-3-yl)-2-fluoro-phenyl]-3-(2-fluoro-phenyl)-urea, 1-(4-chloro-3-(1-ethyl-7-(methylamino)-2-oxo-1,2-dihydro-1,6-naphthyridin-3-yl)-2-fluorophenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-(3-fluorophenyl)urea, 1-(4-chloro-5-(7-(2-(dimethylamino)ethylamino)-1-ethyl-2-oxo-1,2-dihydro-1,6-naphthyridin-3-yl)-2-fluorophenyl)-3-phenylurea, 1-(4-chloro-5-(7-(3-(dimethylamino)propylamino)-1-ethyl-2-oxo-1,2-dihydro-1,6-naphthyridin-3-yl)-2-fluorophenyl)-3-phenylurea, 1-(4-bromo-5-(1-ethyl-7-(methylamino)-2-oxo-1,2-dihydro-1,6-naphthyridin-3-yl)-2-fluorophenyl)-3-phenylurea, 1-(benzo[b]thiophen-3-yl)-3-(4-chloro-5-(1-ethyl-7-(methylamino)-2-oxo-1,2,4a,8a-tetrahydro-1,6-naphthyridin-3-yl)-2-fluorophenyl)urea, 1-(4-chloro-3-(1-ethyl-7-(methylamino)-2-oxo-1,2-dihydro-1,6-naphthyridin-3-yl)phenyl)-3-phenylurea, 1-(4-chloro-5-(1-ethyl-7-(2-methoxyethylamino)-2-oxo-1,2-dihydro-1,6-naphthyridin-3-yl)-2-fluorophenyl)-3-(4-fluorophenyl)urea, 1-(4-chloro-5-(1-ethyl-7-(2-methoxyethylamino)-2-oxo-1,2-dihydro-1,6-naphthyridin-3-yl)-2-fluorophenyl)-3-(2-fluorophenyl)urea, 1-(5-(1-ethyl-7-(2-methoxyethylamino)-2-oxo-1,2-dihydro-1,6-naphthyridin-3-yl)-2,4-difluorophenyl)-3-phenylurea, 1-(5-(1-ethyl-7-(2-methoxyethylamino)-2-oxo-1,2-dihydro-1,6-naphthyridin-3-yl)-2-fluoro-4-methylphenyl)-3-phenylurea, 1-(5-(1-ethyl-7-(methylamino)-2-oxo-1,2-dihydro-1,6-naphthyridin-3-yl)-2-fluoro-4-methylphenyl)-3-(2-fluorophenyl)urea, 1-(4-chloro-5-(1-ethyl-7-(3-methoxypropylamino)-2-oxo-1,2-dihydro-1,6-naphthyridin-3-yl)-2-fluorophenyl)-3-phenylurea, 1-(2,4-difluoro-5-(1-isopropyl-7-(methylamino)-2-oxo-1,2-dihydro-1,6-naphthyridin-3-yl)phenyl)-3-(3-fluorophenyl)urea, 1-(2-fluoro-5-(1-isopropyl-7-(methylamino)-2-oxo-1,2-dihydro-1,6-naphthyridin-3-yl)-4-methylphenyl)-3-(3-fluorophenyl)urea, 1-(4-chloro-5-(1-ethyl-2-oxo-7-(tetrahydro-2H-pyran-4-ylamino)-1,2-dihydro-1,6-naphthyridin-3-yl)-2-fluorophenyl)-3-phenylurea, (S)-1-(4-chloro-5-(1-ethyl-7-(1-methoxypropan-2-ylamino)-2-oxo-1,2-dihydro-1,6-naphthyridin-3-yl)-2-fluorophenyl)-3-phenylurea, 1-(5-(1-ethyl-7-(methylamino)-2-oxo-1,2-dihydro-1,6-naphthyridin-3-yl)-2-fluoro-4-methylphenyl)-3-(3-fluorophenyl)urea, 1-(5-(7-(cyclopropylamino)-1-ethyl-2-oxo-1,2-dihydro-1,6-naphthyridin-3-yl)-2-fluoro-4-methylphenyl)-3-(3-fluorophenyl)urea, 1-(4-chloro-5-(1-ethyl-7-(1-methylpiperidin-4-ylamino)-2-oxo-1,2-dihydro-1,6-naphthyridin-3-yl)-2-fluorophenyl)-3-phenylurea, 1-(4-chloro-5-(1-ethyl-2-oxo-7-(THF-3-ylamino)-1,2-dihydro-1,6-naphthyridin-3-yl)-2-fluorophenyl)-3-phenylurea, 1-(4-chloro-5-(1-ethyl-7-(1-methylpyrrolidin-3-ylamino)-2-oxo-1,2-dihydro-1,6-naphthyridin-3-yl)-2-fluorophenyl)-3-phenylurea, 1-(4-bromo-5-(1-ethyl-7-(methylamino)-2-oxo-1,2-dihydro-1,6-naphthyridin-3-yl)-2-fluorophenyl)-3-(3-fluorophenyl)urea, 1-(4-bromo-5-(1-ethyl-7-(2-methoxyethylamino)-2-oxo-1,2-dihydro-1,6-naphthyridin-3-yl)-2-fluorophenyl)-3-phenylurea, 1-(5-(7-acetamido-1-ethyl-2-oxo-1,2-dihydro-1,6-naphthyridin-3-yl)-4-bromo-2-fluorophenyl)-3-phenylurea, 1-(5-(7-acetamido-1-ethyl-2-oxo-1,2-dihydro-1,6-naphthyridin-3-yl)-4-chloro-2-fluorophenyl)-3-phenylurea, 1-(4-chloro-5-(1-ethyl-7-(methylamino)-2-oxo-1,2-dihydro-1,6-naphthyridin-3-yl)-2-fluorophenyl)-3-(3,5-difluorophenyl)urea, 1-(4-bromo-2-fluoro-5-(1-methyl-7-(methylamino)-2-oxo-1,2-dihydro-1,6-naphthyridin-3-yl)phenyl)-3-phenylurea, 1-(5-(7-amino-1-ethyl-2-oxo-1,2-dihydro-1,6-naphthyridin-3-yl)-4-bromo-2-fluorophenyl)-3-phenylurea, 1-(5-(7-amino-1-ethyl-2-oxo-1,2-dihydro-1,6-naphthyridin-3-yl)-2-fluoro-4-methylphenyl)-3-(3-fluorophenyl)urea, 1-(benzo[b]thiophen-3-yl)-3-(5-(1-ethyl-7-(methylamino)-2-oxo-1,2-dihydro-1,6-naphthyridin-3-yl)-2-fluoro-4-methylphenyl)urea, 1-(3,5-difluorophenyl)-3-(5-(1-ethyl-7-(methylamino)-2-oxo-1,2-dihydro-1,6-naphthyridin-3-yl)-2-fluoro-4-methylphenyl)urea, 1-(2,5-difluorophenyl)-3-(5-(1-ethyl-7-(methylamino)-2-oxo-1,2-dihydro-1,6-naphthyridin-3-yl)-2-fluoro-4-methylphenyl)urea, 1-(2,5-difluorophenyl)-3-(5-(1-ethyl-7-(methylamino)-2-oxo-1,2,4a,8a-tetrahydro-1,6-naphthyridin-3-yl)-2,4-difluorophenyl)urea, 1-(3,5-difluorophenyl)-3-(5-(1-ethyl-7-(methylamino)-2-oxo-1,2,4a,8a-tetrahydro-1,6-naphthyridin-3-yl)-2,4-difluorophenyl)urea, N-(3-(2-bromo-4-fluoro-5-(3-phenylureido)phenyl)-1-ethyl-2-oxo-1,2-dihydro-1,6-naphthyridin-7-yl)-2-cyanoacetamide, N-(3-(2-chloro-4-fluoro-5-(3-phenylureido)phenyl)-1-ethyl-2-oxo-1,2-dihydro-1,6-naphthyridin-7-yl)-2-cyanoacetamide, 1-(5-(7-acetamido-1-ethyl-2-oxo-1,2-dihydro-1,6-naphthyridin-3-yl)-2,4-difluorophenyl)-3-phenylurea, N-(3-(2-chloro-5-(3-(3,5-difluorophenyl)ureido)-4-fluorophenyl)-1-ethyl-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(2,5-difluorophenyl)urea, 1-(3-chloro-5-fluorophenyl)-3-(5-(1-ethyl-7-(methylamino)-2-oxo-1,2-dihydro-1,6-naphthyridin-3-yl)-2-fluoro-4-methylphenyl)urea, 3-(3-(2-chloro-4-fluoro-5-(3-phenylureido)phenyl)-1-ethyl-2-oxo-1,2-dihydro-1,6-naphthyridin-7-yl)-1,1-dimethylurea, 1-(4-chloro-5-(1-ethyl-7-(methylamino)-2-oxo-1,2-dihydro-1,6-naphthyridin-3-yl)-2-fluorophenyl)-3-(3-chloro-5-fluorophenyl)urea, 1-(4-chloro-5-(1-ethyl-7-(methylamino)-2-oxo-1,2-dihydro-1,6-naphthyridin-3-yl)-2-fluorophenyl)-3-(3-fluoro-5-methylphenyl)urea, methyl(3-(2-chloro-4-fluoro-5-(3-phenylureido)phenyl)-1-ethyl-2-oxo-1,2-dihydro-1,6-naphthyridin-7-yl)carbamate, N-(3-(2-chloro-4-fluoro-5-(3-phenylureido)phenyl)-1-ethyl-2-oxo-1,2-dihydro-1,6-naphthyridin-7-yl)-2-methoxyacetamide, 2-cyano-N-(3-(2,4-difluoro-5-(3-phenylureido)phenyl)-1-ethyl-2-oxo-1,2-dihydro-1,6-naphthyridin-7-yl)acetamide, 1-(4-cyano-5-(1-ethyl-7-(methylamino)-2-oxo-1,2-dihydro-1,6-naphthyridin-3-yl)-2-fluorophenyl)-3-phenylurea, 1-(4-chloro-2-fluoro-5-(1-isopropyl-7-(methylamino)-2-oxo-1,2-dihydro-1,6-naphthyridin-3-yl)phenyl)-3-(3-fluorophenyl)urea, N-(1-ethyl-3-(4-fluoro-5-(3-(3-fluorophenyl)ureido)-2-methylphenyl)-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea, N-(1-ethyl-3-(4-fluoro-2-methyl-5-(3-phenylureido) phenyl)-2-oxo-1,2-dihydro-1,6-naphthyridin-7-yl) acetamide, N-(3-(2-chloro-4-fluoro-5-(3-phenylureido) phenyl)-1-ethyl-2-oxo-1,2-dihydro-1,6-naphthyridin-7-yl)-3-hydroxyazetidine-1-carboxamide, 1-(5-(1-ethyl-7-(methylamino)-2-oxo-1,2-dihydro-1,6-naphthyridin-3-yl)-2-fluoro-4-methylphenyl)-3-(3-((4-methylpiperazin-1-yl)methyl)phenyl)urea, 1-(4-bromo-5-(1-ethyl-7-(methylamino)-2-oxo-1,2-dihydro-1,6-naphthyridin-3-yl)-2-fluorophenyl)-3-(3-((4-methylpiperazin-1-yl)methyl)phenyl)urea, (R)—N-(3-(2-chloro-4-fluoro-5-(3-phenylureido)phenyl)-1-ethyl-2-oxo-1,2-dihydro-1,6-naphthyridin-7-yl)-3-(dimethylamino)pyrrolidine-1-carboxamide, (S)—N-(3-(2-chloro-4-fluoro-5-(3-phenylureido)phenyl)-1-ethyl-2-oxo-1,2-dihydro-1,6-naphthyridin-7-yl) pyrrolidine-2-carboxamide, N-(3-(2-chloro-4-fluoro-5-(3-phenylureido)phenyl)-1-isopropyl-2-oxo-1,2-dihydro-1,6-naphthyridin-7-yl)acetamide, 1-(4-chloro-5-(1-ethyl-7-(methylamino)-2-oxo-1,2-dihydro-1,6-naphthyridin-3-yl)-2-fluorophenyl)-3-(4-fluoro-3-((4-methylpiperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-fluoro-5-((4-methylpiperazin-1-yl)methyl)phenyl)urea, 1-(5-(1-ethyl-7-(methylamino)-2-oxo-1,2-dihydro-1,6-naphthyridin-3-yl)-2-fluoro-4-methylphenyl)-3-(4-fluoro-3-((4-methylpiperazin-1-yl)methyl)phenyl)urea, 1-(5-(1-ethyl-7-(methylamino)-2-oxo-1,2-dihydro-1,6-naphthyridin-3-yl)-2,4-difluorophenyl)-3-(4-fluoro-3-((4-methylpiperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-cyanophenyl)urea, 1-(4-chloro-5-(1-ethyl-7-((3-morpholinopropyl)amino)-2-oxo-1,2-dihydro-1,6-naphthyridin-3-yl)-2-fluorophenyl)-3-phenylurea, 1-(5-(7-amino-1-ethyl-2-oxo-1,2-dihydro-1,6-naphthyridin-3-yl)-2-fluoro-4-methylphenyl)-3-(4-fluoro-3-((4-methylpiperazin-1-yl)methyl)phenyl)urea, 1-(4-chloro-5-(1-ethyl-7-(methylamino)-2-oxo-1,2-dihydro-1,6-naphthyridin-3-yl)-2-fluorophenyl)-3-(3-((dimethylamino)methyl)-4-fluorophenyl)urea, 1-(4-chloro-5-(1-ethyl-7-(methylamino)-2-oxo-1,2-dihydro-1,6-naphthyridin-3-yl)-2-fluorophenyl)-3-(4-fluoro-3-(morpholinomethyl)phenyl)urea, (S)—N-(3-(2-chloro-4-fluoro-5-(3-phenylureido)phenyl)-1-ethyl-2-oxo-1,2-dihydro-1,6-naphthyridin-7-yl)-3-(dimethylamino)pyrrolidine-1-carboxamide, 1-(4-chloro-5-(1-ethyl-7-(methylamino)-2-oxo-1,2-dihydro-1,6-naphthyridin-3-yl)-2-fluorophenyl)-3-(4-fluoro-3-(pyrrolidin-1-ylmethyl)phenyl)urea, 3-(3-(2-chloro-4-fluoro-5-(3-(3-fluorophenyl)ureido)phenyl)-1-isopropyl-2-oxo-1,2-dihydro-1,6-naphthyridin-7-yl)-1,1-dimethylurea, N-(3-(2-chloro-4-fluoro-5-(3-(3-fluorophenyl)ureido)phenyl)-1-isopropyl-2-oxo-1,2-dihydro-1,6-naphthyridin-7-yl)acetamide, N-(1-ethyl-3-(4-fluoro-5-(3-(4-fluoro-3-((4-methylpiperazin-1-yl) methyl)phenyl)ureido)-2-methylphenyl)-2-oxo-1,2-dihydro-1,6-naphthyridin-7-yl)formamide, 3-(1-ethyl-3-(4-fluoro-2-methyl-5-(3-phenylureido)phenyl)-2-oxo-1,2-dihydro-1,6-naphthyridin-7-yl)-1,1-dimethylurea, N-(3-(2-chloro-4-fluoro-5-(3-phenylureido)phenyl)-1-ethyl-2-oxo-1,2-dihydro-1,6-naphthyridin-7-yl)-3-(dimethylamino)azetidine-1-carboxamide, 3-(3-(2-chloro-4-fluoro-5-(3-phenylureido)phenyl)-1-isopropyl-2-oxo-1,2-dihydro-1,6-naphthyridin-7-yl)-1,1-dimethylurea, 3-(3-(5-(3-(benzo[b]thiophen-3-yl)ureido)-4-fluoro-2-methylphenyl)-1-ethyl-2-oxo-1,2-dihydro-1,6-naphthyridin-7-yl)-1,1-dimethylurea, 3-(3-(2-bromo-4-fluoro-5-(3-phenylureido)phenyl)-1-ethyl-2-oxo-1,2-dihydro-1,6-naphthyridin-7-yl)-1,1-dimethylurea, 3-(1-ethyl-3-(4-fluoro-5-(3-(3-fluorophenyl)ureido)-2-methylphenyl)-2-oxo-1,2-dihydro-1,6-naphthyridin-7-yl)-1,1-dimethylurea, N-(3-(2-chloro-4-fluoro-5-(3-(4-fluoro-3-(morpholinomethyl)phenyl)ureido)phenyl)-1-ethyl-2-oxo-1,2-dihydro-1,6-naphthyridin-7-yl) formamide, 3-(3-(5-(3-(3,5-difluorophenyl)ureido)-4-fluoro-2-methylphenyl)-1-ethyl-2-oxo-1,2-dihydro-1,6-naphthyridin-7-yl)-1,1-dimethylurea, N-(3-(4-fluoro-2-methyl-5-(3-phenylureido)phenyl)-1-isopropyl-2-oxo-1,2-dihydro-1,6-naphthyridin-7-yl) azetidine-1-carboxamide, N-(1-ethyl-3-(4-fluoro-2-methyl-5-(3-phenylureido)phenyl)-2-oxo-1,2-dihydro-1,6-naphthyridin-7-yl)azetidine-1-carboxamide, 1-(5-(1-ethyl-7-((6-methylpyridin-3-yl)amino)-2-oxo-1,2-dihydro-1,6-naphthyridin-3-yl)-2-fluoro-4-methylphenyl)-3-phenylurea, 3-(3-(2,4-difluoro-5-(3-phenylureido)phenyl)-1-ethyl-2-oxo-1,2-dihydro-1,6-naphthyridin-7-yl)-1,1-dimethylurea, 3-(dimethylamino)-N-(1-ethyl-3-(4-fluoro-2-methyl-5-(3-phenylureido)phenyl)-2-oxo-1,2-dihydro-1,6-naphthyridin-7-yl)azetidine-1-carboxamide, 1-(5-(1-ethyl-7-(methylamino)-2-oxo-1,2-dihydro-1,6-naphthyridin-3-yl)-2-fluoro-4-iodophenyl)-3-phenylurea, and 1-(5-(1-ethyl-7-((1-methyl-1H-pyrazol-4-yl) amino)-2-oxo-1,2-dihydro-1,6-naphthyridin-3-yl)-2-fluoro-4-methylphenyl)-3-phenylurea.]

[5. The method of claim 4 wherein the compound is selected from the group consisting of 1-(5-(1-ethyl-7-(methylamino)-2-oxo-1,2-dihydro-1,6-naphthyridin-3-yl)-2-fluoro-4-methylphenyl)-3-(naphthalen-1-yl)urea, 1-(4-chloro-5-(1-ethyl-7-(methylamino)-2-oxo-1,2-dihydro-1,6-naphthyridin-3-yl)-2-fluorophenyl)-3-phenylurea, 1-(4-chloro-5-(1-ethyl-7-(methylamino)-2-oxo-1,2-dihydro-1,6-naphthyridin-3-yl)-2-fluorophenyl)-3-(2,3-difluorophenyl)urea, 1-(5-(1-ethyl-7-(methylamino)-2-oxo-1,2-dihydro-1,6-naphthyridin-3-yl)-2,4-difluorophenyl)-3-phenylurea, 1-(benzo[b]thiophen-3-yl)-3-(5-(1-ethyl-7-(methylamino)-2-oxo-1,2-dihydro-1,6-naphthyridin-3-yl)-2,4-difluorophenyl)urea, 1-(5-(7-amino-1-ethyl-2-oxo-1,2-dihydro-1,6-naphthyridin-3-yl)-4-chloro-2-fluorophenyl)-3-(3-fluorophenyl)urea, 1-(5-(7-amino-1-ethyl-2-oxo-1,2-dihydro-1,6-naphthyridin-3-yl)-4-chloro-2-fluorophenyl)-3-phenylurea, 1-(5-(1-ethyl-7-(methylamino)-2-oxo-1,2-dihydro-1,6-naphthyridin-3-yl)-2-fluoro-4-methylphenyl)-3-phenylurea, 1-[4-chloro-5-(1-ethyl-7-methylamino-2-oxo-1,2-dihydro-[1,6]naphthyridin-3-yl)-2-fluoro-phenyl]-3-(3-fluoro-phenyl)-urea, 1-(4-bromo-5-(1-ethyl-7-(methylamino)-2-oxo-1,2-dihydro-1,6-naphthyridin-3-yl)-2-fluorophenyl)-3-phenylurea, 1-(benzo[b]thiophen-3-yl)-3-(4-chloro-5-(1-ethyl-7-(methylamino)-2-oxo-1,2,4a,8a-tetrahydro-1,6-naphthyridin-3-yl)-2-fluorophenyl)urea, 1-(5-(1-ethyl-7-(methylamino)-2-oxo-1,2-dihydro-1,6-naphthyridin-3-yl)-2-fluoro-4-methylphenyl)-3-(3-fluorophenyl)urea, 1-(5-(7-amino-1-ethyl-2-oxo-1,2-dihydro-1,6-naphthyridin-3-yl)-4-bromo-2-fluorophenyl)-3-phenylurea, 1-(benzo[b] thiophen-3-yl)-3-(5-(1-ethyl-7-(methylamino)-2-oxo-1,2-dihydro-1,6-naphthyridin-3-yl)-2-fluoro-4-methylphenyl)urea, 3-(3-(2-chloro-4-fluoro-5-(3-phenylureido)phenyl)-1-ethyl-2-oxo-1,2-dihydro-1,6-naphthyridin-7-yl)-1,1-dimethylurea, N-(1-ethyl-3-(4-fluoro-5-(3-(3-fluorophenyl)ureido)-2-methylphenyl)-2-oxo-1,2-dihydro-1,6-naphthyridin-7-yl)acetamide, N-(1-ethyl-3-(4-fluoro-2-methyl-5-(3-phenylureido)phenyl)-2-oxo-1,2-dihydro-1,6-naphthyridin-7-yl)acetamide, and 3-(1-ethyl-3-(4-fluoro-2-methyl-5-(3-phenylureido)phenyl)-2-oxo-1,2-dihydro-1,6-naphthyridin-7-yl)-1,1-dimethylurea.]

[6. The method of claim 4 wherein the compound is 1-(5-(1-ethyl-7-(methylamino)-2-oxo-1,2-dihydro-1,6-naphthyridin-3-yl)-2-fluoro-4-methylphenyl)-3-(naphthalen-1-yl)urea.]

[7. The method of claim 4 wherein the compound is 1-(4-chloro-5-(1-ethyl-7-(methylamino)-2-oxo-1,2-dihydro-1,6-naphthyridin-3-yl)-2-fluorophenyl)-3-(2,3-difluorophenyl)urea.]

8. The method of claim [4] *1,* wherein the compound is 1-(4-bromo-5-(1-ethyl-7-(methylamino)-2-oxo-1,2-dihydro-1,6-naphthyridin-3-yl)-2-fluorophenyl)-3-phenylurea.

[9. The method of claim 4 wherein the compound is 1-(5-(1-ethyl-7-(methylamino)-2-oxo-1,2-dihydro-1,6-naphthyridin-3-yl)-2-fluoro-4-methylphenyl)-3-phenylurea.]

10. The method of claim [4] *1,* wherein the compound is 1-(benzo[b]thiophen-3-yl)-3-(5-(1-ethyl-7-(methylamino)-2-oxo-1,2-dihydro-1,6-naphthyridin-3-yl)-2-fluoro-4-methylphenyl)urea.

[11. The method of claim 4 wherein the compound is 1-[4-chloro-5-(1-ethyl-7-methylamino-2-oxo-1,2-dihydro-[1,6]naphthyridin-3-yl)-2-fluoro-phenyl]-3-(3-fluoro-phenyl)-urea.]

12. The method of claim [4] *1,* wherein the compound is 1-(5-(7-amino-1-ethyl-2-oxo-1,2-dihydro-1,6-naphthyridin-3-yl)-4-bromo-2-fluorophenyl)-3-phenylurea.

[13. The method of claim/wherein the compound is 1-(5-(7-amino-1-ethyl-2-oxo-1,2-dihydro-1,6-naphthyridin-3-yl)-4-chloro-2-fluorophenyl)-3-phenylurea.]

[14. The method of claim 4 wherein the compound is 1-(4-chloro-5-(1-ethyl-7-(methylamino)-2-oxo-1,2-dihydro-1,6-naphthyridin-3-yl)-2-fluorophenyl)-3-phenylurea.]

[15. The method of claim 1 wherein the disease is gastrointestinal stromal tumors.]

[16. The method of claim 1 wherein the disease is ovarian cancer.]

[17. The method of claim 1 wherein the disease is melanoma.]

[18. The method of claim 1 wherein the disease is acute myeloid leukemia.]

[19. The method of claim 1 wherein the disease is germ cell tumors of the seminoma or dysgerminoma.]

[20. The method of claim 1 wherein the disease is mastocytosis.]

[21. The method of claim 1 wherein the disease is mast cell leukemia.]

* * * * *